(12) United States Patent
Jung et al.

(10) Patent No.: US 7,973,164 B2
(45) Date of Patent: Jul. 5, 2011

(54) QUINOLINE DERIVATIVES

(75) Inventors: Frederic Henri Jung, Reims (FR); Patrick Ple, Reims (FR)

(73) Assignee: AstraZeneca AB, Sodertalje (SE)

( * ) Notice: Subject to any disclaimer, the term of this patent is extended or adjusted under 35 U.S.C. 154(b) by 246 days.

(21) Appl. No.: 12/280,848

(22) PCT Filed: Mar. 1, 2007

(86) PCT No.: PCT/GB2007/000719
§ 371 (c)(1),
(2), (4) Date: Aug. 27, 2008

(87) PCT Pub. No.: WO2007/099326
PCT Pub. Date: Sep. 7, 2007

(65) Prior Publication Data
US 2009/0076074 A1  Mar. 19, 2009

(30) Foreign Application Priority Data

Mar. 2, 2006 (EP) .................... 06300181
Oct. 31, 2006 (EP) .................... 06301102

(51) Int. Cl.
*C07D 215/38* (2006.01)
(52) U.S. Cl. .................... 546/160; 546/153
(58) Field of Classification Search .................. 546/153, 546/160; 514/312, 313
See application file for complete search history.

(56) References Cited

U.S. PATENT DOCUMENTS

| | | | |
|---|---|---|---|
| 5,457,105 A | 10/1995 | Barker | |
| 5,616,582 A | 4/1997 | Barker | |
| 5,821,246 A | 10/1998 | Brown et al. | |
| 5,866,572 A | 2/1999 | Barker et al. | |
| 6,017,919 A | 1/2000 | Inaba et al. | |
| 6,399,602 B1 | 6/2002 | Barker et al. | |
| 6,531,291 B1 | 3/2003 | Kabbash et al. | |
| 6,593,333 B1 | 7/2003 | Cumming | |
| 6,716,847 B2 | 4/2004 | Cumming | |
| 6,881,553 B2 | 4/2005 | Kabbash et al. | |
| 6,897,214 B2 | 5/2005 | Barker et al. | |
| 6,919,338 B2 | 7/2005 | Mortlock et al. | |
| 6,977,259 B2 | 12/2005 | Mortlock et al. | |
| 7,037,925 B2 | 5/2006 | Larsson et al. | |
| 7,067,532 B2 | 6/2006 | Boyle et al. | |
| 7,074,800 B1 | 7/2006 | Stokes et al. | |
| 7,081,461 B1 | 7/2006 | Mortlock et al. | |
| 7,105,669 B1 | 9/2006 | Mortlock et al. | |
| 7,208,500 B2 * | 4/2007 | Lou et al. | 514/301 |
| 7,235,559 B1 | 6/2007 | Mortlock et al. | |
| 7,253,184 B2 | 8/2007 | Boyle et al. | |
| 7,262,201 B1 | 8/2007 | Hennequin et al. | |
| 7,268,230 B2 | 9/2007 | Hennequin | |
| 7,320,989 B2 * | 1/2008 | Anderson et al. | 514/313 |
| 7,402,583 B2 | 7/2008 | Boyle et al. | |
| 7,402,585 B2 | 7/2008 | Jung et al. | |
| 7,652,009 B2 * | 1/2010 | Kim et al. | 514/252.04 |

| | | |
|---|---|---|
| 2006/0160803 A1 | 7/2006 | Adams et al. |
| 2009/0036474 A1 | 2/2009 | Ple et al. |
| 2009/0036485 A1 | 2/2009 | Jung et al. |
| 2009/0042910 A1 | 2/2009 | Jung et al. |
| 2009/0076075 A1 | 3/2009 | Jung et al. |
| 2009/0233924 A1 | 9/2009 | Ple et al. |
| 2009/0233950 A1 | 9/2009 | Jung et al. |

FOREIGN PATENT DOCUMENTS

| | | |
|---|---|---|
| EP | 0566226 | 10/1993 |
| EP | 0837063 | 4/1998 |
| EP | 1541563 | 6/2005 |
| EP | 1541564 | 6/2005 |
| EP | 1661889 | 5/2006 |
| WO | WO 92/20642 | 11/1992 |
| WO | WO 96/09294 | 3/1996 |
| WO | WO 96/15118 | 5/1996 |
| WO | WO 96/39145 | 12/1996 |
| WO | WO 97/03069 | 1/1997 |
| WO | WO 97/29079 | 8/1997 |
| WO | WO 97/30034 | 8/1997 |
| WO | WO 99/47529 | 9/1999 |
| WO | WO 00/20402 | 4/2000 |
| WO | WO 00/21955 | 4/2000 |
| WO | WO 00/47212 | 8/2000 |
| WO | WO 01/19788 | 3/2001 |
| WO | WO 01/21594 | 3/2001 |
| WO | WO 01/21595 | 3/2001 |
| WO | WO 01/21596 | 3/2001 |
| WO | WO 01/21597 | 3/2001 |
| WO | WO 01/55116 | 8/2001 |
| WO | WO 02/00649 | 1/2002 |
| WO | WO 02/17712 | 3/2002 |
| WO | WO 02/36570 | 5/2002 |
| WO | WO 02/44166 | 6/2002 |
| WO | WO 02/051831 | 7/2002 |

(Continued)

*Primary Examiner* — D. Margaret Seaman
(74) *Attorney, Agent, or Firm* — Morgan, Lewis & Bockius LLP

(57) ABSTRACT

The invention concerns quinoline derivatives of Formula I

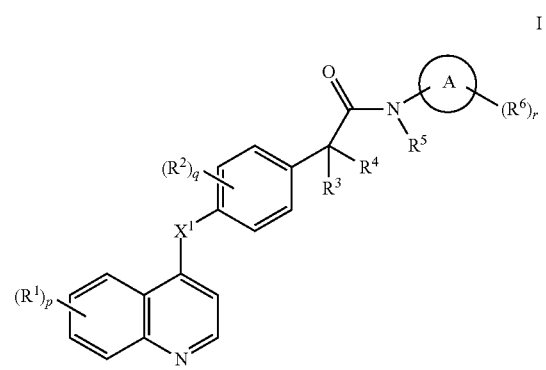

I or a pharmaceutically-acceptable salt thereof, wherein each of $X^1$, p, $R^1$, q, $R^2$, $R^3$, $R^4$, $R^5$, Ring A, r and $R^6$ has any of the meanings defined hereinbefore in the description; processes for their preparation, pharmaceutical compositions containing them and their use in the manufacture of a medicament for use in the treatment of cell proliferative disorders.

15 Claims, No Drawings

FOREIGN PATENT DOCUMENTS

| | | |
|---|---|---|
| WO | WO 02/092571 | 11/2002 |
| WO | WO 03/037274 | 5/2003 |
| WO | WO 03/040108 | 5/2003 |
| WO | WO 03/040109 | 5/2003 |
| WO | WO 03/055491 | 7/2003 |
| WO | WO 03/064413 | 8/2003 |
| WO | WO 03/099771 | 12/2003 |
| WO | WO 2004/007472 | 1/2004 |
| WO | WO 2004/024705 | 3/2004 |
| WO | WO 2004/058752 | 7/2004 |
| WO | WO 2004/058781 | 7/2004 |
| WO | WO 2004/094410 | 11/2004 |
| WO | WO 2004/098528 | 11/2004 |
| WO | WO 2004/105764 | 12/2004 |
| WO | WO 2004/108704 | 12/2004 |
| WO | WO 2004/113324 | 12/2004 |
| WO | WO 2005/014582 | 2/2005 |
| WO | WO 2005/021554 | 3/2005 |
| WO | WO 2005/023771 | 3/2005 |
| WO | WO 2005/030140 | 4/2005 |
| WO | WO 2006/040520 | 4/2006 |
| WO | WO 2006/040522 | 4/2006 |
| WO | WO 2006/040526 | 4/2006 |
| WO | WO 2006/076706 | 7/2006 |
| WO | 2006117552 | * 11/2006 |
| WO | 2006117570 | * 11/2006 |
| WO | WO 2006/117552 | 11/2006 |
| WO | WO 2006/117570 | 11/2006 |
| WO | WO 2007/099317 | 9/2007 |
| WO | WO 2007/099323 | 9/2007 |
| WO | WO 2007/099335 | 9/2007 |
| WO | WO 2007/113548 | 10/2007 |
| WO | WO 2007/113565 | 10/2007 |

* cited by examiner

QUINOLINE DERIVATIVES

RELATED APPLICATIONS

The present application is a U.S. National Phase Application of International Application No. PCT/GB2007/000719 (filed Mar. 1, 2007) which claims the benefit of European Patent Application No. 06300181.2 (filed Mar. 2, 2006) and European Patent Application No. 06301102.7 (filed Oct. 31, 2006), all of which are hereby incorporated by reference in their entirety.

The invention concerns certain novel quinoline derivatives, or pharmaceutically-acceptable salts thereof, which possess anti-cancer activity and are accordingly useful in methods of treatment of the human or animal body. The invention also concerns processes for the manufacture of said quinoline derivatives, pharmaceutical compositions containing them and their use in therapeutic methods, for example in the manufacture of medicaments for use in the prevention or treatment of cancers in a warm-blooded animal such as man, including use in the prevention or treatment of solid tumour disease.

Many of the current treatment regimes for the abnormal cell growth found in cell proliferation diseases such as psoriasis and cancer utilise compounds which inhibit DNA synthesis. Such compounds are toxic to cells generally but their toxic effect on rapidly dividing cells such as tumour cells can be beneficial. Alternative approaches to anti-cancer agents which act by mechanisms other than the inhibition of DNA synthesis have the potential to display enhanced selectivity of action.

Eukaryotic cells are continually responding to many diverse extracellular signals that enable communication between cells within an organism. These signals regulate a wide variety of physical responses in the cell including proliferation, differentiation, apoptosis and motility. The extracellular signals take the form of a diverse variety of soluble factors including growth factors as well as paracrine, autocrine and endocrine factors. By binding to specific transmembrane receptors, growth factor ligands communicate extracellular signals to the intracellular signalling pathways, thereby causing the individual cell to respond to extracellular signals. Many of these signal transduction processes utilise the reversible process of the phosphorylation of proteins involving specific kinases and phosphatases.

As phosphorylation is such an important regulatory mechanism in the signal transduction process, it is not surprising that aberrations in the process result in abnormal cell differentiation, transformation and growth. For example, it has been discovered that a cell may become cancerous by virtue of the transformation of a portion of its DNA into an oncogene. Several such oncogenes encode proteins which are receptors for growth factors, for example tyrosine kinase enzymes. Tyrosine kinases may also be mutated to constitutively active forms that result in the transformation of a variety of human cells. Alternatively, the over-expression of normal tyrosine kinase enzymes may also result in abnormal cell proliferation.

Tyrosine kinase enzymes may be divided into two groups:—the receptor tyrosine kinases and the non-receptor tyrosine kinases. About 90 tyrosine kinase have been identified in the human genome, of which about 60 are of the receptor type and about 30 are of the non-receptor type. These can be categorised into 20 receptor tyrosine kinase sub-families according to the families of growth factors that they bind and into 10 non-receptor tyrosine kinase sub-families (Robinson et al, *Oncogene*, 2000, 19, 5548-5557). The classification includes the EGF family of receptor tyrosine kinases such as the EGF, TGFα, Neu and erbB receptors, the insulin family of receptor tyrosine kinases such as the insulin and IGF1 receptors and insulin-related receptor (IRR) and the Class III family of receptor tyrosine kinases such as the platelet-derived growth factor (PDGF) receptor tyrosine kinases, for example the PDGFα and PDGFβ receptors, the stem cell factor receptor tyrosine kinase (SCF RTK, commonly known as c-Kit), the fms-related tyrosine kinase 3 (Flt3) receptor tyrosine kinase and the colony-stimulating factor 1 receptor (CSF-1R) tyrosine kinase.

It has been discovered that such mutated and over-expressed forms of tyrosine kinases are present in a large proportion of common human cancers such as the leukaemias, breast cancer, prostate cancer, non-small cell lung cancer (NSCLC) including adenocarcinomas and squamous cell cancer of the lung, gastrointestinal cancer including colon, rectal and stomach cancer, bladder cancer, oesophageal cancer, ovarian cancer and pancreatic cancer. As further human tumour tissues are tested, it is expected that the widespread prevalence and relevance of tyrosine kinases will be further established. For example, it has been shown that EGFR tyrosine kinase is mutated and/or over-expressed in several human cancers including in tumours of the lung, head and neck, gastrointestinal tract, breast, oesophagus, ovary, uterus, bladder and thyroid.

Platelet-derived growth factor (PDGF) is a major mitogen for connective tissue cells and other cell types. The PDGF receptors comprising PDGFα and PDGFβ receptor isozymes display enhanced activity in blood vessel disease (for example atherosclerosis and restenosis, for example in the process of restenosis subsequent to balloon angioplasty and heart arterial by-pass surgery). Such enhanced PDGF receptor kinase activity is also observed in other cell proliferative disorders such as fibrotic diseases (for example kidney fibrosis, hepatic cirrhosis, lung fibrosis and multicystic renal dysplasia), glomerulonephritis, inflammatory diseases (for example rheumatoid arthritis and inflammatory bowel disease), multiple sclerosis, psoriasis, hypersensitivity reactions of the skin, allergic asthma, insulin-dependent diabetes, diabetic retinopathy and diabetic nephropathy.

The PDGF receptors can also contribute to cell transformation in cancers and leukaemias by autocrine stimulation of cell growth. It has been shown that PDGF receptor kinases are mutated and/or over-expressed in several human cancers including in tumours of the lung (non-small cell lung cancer and small cell lung cancer), gastrointestine (such as colon, rectal and stomach tumours), prostate, breast, kidney, liver, brain (such as glioblastoma), oesophagus, ovary, pancreas and skin (such as dermatofibrosarcoma protruberans) and in leukaemias and lymphomas such as chronic myelogenous leukaemia (CML), chronic myelomonocytic leukaemia (CMML), acute lymphocyte leukaemia (ALL) and multiple myeloma. Enhanced cell signalling by way of the PDGF receptor tyrosine kinases can contribute to a variety of cellular effects including cell proliferation, cellular mobility and invasiveness, cell permeability and cellular apoptosis.

Accordingly, antagonism of the activity of PDGF receptor kinases is expected to be beneficial in the treatment of a number of cell proliferative disorders such as cancer, especially in inhibiting tumour growth and metastasis and in inhibiting the progression of leukaemia.

In addition, PDGF is involved in angiogenesis, the process of forming new blood vessels, that is critical for continuing tumour growth. Normally, angiogenesis plays an important role in processes such as embryonic development, wound healing and several components of female reproductive function. However, undesirable or pathological angiogenesis has been associated with a number of disease states including diabetic retinopathy, psoriasis, cancer, rheumatoid arthritis, atheroma, Kaposi's sarcoma and haemangioma. Angiogenesis is stimulated via the promotion of the growth of endothelial cells. Several polypeptides with in vitro endothelial cell growth promoting activity have been identified including acidic and basic fibroblast growth factors (aFGF and bFGF) and vascular endothelial growth factor (VEGF). By virtue of the restricted expression of its receptors, the growth factor activity of VEGF, in contrast to that of aFGF and bFGF, is relatively specific towards endothelial cells. Recent evidence indicates that VEGF is an important stimulator of both normal and pathological angiogenesis and vascular permeability. This cytokine induces a vascular sprouting phenotype by inducing endothelial cell proliferation, protease expression and migration which subsequently leads to the formation of capillary tubes that promote the formation of the hyperpermeable, immature vascular network which is characteristic of pathological angiogenesis. The receptor tyrosine kinase (RTK) sub-family that binds VEGF comprises the kinase insert domain-containing receptor KDR (also referred to as Flk-1), the fms-like tyrosine kinase receptor Flt-1 and the fms-like tyrosine kinase receptor Flt-4. Two of these related RTKs, namely Flt-1 and KDR, have been shown to bind VEGF with high affinity.

Accordingly, antagonism of the activity of VEGF is expected to be beneficial in the treatment of a number of disease states that are associated with angiogenesis and/or increased vascular permeability such as cancer, especially in inhibiting the development of tumours.

It is known that several compounds with PDGF receptor kinase inhibitory activity are progressing toward clinical development. The 2-anilinopyrimidine derivative known as imatinib (STI571; *Nature Reviews*, 2002, 1, 493-502; *Cancer Research*, 1996, 56, 100-104) has been shown to inhibit PDGF receptor kinase activity although its current clinical use is for the treatment of CML based on its additional activity as an inhibitor of BCR-ABL kinase. STI571 inhibits the growth of glioblastoma tumours arising from injection into the brains of nude mice of the human glioblastoma lines U343 and U87 (*Cancer Research*, 2000, 60, 5143-5150). The compound also inhibits the in vivo growth of dermatofibrosarcoma protruberans cell cultures (*Cancer Research*, 2001, 61, 5778-5783). Based on the PDGF receptor kinase inhibitory activity of the compound, clinical trials are being carried out in glioblastoma and in prostate cancer. Several other PDGF receptor kinase inhibitors are being investigated including quinoline, quinazoline and quinoxaline derivatives (*Cytokine & Growth Factor Reviews*, 2004, 15, 229-235).

It is known from International Patent Application WO 92/20642 that certain aryl and heteroaryl compounds inhibit EGF and/or PDGF receptor tyrosine kinase. There is the disclosure of certain quinoline derivatives therein but no specific mention is made therein of 2-phenylacetamide derivatives; in particular, there is no specific mention made therein of quinolin-4-yloxy-substituted 2-phenylacetamide derivatives.

It is disclosed in many published patent applications such as International Patent Application WO 96/09294 that 4-anilinoquinazolines, 4-aryloxyquinazolines, 4-anilinoquinolines or 4-aryloxyquinolines possess tyrosine kinase enzyme inhibitory activity. However, there is no specific mention made therein of quinolin-4-yloxy-substituted 2-phenylacetamide compounds.

For example, it is known from International Patent Applications WO 02/36570 and WO 02/44166 that certain aryl and heteroaryl compounds inhibit MEK receptor tyrosine kinase. There is the disclosure therein of certain quinoline derivatives therein but no specific mention is made therein of 2-phenylacetamide derivatives; in particular, there is no specific mention made therein of quinolin-4-yloxy-substituted 2-phenylacetamide derivatives.

For example, it is known from International Patent Application WO 02/092571 that certain 3-carbamoylquinoline compounds inhibit JAK kinase. There is the disclosure therein of certain quinolin-4-ylamino-substituted 2-phenylacetamide derivatives but there is no specific mention made therein of N-aryl- or N-heteroaryl-2-phenylacetamide derivatives.

It is known from International Patent Application WO 2005/021554 that thienopyridine-substituted 2-phenylacetamide compounds inhibit VEGF receptor tyrosine kinases and provide an antiangiogenic effect. There is the disclosure in example 87 therein of a single quinolin-4-yloxy-substituted 2-phenylacetamide, namely of the compound N-(5-chloropyridin-2-yl)-2-[4-(7-methoxyquinolin-4-yloxy)phenyl]acetamide.

We have now found that surprisingly certain novel quinolin-4-yloxy-substituted 2-phenylacetamide compounds possess potent activity against cell proliferative disorders. It is believed that the compounds provide a useful treatment of cell proliferative disorders, for example to provide an antitumour effect, by way of a contribution from inhibition of PDGF receptor tyrosine kinases.

A further characteristic of hyperproliferative diseases such as cancer is damage to the cellular pathways that control progress through the cell cycle which, in normal eukaryotic cells, involves an ordered cascade of protein phosphorylation. As for signal transduction mechanisms, several families of protein kinases appear to play critical roles in the cell cycle cascade. The most widely studied of these cell cycle regulators is the cyclin dependent kinase family (the CDKs). Activity of specific CDKs at specific times is essential both to initiate and coordinate progress through the cell cycle. For example, the CDK4 protein appears to control entry into the cell cycle (the G0-G1-S transition) by phosphorylating the retinoblastoma gene product pRb which stimulates the release of the transcription factor E2F from pRb which, in turn, acts to increase the transcription of genes necessary for entry into S phase. The catalytic activity of CDK4 is stimulated by binding to a partner protein, Cyclin D. One of the first demonstrations of a direct link between cancer and the cell cycle was made with the observation that the Cyclin D1 gene was amplified and Cyclin D protein levels increased in many human tumours.

More recently, protein kinases that are structurally distinct from the CDK family have been identified which play critical roles in regulating the cell cycle and which also appear to be important in oncogenesis. They include the human homologues of the *Drosophila aurora* and *S. cerevisiae* Ipl1 proteins. The three human homologues of these genes Aurora-A, Aurora-B and Aurora-C encode cell cycle regulated serine-threonine protein kinases that show a peak of expression and kinase activity through G2 and mitosis. Several observations implicate the involvement of human aurora proteins in cancer, especially Aurora-A and Aurora-B. Abrogation of Aurora-A expression and function by antisense oligonucleotide treatment of human tumour cell lines leads to cell cycle arrest and exerts an anti-proliferative effect. Additionally, small molecule inhibitors of Aurora-A and Aurora-B have been demonstrated to have an anti-proliferative effect in human tumour cells.

It is disclosed in International Patent Application WO 01/55116 that certain 4-heteroarylaminoquinolines possess Aurora kinase enzyme inhibitory activity. However, there is no specific mention made therein of quinolin-4-yloxy-substituted 2-phenylacetamide compounds.

It is disclosed in International Patent Applications WO 01/21594, WO 01/21596 and WO 01/21597 that certain quinazoline derivatives that carry an anilino or phenoxy group linked to the 4-position of the quinazoline ring possess Aurora kinase inhibitory activity. There is no mention therein of 2-phenylacetamide derivatives; in particular, there is no specific mention made therein of quinazoline-substituted or quinoline-substituted 2-phenylacetamide derivatives.

It is disclosed in International Patent Applications WO 02/00649, WO 03/055491, WO 04/058752, WO 04/058781 and WO 04/094410 that certain quinazoline derivatives that carry a heteroaryl group linked to the 4-position of the quinazoline ring by, for example, a NH or O group possess Aurora kinase inhibitory activity. There is no mention therein of 2-phenylacetamide derivatives; in particular, there is no specific mention made therein of quinazoline-substituted or quinoline-substituted 2-phenylacetamide derivatives.

As stated above, we have now found that surprisingly certain novel quinolin-4-yloxy-substituted 2-phenylacetamide compounds possess potent activity against cell proliferative disorders. Without wishing to imply that the compounds disclosed in the present invention possess pharmacological activity only by virtue of an effect on one or two biological processes, it is believed that the compounds provide a useful treatment of cell proliferative disorders, for example to provide an anti-tumour effect, by way of a contribution from inhibition of PDGF receptor tyrosine kinases. In particular, it is believed that the compounds of the present invention provide a useful treatment of cell proliferative disorders by way of a contribution from inhibition of the PDGFα and/or PDGFβ receptor tyrosine kinases.

Many of the compounds of the present invention possess potent inhibitory activity against the PDGF receptor family of tyrosine kinases, for example the PDGFα and/or PDGFβreceptor tyrosine kinases, whilst possessing less potent inhibitory activity against other tyrosine kinase enzymes, for example against one or more other Class III family receptor tyrosine kinases such as Flt3 receptor tyrosine kinase and the CSF-1R tyrosine kinase, against the EGF receptor tyrosine kinase, or against VEGF receptor tyrosine kinases such as KDR and Flt-1. Furthermore, certain compounds of the present invention possess substantially better potency against the PDGF receptor family of tyrosine kinases, particularly against the PDGFβ receptor tyrosine kinase than against EGF receptor tyrosine kinase or VEGF receptor tyrosine kinases such as KDR. Such compounds possess sufficient potency that they may be used in an amount sufficient to inhibit the PDGF receptor family of tyrosine kinases, particularly PDGFβ receptor tyrosine kinase whilst demonstrating little activity against EGF receptor tyrosine kinase or against VEGF receptor tyrosine kinases such as KDR.

According to one aspect of the invention there is provided a quinoline derivative of the Formula I

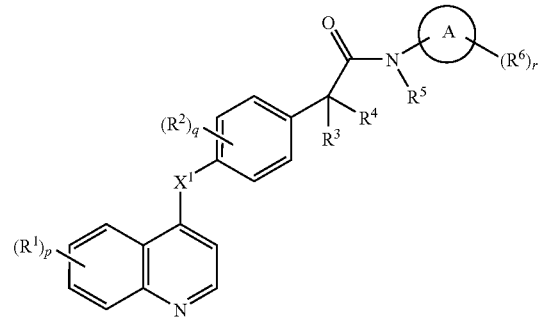

I wherein $X^1$ is O or $N(R^7)$ where $R^7$ is hydrogen or (1-8C) alkyl;

p is 0, 1, 2 or 3;

each $R^1$ group, which may be the same or different, is selected from halogeno, trifluoromethyl, cyano, hydroxy, mercapto, amino, carboxy, (1-6C)alkoxycarbonyl, carbamoyl, (1-8C)alkyl, (2-8C)alkenyl, (2-8C)alkynyl, (1-6C) alkoxy, (2-6C)alkenyloxy, (2-6C)alkynyloxy, (1-6C)alkylthio, (1-6C)alkylsulphinyl, (1-6C)alkylsulphonyl, (1-6C) alkylamino, di-[(1-6C)alkyl]amino, N-(1-6C) alkylcarbamoyl, N,N-di-[(1-6C)alkyl]carbamoyl, N-(1-6C) alkylsulphamoyl, N,N-di-[(1-6C)alkyl]sulphamoyl, (2-6C) alkanoyl, (2-6C)alkanoylamino and N-(1-6C)alkyl-(2-6C) alkanoylamino, or from a group of the formula:

$Q^1-X^2-$ wherein $X^2$ is selected from O, S, SO, $SO_2$, $N(R^8)$, CO, $CON(R^8)$, $N(R^8)CO$, $OC(R^8)_2$ and $N(R^8)C(R^8)_2$, wherein each $R^8$ is hydrogen or (1-8C)alkyl, and $Q^1$ is aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl, and wherein any aryl, (3-8C)cycloalkyl, (3-8C)cycloalkenyl, heteroaryl or heterocyclyl group within a $R^1$ substituent optionally bears 1, 2 or 3 substituents, which may be the same or different, selected from halogeno, trifluoromethyl, cyano, nitro, hydroxy, amino, carboxy, carbamoyl, ureido, (1-8C) alkyl, (2-8C)alkenyl, (2-8C)alkynyl, (1-6C)alkoxy, (2-6C) alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (2-6C)alkanoylamino, N-(1-6C)alkyl-(2-6C)alkanoylamino, N-(1-6C)alkylureido, N'-(1-6C)alkylureido, N',N'-di-[(1-6C)alkyl]ureido, N,N'-di-[(1-6C)alkyl] ureido, N,N',N'-tri-[(1-6C)alkyl]ureido, N-(1-6C) alkylsulphamoyl, N,N-di-[(1-6C)alkyl]sulphamoyl, (1-6C) alkanesulphonylamino and N-(1-6C)alkyl-(1-6C) alkanesulphonylamino, or from a group of the formula:

$-X^3-R^9$ wherein $X^3$ is a direct bond or is selected from O and $N(R^{10})$, wherein $R^{10}$ is hydrogen or (1-8C)alkyl, and $R^9$ is halogeno-(1-6C)alkyl, hydroxy-(1-6C)alkyl, mercapto-(1-6C)alkyl, (1-6C)alkoxy-(1-6C)alkyl, (1-6C)alkylthio-(1-6C)alkyl, (1-6C)alkylsulphinyl-(1-6C)alkyl, (1-6C)alkylsulphonyl-(1-6C)alkyl, cyano-(1-6C)alkyl, amino-(1-6C)alkyl, (1-6C) alkylamino-(1-6C)alkyl, di-[(1-6C)alkyl]amino-(1-6C) alkyl, (2-6C)alkanoylamino-(1-6C)alkyl, N-(1-6C)alkyl-(2-6C)alkanoylamino-(1-6C)alkyl, (1-6C)

alkoxycarbonylamino-(1-6C)alkyl, ureido-(1-6C)alkyl, N-(1-6C)alkylureido-(1-6C)alkyl, N'-(1-6C)alkylureido-(1-6C)alkyl, N',N'-di-[(1-6C)alkyl]ureido-(1-6C)alkyl, N,N'-di-[(1-6C)alkyl]ureido-(1-6C)alkyl or N,N',N'-tri-[(1-6C)alkyl]ureido-(1-6C)alkyl, or from a group of the formula:

$$-X^4-Q^2$$

wherein $X^4$ is a direct bond or is selected from O, CO and N($R^{11}$), wherein $R^{11}$ is hydrogen or (1-8C)alkyl, and $Q^2$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, hydroxy, (1-8C)alkyl and (1-6C)alkoxy, and wherein any aryl, heteroaryl or heterocyclyl group within a substituent on $R^1$ optionally bears a (1-3C)alkylenedioxy group, and wherein any heterocyclyl group within a $R^1$ substituent optionally bears 1 or 2 oxo or thioxo substituents, and wherein any CH, $CH_2$ or $CH_3$ group within a $R^1$ substituent optionally bears on each said CH, $CH_2$ or $CH_3$ group one or more halogeno or (1-8C)alkyl substituents and/or a substituent selected from hydroxy, mercapto, amino, cyano, carboxy, carbamoyl, ureido, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylureido, N'-(1-6C)alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, and wherein adjacent carbon atoms in any (2-6C)alkylene chain within a $R^1$ substituent are optionally separated by the insertion into the chain of a group selected from O, S, SO, $SO_2$, N($R^{12}$), CO, CH(O$R^{12}$), CON($R^{12}$), N($R^{12}$)CO, N($R^{12}$)CON($R^{12}$), $SO_2$N($R^{12}$), N($R^{12}$)$SO_2$, CH=CH and C≡C wherein $R^{12}$ is hydrogen or (1-8C)alkyl, or, when the inserted group is N($R^{12}$), $R^{12}$ may also be (2-6C)alkanoyl;

q is 0, 1 or 2;

each $R^2$ group, which may be the same or different, is selected from halogeno, trifluoromethyl, cyano, carboxy, hydroxy, amino, carbamoyl, (1-8C)alkyl, (2-8C)alkenyl, (2-8C)alkynyl, (1-6C)alkoxy, (1-6C)alkylamino, di-[(1-6C)alkyl]amino, N-(1-6C)alkylcarbamoyl, N,N-di-[(1-6C)alkyl]carbamoyl, halogeno-(1-6C)alkyl, hydroxy-(1-6C)alkyl, (1-6C)alkoxy-(1-6C)alkyl, cyano-(1-6C)alkyl, carboxy-(1-6C)alkyl, (1-6C)alkoxycarbonyl-(1-6C)alkyl, amino-(1-6C)alkyl, (1-6C)alkylamino-(1-6C)alkyl, di-[(1-6C)alkyl]amino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (2-6C)alkanoylamino-(1-6C)alkyl and N-(1-6C)alkyl-(2-6C)alkanoylamino-(1-6C)alkyl;

$R^3$ is hydrogen, (1-8C)alkyl, (2-8C)alkenyl or (2-8C)alkynyl;

$R^4$ is hydrogen, (1-8C)alkyl, (2-8C)alkenyl, (2-8C)alkynyl, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl, di-[(1-6C)alkyl]amino-(1-6C)alkyl, carbamoyl-(1-6C)alkyl, N-(1-6C)alkylcarbamoyl-(1-6C)alkyl, N,N-di-[(1-6C)alkyl]carbamoyl-((1-6C)alkyl, (1-6C)alkoxycarbonyl-(1-6C)alkyl, (2-6C)alkanoylamino-(1-6C)alkyl or N-(1-6C)alkyl-(2-6C)alkanoylamino-(1-6C)alkyl;

or $R^3$ and $R^4$ together with the carbon atom to which they are attached form a (3-8C)cycloalkyl group;

$R^5$ is hydrogen, (1-8C)alkyl, (2-8C)alkenyl or (2-8C)alkynyl or a group of the formula:

$$-X^5-R^{13}$$

wherein $X^5$ is a direct bond or is selected from O and N($R^{14}$), wherein $R^{14}$ is hydrogen or (1-8C)alkyl, and $R^{13}$ is halogeno-(1-6C)alkyl, hydroxy-(1-6C)alkyl, (1-6C)alkoxy-(1-6C)alkyl or cyano-(1-6C)alkyl;

Ring A is a 6-membered monocyclic or a 10-membered bicyclic aryl ring or a 5- or 6-membered monocyclic or a 9- or 10-membered bicyclic heteroaryl ring with up to three ring heteroatoms selected from oxygen, nitrogen and sulphur;

r is 0, 1, 2 or 3; and each $R^6$ group, which may be the same or different, is selected from halogeno, trifluoromethyl, cyano, hydroxy, mercapto, amino, carboxy, carbamoyl, sulphamoyl, ureido, (1-8C)alkyl, (2-8C)alkenyl, (2-8C)alkynyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

$$-X^6-R^{15}$$

wherein $X^6$ is a direct bond or is selected from O and N($R^{16}$), wherein $R^{16}$ is hydrogen or (1-8C)alkyl, and $R^{15}$ is halogeno-(1-6C)alkyl, hydroxy-(1-6C)alkyl, mercapto-(1-6C)alkyl, (1-6C)alkoxy-(1-6C)alkyl, (1-6C)alkylthio-(1-6C)alkyl, (1-6C)alkylsulphinyl-(1-6C)alkyl, (1-6C)alkylsulphonyl-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, carboxy-(1-6C)alkyl, (1-6C)alkoxycarbonyl-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, sulphamoyl-(1-6C)alkyl, N-(1-6C)alkylsulphamoyl-(1-6C)alkyl, N,N-di-[(1-6C)alkyl]sulphamoyl-(1-6C)alkyl, ureido-(1-6C)alkyl, N-(1-6C)alkylureido-(1-6C)alkyl, N'-(1-6C)alkylureido-(1-6C)alkyl, N',N'-di-[(1-6C)alkyl]ureido-(1-6C)alkyl, N,N'-di-[(1-6C)alkyl]ureido-(1-6C)alkyl, N,N',N'-tri-[(1-6C)alkyl]ureido-(1-6C)alkyl, (1-6C)alkanesulphonylamino-(1-6C)alkyl or N-(1-6C)alkyl-(1-6C)alkanesulphonylamino-(1-6C)alkyl, or from a group of the formula:

$$-X^7-Q^3$$

wherein $X^7$ is a direct bond or is selected from O, S, SO, $SO_2$, N($R^{17}$), CO, CH(O$R^{17}$), CON($R^{17}$), N($R^{17}$)CO, N($R^{17}$)CON ($R^{17}$), $SO_2$N($R^{17}$), N($R^{17}$)$SO_2$, C($R^{17}$)$_2$O, C($R^{17}$)$_2$S and C($R^{17}$)$_2$N($R^{17}$), wherein each $R^{17}$ is hydrogen or (1-8C)alkyl, and $Q^3$ is aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl, or two $R^6$ groups together form a bivalent group that spans adjacent ring positions on Ring A selected from OC($R^{18}$)$_2$O, OC($R^{18}$)$_2$C($R^{18}$)$_2$O, OC($R^{18}$)$_2$C($R^{18}$)$_2$, C($R^{18}$)$_2$OC($R^{18}$)$_2$, OC($R^{18}$)$_2$C($R^{18}$)$_2$C($R^{18}$)$_2$, C($R^{18}$)$_2$C($R^{18}$)$_2$C($R^{18}$)$_2$, OC($R^{18}$)$_2$N($R^{19}$), N($R^{19}$)$_2$C($R^{18}$)$_2$N($R^{19}$), N($R^{19}$)C($R^{18}$)$_2$C($R^{18}$)$_2$, N($R^{19}$)C($R^{18}$)$_2$C($R^{18}$)$_2$, OC($R^{18}$)$_2$C($R^{18}$)$_2$N ($R^{19}$), C($R^{18}$)$_2$N($R^{19}$)C($R^{18}$)$_2$, CO.N($R^{18}$)C($R^{18}$)$_2$, N($R^{18}$)

$CO.C(R^{18})_2$, $N(R^{19})C(R^{18})_2CO$, $CO.N(R^{18})CO$, $N(R^{19})N(R^{18})CO$, $N(R^{18})CO.N(R^{18})$, $O.CO.N(R^{18})$, $O.CO.C(R^{18})_2$ and $CO.OC(R^{18})_2$ wherein each $R^{18}$ is hydrogen, (1-8C)alkyl, (2-8C)alkenyl or (2-8C)alkynyl, and wherein $R^{19}$ is hydrogen, (1-8C)alkyl, (2-8C)alkenyl, (2-8C)alkynyl or (2-6C)alkanoyl, and wherein any aryl, (3-8C)cycloalkyl, (3-8C)cycloalkenyl, heteroaryl or heterocyclyl group within an $R^6$ group optionally bears 1, 2 or 3 substituents, which may be the same or different, selected from halogen, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—$X^8$—$R^{20}$ wherein $X^8$ is a direct bond or is selected from O and $N(R^{21})$, wherein $R^{21}$ is hydrogen or (1-8C)alkyl, and $R^{20}$ is halogeno-(1-6C)alkyl, hydroxy-(1-6C)alkyl, mercapto-(1-6C)alkyl, (1-6C)alkoxy-(1-6C)alkyl, (1-6C)alkylthio-(1-6C)alkyl, (1-6C)alkylsulphinyl-(1-6C)alkyl, (1-6C)alkylsulphonyl-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl or N-(1-6C)alkyl-(2-6C)alkanoylamino-(1-6C)alkyl, or from a group of the formula:

—$X^9$-$Q^4$ wherein $X^9$ is a direct bond or is selected from O, CO and $N(R^{22})$, wherein $R^{22}$ is hydrogen or (1-8C)alkyl, and $Q^4$ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, hydroxy, (1-8C)alkyl and (1-6C)alkoxy, and wherein any aryl, heteroaryl or heterocyclyl group within an $R^6$ group optionally bears a (1-3C)alkylenedioxy group, and wherein any heterocyclyl group within an $R^6$ group optionally bears 1 or 2 oxo or thioxo substituents, and wherein any CH, $CH_2$ or $CH_3$ group within an $R^6$ group optionally bears on each said CH, $CH_2$ or $CH_3$ group one or more halogeno or (1-8C)alkyl substituents and/or a substituent selected from hydroxy, mercapto, amino, cyano, carboxy, carbamoyl, ureido, (2-8C)alkenyl, (2-8C)alkynyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, and wherein adjacent carbon atoms in any (2-6C)alkylene chain within an $R^6$ group are optionally separated by the insertion into the chain of a group selected from O, S, SO, $SO_2$, $N(R^{23})$, $N(R^{23})CO$, $CON(R^{23})$, $N(R^{23})CON(R^{23})$, CO, $CH(OR^{23})$, $N(R^{23})SO_2$, $SO_2N(R^{23})$, CH=CH and C≡C wherein $R^{23}$ is hydrogen or (1-8C)alkyl, or, when the inserted group is $N(R^{23})$, $R^{23}$ may also be (2-6C)alkanoyl;

or a pharmaceutically-acceptable salt thereof, provided that the compound N-(5-chloropyridin-2-yl)-2-[4-(7-methoxyquinolin-4-yloxy)phenyl]acetamide is excluded.

In this specification the generic term "(1-8C)alkyl" includes both straight-chain and branched-chain alkyl groups such as propyl, isopropyl and tert-butyl, and also (3-8C)cycloalkyl groups such as cyclopropyl, cyclobutyl, cyclopentyl, cyclohexyl and cycloheptyl, and also (3-6C)cycloalkyl-(1-2C)alkyl groups such as cyclopropylmethyl, 2-cyclopropylethyl, cyclobutylmethyl, 2-cyclobutylethyl, cyclopentylmethyl, 2-cyclopentylethyl, cyclohexylmethyl and 2-cyclohexylethyl. However references to individual alkyl groups such as "propyl" are specific for the straight-chain version only, references to individual branched-chain alkyl groups such as "isopropyl" are specific for the branched-chain version only and references to individual cycloalkyl groups such as "cyclopentyl" are specific for that 5-membered ring only. An analogous convention applies to other generic terms, for example (1-6C)alkoxy includes (3-6C)cycloalkyloxy groups and (3-5C)cycloalkyl-(1-2C)alkoxy groups, for example methoxy, ethoxy, propoxy, isopropoxy, cyclopropyloxy, cyclobutyloxy, cyclopentyloxy, cyclohexyloxy, cyclopropylmethoxy, 2-cyclopropylethoxy, cyclobutylmethoxy, 2-cyclobutylethoxy and cyclopentylmethoxy; (1-6C)alkylamino includes (3-6C)cycloalkylamino groups and (3-5C)cycloalkyl-(1-2C)alkylamino groups, for example methylamino, ethylamino, propylamino, cyclopropylamino, cyclobutylamino, cyclohexylamino, cyclopropylmethylamino, 2-cyclopropylethylamino, cyclobutylmethylamino, 2-cyclobutylethylamino and cyclopentylmethylamino; and di-[(1-6Calkyl]amino includes di-[(3-6C)cycloalkyl]amino groups and di-[(3-5C)cycloalkyl-(1-2C)alkyl]amino groups, for example dimethylamino, diethylamino, dipropylamino, N-cyclopropyl-N-methylamino, N-cyclobutyl-N-methylamino, N-cyclohexyl-N-ethylamino, N-cyclopropylmethyl-N-methylamino, N-(2-cyclopropylethyl)-N-methylamino and N-cyclopentylmethyl-N-methylamino.

It is to be understood that, insofar as certain of the compounds of Formula I defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

It is to be understood that certain compounds of Formula I defined above may exhibit the phenomenon of tautomerism. In particular, tautomerism may affect heteroaryl rings within the definition of Ring A or heterocyclic groups within the $R^1$ and $R^6$ groups that bear 1 or 2 oxo or thioxo substituents. It is to be understood that the present invention includes in its definition any such tautomeric form, or a mixture thereof, which possesses the above-mentioned activity and is not to be limited merely to any one tautomeric form utilised within the formulae drawings or named in the Examples. For example, Ring A may be a pyrazolyl group. When, for example, such a pyrazolyl group is linked to the N atom of the $CON(R^5)$ group from the 3-position, a tautomeric mixture of compounds comprising a 1H-pyrazol-3-yl group and a 1H-pyrazol-5-yl group may be present. In general, just one of any such tautomeric forms is named in the Examples that follow hereinafter or is presented in any relevant formulae drawings that follow hereinafter.

In structural Formula I, it is to be understood that there is a hydrogen atom at the 2-position on the quinoline ring. It is to be understood thereby that the $R^1$ substituents may only be located at the 3-, 5-, 6-, 7- or 8-positions on the quinoline ring i.e. that the 2-position remains unsubstituted. Conveniently, the 3-position on the quinoline ring also remains unsubstituted or the $R^1$ substituent at the 3-position on the quinoline ring is a cyano group. More conveniently, $R^1$ substituents may only be located at the 5-, 6- or 7-positions on the quinoline ring. Yet more conveniently, $R^1$ substituents may only be located at the 6- and/or 7-positions on the quinoline ring.

In structural Formula I, it is further to be understood that any $R^2$ group that may be present on the central phenyl group may be located at any available position. Conveniently, no $R^2$ group is present (q=0). Alternatively, there is a single $R^2$ group. More conveniently, there is a single $R^2$ group that is located at the 2-position (relative to the $C(R^3)(R^4)$ group).

In structural Formula I, it is to be understood that any $R^6$ group may be located at any available position on Ring A. For example, an $R^6$ group may be located at the 3- or 4-position (relative to the $CON(R^5)$ group) when Ring A is a 6-membered ring or, for example, it may be located at the 3-position (relative to the $CON(R^5)$ group) when Ring A is a 5-membered ring.

Suitable values for the generic radicals referred to above include those set out below.

A suitable value for any one of the 'Q' groups ($Q^1$ to $Q^4$) within the $R^1$ or $R^6$ groups when the 'Q' group is aryl or for the aryl group within any 'Q' group is, for example, phenyl or naphthyl, preferably phenyl.

A suitable value for any one of the 'Q' groups ($Q^1$ or $Q^3$) within the $R^1$ or $R^6$ groups when the 'Q' group is (3-8C) cycloalkyl or for the (3-8C)cycloalkyl group within any 'Q' group is, for example, cyclopropyl, cyclobutyl, cyclopentyl, cyclohexyl, cycloheptyl, bicyclo[2.2.1]heptyl or cyclooctyl.

A suitable value for the (3-8C)cycloalkyl group formed when $R^3$ and $R^4$ together with the carbon atom to which they are attached form a (3-8C)cycloalkyl group is, for example, cyclopropyl, cyclobutyl, cyclopentyl, cyclohexyl or cycloheptyl.

A suitable value for any one of the 'Q' groups ($Q^1$ or $Q^3$) within the $R^1$ or $R^6$ groups when the 'Q' group is (3-8C) cycloalkenyl or for the (3-8C)cycloalkenyl group within any 'Q' group is, for example, cyclobutenyl, cyclopentenyl, cyclohexenyl, cycloheptenyl or cyclooctenyl.

A suitable value for any one of the 'Q' groups ($Q^1$ to $Q^4$) within the $R^1$ or $R^6$ groups when the 'Q' group is heteroaryl or for the heteroaryl group within any 'Q' group is, for example, an aromatic 5- or 6-membered monocyclic ring or a 9- or 10-membered bicyclic ring with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl.

A suitable value for any one of the 'Q' groups ($Q^1$ to $Q^4$) within the $R^1$ or $R^6$ groups when the 'Q' group is heterocyclyl or for the heterocyclyl group within any 'Q' group is, for example, a non-aromatic saturated or partially saturated 3 to 10 membered monocyclic or bicyclic ring with up to five heteroatoms selected from oxygen, nitrogen and sulphur, for example oxiranyl, oxetanyl, tetrahydrofuranyl, tetrahydropyranyl, oxepanyl, tetrahydrothienyl, 1,1-dioxotetrahydrothienyl, tetrahydrothiopyranyl, 1,1-dioxotetrahydrothiopyranyl, aziridinyl, azetidinyl, pyrrolinyl, pyrrolidinyl, imidazolinyl, imidazolidinyl, pyrazolinyl, pyrazolidinyl, morpholinyl, tetrahydro-1,4-thiazinyl, 1,1-dioxotetrahydro-1,4-thiazinyl, piperidinyl, homopiperidinyl, piperazinyl, homopiperazinyl, 2-azabicyclo[2.2.1]heptyl, quinuclidinyl, chromanyl, isochromanyl, indolinyl, isoindolinyl, dihydropyridinyl, tetrahydropyridinyl, dihydropyrimidinyl or tetraliydropyrimidinyl, preferably tetrahydrofuranyl, tetrahydropyranyl, tetrahydrothiopyranyl, pyrrolinyl, pyrrolidinyl, morpholinyl, piperidinyl, piperazinyl, indolinyl or isoindolinyl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 4-oxo-1,4-dihydropyridinyl, 2,5-dioxopyrrolidinyl, 2,5-dioxoimidazolidinyl or 2,6-dioxopiperidinyl.

A suitable value for any 'Q' group when it is heteroaryl-(1-6C)alkyl is, for example, heteroarylmethyl, 2-heteroarylethyl and 3-heteroarylpropyl. The invention comprises corresponding suitable values for 'Q' groups when, for example, rather than a heteroaryl-(1-6C)alkyl group, an aryl-(1-6C) alkyl, (3-8C)cycloalkyl-(1-6C)alkyl, (3-8C)cycloalkenyl-(1-6C)alkyl or heterocyclyl-(1-6C)alkyl group is present.

A suitable value for Ring A when it is a 6-membered monocyclic or a 10-membered bicyclic aryl ring or a 5- or 6-membered monocyclic or a 9- or 10-membered bicyclic heteroaryl ring with up to three ring heteroatoms selected from oxygen, nitrogen and sulphur is, for example, phenyl, naphthyl, furyl, pyrrolyl, thienyl, oxazolyl, isoxazolyl, imidazolyl, pyrazolyl, thiazolyl, isothiazolyl, oxadiazolyl, thiadiazolyl, triazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl. Conveniently, Ring A is a phenyl, furyl, pyrrolyl, thienyl, oxazolyl, isoxazolyl, imidazolyl, pyrazolyl, thiazolyl, pyridyl, pyrimidinyl, pyrazinyl or pyridazinyl ring. Conveniently, Ring A is a phenyl, pyridyl, pyrimidinyl, pyrazinyl or pyridazinyl ring. A suitable value for Ring A when it is a 5-membered monocyclic heteroaryl ring with up to three ring heteroatoms selected from oxygen, nitrogen and sulphur is, for example, furyl, pyrrolyl, thienyl, oxazolyl, isoxazolyl, imidazolyl, pyrazolyl, thiazolyl, isothiazolyl, oxadiazolyl, thiadiazolyl or triazolyl. Conveniently, Ring A is an oxazolyl, isoxazolyl, imidazolyl, pyrazolyl, thiazolyl, isothiazolyl, oxadiazolyl or thiadiazolyl ring.

Suitable values for any of the 'R' groups ($R^1$ to $R^{23}$), or for various groups within an $R^1$, $R^2$ or $R^6$ substituent include:—

| | |
|---|---|
| for halogeno | fluoro, chloro, bromo and iodo; |
| for (1-8C)alkyl: | methyl, ethyl, propyl, isopropyl, tert-butyl, cyclobutyl, cyclohexyl, cyclohexylmethyl and 2-cyclopropylethyl; |
| for (2-8C)alkenyl: | vinyl, isopropenyl, allyl and but-2-enyl; |

-continued

| | |
|---|---|
| for (2-8C)alkynyl: | ethynyl, 2-propynyl and but-2-ynyl; |
| for (1-6C)alkoxy: | methoxy, ethoxy, propoxy, isopropoxy and butoxy; |
| for (2-6C)alkenyloxy: | vinyloxy and allyloxy; |
| for (2-6C)alkynyloxy: | ethynyloxy and 2-propynyloxy; |
| for (1-6C)alkylthio: | methylthio, ethylthio and propylthio; |
| for (1-6C)alkylsulphinyl: | methylsulphinyl and ethylsulphinyl; |
| for (1-6C)alkylsulphonyl: | methylsulphonyl and ethylsulphonyl; |
| for (1-6C)alkylamino: | methylamino, ethylamino, propylamino, isopropylamino and butylamino; |
| for di-[(1-6C)alkyl]amino: | dimethylamino, diethylamino, N-ethyl-N-methylamino and diisopropylamino; |
| for (1-6C)alkoxycarbonyl: | methoxycarbonyl, ethoxycarbonyl, propoxycarbonyl and tert-butoxycarbonyl; |
| for N-(1-6C)alkylcarbamoyl: | N-methylcarbamoyl, N-ethylcarbamoyl and N-propylcarbamoyl; |
| for N,N-di-[(1-6C)alkyl]carbamoyl: | N,N-dimethylcarbamoyl, N-ethyl-N-methylcarbamoyl and N,N-diethylcarbamoyl; |
| for (2-6C)alkanoyl: | acetyl, propionyl and isobutyryl; |
| for (2-6C)alkanoyloxy: | acetoxy and propionyloxy; |
| for (2-6C)alkanoylamino: | acetamido and propionamido; |
| for N-(1-6C)alkyl-(2-6C)alkanoylamino: | N-methylacetamido and N-methylpropionamido; |
| for N'-(1-6C)alkylureido: | N'-methylureido and N'-ethylureido; |
| for N',N'-di-[(1-6C)alkyl]ureido: | N',N'-dimethylureido and N'-methyl-N'-ethylureido; |
| for N-(1-6C)alkylureido: | N-methylureido and N-ethylureido; |
| for N,N'-di-[(1-6C)alkyl]ureido: | N,N'-dimethylureido, N-methyl-N'-ethylureido and N-ethyl-N'-methylureido; |
| for N,N',N'-tri-[(1-6C)alkyl]ureido: | N,N',N'-trimethylureido, N-ethyl-N',N'-dimethylureido and N-methyl-N',N'-diethylureido; |
| for N-(1-6C)alkylsulphamoyl: | N-methylsulphamoyl and N-ethylsulphamoyl; |
| for N,N-di-[(1-6C)alkyl]sulphamoyl: | N,N-dimethylsulphamoyl; |
| for (1-6C)alkanesulphonylamino: | methanesulphonylamino and ethanesulphonylamino; |
| for N-(1-6C)alkyl-(1-6C)alkanesulphonylamino: | N-methylmethanesulphonylamino and N-methylethanesulphonylamino; |
| for halogeno-(1-6C)alkyl: | chloromethyl, 2-fluoroethyl, 2-chloroethyl, 1-chloroethyl, 2,2-difluoroethyl, 2,2,2-trifluoroethyl, 3-fluoropropyl, 3-chloropropyl, 3,3-difluoropropyl and 3,3,3-trifluoropropyl; |
| for hydroxy-(1-6C)alkyl: | hydroxymethyl, 2-hydroxyethyl, 1-hydroxyethyl and 3-hydroxypropyl; |
| for mercapto-(1-6C)alkyl: | mercaptomethyl, 2-mercaptoethyl, 1-mercaptoethyl and 3-mercaptopropyl; |
| for (1-6C)alkoxy-(1-6C)alkyl: | methoxymethyl, ethoxymethyl, 1-methoxyethyl, 2-methoxyethyl, 2-ethoxyethyl and 3-methoxypropyl; |
| for (1-6C)alkylthio-(1-6C)alkyl: | methylthiomethyl, ethylthiomethyl, 2-methylthioethyl, 1-methylthioethyl and 3-methylthiopropyl; |
| for (1-6C)alkylsulphinyl-(1-6C)alkyl: | methylsulphinylmethyl, ethylsulphinylmethyl, 2-methylsulphinylethyl, 1-methylsulphinylethyl and 3-methylsulphinylpropyl; |
| for (1-6C)alkylsulphonyl-(1-6C)alkyl: | methylsulphonylmethyl, ethylsulphonylmethyl, 2-methylsulphonylethyl, 1-methylsulphonylethyl and 3-methylsulphonylpropyl; |
| for cyano-(1-6C)alkyl: | cyanomethyl, 2-cyanoethyl, 1-cyanoethyl and 3-cyanopropyl; |
| for amino-(1-6C)alkyl: | aminomethyl, 2-aminoethyl, 1-aminoethyl, 3-aminopropyl, 1-aminopropyl and 5-aminopropyl; |
| for (1-6C)alkylamino-(1-6C)alkyl: | methylaminomethyl, ethylaminomethyl, 1-methylaminoethyl, 2-methylaminoethyl, 2-ethylaminoethyl and 3-methylaminopropyl; |
| for di-[(1-6C)alkyl]amino-(1-6C)alkyl: | dimethylaminomethyl, diethylaminomethyl, 1-dimethylaminoethyl, 2-dimethylaminoethyl and 3-dimethylaminopropyl; |
| for (2-6C)alkanoylamino-(1-6C)alkyl: | acetamidomethyl, propionamidomethyl, 2-acetamidoethyl and 1-acetamidoethyl; |
| for N-(1-6C)alkyl-(2-6C)alkanoylamino-(1-6C)alkyl: | N-methylacetamidomethyl, N-methylpropionamidomethyl, 2-(N-methylacetamido)ethyl and 1-(N-methylacetamido)ethyl; |
| for (1-6C)alkoxycarbonylamino-(1-6C)alkyl: | methoxycarbonylaminomethyl, ethoxycarbonylaminomethyl, tert-butoxycarbonylaminomethyl and 2-methoxycarbonylaminoethyl. |
| for ureido-(1-6C)alkyl: | ureidomethyl, 2-ureidoethyl and 1-ureidoethyl; |
| for N'-(1-6C)alkylureido-(1-6C)alkyl: | N'-methylureidomethyl, 2-(N'-methylureido)ethyl and 1-(N'-methylureido)ethyl; |
| for N',N'-di-[(1-6C)alkyl]ureido-(1-6C)alkyl: | N',N'-dimethylureidomethyl, 2-(N',N'-dimethylureido)ethyl and 1-(N',N'-dimethylureido)ethyl; |

-continued

| | |
|---|---|
| for N-(1-6C)alkylureido-(1-6C)alkyl: | N-methylureidomethyl, 2-(N-methylureido)ethyl and 1-(N-methylureido)ethyl; |
| for N,N'-di-[(1-6C)alkyl]ureido-(1-6C)alkyl: | N,N'-dimethylureidomethyl, 2-(N,N'-dimethylureido)ethyl and 1-(N,N'-dimethylureido)ethyl; |
| for N,N',N'-tri-[(1-6C)alkyl]ureido-(1-6C)alkyl: | N,N',N'-trimethylureidomethyl, 2-(N,N',N'-trimethylureido)ethyl and 1-(N,N',N'-trimethylureido)ethyl; |
| for carboxy-(1-6C)alkyl: | carboxymethyl, 1-carboxyethyl, 2-carboxyethyl, 3-carboxypropyl and 4-carboxybutyl; |
| for (1-6C)alkoxycarbonyl-(1-6C)alkyl: | methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl; |
| for carbamoyl-(1-6C)alkyl: | carbamoylmethyl, 1-carbamoylethyl, 2-carbamoylethyl and 3-carbamoylpropyl; |
| for N-(1-6C)alkylcarbamoyl-(1-6C)alkyl: | N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl; |
| for N,N-di-[(1-6C)alkyl]carbamoyl-(1-6C)alkyl: | N,N-dimethylcarbamoylmethyl, N-ethyl-N-methylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl, 3-(N,N-dimethylcarbamoyl)propyl and 4-(N,N-dimethylcarbamoyl)butyl; |
| for sulphamoyl-(1-6C)alkyl: | sulphamoylmethyl, 1-sulphamoylethyl, 2-sulphamoylethyl and 3-sulphamoylpropyl; |
| for N-(1-6C)alkylsulphamoyl-(1-6C)alkyl: | N-methylsulphamoylmethyl, 1-(N-methylsulphamoyl)ethyl, 2-(N-methylsulphamoyl)ethyl, and 3-(N-methylsulphamoyl)propyl; |
| for N,N-di-[(1-6C)alkyl]sulphamoyl-(1-6C)alkyl: | N,N-dimethylsulphamoylmethyl, 1-(N,N-dimethylsulphamoyl)ethyl, 2-(N,N-dimethylsulphamoyl)ethyl and 3-(N,N-dimethylsulphamoyl)propyl; |
| for (1-6C)alkanesulphonylamino-(1-6C)alkyl: | methanesulphonylaminomethyl, 2-(methanesulphonylamino)ethyl and 1-(methanesulphonylamino)ethyl; and |
| for N-(1-6C)alkyl-(1-6C)alkanesulphonylamino-(1-6C)alkyl: | N-methylmethanesulphonylaminomethyl, 2-(N-methylmethanesulphonylamino)ethyl and 1-(N-methylmethanesulphonylamino)ethyl. |

A suitable value for a (1-3C)alkylenedioxy group that may be present within a $R^1$ or $R^6$ group is, for example, methylenedioxy, ethylidenedioxy, isopropylidenedioxy or ethylenedioxy and the oxygen atoms thereof occupy adjacent ring positions.

When, as defined hereinbefore, an $R^1$ group forms a group of the formula $Q^1$-$X^2$— and, for example, $X^2$ is a $OC(R^8)_2$ linking group, it is the carbon atom, not the oxygen atom, of the $OC(R^8)_2$ linking group which is attached to the quinoline ring and the oxygen atom is attached to the $Q^1$ group. Similarly, when, as defined hereinbefore, an $R^6$ group forms a group of the formula —$X^7$-$Q^3$ and, for example, $X^7$ is a $C(R^{17})_2O$ linking group, it is the oxygen atom of the $C(R^{17})_2O$ linking group which is attached to the $Q^3$ group.

A suitable (2-6C)alkylene chain within a $R^1$ or $R^6$ group is, for example, an ethylene, trimethylene, tetramethylene or pentamethylene chain.

As defined hereinbefore, adjacent carbon atoms in any (2-6C)alkylene chain within a $R^1$ or $R^6$ group may be optionally separated by the insertion into the chain of a group such as O, $CON(R^{12})$ or $CON(R^{23})$ respectively, and C≡C. For example, insertion of an O atom into the alkylene chain within a 4-methoxybutoxy group gives rise to, for example, a 2-(2-methoxyethoxy)ethoxy group, for example, insertion of a C≡C group into the ethylene chain within a 2-hydroxyethoxy group gives rise to a 4-hydroxybut-2-ynyloxy group and, for example, insertion of a CONH group into the ethylene chain within a 3-methoxypropoxy group gives rise to, for example, a 2-(2-methoxyacetamido)ethoxy group.

When, as defined hereinbefore, any CH, $CH_2$ or $CH_3$ group within a $R^1$ or $R^6$ group optionally bears on each said CH, $CH_2$ or $CH_3$ group one or more halogeno or (1-8C)alkyl substituents, there is suitably 1 halogeno or (1-8C)alkyl substituent present on each said CH group, there are suitably 1 or 2 such substituents present on each said $CH_2$ group and there are suitably 1, 2 or 3 such substituents present on each said $CH_3$ group.

When, as defined hereinbefore, any CH, $CH_2$ or $CH_3$ group within a $R^1$ or $R^6$ group optionally bears on each said CH, $CH_2$ or $CH_3$ group a substituent as defined hereinbefore, suitable $R^1$ or $R^6$ groups so formed include, for example, hydroxy-substituted (1-8C)alkyl groups such as hydroxymethyl, 1-hydroxyethyl and 2-hydroxyethyl, hydroxy-substituted (1-6C)alkoxy groups such as 2-hydroxypropoxy and 3-hydroxypropoxy, (1-6C)alkoxy-substituted (1-6C)alkoxy groups such as 2-methoxyethoxy and 3-ethoxypropoxy, hydroxy-substituted amino-(2-6C)alkoxy groups such as 3-amino-2-hydroxypropoxy, hydroxy-substituted (1-6C) alkylamino-(2-6C)alkoxy groups such as 2-hydroxy-3-methylaminopropoxy, hydroxy-substituted di-[(1-6C)alkyl] amino-(2-6C)alkoxy groups such as 3-dimethylamino-2-hydroxypropoxy, hydroxy-substituted amino-(2-6C) alkylamino groups such as 3-amino-2-hydroxypropylamino, hydroxy-substituted (1-6C)alkylamino-(2-6C)alkylamino groups such as 2-hydroxy-3-methylaminopropylamino and hydroxy-substituted di-[(1-6C)alkyl]amino-(2-6C)alkylamino groups such as 3-dimethylamino-2-hydroxypropylamino.

When, as defined hereinbefore, any CH, $CH_2$ or $CH_3$ group within a $R^1$ or $R^6$ group optionally bears on each said CH, $CH_2$ or $CH_3$ group a substituent as defined hereinbefore, suitable $R^1$ or $R^6$ groups so formed also include, for example, hydroxy-substituted (1-6C)alkylamino-(1-6C)alkyl groups such as 2-hydroxy-3-methylaminopropyl and 2-hydroxyethylaminomethyl and hydroxy-substituted di-[(1-6C)alkyl] amino-(1-6C)alkyl groups such as 3-dimethylamino-2-hydroxypropyl and di-(2-hydroxyethyl)aminomethyl.

It is further to be understood that when, as defined hereinbefore, any CH, $CH_2$ or $CH_3$ group within a $R^1$ or $R^6$ group optionally bears on each said CH, $CH_2$ or $CH_3$ group a substituent as defined hereinbefore, such an optional substituent may be present on a CH, $CH_2$ or $CH_3$ group within the hereinbefore defined substituents that may be present on an aryl, heteroaryl or heterocyclyl group within a $R^1$ or $R^6$ group. For example, if the $R^1$ or $R^6$ group includes an aryl or heteroaryl group that is substituted by a (1-8C)alkyl group, the (1-8C) alkyl group may be optionally substituted on a CH, $CH_2$ or $CH_3$ group therein by one of the hereinbefore defined substituents therefor. For example, if the $R^1$ or $R^6$ group includes a heteroaryl group that is substituted by, for example, a (1-6C) alkylamino-(1-6C)alkyl group, the terminal $CH_3$ group of the (1-6C)alkylamino group may be further substituted by, for example, a (1-6C)alkylsulphonyl group or a (2-6C)alkanoyl group. Further, for example, if the $R^1$ or $R^6$ group includes a heterocyclyl group such as a piperidinyl or piperazinyl group that is substituted on a nitrogen atom thereof by, for example, a (2-6C)alkanoyl group, the terminal $CH_3$ group of the (2-6C) alkanoyl group may be further substituted by, for example, a di-[(1-6C)alkyl]amino group. For example, the $R^1$ or $R^6$ group may include a N-(2-dimethylaminoacetyl)piperidin-4-yl group or a 4-(2-dimethylaminoacetyl)piperazin-1-yl group. Further, for example, if the $R^1$ or $R^6$ group includes a heterocyclyl group such as a azetidinyl, piperidinyl or piperazinyl group that is substituted on a nitrogen atom thereof by, for example, a (2-6C)alkanoyl group, a $CH_2$ group of the (2-6C)alkanoyl group may be further substituted by, for example, a hydroxy group. For example, the $R^1$ or $R^6$ group may include a N-(2-hydroxypropionyl)piperidin-4-yl group.

As defined hereinbefore, two $R^6$ groups together may form a bivalent group, for example $OC(R^{18})_2O$, that spans adjacent ring positions on Ring A. When Ring A is, for example, a phenyl group, a suitable group so formed is a 2,3-methylenedioxyphenyl or a 3,4-methylenedioxyphenyl group. When a further optional $R^6$ group is present, for example a halogeno group, a suitable group so formed is, for example, a 6-fluoro-2,3-methylenedioxyphenyl group. Further, when Ring A is, for example, a phenyl group and two $R^6$ groups together form, for example, a $OC(R^{18})_2C(R^{18})_2$ group, a suitable group so formed is, for example, a 2,3-dihydrobenzofuran-5-yl group or a 2,3-dihydrobenzofuran-6-yl group. Further, when Ring A is, for example, a phenyl group and two $R^6$ groups together form, for example, a $N(R^{19})C(R^{18})_2C(R^{18})_2$ group, a suitable group so formed is, for example, an indolin-5-yl or a indolin-6-yl group. Further, when Ring A is, for example, a phenyl group and two $R^6$ groups together form, for example, a $N(R^{18})CO.C(R^{18})_2$ group, a suitable group so formed is, for example, a 2-oxoindolin-5-yl group or a 2-oxoindolin-6-yl group.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulphuric, trifluoroacetic or citric acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine. A further suitable pharmaceutically-acceptable salt of a compound of the Formula I is, for example, a salt formed within the human or animal body after administration of a compound of the Formula I.

It is further to be understood that a suitable pharmaceutically-acceptable solvate of a compound of the Formula I also forms an aspect of the present invention. A suitable pharmaceutically-acceptable solvate is, for example, a hydrate such as a hemi-hydrate, a mono-hydrate, a di-hydrate or a tri-hydrate or an alternative quantity thereof.

It is further to be understood that a suitable pharmaceutically-acceptable pro-drug of a compound of the Formula I also forms an aspect of the present invention. Accordingly, the compounds of the invention may be administered in the form of a pro-drug, that is a compound that is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula I and in vivo cleavable amide derivatives that may be formed at a carboxy group or an amino group in a compound of the Formula I.

Accordingly, the present invention includes those compounds of the Formula I as defined hereinbefore when made available by organic synthesis and when made available within the human or animal body by way of cleavage of a pro-drug thereof. Accordingly, the present invention includes those compounds of the Formula I that are produced by organic synthetic means and also such compounds that are produced in the human or animal body by way of metabolism of a precursor compound, that is a compound of the Formula I may be a synthetically-produced compound or a metabolically-produced compound.

A suitable pharmaceutically-acceptable pro-drug of a compound of the Formula I is one that is based on reasonable medical judgement as being suitable for administration to the human or animal body without undesirable pharmacological activities and without undue toxicity.

Various forms of pro-drug have been described, for example in the following document:— a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);

d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically-acceptable pro-drug of a compound of the Formula I that possesses a carboxy group is, for example, an in vivo cleavable ester thereof. An in vivo cleavable ester of a compound of the Formula I containing a carboxy group is, for example, a pharmaceutically-acceptable ester which is cleaved in the human or animal body to produce the parent acid. Suitable pharmaceutically-acceptable esters for carboxy include (1-6C)alkyl esters such as methyl, ethyl and tert-butyl, (1-6C)alkoxymethyl esters such as methoxymethyl esters, (1-6C)alkanoyloxymethyl esters such as pivaloyloxymethyl esters, 3-phthalidyl esters, (3-8C)cycloalkylcarbonyloxy-(1-6C)alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and (1-6C)alkoxycarbonyloxy-(1-6C)alkyl esters such as methoxycarbonyloxymethyl and 1-methoxycarbonyloxyethyl esters.

A suitable pharmaceutically-acceptable pro-drug of a compound of the Formula I that possesses a hydroxy group is, for example, an in vivo cleavable ester or ether thereof. An in vivo cleavable ester or ether of a compound of the Formula I containing a hydroxy group is, for example, a pharmaceutically-acceptable ester or ether which is cleaved in the human or animal body to produce the parent hydroxy compound. Suitable pharmaceutically-acceptable ester forming groups for a hydroxy group include inorganic esters such as phosphate esters (including phosphoramidic cyclic esters). Further suitable pharmaceutically-acceptable ester forming groups for a hydroxy group include (1-10C)alkanoyl groups such as acetyl, benzoyl, phenylacetyl and substituted benzoyl and phenylacetyl groups, (1-10C)alkoxycarbonyl groups such as ethoxycarbonyl, N,N-[di-(1-4C)alkyl]carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(1-4C)alkylpiperazin-1-ylmethyl. Suitable pharmaceutically-acceptable ether forming groups for a hydroxy group include α-acyloxyalkyl groups such as acetoxymethyl and pivaloyloxymethyl groups.

A suitable pharmaceutically-acceptable pro-drug of a compound of the Formula I that possesses a carboxy group is, for example, an in vivo cleavable amide thereof, for example an amide formed with an amine such as ammonia, a (1-4C)alkylamine such as methylamine, a di-(1-4C)alkylamine such as dimethylamine, N-ethyl-N-methylamine or diethylamine, a (1-4C)alkoxy-(2-4C)alkylamine such as 2-methoxyethylamine, a phenyl-(1-4C)alkylamine such as benzylamine and amino acids such as glycine or an ester thereof.

A suitable pharmaceutically-acceptable pro-drug of a compound of the Formula I that possesses an amino group is, for example, an in vivo cleavable amide derivative thereof. Suitable pharmaceutically-acceptable amides from an amino group include, for example an amide formed with (1-10C)alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(1-4C)alkylpiperazin-1-ylmethyl.

The in vivo effects of a compound of the Formula I may be exerted in part by one or more metabolites that are formed within the human or animal body after administration of a compound of the Formula I. As stated hereinbefore, the in vivo effects of a compound of the Formula I may also be exerted by way of metabolism of a precursor compound (a pro-drug).

Particular novel compounds of the invention include, for example, quinoline derivatives of the Formula I, or pharmaceutically-acceptable salts thereof, wherein, unless otherwise stated, each of $X^1$, p, $R^1$, q, $R^2$, $R^3$, $R^4$, $R^5$, Ring A, r and $R^6$ has any of the meanings defined hereinbefore or in paragraphs (a) to (iii) hereinafter:—

(a) $X^1$ is O or NH;
(b) $X^1$ is O;
(c) $X^1$ is NH;
(d) p is 0, 1, 2 or 3, and each $R^1$ group that is present is selected from halogeno, trifluoromethyl, cyano, hydroxy, amino, carboxy, (1-6C)alkoxycarbonyl, carbamoyl, (1-8C)alkyl, (2-8C)alkenyl, (2-8C)alkynyl, (1-6C)alkoxy, (2-6C)alkenyloxy, (2-6C)alkynyloxy, (1-6C)alkylamino, di-[(1-6C)alkyl]amino, N-(1-6C)alkylcarbamoyl and N,N-di-[(1-6C)alkyl]carbamoyl, or from a group of the formula:

$$Q^1\text{-}X^2\text{—}$$

wherein $X^2$ is selected from O, $N(R^8)$, CO, $CON(R^8)$, $N(R^8)CO$ and $OC(R^8)_2$ wherein $R^8$ is hydrogen or (1-8C)alkyl, and $Q^1$ is aryl, aryl-(1-6C)alkyl, (3-8C)cycloalkyl-(1-6C)alkyl, heteroaryl, heteroaryl-(1-6C)alkyl, heterocyclyl or heterocyclyl-(1-6C)alkyl, and wherein any aryl, (3-8C)cycloalkyl, heteroaryl or heterocyclyl group within a substituent on $R^1$ optionally bears 1, 2 or 3 substituents, which may be the same or different, selected from halogeno, trifluoromethyl, hydroxy, amino, carbamoyl, (1-8C)alkyl, (2-8C)alkenyl, (2-8C)alkynyl, (1-6C)alkoxy, (1-6C)alkylsulphonyl, (1-6C)alkylamino, di-[(1-6C)alkyl]amino, (2-6C)alkanoyl, N-(1-6C)alkylcarbamoyl, N,N-di-[(1-6C)alkyl]carbamoyl, (2-6C)alkanoylamino and N-(1-6C)alkyl-(2-6C)alkanoylamino, or from a group of the formula:

$$—X^3—R^9$$

wherein $X^3$ is a direct bond or is selected from O and $N(R^{10})$, wherein $R^{10}$ is hydrogen or (1-8C)alkyl, and $R^9$ is halogeno-(1-6C)alkyl, hydroxy-(1-6C)alkyl, (1-6C)alkoxy-(1-6C)alkyl, (1-6C)alkylsulphonyl-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl or N-(1-6C)alkyl-(2-6C)alkanoylamino-(1-6C)alkyl, or from a group of the formula:

$$—X^4\text{-}Q^2$$

wherein $X^4$ is a direct bond or is selected from O, CO and $N(R^{11})$, wherein $R^{11}$ is hydrogen or (1-8C)alkyl, and $Q^2$ is heterocyclyl or heterocyclyl-(1-6C)alkyl which optionally bears 1 or 2 substituents, which may be the same or different, selected from halogeno, (1-8C)alkyl and (1-6C)alkoxy, and wherein any heterocyclyl group within a substituent on $R^1$ optionally bears a (1-3C)alkylenedioxy group, and wherein any heterocyclyl group within a substituent on $R^1$ optionally bears 1 or 2 oxo substituents, and wherein any CH, $CH_2$ or $CH_3$ group within a $R^1$ substituent optionally bears on each said CH, $CH_2$ or $CH_3$ group one or more halogeno or (1-8C)alkyl groups and/or a substituent selected from hydroxy, amino, cyano, carboxy, carbamoyl, ureido, (1-6C)alkoxy, (1-6C)alkylthio, (1-6C)alkyl-sulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, and wherein adjacent carbon atoms in any (2-6C)alkylene chain within a $R^1$ substituent are optionally separated by the insertion into the chain of a group selected from O, $N(R^{12})$, $CON(R^{12})$, $N(R^{12})CO$, CH=CH and C≡C wherein $R^{12}$ is hydrogen or (1-8C)alkyl, or, when the inserted group is $N(R^{12})$, $R^{12}$ may also be (2-6C)alkanoyl;

(e) p is 1 or 2 and the $R^1$ groups are located at the 6- and/or 7-positions and the $R^1$ group at the 6-position is selected from halogeno, trifluoromethyl, cyano, hydroxy, amino, carboxy, (1-6C)alkoxycarbonyl, carbamoyl, (1-8C)alkyl, (2-8C)alkenyl, (2-8C)alkynyl, (1-6C)alkoxy, (2-6C)alkenyloxy, (2-6C)alkynyloxy, (1-6C)alkylamino, di-[(1-6C)alkyl]amino, N-(1-6C)alkylcarbamoyl and N,N-di-[(1-6C)alkyl]carbamoyl, and the $R^1$ group at the 7-position is selected from halogeno, trifluoromethyl, cyano, hydroxy, amino, carboxy, (1-6C)alkoxycarbonyl, carbamoyl, (1-8C)alkyl, (2-8C)alkenyl, (2-8C)alkynyl, (1-6C)alkoxy, (2-6C)alkenyloxy, (2-6C)alkynyloxy, (1-6C)alkylamino, di-[(1-6C)alkyl]amino, N-(1-6C)alkylcarbamoyl and N,N-di-[(1-6C)alkyl]carbamoyl, or from a group of the formula:

$$Q^1-X^2-$$

wherein $X^2$ is selected from O, $N(R^8)$, CO, $CON(R^8)$, $N(R^8)CO$ and $OC(R^8)_2$ wherein $R^8$ is hydrogen or (1-8C)alkyl, and $Q^1$ is aryl, aryl-(1-6C)alkyl, (3-8C)cycloalkyl-(1-6C)alkyl, heteroaryl, heteroaryl-(1-6C)alkyl, heterocyclyl or heterocyclyl-(1-6C)alkyl, and wherein any aryl, (3-8C)cycloalkyl, heteroaryl or heterocyclyl group within a substituent on $R^1$ optionally bears 1, 2 or 3 substituents, which may be the same or different, selected from halogeno, trifluoromethyl, hydroxy, amino, carbamoyl, (1-8C)alkyl, (2-8C)alkenyl, (2-8C)alkynyl, (1-6C)alkoxy, (1-6C)alkylsulphonyl, (1-6C)alkylamino, di-[(1-6C)alkyl]amino, (2-6C)alkanoyl, N-(1-6C)alkylcarbamoyl, N,N-di-[(1-6C)alkyl]carbamoyl, (2-6C)alkanoylamino and N-(1-6C)alkyl-(2-6C)alkanoylamino, or from a group of the formula:

$$-X^3-R^9$$

wherein $X^3$ is a direct bond or is selected from O and $N(R^{10})$, wherein $R^{10}$ is hydrogen or (1-8C)alkyl, and $R^9$ is halogeno-(1-6C)alkyl, hydroxy-(1-6C)alkyl, (1-6C)alkoxy-(1-6C)alkyl, (1-6C)alkylsulphonyl-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl or N-(1-6C)alkyl-(2-6C)alkanoylamino-(1-6C)alkyl, or from a group of the formula:

$$-X^4-Q^2$$

wherein $X^4$ is a direct bond or is selected from O, CO and $N(R^{11})$, wherein $R^{11}$ is hydrogen or (1-8C)alkyl, and $Q^2$ is heterocyclyl or heterocyclyl-(1-6C)alkyl which optionally bears 1 or 2 substituents, which may be the same or different, selected from halogeno, (1-8C)alkyl and (1-6C)alkoxy, and wherein any heterocyclyl group within a substituent on $R^1$ optionally bears a (1-3C)alkylenedioxy group, and wherein any heterocyclyl group within a substituent on $R^1$ optionally bears 1 or 2 oxo substituents, and wherein any CH, $CH_2$ or $CH_3$ group within a $R^1$ substituent optionally bears on each said CH, $CH_2$ or $CH_3$ group one or more halogeno or (1-8C)alkyl groups and/or a substituent selected from hydroxy, amino, cyano, carboxy, carbamoyl, ureido, (1-6C)alkoxy, (1-6C)alkylthio, (1-6C)alkyl-sulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, and wherein adjacent carbon atoms in any (2-6C)alkylene chain within a $R^1$ substituent are optionally separated by the insertion into the chain of a group selected from O, $N(R^{12})$, $CON(R^{12})$, $N(R^{12})CO$, CH=CH and C≡C wherein $R^{12}$ is hydrogen or (1-8C)alkyl, or, when the inserted group is $N(R^{12})$, $R^{12}$ may also be (2-6C)alkanoyl;

(f) p is 1, 2 or 3 and one $R^1$ group is a 3-cyano group and any other $R^1$ groups may be located at the 5-, 6- or 7-position or at the 5- and 7-positions or at the 6- and 7-positions and each other $R^1$ group is selected from fluoro, chloro, trifluoromethyl, cyano, hydroxy, amino, carboxy, methoxycarbonyl, ethoxycarbonyl, carbamoyl, methyl, ethyl, propyl, butyl, vinyl, allyl, but-3-enyl, ethynyl, 2-propynyl, but-3-ynyl, methoxy, ethoxy, propoxy, isopropoxy, butoxy, allyloxy, but-3-enyloxy, ethynyloxy, 2-propynyloxy, but-3-ynyloxy, methylamino, ethylamino, propylamino, dimethylamino, diethylamino, dipropylamino, N-methylcarbamoyl, N-ethylcarbamoyl, N,N-dimethylcarbamoyl and N,N-diethylcarbamoyl, or from a group of the formula:

$$Q^1-X^2-$$

wherein $X^2$ is selected from O, NH, CO, CONH, NHCO and $OCH_2$ and $Q^1$ is phenyl, benzyl, cyclopropylmethyl, 2-thienyl, 1-imidazolyl, 1,2,3-triazol-1-yl, 1,2,4-triazol-1-yl, 2-, 3- or 4-pyridyl, 2-imidazol-1-ylethyl, 3-imidazol-1-ylpropyl, 2-(1,2,3-triazolyl)ethyl, 3-(1,2,3-triazolyl)propyl, 2-(1,2,4-triazolyl)ethyl, 3-(1,2,4-triazolyl)propyl, 2-, 3- or 4-pyridylmethyl, 2-(2-, 3- or 4-pyridyl)ethyl, 3-(2-, 3- or 4-pyridyl)propyl, tetrahydrofuran-3-yl, 3- or 4-tetrahydropyranyl, 1-, 2- or 3-pyrrolidinyl, morpholino, 1,1-dioxotetrahydro-4H-1,4-thiazin-4-yl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 4-pyrrolidin-1-ylbutyl, 2-morpholinoethyl, 3-morpholinopropyl, 4-morpholinobutyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 4-piperidinobutyl, 2-piperidin-3-ylethyl, 3-piperidin-3-ylpropyl, 2-piperidin-4-ylethyl, 3-piperidin-4-ylpropyl, 2-homopiperidin-1-ylethyl, 3-homopiperidin-1-ylpropyl, 2-(1,2,3,6-tetrahydropyridin-1-yl)ethyl, 3-(1,2,3,6-tetrahydropyridin-1-yl)propyl, 4-(1,2,3,6-tetrahydropyridin-1-yl)butyl, 2-piperazin-1-ylethyl, 3-piperazin-1-ylpropyl, 4-piperazin-1-ylbutyl, 2-homopiperazin-1-ylethyl or 3-homopiperazin-1-ylpropyl, and wherein any aryl, (3-8C)cycloalkyl, heteroaryl or heterocyclyl group within a substituent on $R^1$ optionally bears 1, 2 or 3 substituents, which may be the same or different, selected from fluoro, chloro, trifluoromethyl, hydroxy, amino, carbamoyl, methyl, ethyl, allyl, 2-propynyl, methoxy, methylsulphonyl, methylamino, dimethylamino, acetyl, propionyl, isobutyryl, N-methylcarbamoyl, N,N-dimethylcarbamoyl, methylenedioxy, ethylidendioxy and isopropylidenedioxy, or optionally bears 1 substituent selected from a group of the formula:

—X$^3$—R$^9$ wherein X$^3$ is a direct bond or is selected from O and NH and R$^9$ is 2-fluoroethyl, 2,2-difluoroethyl, 2,2,2-trifluoroethyl, 3-fluoropropyl, 3,3-difluoropropyl, 3,3,3-trifluoropropyl, 2-hydroxyethyl, 3-hydroxypropyl, 2-methoxyethyl, 3-methoxypropyl, cyanomethyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl or N-methylacetamidomethyl, and from a group of the formula:

—X$^4$-Q$^2$ wherein X$^4$ is a direct bond or is selected from O, CO and NH and Q$^2$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within a substituent on R$^1$ optionally bears 1 or 2 oxo substituents, and wherein any CH, CH$_2$ or CH$_3$ group within a R$^1$ substituent optionally bears on each said CH, CH$_2$ or CH$_3$ group one or more fluoro, chloro or methyl groups or a substituent selected from hydroxy, amino, cyano, methoxy, methylsulphonyl, methylamino, dimethylamino, diisopropylamino, N-ethyl-N-methylamino, N-isopropyl-N-methylamino, acetyl, acetamido and N-methylacetamido, and wherein adjacent carbon atoms in any (2-6C)alkylene chain within a R$^1$ substituent are optionally separated by the insertion into the chain of a group selected from O, NH, N(Me), N(COMe), CONH, NHCO, CH═CH and C≡C;

(g) p is 2 and the R$^1$ groups are located at the 5- and 7-positions or at the 6- and 7-positions and the R$^1$ groups, which may be the same or different, are selected from cyano, hydroxy, amino, carboxy, methoxycarbonyl, ethoxycarbonyl, carbamoyl, methyl, ethyl, propyl, butyl, vinyl, ethynyl, methoxy, ethoxy, propoxy, isopropoxy, butoxy, but-3-enyloxy, methylamino, ethylamino, dimethylamino, diethylamino, N-methylcarbamoyl, N-ethylcarbamoyl, N,N-dimethylcarbamoyl, N,N-diethylcarbamoyl, cyclopentyloxy, cyclohexyloxy, phenoxy, benzyloxy, tetrahydrofuran-3-yloxy, tetrahydropyran-3-yloxy, tetrahydropyran-4-yloxy, cyclopropylmethoxy, 2-imidazol-1-ylethoxy, 3-imidazol-1-ylpropoxy, 2-(1,2,3-triazol-1-yl)ethoxy, 3-(1,2,3-triazol-1-yl)propoxy, 2-(1,2,4-triazol-1-yl)ethoxy, 3-(1,2,4-triazol-1-yl)propoxy, pyrid-2-ylmethoxy, pyrid-3-ylmethoxy, pyrid-4-ylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, pyrrolidin-1-yl, morpholino, piperidino, piperazin-1-yl, pyrrolidin-1-ylcarbonyl, morpholinocarbonyl, piperidinocarbonyl, piperazin-1-ylcarbonyl, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, piperidin-4-ylmethoxy, 2-piperidin-3-ylethoxy, 3-piperidin-3-ylpropoxy, 2-piperidin-4-ylethoxy, 3-piperidin-4-ylpropoxy, 2-homopiperidin-1-ylethoxy, 3-homopiperidin-1-ylpropoxy, 2-(1,2,3,6-tetrahydropyridin-1-yl)ethoxy 3-(1,2,3,6-tetrahydropyridin-1-yl)propoxy, 4-(1,2,3,6-tetrahydropyridin-1-yl)butoxy, 2-piperazin-1-ylethoxy, 3-piperazin-1-ylpropoxy, 4-piperazin-1-ylbutoxy, 2-homopiperazin-1-ylethoxy, 3-homopiperazin-1-ylpropoxy, 2-pyrrolidin-1-ylethylamino, 3-pyrrolidin-1-ylpropylamino, 4-pyrrolidin-1-ylbutylamino, pyrrolidin-3-ylamino, pyrrolidin-2-ylmethylamino, 2-pyrrolidin-2-ylethylamino, 3-pyrrolidin-2-ylpropylamino, 2-morpholinoethylamino, 3-morpholinopropylamino, 4-morpholinobutylamino, 2-(1,1-dioxotetrahydro-4H-1,4-thiazin-4-yl)ethylamino, 3-(1,1-dioxotetrahydro-4H-1,4-thiazin-4-yl)propylamino, 2-piperidinoethylamino, 3-piperidinopropylamino, 4-piperidinobutylamino, piperidin-3-ylamino, piperidin-4-ylamino, piperidin-3-ylmethylamino, 2-piperidin-3-ylethylamino, piperidin-4-ylmethylamino, 2-piperidin-4-ylethylamino, 2-homopiperidin-1-ylethylamino, 3-homopiperidin-1-ylpropylamino, 2-piperazin-1-ylethylamino, 3-piperazin-1-ylpropylamino, 4-piperazin-1-ylbutylamino, 2-homopiperazin-1-ylethylamino or 3-homopiperazin-1-ylpropylamino, and wherein any phenyl, imidazolyl, triazolyl, pyridyl or heterocyclyl group within a substituent on R$^1$ optionally bears 1 or 2 substituents, which may be the same or different, selected from fluoro, chloro, trifluoromethyl, hydroxy, amino, carbamoyl, methyl, ethyl, methoxy, ethoxy, N-methylcarbamoyl, N,N-dimethylcarbamoyl, methylenedioxy, ethylidendioxy and isopropylidenedioxy, and a pyrrolidin-2-yl, piperidin-3-yl, piperidin-4-yl, piperazin-1-yl or homopiperazin-1-yl group within a R$^1$ substituent is optionally N-substituted with allyl, 2-propynyl, methylsulphonyl, ethylsulphonyl, acetyl, propionyl, isobutyryl, 2-fluoroethyl, 2,2-difluoroethyl, 2,2,2-trifluoroethyl, 3-fluoropropyl, 3,3-difluoropropyl, 3,3,3-trifluoropropyl, 2-methoxyethyl, 3-methoxypropyl, cyanomethyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on R$^1$ optionally bears 1 or 2 oxo substituents, and wherein any CH, CH$_2$ or CH$_3$ group within a R$^1$ substituent optionally bears on each said CH, CH$_2$ or CH$_3$ group one or more fluoro, chloro or methyl groups or a substituent selected from hydroxy, amino, methoxy, methylsulphonyl, methylamino, dimethylamino, diisopropylamino, N-ethyl-N-methylamino, N-isopropyl-N-methylamino, N-methyl-N-propylamino, acetamido and N-methylacetamido, and wherein adjacent carbon atoms in any (2-6C)alkylene chain within a R$^1$ substituent are optionally separated by the insertion into the chain of a group selected from O, NH, N(Me), CH═CH and C≡C;

(h) p is 2 and the R$^1$ groups are located at the 6- and 7-positions and the R$^1$ groups, which may be the same or different, are selected from cyano, hydroxy, amino, methoxycarbonyl, ethoxycarbonyl, carbamoyl, methyl, ethyl, methoxy, ethoxy, propoxy, isopropoxy, butoxy, methylamino, ethylamino, dimethylamino, diethylamino, N-methylcarbamoyl, N-ethylcarbamoyl, N,N-dimethylcarbamoyl, N,N-diethylcarbamoyl, pyrrolidin-1-ylcarbonyl, morpholinocarbonyl, piperidinocarbonyl, piperazin-1-ylcarbonyl, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 3-(1,2,3,6-tetrahydropyridin-1-yl)propoxy, 2-piperazin-1-ylethoxy, 3-piperazin-1-ylpropoxy, 2-homopiperazin-1-ylethoxy and 3-homopiperazin-1-ylpropoxy, and wherein any heterocyclyl group within a substituent on $R^1$ optionally bears 1 or 2 substituents, which may be the same or different, selected from fluoro, chloro, trifluoromethyl, hydroxy, amino, methyl, ethyl, methoxy, methylenedioxy, ethylidendioxy and isopropylidenedioxy, and a pyrrolidin-2-yl, pyrrolidin-3-yl, piperidin-3-yl, piperidin-4-yl, piperazin-1-yl or homopiperazin-1-yl group within a $R^1$ substituent is optionally N-substituted with methyl, ethyl, propyl, allyl, 2-propynyl, methylsulphonyl, acetyl, propionyl, isobutyryl, 2-fluoroethyl, 2,2-difluoroethyl, 2,2,2-trifluoroethyl or cyanomethyl, and wherein any heterocyclyl group within a substituent on $R^1$ optionally bears 1 or 2 oxo substituents, and wherein any CH, $CH_2$ or $CH_3$ group within a $R^1$ substituent optionally bears on each said CH, $CH_2$ or $CH_3$ group one or more chloro groups or a substituent selected from hydroxy, amino, methoxy, methylsulphonyl, methylamino, dimethylamino, diisopropylamino, N-ethyl-N-methylamino and N-isopropyl-N-methylamino, and wherein adjacent carbon atoms in any (2-6C)alkylene chain within a $R^1$ substituent are optionally separated by the insertion into the chain of a group selected from O, NH, CH=CH and C≡C;

(i) p is 2 and the $R^1$ groups are located at the 6- and 7-positions and the $R^1$ groups, which may be the same or different, are selected from hydroxy, amino, methoxycarbonyl, ethoxycarbonyl, carbamoyl, methyl, ethyl, methoxy, ethoxy, propoxy, isopropoxy, butoxy, methylamino, ethylamino, dimethylamino, diethylamino, N-methylcarbamoyl, N-ethylcarbamoyl, N,N-dimethylcarbamoyl, N,N-diethylcarbamoyl, pyrrolidin-1-ylcarbonyl, morpholinocarbonyl, piperidinocarbonyl, piperazin-1-ylcarbonyl, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, 3-piperidinyloxy, 4-piperidinyloxy, piperidin-3-ylmethoxy, piperidin-4-ylmethoxy, 2-piperidin-3-ylethoxy, 2-piperidin-4-ylethoxy, 2-homopiperidin-1-ylethoxy, 3-homopiperidin-1-ylpropoxy, 3-(1,2,3,6-tetrahydropyridin-1-yl)propoxy, 2-piperazin-1-ylethoxy, 3-piperazin-1-ylpropoxy, 2-homopiperazin-1-ylethoxy and 3-homopiperazin-1-ylpropoxy, and wherein any heterocyclyl group within a substituent on $R^1$ optionally bears 1 or 2 substituents, which may be the same or different, selected from fluoro, chloro, trifluoromethyl, hydroxy, amino, methyl, ethyl, methoxy, methylenedioxy, ethylidendioxy and isopropylidenedioxy, and a pyrrolidin-2-yl, pyrrolidin-3-yl, piperidin-3-yl, piperidin-4-yl, piperazin-1-yl or homopiperazin-1-yl group within a $R^1$ substituent is optionally N-substituted with methyl, ethyl, propyl, allyl, 2-propynyl, methylsulphonyl, acetyl, propionyl, isobutyryl, 2-fluoroethyl, 2,2-difluoroethyl, 2,2,2-trifluoroethyl or cyanomethyl, and wherein any heterocyclyl group within a substituent on $R^1$ optionally bears 1 or 2 oxo substituents, and wherein any CH, $CH_2$ or $CH_3$ group within a $R^1$ substituent optionally bears on each said CH, $CH_2$ or $CH_3$ group one or more chloro groups or a substituent selected from hydroxy, amino, methoxy, methylsulphonyl, methylamino, dimethylamino, diisopropylamino, N-ethyl-N-methylamino and N-isopropyl-N-methylamino, and wherein adjacent carbon atoms in any (2-6C)alkylene chain within a $R^1$ substituent are optionally separated by the insertion into the chain of a group selected from O, NH, CH=CH and C≡C;

(j) p is 2 and the $R^1$ groups are located at the 6- and 7-positions and the $R^1$ group at the 6-position is selected from cyano, hydroxy, methoxycarbonyl, ethoxycarbonyl, carbamoyl, methoxy, ethoxy, propoxy, N-methylcarbamoyl, N-ethylcarbamoyl, N,N-dimethylcarbamoyl, N,N-diethylcarbamoyl, pyrrolidin-1-ylcarbonyl, morpholinocarbonyl, piperidinocarbonyl and piperazin-1-ylcarbonyl, and the $R^1$ group at the 7-position is selected from methoxy, ethoxy, propoxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 3-(1,2,3,6-tetrahydropyridin-1-yl)propoxy, 2-piperazin-1-ylethoxy, 3-piperazin-1-ylpropoxy, 2-homopiperazin-1-ylethoxy and 3-homopiperazin-1-ylpropoxy, and wherein any heterocyclyl group within a substituent on $R^1$ optionally bears 1 or 2 substituents, which may be the same or different, selected from fluoro, chloro, trifluoromethyl, hydroxy, amino, methyl, ethyl, methoxy, methylenedioxy, ethylidendioxy and isopropylidenedioxy, and a pyrrolidin-2-yl, pyrrolidin-3-yl, piperidin-3-yl, piperidin-4-yl, piperazin-1-yl or homopiperazin-1-yl group within a $R^1$ substituent is optionally N-substituted with methyl, ethyl, propyl, allyl, 2-propynyl, methylsulphonyl, acetyl, propionyl, isobutyryl, 2-fluoroethyl, 2,2-difluoroethyl, 2,2,2-trifluoroethyl or cyanomethyl, and wherein any heterocyclyl group within a substituent on $R^1$ optionally bears 1 or 2 oxo substituents, and wherein any CH, $CH_2$ or $CH_3$ group within a $R^1$ substituent optionally bears on each said CH, $CH_2$ or $CH_3$ group one or more chloro groups or a substituent selected from hydroxy, amino, methoxy, methylsulphonyl, methylamino, dimethylamino, diisopropylamino, N-ethyl-N-methylamino and N-isopropyl-N-methylamino;

(k) q is 0;

(l) q is 1 or 2 and each $R^2$ group, which may be the same or different, is selected from halogeno, trifluoromethyl, cyano, carbamoyl, hydroxy, amino, (1-8C)alkyl, (2-8C)alkenyl, (2-8C)alkynyl, (1-6C)alkoxy, (1-6C)alkylamino, di-[(1-6C)alkyl]amino, N-(1-6C)alkylcarbamoyl and N,N-di-[(1-6C)alkyl]carbamoyl;

(m) q is 1 or 2 and each R² group, which may be the same or different, is selected from halogeno, trifluoromethyl, cyano, hydroxy, amino, (1-8C)alkyl, (2-8C)alkenyl, (2-8C)alkynyl, (1-6C)alkoxy, (1-6C)alkylamino and di-[(1-6C)alkyl]amino;

(n) q is 1 or 2 and each R² group, which may be the same or different, is selected from fluoro, chloro, trifluoromethyl, cyano, hydroxy, amino, methyl, methoxy, methylamino and dimethylamino;

(o) q is 1 and the R² group which is located at the 2-position (relative to the C(R³)(R⁴) group) is a (1-6C)alkoxy group;

(p) q is 1 and the R² group which is located at the 2-position (relative to the C(R³)(R⁴) group) is selected from fluoro, chloro, trifluoromethyl, cyano, carbamoyl, hydroxy, amino, methyl, methoxy, methylamino, dimethylamino, N-methylcarbamoyl and N,N-dimethylcarbamoyl;

(q) q is 1 and the R² group which is located at the 2-position (relative to the C(R³)(R⁴) group) is selected from fluoro, chloro, trifluoromethyl, cyano, hydroxy, amino, methyl, methoxy, methylamino and dimethylamino;

(r) q is 1 and the R² group which is located at the 2-position (relative to the C(R³)(R⁴) group) is selected from fluoro, chloro, cyano, methyl and methoxy;

(s) q is 1 and the R² group which is located at the 2-position (relative to the C(R³)(R⁴) group) is a methoxy group;

(t) R³ is hydrogen, methyl or ethyl;

(u) R³ is hydrogen;

(v) R⁴ is hydrogen, methyl, ethyl, propyl, 2-fluoroethyl, 2,2-difluoroethyl, 2,2,2-trifluoroethyl, 3-fluoropropyl, 3,3-difluoropropyl, 3,3,3-trifluoropropyl, 2-hydroxyethyl, 3-hydroxypropyl, 2-methoxyethyl, 3-methoxypropyl, cyanomethyl, 2-cyanoethyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl or N-methylacetamidomethyl;

(w) R⁴ is hydrogen, methyl or ethyl;

(x) R⁴ is hydrogen;

(y) R³ and R⁴ together with the carbon atom to which they are attached form a cyclopropyl, cyclobutyl, cyclopentyl or cyclohexyl group;

(z) R⁵ is hydrogen, methyl, ethyl, propyl, allyl, 2-propynyl, 2-fluoroethyl, 2,2-difluoroethyl, 2,2,2-trifluoroethyl, 3-fluoropropyl, 3,3-difluoropropyl, 3,3,3-trifluoropropyl, 2-hydroxyethyl, 3-hydroxypropyl, 2-methoxyethyl, 3-methoxypropyl, cyanomethyl, 2-cyanoethyl or 3-cyanopropyl;

(aa) R⁵ is methyl or ethyl;

(bb) R⁵ is hydrogen;

(cc) Ring A is a 6-membered monocyclic aryl ring or a 5- or 6-membered monocyclic heteroaryl ring with up to three ring heteroatoms selected from oxygen, nitrogen and sulphur;

(dd) Ring A is a phenyl ring;

(ee) Ring A is a 6-membered monocyclic heteroaryl ring with up to three nitrogen heteroatoms;

(ff) Ring A is a 5-membered monocyclic heteroaryl ring with up to three ring heteroatoms selected from oxygen, nitrogen and sulphur;

(gg) Ring A is a phenyl, furyl, pyrrolyl, thienyl, oxazolyl, isoxazolyl, imidazolyl, pyrazolyl, thiazolyl, isothiazolyl, oxadiazolyl, thiadiazolyl, pyridyl, pyrimidinyl, pyrazinyl or pyridazinyl ring;

(hh) Ring A is a phenyl, pyridyl, pyrimidinyl, pyrazinyl or pyridazinyl ring;

(ii) Ring A is a furyl, pyrrolyl, thienyl, oxazolyl, isoxazolyl, imidazolyl, pyrazolyl, thiazolyl, isothiazolyl, oxadiazolyl or thiadiazolyl ring;

(jj) when Ring A is a 6-membered ring, and one or two R⁶ groups are present, one R⁶ group is located at the 3- or 4-position (relative to the CON(R⁵) group);

(kk) when Ring A is a 5-membered ring, and one or two R⁶ groups are present, one R⁶ group is located at the 3-position (relative to the CON(R⁵) group);

(ll) Ring A is a phenyl, pyridyl, pyrimidinyl, pyrazinyl or pyridazinyl ring that bears one or two R⁶ groups and one R⁶ group is located at the 3- or 4-position (relative to the CON(R⁵) group);

(mm) Ring A is a furyl, pyrrolyl, thienyl, oxazolyl, isoxazolyl, imidazolyl, pyrazolyl, thiazolyl, isothiazolyl, oxadiazolyl or thiadiazolyl ring that bears one or two R⁶ groups and one R⁶ group is located at the 3-position (relative to the CON(R⁵) group);

(nn) Ring A is a 9- or 10-membered bicyclic heteroaryl ring with up to three ring heteroatoms selected from oxygen, nitrogen and sulphur;

(oo) Ring A is a benzofuranyl, indolyl, benzothienyl, benzoxazolyl, benzimidazolyl, benzothiazolyl, indazolyl, benzotriazolyl, 1H-pyrrolo[3,2-b]pyridinyl, quinolyl, isoquinolyl, quinazolinyl, quinoxalinyl or naphthyridinyl ring;

(pp) r is 0, 1, 2 or 3 and each R⁶ group that is present, which may be the same or different, is selected from halogeno, trifluoromethyl, cyano, hydroxy, amino, (1-8C)alkyl, (2-8C)alkenyl, (2-8C)alkynyl, (1-6C)alkoxy, (1-6C)alkylamino, di-[(1-6C)alkyl]amino, (2-6C)alkanoylamino and N-(1-6C)alkyl-(2-6C)alkanoylamino;

(qq) r is 1 or 2 and each R⁶ group, which may be the same or different, is selected from fluoro, chloro, trifluoromethyl, cyano, hydroxy, amino, methyl, ethyl, propyl, isopropyl, butyl, sec-butyl, isobutyl, tert-butyl, methoxy, ethoxy, methylamino, ethylamino, dimethylamino and diethylamino;

(rr) r is 1 and the R⁶ group is selected from fluoro, chloro, trifluoromethyl, hydroxy, amino, methyl, ethyl, propyl, isopropyl, butyl, sec-butyl, isobutyl, tert-butyl, methoxy, ethoxy, methylamino, ethylamino, dimethylamino and diethylamino;

(ss) r is 1, 2 or 3 and one R⁶ group is a group of the formula:

—X⁶—R¹⁵ wherein X⁶ is a direct bond or is selected from O and N(R¹⁶), wherein R¹⁶ is hydrogen or (1-8C)alkyl, and R¹⁵ is halogeno-(1-6C)alkyl, hydroxy-(1-6C)alkyl, mercapto-(1-6C)alkyl, (1-6C)alkoxy-(1-6C)alkyl, (1-6C)alkylthio-(1-6C)alkyl, (1-6C)alkylsulphinyl-(1-6C)alkyl, (1-6C)alkylsulphonyl-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, carboxy-(1-6C)alkyl, (1-6C)alkoxycarbonyl-(1-6C)alkyl, carbamoyl-(1-6C)alkyl, N-(1-6C)alkylcarbamoyl-(1-6C)alkyl or N,N-di-[(1-6C)alkyl]carbamoyl-(1-6C)alkyl provided that, when X⁶ is O or N(R¹⁶), there are at least two carbon atoms between X⁶ and any heteroatom in the R¹⁵ group, and any other R⁶ group that is present is selected from halogeno, trifluoromethyl, cyano, hydroxy, amino, (1-8C)alkyl, (2-8C)alkenyl, (2-8C)alkynyl, (1-6C)alkoxy, (1-6C)alkylamino, di-[(1-6C)alkyl]amino, (2-6C)alkanoylamino and N-(1-6C)alkyl-(2-6C)alkanoylamino, and wherein any CH, CH₂ or CH₃ group within an R⁶ group optionally bears on each said CH, CH₂ or CH₃ group one or more halogeno or (1-8C)alkyl substituents and/or a substituent selected from hydroxy, amino, cyano, carboxy, carbamoyl, ureido, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoylamino and N-(1-6C)alkyl-(2-6C)alkanoylamino;

(tt) r is 1, 2 or 3 and one $R^6$ group is a group of the formula:

—$X^7$-$Q^3$ wherein $X^7$ is a direct bond or is selected from O, N($R^{17}$), CON($R^{17}$), N($R^{17}$)CO and C($R^{17}$)$_2$O, wherein each $R^{17}$ is hydrogen or (1-8C)alkyl, and $Q^3$ is aryl, aryl-(1-6C)alkyl, (3-8C)cycloalkyl, (3-8C)cycloalkyl-(1-6C)alkyl, heteroaryl, heteroaryl-(1-6C)alkyl, heterocyclyl or heterocyclyl-(1-6C)alkyl provided that, when $X^7$ is selected from O, N($R^{17}$), CON($R^{17}$) or C($R^{17}$)$_2$O, there are at least two carbon atoms between $X^7$ and any heteroatom in $Q^3$ that is not in a heteroaryl ring, and any other $R^6$ group that is present is selected from halogeno, trifluoromethyl, cyano, hydroxy, amino, (1-8C)alkyl, (2-8C)alkenyl, (2-8C)alkynyl, (1-6C)alkoxy, (1-6C)alkylamino, di-[(1-6C)alkyl]amino, (2-6C)alkanoylamino and N-(1-6C)alkyl-(2-6C)alkanoylamino, and wherein any aryl, (3-8C)cycloalkyl, heteroaryl or heterocyclyl group within an $R^6$ group optionally bears 1, 2 or 3 substituents, which may be the same or different, selected from halogeno, trifluoromethyl, cyano, hydroxy, amino, carboxy, carbamoyl, ureido, (1-8C)alkyl, (2-8C)alkenyl, (2-8C)alkynyl, (1-6C)alkoxy, (1-6C)alkylamino and di-[(1-6C)alkyl]amino, or from a group of the formula:

—$X^8$—$R^{20}$ wherein $X^8$ is a direct bond or is selected from O and N($R^{21}$), wherein $R^{21}$ is hydrogen or (1-8C)alkyl, and $R^{20}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, and wherein any heterocyclyl group within an $R^6$ group optionally bears 1 or 2 oxo or thioxo substituents, and wherein any CH, CH$_2$ or CH$_3$ group within an $R^6$ group optionally bears on each said CH, CH$_2$ or CH$_3$ group one or more halogeno or (1-8C)alkyl substituents and/or a substituent selected from hydroxy, amino, cyano, carboxy, carbamoyl, ureido, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoylamino and N-(1-6C)alkyl-(2-6C)alkanoylamino;

(uu) r is 1, 2 or 3 and one $R^6$ group is a group of the formula:

—$X^6$—$R^{15}$ wherein $X^6$ is a direct bond or is selected from O and N($R^{16}$), wherein $R^{16}$ is hydrogen or (1-8C)alkyl, and $R^{15}$ is hydroxy-(1-6C)alkyl, (1-6C)alkoxy-(1-6C)alkyl, (1-6C)alkylthio-(1-6C)alkyl, (1-6C)alkylsulphinyl-(1-6C)alkyl, (1-6C)alkylsulphonyl-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, aryl, aryl-(1-6C)alkyl, (3-8C)cycloalkyl, (3-8C)cycloalkyl-(1-6C)alkyl, heteroaryl, heteroaryl-(1-6C)alkyl, heterocyclyl or heterocyclyl-(1-6C)alkyl, provided that, when $X^6$ is O or N($R^{16}$), there are at least two carbon atoms between $X^6$ and any heteroatom in the $R^{16}$ group, and any other $R^6$ group that is present is selected from halogeno, trifluoromethyl, cyano, hydroxy, amino, (1-8C)alkyl, (2-8C)alkenyl, (2-8C)alkynyl, (1-6C)alkoxy, (1-6C)alkylamino, di-[(1-6C)alkyl]amino, (2-6C)alkanoylamino and N-(1-6C)alkyl-(2-6C) alkanoylamino, and wherein any aryl, (3-8C)cycloalkyl, heteroaryl or heterocyclyl group within the $R^6$ group optionally bears 1 or 2 substituents, which may be the same or different, selected from halogeno, trifluoromethyl, cyano, hydroxy, amino, (1-8C)alkyl, (1-6C)alkoxy, (1-6C)alkylamino and di-[(1-6C)alkyl]amino, or from a group of the formula:

—$X^8$—$R^{20}$ wherein $X^8$ is a direct bond and $R^{20}$ is halogeno-(1-6C)alkyl, hydroxy-(1-6C)alkyl, (1-6C)alkoxy-(1-6C)alkyl, cyano-(1-6C)alkyl, amino-(1-6C)alkyl, (1-6C)alkylamino-(1-6C)alkyl or di-[(1-6C)alkyl]amino-(1-6C)alkyl, and wherein any CH, CH$_2$ or CH$_3$ group within the $R^6$ group optionally bears on each said CH, CH$_2$ or CH$_3$ group 1, 2 or 3 halogeno or (1-8C)alkyl substituents and/or a substituent selected from hydroxy, amino, cyano, (3-8C)alkenyl, (3-8C)alkynyl, (1-6C)alkoxy, (1-6C)alkylsulphonyl, (1-6C)alkylamino, di-[(1-6C)alkyl]amino, (2-6C)alkanoylamino and N-(1-6C)alkyl-(2-6C)alkanoylamino;

(vv) r is 1, 2 or 3 and one $R^6$ group is a group of the formula:

—$X^6$—$R^{15}$ wherein $X^6$ is a direct bond or is selected from O and N($R^{16}$), wherein $R^{16}$ is hydrogen or (1-8C)alkyl, and $R^{15}$ is hydroxy-(1-6C)alkyl, (1-6C)alkoxy-(1-6C)alkyl, amino-(1-6C)alkyl, (1-6C)alkylamino-(1-6C)alkyl, di-[(1-6C)alkyl]amino-(1-6C)alkyl, aryl, aryl-(1-6C)alkyl, (3-8C)cycloalkyl, (3-8C)cycloalkyl-(1-6C)alkyl, heteroaryl, heteroaryl-(1-6C)alkyl, heterocyclyl or heterocyclyl-(1-6C)alkyl, provided that, when $X^6$ is O or N($R^{16}$), there are at least two carbon atoms between $X^6$ and any heteroatom in the $R^{15}$ group, and any other $R^6$ group that is present is selected from halogeno, trifluoromethyl, cyano, hydroxy, amino, (1-8C)alkyl, (1-6C)alkoxy, (1-6C)alkylamino, di-[(1-6C)alkyl]amino, (2-6C)alkanoylamino and N-(1-6C)alkyl-(2-6C)alkanoylamino, and wherein any aryl, (3-8C)cycloalkyl, heteroaryl or heterocyclyl group within the $R^6$ group optionally bears 1 or 2 substituents, which may be the same or different, selected from halogeno, trifluoromethyl, hydroxy, amino, (1-8C)alkyl, (1-6C)alkoxy, (1-6C)alkylamino, di-[(1-6C)alkyl]amino, hydroxy-(1-6C)alkyl, amino-(1-6C)alkyl, (1-6C)alkylamino-(1-6C)alkyl and di-[(1-6C)alkyl]amino-(1-6C)alkyl;

(ww) r is 1 or 2 and one $R^6$ group is a group of the formula:

—$X^6$—$R^{15}$ wherein $X^6$ is a direct bond or is selected from O, NH and N(Me), and $R^{15}$ is hydroxymethyl, 1-hydroxyethyl, 2-hydroxyethyl, 1-hydroxy-1-methylethyl, 3-hydroxypropyl, methoxymethyl, 1-methoxyethyl, 2-methoxyethyl, 1-methoxy-1-methylethyl, 3-methoxypropyl, cyanomethyl, 1-cyanoethyl, 2-cyanoethyl, 1-cyano-1-methylethyl, 3-cyanopropyl, aminomethyl, 1-aminoethyl, 2-aminoethyl, 1-amino-1-methylethyl, 3-aminopropyl, methylaminomethyl, 1-methylaminoethyl, 2-methylaminoethyl, 1-methylamino-1-methylethyl, 3-methylaminopropyl, ethylaminomethyl, 1-ethylaminoethyl, 2-ethylaminoethyl, 1-ethylamino-1-methylethyl, 3-ethylaminopropyl, isopropylaminomethyl, 1-isopropylaminoethyl, dimethylaminomethyl, 1-dimethylaminoethyl, 2-dimethylaminoethyl, 1-dimethylamino-1-methylethyl, 3-dimethylaminopropyl, phenyl, benzyl, cyclopropyl, cyclobutyl, cyclopentyl, cyclohexyl, furyl, thienyl, oxazolyl, imidazolyl, thiazolyl, pyridyl, pyrimidinyl, tetrahydrofuranyl, tetrahydropyranyl, tetrahydrothiopyranyl, pyrrolinyl, pyrrolidinyl, imidazolidinyl, pyrazolidinyl, morpholinyl, tetrahydro-1,4-thiazinyl, piperidinyl, homopiperidinyl, piperazinyl, homopiperazinyl, indolinyl, isoindolinyl, pyrrolinylmethyl, pyrrolidinylmethyl, 2-pyrrolidinylethyl, 3-pyrrolidinylpropyl, imidazolidinylmethyl, pyrazolidinylmethyl, morpholinylmethyl, 2-(morpholinyl)ethyl, 3-(morpholinyl)propyl, tetrahydro-1,4-thiazinylmethyl, 2-(tetrahydro-1,4-thiazinyl)ethyl, 3-(tetrahydro-1,4-thiazinyl)propyl, piperidinylmethyl, 2-(piperidinyl)ethyl, 3-(piperidinyl)propyl, homopiperidinylmethyl, piperazinylmethyl, 2-(piperazinyl)ethyl, 3-(piperazinyl)propyl or homopiperazinylmethyl, provided that, when $X^6$ is O, NH or N(Me), there are at least two carbon atoms between $X^6$ and any heteroatom in the $R^{15}$ group, and wherein any aryl, (3-8C)cycloalkyl, heteroaryl or heterocyclyl group within the $R^6$ group optionally bears 1 or 2 substituents, which may be the same or different, selected from fluoro, chloro, trifluoromethyl, hydroxy, amino, methyl, ethyl, methoxy, ethoxy, methylamino, dimethylamine, hydroxymethyl, 2-hydroxyethyl, 3-hydroxypropyl, aminomethyl, 2-aminoethyl, 3-aminopropyl, methylaminomethyl, 2-methylaminoethyl, 3-methylaminopropyl, dimethylaminomethyl, 2-dimethylaminoethyl and 3-dimethylaminopropyl, and any other $R^6$ group that is present is selected from fluoro, chloro, trifluoromethyl, cyano, hydroxy, amino, methyl, methoxy, methylamino and dimethylamino;

(xx) r is 1 or 2 and the first $R^6$ group is a group of the formula:

wherein $X^6$ is a direct bond or O and $R^{15}$ is hydroxymethyl, 1-hydroxyethyl, 2-hydroxyethyl, 3-hydroxypropyl, methoxymethyl, 1-methoxyethyl, 2-methoxyethyl, 1-methoxy-1-methylethyl, 3-methoxypropyl, cyanomethyl, 1-cyanoethyl, 2-cyanoethyl, 3-cyanopropyl, aminomethyl, 1-aminoethyl, 2-aminoethyl, 3-aminopropyl, methylaminomethyl, 1-methylaminoethyl, 2-methylaminoethyl, 3-methylaminopropyl, ethylaminomethyl, 1-ethylaminoethyl, 2-ethylaminoethyl, 1-ethylamino-1-methylethyl, 3-ethylaminopropyl, isopropylaminomethyl, 1-isopropylaminoethyl, dimethylaminomethyl, 1-dimethylaminoethyl, 2-dimethylaminoethyl, 3-dimethylaminopropyl, phenyl, benzyl, cyclopropyl, cyclopentyl, cyclohexyl, thienyl, imidazolyl, thiazolyl, thiadiazolyl, pyrrolidinyl, morpholinyl, tetrahydro-1,4-thiazinyl, piperidinyl, homopiperidinyl, piperazinyl, homopiperazinyl, pyrrolidinylmethyl, 2-(pyrrolidinyl)ethyl, 3-(pyrrolidinyl)propyl, morpholinylmethyl, 2-(morpholinyl)ethyl, 3-(morpholinyl)propyl, piperidinylmethyl, 2-(piperidinyl)ethyl, 3-(piperidinyl)propyl, homopiperidinylmethyl, piperazinylmethyl, 2-(piperazinyl)ethyl, 3-(piperazinyl)propyl or homopiperazinylmethyl, provided that, when $X^6$ is O, there are at least two carbon atoms between $X^6$ and any heteroatom in the $R^{15}$ group, and wherein any aryl, (3-8C)cycloalkyl, heteroaryl or heterocyclyl group within the $R^6$ group optionally bears a substituent selected from fluoro, chloro, trifluoromethyl, hydroxy, amino, methyl, methoxy, methylamino and dimethylamino and any such aryl, (3-8C)cycloalkyl, heteroaryl or heterocyclyl group within the $R^6$ group optionally bears a further substituent selected from hydroxymethyl, cyanomethyl, aminomethyl, methylaminomethyl and dimethylaminomethyl, and any second $R^6$ group that is present is selected from fluoro, chloro, trifluoromethyl, cyano, hydroxy, amino, methyl, methoxy, methylamino and dimethylamino;

(yy) r is 1 or 2 and the first $R^6$ group is selected from hydroxymethyl, 1-hydroxyethyl, 2-hydroxyethyl, methoxymethyl, 1-methoxyethyl, 2-methoxyethyl, cyanomethyl, 1-cyanoethyl, 2-cyanoethyl, aminomethyl, 1-aminoethyl, 2-aminoethyl, methylaminomethyl, 1-methylaminoethyl, 2-methylaminoethyl, ethylaminomethyl, 1-ethylaminoethyl, 2-ethylaminoethyl, isopropylaminomethyl, 1-isopropylaminoethyl, 2-isopropylaminoethyl, dimethylaminomethyl, 1-dimethylaminoethyl, 2-dimethylaminoethyl, phenyl, benzyl, cyclopropyl, cyclopentyl, cyclohexyl, thienyl, imidazolyl, thiazolyl, thiadiazolyl, pyrrolidinyl, morpholinyl, tetrahydro-1,4-thiazinyl, piperidinyl, homopiperidinyl, piperazinyl, homopiperazinyl, pyrrolidinylmethyl, 2-(pyrrolidinyl)ethyl, morpholinylmethyl, 2-(morpholinyl)ethyl, piperidinylmethyl, 2-(piperidinyl)ethyl, homopiperidinylmethyl, piperazinylmethyl, 2-(piperazinyl)ethyl and homopiperazinylmethyl, and wherein any aryl, (3-8C)cycloalkyl, heteroaryl or heterocyclyl group within the $R^6$ group optionally bears a substituent selected from fluoro, chloro, trifluoromethyl, hydroxy, amino, methyl, methoxy, methylamino and dimethylamino and any such aryl, (3-8C)cycloalkyl, heteroaryl or heterocyclyl group within the $R^6$ group optionally bears a further substituent selected from hydroxymethyl, cyanomethyl, aminomethyl, methylaminomethyl and dimethylaminomethyl, and any second $R^6$ group that is present is selected from fluoro, chloro, trifluoromethyl, cyano, hydroxy, amino, methyl, methoxy, methylamino and dimethylamino;

(zz) r is 1 or 2 and the first $R^6$ group is selected from fluoro, chloro, cyano, hydroxy, amino, methyl, ethyl, propyl, isopropyl, butyl, sec-butyl, isobutyl, tert-butyl, cyclopropyl, cyclobutyl, cyclopentyl, methoxy, ethoxy, methylamino, ethylamino, propylamino, isopropylamino, cyclopropylamino, 2-hydroxyethylamino, 2-methoxyethylamino, dimethylamino, N-cyclopropyl-N-methylamino, acetyl, hydroxymethyl, 1-hydroxyethyl, aminomethyl, methylaminomethyl, ethylaminomethyl, propylaminomethyl, isopropylaminomethyl, cyclopropylaminomethyl, 2-hydroxyethylaminomethyl, dimethylaminomethyl, diethylaminomethyl, N-ethyl-N-methylaminomethyl, cyclopropylaminomethyl, N-cyclopropyl-N-methylaminomethyl, furylmethylaminomethyl, pyrrolylmethylaminomethyl, pyridylmethylaminomethyl, phenyl, furyl, thienyl, imidazolyl, oxazolyl, thiazolyl, pyrrolidinyl, morpholinyl, piperidinyl, homopiperidinyl, piperazinyl, homopiperazinyl, azetidinylmethyl, pyrrolidinylmethyl, morpholinylmethyl, piperidinylmethyl, homopiperidinylmethyl, piperazinylmethyl and homopiperazinylmethyl, and wherein any aryl, (3-8C)cycloalkyl, heteroaryl or heterocyclyl group within the $R^6$ group optionally bears a substituent selected from fluoro, chloro, trifluoromethyl, hydroxy, amino, methyl, methoxy, methylamino, dimethylamino, hydroxymethyl, cyanomethyl, aminomethyl, methylaminomethyl and dimethylaminomethyl, and any second $R^6$ group that is present is selected from fluoro, chloro, trifluoromethyl, cyano, hydroxy, amino, methyl, methoxy, methylamino and dimethylamino;

(aaa) r is 1 and the $R^6$ group is selected from fluoro, chloro, trifluoromethyl, hydroxy, amino, methyl, ethyl, propyl, isopropyl, butyl, sec-butyl, isobutyl, tert-butyl, cyclopropyl, cyclobutyl, cyclopentyl, hydroxymethyl, 2-hydroxyethyl, methoxymethyl, 2-methoxyethyl, methylaminomethyl, ethylaminomethyl, isopropylaminomethyl, cyclopropylaminomethyl, dimethylaminomethyl, methoxy, ethoxy, methylamino, ethylamino, dimethylamino and diethylamino;

(bbb) two $R^6$ groups together form a bivalent group that spans adjacent ring positions on Ring A selected from $OC(R^{18})_2O$, $OC(R^{18})_2C(R^{18})_2O$, $OC(R^{18})_2C(R^{18})_2$, $C(R^{18})_2OC(R^{18})_2$, $C(R^{18})_2C(R^{18})_2C(R^{18})_2$, $C(R^{18})_2C(R^{18})_2C(R^{18})_2$, $OC(R^{18})_2N(R^{19})$, $N(R^{19})C(R^{18})_2$, $N(R^{19})$, $N(R^{19})C(R^{18})_2C(R^{18})_2$, $N(R^{19})C(R^{18})_2C(R^{18})_2C(R^{18})_2$ and $C(R^{18})_2N(R^{19})C(R^{18})_2$, wherein each of $R^{18}$ and $R^{19}$ is hydrogen, (1-8C)alkyl, (2-8C)alkenyl or (2-8C)alkynyl;

(ccc) two $R^6$ groups together form a bivalent group that spans adjacent ring positions on Ring A selected from $OC(R^{18})_2O$, $OC(R^{18})_2C(R^{18})_2O$, $C(R^{18})_2OC(R^{18})_2$, $OC(R^{18})_2N(R^{19})$, $N(R^{19})C(R^{18})_2N(R^{19})$, $N(R^{19})C(R^{18})_2C(R^{18})_2$, $N(R^{19})C(R^{18})_2C(R^{18})_2C(R^{18})_2$ and $C(R^{18})_2N(R^{19})C(R^{18})_2$, wherein each of $R^{18}$ and $R^{19}$ is hydrogen, methyl, ethyl or propyl;

(ddd) two $R^6$ groups together form a bivalent group that spans adjacent ring positions on Ring A selected from $OCH_2O$, $OCH_2CH_2O$, $OCH_2NH$, $NHCH_2CH_2$ and $NHCH_2CH_2CH_2$;

(eee) two $R^6$ groups together form a bivalent group that spans adjacent ring positions on Ring A selected from $OCH_2O$ and $OCH_2CH_2O$;

(fff) p is 0 or p is 1 or 2 and the $R^1$ groups are located at the 6- and/or 7-positions and are selected from halogeno, trifluoromethyl, cyano, hydroxy, amino, carbamoyl, (1-6C)alkoxycarbonyl, (1-8C)alkyl, (2-8C)alkenyl, (2-8C)alkynyl, (1-6C)alkoxy, (2-6C)alkenyloxy, (2-6C)alkynyloxy, (1-6C)alkylamino, di-[(1-6C)alkyl]amino, N-(1-6C)alkylcarbamoyl and N,N-di-[(1-6C)alkyl]carbamoyl, and q is 1 and the $R^2$ group is located at the 2-position (relative to the $C(R^3)(R^4)$ group) and is selected from halogeno, trifluoromethyl, cyano, carbamoyl, hydroxy, amino, (1-8C)alkyl, (2-8C)alkenyl, (2-8C)alkynyl, (1-6C)alkoxy, (1-6C)alkylamino, di-[(1-6C)alkyl]amino, N-(1-6C)alkylcarbamoyl and N,N-di-[(1-6C)alkyl]carbamoyl;

(ggg) p is 0 or p is 1 or 2 and the $R^1$ groups are located at the 6- and/or 7-positions and are selected from fluoro, chloro, trifluoromethyl, cyano, hydroxy, amino, carbamoyl, methoxycarbonyl, ethoxycarbonyl, methyl, ethyl, methoxy, ethoxy, methylamino, dimethylamino, N-methylcarbamoyl and N,N-dimethylcarbamoyl, and q is 1 and the $R^2$ group which is located at the 2-position (relative to the $C(R^3)(R^4)$ group) is selected from fluoro, chloro, trifluoromethyl, cyano, carbamoyl, hydroxy, amino, methyl, ethyl, methoxy, ethoxy, methylamino, dimethylamino, N-methylcarbamoyl and N,N-dimethylcarbamoyl;

(hhh) p is 0 or p is 1 or 2 and the $R^1$ groups are located at the 6- and/or 7-positions and are selected from fluoro, chloro, cyano, carbamoyl, methoxycarbonyl, methoxy, ethoxy, N-methylcarbamoyl and N,N-dimethylcarbamoyl, and q is 1 and the $R^2$ group which is located at the 2-position (relative to the $C(R^3)(R^4)$ group) is selected from carbamoyl, methoxy, ethoxy, N-methylcarbamoyl and N,N-dimethylcarbamoyl; and (iii) p is 0 or p is 1 or 2 and the $R^1$ groups are located at the 6- and/or 7-positions and are selected from fluoro, cyano, carbamoyl, methoxycarbonyl, methoxy, ethoxy, N-methylcarbamoyl and N,N-dimethylcarbamoyl, and q is 1 and the $R^2$ group which is located at the 2-position (relative to the $C(R^3)(R^4)$ group) is selected from methoxy and ethoxy.

A particular compound of the invention is a quinoline derivative of the Formula I wherein:—

$X^1$ is O;

p is 2 and the $R^1$ groups are located at the 6- and 7-positions and the $R^1$ group at the 6-position is selected from cyano, hydroxy, methoxycarbonyl, ethoxycarbonyl, carbamoyl, methoxy, ethoxy, propoxy, N-methylcarbamoyl, N-ethylcarbamoyl, N,N-dimethylcarbamoyl, N,N-diethylcarbamoyl, pyrrolidin-1-ylcarbonyl, morpholinocarbonyl, piperidinocarbonyl and piperazin-1-ylcarbonyl, and the $R^1$ group at the 7-position is selected from methoxy, ethoxy, propoxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-molpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 3-(1,2,3,6-tetrahydropyridin-1-yl)propoxy, 2-piperazin-1-ylethoxy, 3-piperazin-1-ylpropoxy, 2-homopiperazin-1-ylethoxy and 3-homopiperazin-1-ylpropoxy, and wherein any heterocyclyl group within a substituent on $R^1$ optionally bears 1 or 2 substituents, which may be the same or different, selected from fluoro, chloro, trifluoromethyl, hydroxy, amino, methyl, ethyl, methoxy, methylenedioxy, ethylidendioxy and isopropylidenedioxy, and a pyrrolidin-2-yl, pyrrolidin-3-yl, piperidin-3-yl, piperidin-4-yl, piperazin-1-yl or homopiperazin-1-yl group within a $R^1$ substituent is optionally N-substituted with methyl, ethyl, propyl, allyl, 2-propynyl, methylsulphonyl, acetyl, propionyl, isobutyryl, 2-fluoroethyl, 2,2-difluoroethyl, 2,2,2-trifluoroethyl or cyanomethyl, and wherein any heterocyclyl group within a substituent on $R^1$ optionally bears 1 or 2 oxo substituents, and wherein any CH, $CH_2$ or $CH_3$ group within a $R^1$ substituent optionally bears on each said CH, $CH_2$ or $CH_3$ group one or more chloro groups or a substituent selected from hydroxy, amino, methoxy, methylsulphonyl, methylamino, dimethylamino, diisopropylamino, N-ethyl-N-methylamino and N-isopropyl-N-dimethylamino;

q is 0 or q is 1 and the $R^2$ group which is located at the 2- or 3-position (relative to the $C(R^3)(R^4)$ group) is selected from fluoro, chloro, trifluoromethyl, cyano, hydroxy, amino, methyl, methoxy, methylamino and dimethylamino;

each of $R^3$ and $R^4$ is hydrogen;

$R^5$ is hydrogen, methyl or ethyl;

Ring A is a phenyl, pyridyl, pyrimidinyl, pyrazinyl or pyridazinyl ring; and r is 0 or r is 1 or 2 and one $R^6$ group is located at the 3- or 4-position (relative to the $CON(R^5)$ group), and each $R^6$ group, which may be the same or different, is selected from fluoro, chloro, trifluoromethyl, cyano, hydroxy, amino, methyl, methoxy, methylamino and dimethylamino, or r is 1 or 2 and one $R^6$ group is located at the 3- or 4-position (relative to the $CON(R^5)$ group) and is a group of the formula:

—$X^6$—$R^{15}$ wherein $X^6$ is a direct bond or O and $R^{15}$ is hydroxymethyl, 1-hydroxyethyl, 2-hydroxyethyl, 3-hydroxypropyl, methoxymethyl, 1-methoxyethyl, 2-methoxyethyl, 1-methoxy-1-methylethyl, 3-methoxypropyl, cyanomethyl, 1-cyanoethyl, 2-cyanoethyl, 3-cyanopropyl, aminomethyl, 1-aminoethyl, 2-aminoethyl, 3-aminopropyl, methylaminomethyl, 1-methylaminoethyl, 2-methylaminoethyl, 3-methylaminopropyl, ethylaminomethyl, 1-ethylaminoethyl, 2-ethylaminoethyl, 1-ethylamino-1-methylethyl, 3-ethylaminopropyl, isopropylaminomethyl, 1-isopropylaminoethyl, dimethylaminomethyl, 1-dimethylaminoethyl, 2-dimethylaminoethyl, 3-dimethylaminopropyl, phenyl, benzyl, cyclopropyl, cyclopentyl, cyclohexyl, thienyl, imidazolyl, thiazolyl, thiadiazolyl, pyrrolidinyl, morpholinyl, tetrahydro-1,4-thiazinyl, piperidinyl, homopiperidinyl, piperazinyl, homopiperazinyl, pyrrolidinylmethyl, 2-(pyrrolidinyl)ethyl, 3-(pyrrolidinyl)propyl, morpholinylmethyl, 2-(morpholinyl)ethyl, 3-(morpholinyl)propyl, piperidinylmethyl, 2-(piperidinyl)ethyl, 3-(piperidinyl)propyl, homopiperidinylmethyl, piperazinylmethyl, 2-(piperazinyl)ethyl, 3-(piperazinyl)propyl or homopiperazinylmethyl, provided that, when $X^6$ is O, there are at least two carbon atoms between $X^6$ and any heteroatom in the $R^{15}$ group, and wherein any aryl, (3-8C)cycloalkyl, heteroaryl or heterocyclyl group within the $R^6$ group optionally bears a substituent selected from fluoro, chloro, trifluoromethyl, hydroxy, amino, methyl, methoxy, methylamino and dimethylamino and any such aryl, (3-8C)cycloalkyl, heteroaryl or heterocyclyl group within the $R^6$ group optionally bears a further substituent selected from hydroxymethyl, cyanomethyl, aminomethyl, methylaminomethyl and dimethylaminomethyl, and any second $R^6$ group that is present is selected from fluoro, chloro, trifluoromethyl, cyano, hydroxy, amino, methyl, methoxy, methylamino and dimethylamino;

or a pharmaceutically-acceptable salt thereof.

A further particular compound of the invention is a quinoline derivative of the Formula I wherein:—

$X^1$ is O;

p is 2 and the first $R^1$ group is located at the 6-position and is selected from cyano, carbamoyl, methoxy, N-methylcarbamoyl and N,N-dimethylcarbamoyl, and the second $R^1$ group is located at the 7-position and is selected from methoxy, ethoxy, 2-methoxyethoxy, 3-methoxypropoxy, 2-methylsulphonylethoxy, 3-methylsulphonylpropoxy, 2-(2-methoxyethoxy)ethoxy, 2-pyrrolidin-1-ylethoxy, 3-pyrrolidin-1-ylpropoxy, 2-[(3RS,4SR)-3,4-methylenedioxypyrrolidin-1-yl]ethoxy, 3-[(3RS,4SR)-3,4-methylenedioxypyrrolidin-1-yl]propoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-(1,2,3,6-tetrahydropyridin-1-yl)ethoxy, 3-(1,2,3,6-tetrahydropyridin-1-yl)propoxy, 2-(4-hydroxypiperidin-1-yl)ethoxy, 3-(4-hydroxypiperidin-1-yl)propoxy, 2-piperazin-1-ylethoxy, 3-piperazin-1-ylpropoxy, 4-piperazin-1-ylbutoxy, 2-(4-methylpiperazin-1-yl)ethoxy, 3-(4-methylpiperazin-1-yl)propoxy, 4-(4-methylpiperazin-1-yl)butoxy, 2-(4-allylpiperazin-1-yl)ethoxy, 3-(4-allylpiperazin-1-yl)propoxy, 2-(4-prop-2-ynylpiperazin-1-yl)ethoxy, 3-(4-prop-2-ynylpiperazin-1-yl)propoxy, 2-(4-methylsulphonylpiperazin-1-yl)ethoxy, 3-(4-methylsulphonylpiperazin-1-yl)propoxy, 2-(4-acetylpiperazin-1-yl)ethoxy, 3-(4-acetylpiperazin-1-yl)propoxy, 4-(4-acetylpiperazin-1-yl)butoxy, 2-(4-isobutyrylpiperazin-1-yl)ethoxy, 3-(4-isobutyrylpiperazin-1-yl)propoxy, 4-(4-isobutyrylpiperazin-1-yl)butoxy, 2-[4-(2-fluoroethyl)piperazin-1-yl]ethoxy, 3-[4-(2-fluoroethyl)piperazin-1-yl]propoxy, 2-[4-(2,2,2-trifluoroethyl)piperazin-1-yl]ethoxy, 3-[4-(2,2,2-trifluoroethyl)piperazin-1-yl]propoxy, 2-(4-cyanomethylpiperazin-1-yl)ethoxy, 3-(4-cyanomethylpiperazin-1-yl)propoxy, 2-[2-(4-methylpiperazin-1-yl)ethoxy]ethoxy, 2-(4-pyridyloxy)ethoxy, 3-pyridylmethoxy and 2-cyanopyrid-4-ylmethoxy;

q is 0 or q is 1 and the $R^2$ group which is located at the 2-position (relative to the $C(R^3)(R^4)$ group) is selected from fluoro, chloro, cyano, methyl and methoxy;

each of $R^3$ and $R^4$ is hydrogen;

$R^5$ is hydrogen or methyl;

Ring A is a phenyl, pyridyl, pyrimidinyl, pyrazinyl or pyridazinyl ring; and r is 0 or r is 1 or 2 and one $R^6$ group is located at the 3- or 4-position (relative to the $CON(R^5)$ group), and each $R^6$ group, which may be the same or different, is selected from fluoro, chloro, trifluoromethyl, hydroxy, amino, methyl, methoxy, methylamino and dimethylamino, or r is 1 or 2 and one $R^6$ group is located at the 3- or 4-position (relative to the $CON(R^5)$ group) and is selected from hydroxymethyl, 1-hydroxyethyl, 2-hydroxyethyl, methoxymethyl, 1-methoxyethyl, 2-methoxyethyl, cyanomethyl, 1-cyanoethyl, 2-cyanoethyl, aminomethyl, 1-aminoethyl, 2-aminoethyl, methylaminomethyl, 1-methylaminoethyl, 2-methylaminoethyl, ethylaminomethyl, 1-ethylaminoethyl, 2-ethylaminoethyl, isopropylaminomethyl, 1-isopropylaminoethyl, 2-isopropylaminoethyl, dimethylaminomethyl, 1-dimethylaminoethyl, 2-dimethylaminoethyl, pyrrolidinylmethyl, morpholinylmethyl, piperidinylmethyl and piperazinylmethyl, and wherein any heterocyclyl group within the $R^6$ group optionally bears a substituent selected from fluoro, chloro, trifluoromethyl, hydroxy, amino, methyl, methoxy, methylamino and dimethylamino, and any second $R^6$ group that is present is selected from fluoro, chloro, trifluoromethyl, cyano, hydroxy, amino, methyl, methoxy, methylamino and dimethylamino;

or a pharmaceutically-acceptable salt thereof.

A further particular compound of the invention is a quinoline derivative of the Formula I wherein:—

$X^1$ is O;

p is 2 and the $R^1$ groups, which may be the same or different, are located at the 6- and 7-positions and are selected from cyano, methoxy, ethoxy, propoxy, 2-hydroxyethoxy, 3-hydroxypropoxy, 2-methoxyethoxy, 3-methoxypropoxy, 2-methylsulphonylethoxy, 3-methylsulphonylpropoxy and 2-(2-methoxyethoxy)ethoxy;

q is 0 or q is 1 and the $R^2$ group is fluoro, chloro, methyl or methoxy;

each of $R^3$ and $R^4$ is hydrogen;

$R^5$ is hydrogen, methyl or ethyl;

Ring A is phenyl; and r is 1 or 2 and the first $R^6$ group is located at the 3-position (relative to the $CON(R^5)$ group) and is selected from fluoro, chloro, methoxy, ethoxy, methylamino, ethylamino, dimethylamino, cyclopropylamino, N-cyclopropyl-N-methylamino, hydroxymethyl, aminomethyl, methylaminomethyl, ethylaminomethyl, isopropylaminomethyl, cyclopropylaminomethyl, dimethylaminomethyl, diethylaminomethyl, N-ethyl-N-methylaminomethyl, N-cyclopropyl-N-methylaminomethyl, azetidinylmethyl, pyrrolidinylmethyl, morpholinylmethyl, piperidinylmethyl, homopiperidinylmethyl, piperazinylmethyl and homopiperazinylmethyl, and any second $R^6$ group that is present is selected from fluoro, chloro, methyl, ethyl, methoxy and ethoxy, and wherein any heterocyclyl group within the $R^6$ group optionally bears a methyl, ethyl or hydroxymethyl substituent;
or a pharmaceutically-acceptable salt thereof.

A further particular compound of the invention is a quinoline derivative of the Formula I wherein:—
$X^1$ is O;
p is 2 and the first $R^1$ group is a 6-cyano or 6-methoxy group and the second $R^1$ group is located at the 7-position and is selected from methoxy, ethoxy, 2-hydroxyethoxy and 2-methoxyethoxy;
q is 0 or q is 1 and the $R^2$ group is fluoro;
each of $R^3$ and $R^4$ is hydrogen;
$R^5$ is hydrogen, methyl or ethyl;
Ring A is phenyl; and
r is 1 or 2 and the first $R^6$ group is located at the 3-position (relative to the CON($R^5$) group) and is selected from fluoro, chloro, methoxy, methylamino, ethylamino, dimethylamino, cyclopropylamino, hydroxymethyl, aminomethyl, methylaminomethyl, ethylaminomethyl, propylaminomethyl, isopropylaminomethyl, cyclopropylaminomethyl, dimethylaminomethyl, diethylaminomethyl, N-ethyl-N-methylaminomethyl, N-cyclopropyl-N-methylaminomethyl, azetidin-1-ylmethyl, pyrrolidin-1-ylmethyl, morpholinomethyl, piperidinomethyl and piperazin-1-ylmethyl,
and any second $R^6$ group that is present is selected from fluoro, chloro, methyl, ethyl, methoxy and ethoxy,
and wherein any heterocyclyl group within the $R^6$ group optionally bears a methyl, ethyl or hydroxymethyl substituent;
or a pharmaceutically-acceptable salt, solvate or pro-drug thereof.

A further particular compound of the invention is a quinoline derivative of the Formula I wherein:—
$X^1$ is O;
p is 2 and the $R^1$ groups, which may be the same or different, are located at the 6- and 7-positions and are selected from cyano, methoxy, ethoxy, propoxy, 2-hydroxyethoxy, 3-hydroxypropoxy, 2-methoxyethoxy, 3-methoxypropoxy, 2-methylsulphonylethoxy, 3-methylsulphonylpropoxy and 2-(2-methoxyethoxy)ethoxy;
q is 0 or q is 1 and the $R^2$ group is fluoro, chloro, methyl or methoxy;
each of $R^3$ and $R^4$ is hydrogen;
$R^5$ is hydrogen, methyl or ethyl;
Ring A is pyridyl, pyrimidinyl, pyrazinyl or pyridazinyl; and
r is 0, 1 or 2 and each $R^6$ group that is present is selected from fluoro, chloro, trifluoromethyl, cyano, methyl, ethyl, propyl, isopropyl, tert-butyl, cyclopropyl, cyclobutyl, cyclopentyl, methoxy, ethoxy, methylamino, ethylamino, propylamino, isopropylamino, cyclopropylamino, 2-hydroxyethylamino, 2-methoxyethylamino, dimethylamino, N-cyclopropyl-N-methylamino, acetyl, hydroxymethyl, aminomethyl, methylaminomethyl, ethylaminomethyl, propylaminomethyl, isopropylaminomethyl, cyclopropylaminomethyl, dimethylaminomethyl, diethylaminomethyl, N-ethyl-N-methylaminomethyl, N-cyclopropyl-N-methylaminomethyl, pyrrolidin-1-yl, piperidino, morpholino, piperazin-1-yl, pyrrolidin-1-ylmethyl, morpholinomethyl, piperidinomethyl and piperazin-1-ylmethyl,
and wherein any heterocyclyl group within the $R^6$ group optionally bears a methyl or ethyl substituent;
or a pharmaceutically-acceptable salt thereof.

A further particular compound of the invention is a quinoline derivative of the Formula I wherein:—
$X^1$ is O;
p is 2 and the first $R^1$ group is a 6-cyano or 6-methoxy group and the second $R^1$ group is located at the 7-position and is selected from methoxy, ethoxy, 2-hydroxyethoxy and 2-methoxyethoxy;
q is 0 or q is 1 and the $R^2$ group is fluoro, chloro, methyl or methoxy;
each of $R^3$ and $R^4$ is hydrogen;
$R^5$ is hydrogen, methyl or ethyl;
Ring A is 2-pyridyl, 3-pyridyl, 4-pyridyl, 2-pyrimidinyl, 4-pyrimidinyl, 5-pyrimidinyl, 2-pyrazinyl, 3-pyridazinyl or 4-pyridazinyl; and
r is 0 or r is 1 or 2 and any first $R^6$ group that is present is selected from methylamino, ethylamino, propylamino, isopropylamino, cyclopropylamino, 2-hydroxyethylamino, 2-methoxyethylamino, dimethylamino, N-cyclopropyl-N-methylamino, pyrrolidin-1-yl, piperidino, morpholino and piperazin-1-yl, and any second $R^6$ group that is present is selected from fluoro, chloro, methyl, ethyl, methoxy and ethoxy,
and wherein any heterocyclyl group within the $R^6$ group optionally bears a methyl or ethyl substituent;
or a pharmaceutically-acceptable salt thereof.

A particular compound of the invention is a quinoline derivative of the Formula I wherein:—
$X^1$ is O;
p is 2 and the $R^1$ groups are located at the 6- and 7-positions and the $R^1$ group at the 6-position is selected from cyano, hydroxy, methoxycarbonyl, ethoxycarbonyl, carbamoyl, methoxy, ethoxy, propoxy, N-methylcarbamoyl, N-ethylcarbamoyl, N,N-dimethylcarbamoyl, N,N-diethylcarbamoyl, pyrrolidin-1-ylcarbonyl, morpholinocarbonyl, piperidinocarbonyl and piperazin-1-ylcarbonyl, and the $R^1$ group at the 7-position is selected from methoxy, ethoxy, propoxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 3-(1,2,3,6-tetrahydropyridin-1-yl)propoxy, 2-piperazin-1-ylethoxy, 3-piperazin-1-ylpropoxy, 2-homopiperazin-1-ylethoxy and 3-homopiperazin-1-ylpropoxy,
and wherein any heterocyclyl group within a substituent on $R^1$ optionally bears 1 or 2 substituents, which may be the same or different, selected from fluoro, chloro, trifluoromethyl, hydroxy, amino, methyl, ethyl, methoxy, methylenedioxy, ethylidendioxy and isopropylidenedioxy, and a pyrrolidin-2-yl, pyrrolidin-3-yl, piperidin-3-yl, piperidin-4-yl, piperazin-1-yl or homopiperazin-1-yl group within a $R^1$ substituent is optionally N-substituted with methyl, ethyl, propyl, allyl, 2-propynyl, methylsulphonyl, acetyl, propionyl, isobutyryl, 2-fluoroethyl, 2,2-difluoroethyl, 2,2,2-trifluoroethyl or cyanomethyl,
and wherein any heterocyclyl group within a substituent on $R^1$ optionally bears 1 or 2 oxo substituents,
and wherein any CH, $CH_2$ or $CH_3$ group within a $R^1$ substituent optionally bears on each said CH, $CH_2$ or $CH_3$ group one or more chloro groups or a substituent selected from hydroxy, amino, methoxy, methylsulphonyl, methylamino, dimethylamino, diisopropylamino, N-ethyl-N-methylamino and N-isopropyl-N-methylamino;

q is 0 or q is 1 and the $R^2$ group is selected from fluoro, chloro, trifluoromethyl, cyano, hydroxy, amino, methyl, methoxy, methylamino and dimethylamino;

each of $R^3$ and $R^4$ is hydrogen;

$R^5$ is hydrogen, methyl or ethyl;

Ring A is a furyl, pyrrolyl, thienyl, oxazolyl, isoxazolyl, imidazolyl, pyrazolyl, thiazolyl, isothiazolyl, oxadiazolyl or thiadiazolyl ring; and r is 0 or r is 1 or 2 and one $R^6$ group is located at the 3-position (relative to the CON($R^5$) group), and each $R^6$ group, which may be the same or different, is selected from fluoro, chloro, trifluoromethyl, cyano, hydroxy, amino, methyl, ethyl, propyl, isopropyl, butyl, sec-butyl, isobutyl, tert-butyl, methoxy, ethoxy, methylamino, ethylamino, dimethylamino and diethylamino, or r is 1 or 2 and one $R^6$ group is located at the 3-position (relative to the CON($R^5$) group) and is a group of the formula:

—$X^6$—$R^{15}$ wherein $X^6$ is a direct bond or O and $R^{15}$ is hydroxymethyl, 1-hydroxyethyl, 2-hydroxyethyl, 3-hydroxypropyl, methoxymethyl, 1-methoxyethyl, 2-methoxyethyl, 1-methoxy-1-methylethyl, 3-methoxypropyl, cyanomethyl, 1-cyanoethyl, 2-cyanoethyl, 3-cyanopropyl, aminomethyl, 1-aminoethyl, 2-aminoethyl, 3-aminopropyl, methylaminomethyl, 1-methylaminoethyl, 2-methylaminoethyl, 3-methylaminopropyl, ethylaminomethyl, 1-ethylaminoethyl, 2-ethylaminoethyl, 1-ethylamino-1-methylethyl, 3-ethylaminopropyl, isopropylaminomethyl, 1-isopropylaminoethyl, dimethylaminomethyl, 1-dimethylaminoethyl, 2-dimethylaminoethyl, 3-dimethylaminopropyl, phenyl, benzyl, cyclopropyl, cyclopentyl, cyclohexyl, thienyl, imidazolyl, thiazolyl, thiadiazolyl, pyrrolidinyl, morpholinyl, tetrahydro-1,4-thiazinyl, piperidinyl, homopiperidinyl, piperazinyl, homopiperazinyl, pyrrolidinylmethyl, 2-(pyrrolidinyl)ethyl, 3-(pyrrolidinyl)propyl, morpholinylmethyl, 2-(morpholinyl)ethyl, 3-(morpholinyl)propyl, piperidinylmethyl, 2-(piperidinyl)ethyl, 3-(piperidinyl)propyl, homopiperidinylmethyl, piperazinylmethyl, 2-(piperazinyl)ethyl, 3-(piperazinyl)propyl or homopiperazinylmethyl, provided that, when $X^6$ is O, there are at least two carbon atoms between $X^6$ and any heteroatom in the $R^{15}$ group, and wherein any aryl, (3-8C)cycloalkyl, heteroaryl or heterocyclyl group within the $R^6$ group optionally bears a substituent selected from fluoro, chloro, trifluoromethyl, hydroxy, amino, methyl, methoxy, methylamino and dimethylamino and any such aryl, (3-8C)cycloalkyl, heteroaryl or heterocyclyl group within the $R^6$ group optionally bears a further substituent selected from hydroxymethyl, cyanomethyl, aminomethyl, methylaminomethyl and dimethylaminomethyl, and any second $R^6$ group that is present is selected from fluoro, chloro, trifluoromethyl, cyano, hydroxy, amino, methyl, methoxy, methylamino and dimethylamino;

or a pharmaceutically-acceptable salt thereof.

A further particular compound of the invention is a quinoline derivative of the Formula I wherein:—

$X^1$ is O;

p is 2 and the first $R^1$ group is located at the 6-position and is selected from cyano, carbamoyl, methoxy, N-methylcarbamoyl and N,N-dimethylcarbamoyl, and the second $R^1$ group is located at the 7-position and is selected from methoxy, ethoxy, 2-methoxyethoxy, 3-methoxypropoxy, 2-methylsulphonylethoxy, 3-methylsulphonylpropoxy, 2-(2-methoxyethoxy)ethoxy, 2-pyrrolidin-1-ylethoxy, 3-pyrrolidin-1-ylpropoxy, 2-[(3RS,4SR)-3,4-methylenedioxypyrrolidin-1-yl]ethoxy, 3-[(3RS,4SR)-3,4-methylenedioxypyrrolidin-1-yl]propoxy, 2-molpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-piperidin-3-ylethoxy, 2-(N-methylpiperidin-3-yl)ethoxy, 3-piperidin-3-ylpropoxy, 3-(N-methylpiperidin-3-yl)propoxy, 2-piperidin-4-ylethoxy, 2-(N-methylpiperidin-4-yl)ethoxy, 3-piperidin-4-ylpropoxy, 3-(N-methylpiperidin-4-yl)propoxy, 2-(1,2,3,6-tetrahydropyridin-1-yl)ethoxy, 3-(1,2,3,6-tetrahydropyridin-1-yl)propoxy, 2-(4-hydroxypiperidin-1-yl)ethoxy, 3-(4-hydroxypiperidin-1-yl)propoxy, 2-piperazin-1-ylethoxy, 3-piperazin-1-ylpropoxy, 4-piperazin-1-ylbutoxy, 2-(4-methylpiperazin-1-yl)ethoxy, 3-(4-methylpiperazin-1-yl)propoxy, 4-(4-methylpiperazin-1-yl)butoxy, 2-(4-allylpiperazin-1-yl)ethoxy, 3-(4-allylpiperazin-1-yl)propoxy, 2-(4-prop-2-ynylpiperazin-1-yl)ethoxy, 3-(4-prop-2-ynylpiperazin-1-yl)propoxy, 2-(4-methylsulphonylpiperazin-1-yl)ethoxy, 3-(4-methylsulphonylpiperazin-1-yl)propoxy, 2-(4-acetylpiperazin-1-yl)ethoxy, 3-(4-acetylpiperazin-1-yl)propoxy, 4-(4-acetylpiperazin-1-yl)butoxy, 2-(4-isobutyrylpiperazin-1-yl)ethoxy, 3-(4-isobutyrylpiperazin-1-yl)propoxy, 4-(4-isobutyrylpiperazin-1-yl)butoxy, 2-[4-(2-fluoroethyl)piperazin-1-yl]ethoxy, 3-[4-(2-fluoroethyl)piperazin-1-yl]propoxy, 2-[4-(2,2,2-trifluoroethyl)piperazin-1-yl]ethoxy, 3-[4-(2,2,2-trifluoroethyl)piperazin-1-yl]propoxy, 2-(4-cyanomethylpiperazin-1-yl)ethoxy, 3-(4-cyanomethylpiperazin-1-yl)propoxy, 2-[2-(4-methylpiperazin-1-yl)ethoxy]ethoxy, 2-(4-pyridyloxy)ethoxy, 3-pyridylmethoxy and 2-cyanopyrid-4-ylmethoxy;

q is 0 or q is 1 and the $R^2$ group which is located at the 2-position (relative to the C($R^3$)($R^4$) group) is selected from fluoro, chloro, cyano, methyl and methoxy;

each of $R^3$ and $R^4$ is hydrogen;

$R^5$ is hydrogen or methyl;

Ring A is an oxazolyl, isoxazolyl, imidazolyl, pyrazolyl, thiazolyl, isothiazolyl, oxadiazolyl or thiadiazolyl ring; and r is 0 or r is 1 or 2 and one $R^6$ group is located at the 3-position (relative to the CON($R^5$) group), and each $R^6$ group, which may be the same or different, is selected from fluoro, chloro, trifluoromethyl, hydroxy, amino, methyl, ethyl, propyl, isopropyl, butyl, sec-butyl, isobutyl, tert-butyl, cyclopropyl, cyclobutyl, cyclopentyl, methoxy, ethoxy, methylamino, ethylamino, dimethylamino and diethylamino, or r is 1 or 2 and one $R^6$ group is located at the 3-position (relative to the CON($R^5$) group) and is selected from hydroxymethyl, 1-hydroxyethyl, 2-hydroxyethyl, methoxymethyl, 1-methoxyethyl, 2-methoxyethyl, cyanomethyl, 1-cyanoethyl, 2-cyanoethyl, aminomethyl, 1-aminoethyl, 2-aminoethyl, methylaminomethyl, 1-methylaminoethyl, 2-methylaminoethyl, ethylaminomethyl, 1-ethylaminoethyl, 2-ethylaminoethyl, isopropylaminomethyl, 1-isopropylaminoethyl, 2-isopropylaminoethyl, dimethylaminomethyl, 1-dimethylaminoethyl, 2-dimethylaminoethyl, pyrrolidinylmethyl, morpholinylmethyl, piperidinylmethyl and piperazinylmethyl, and wherein any heterocyclyl group within the $R^6$ group optionally bears a substituent selected from fluoro, chloro, trifluoromethyl, hydroxy, amino, methyl, methoxy, methylamino and dimethylamino, and any second $R^6$ group that is present is selected from fluoro, chloro, trifluoromethyl, cyano, hydroxy, amino, methyl, methoxy, methylamino and dimethylamino;

or a pharmaceutically-acceptable salt thereof.

A further particular compound of the invention is a quinoline derivative of the Formula I wherein:—

$X^1$ is O;

p is 2 and the first $R^1$ group is located at the 6-position and is selected from cyano, carbamoyl, methoxy, N-methylcarbamoyl and N,N-dimethylcarbamoyl, and the second $R^1$ group is located at the 7-position and is selected from methoxy, ethoxy, propoxy, 2-hydroxyethoxy, 3-hydroxypropoxy, 2-methoxyethoxy, 3-methoxypropoxy, 2-methylsulphonylethoxy, 3-methylsulphonylpropoxy and 2-(2-methoxyethoxy)ethoxy;

q is 0 or q is 1 and the $R^2$ group which is located at the 2-position (relative to the $C(R^3)(R^4)$ group) is selected from fluoro, chloro, cyano, methyl and methoxy;

each of $R^3$ and $R^4$ is hydrogen;

$R^5$ is hydrogen or methyl;

Ring A is selected from oxazolyl, isoxazolyl, imidazolyl, pyrazolyl, thiazolyl, isothiazolyl, oxadiazolyl and thiadiazolyl; and r is 0, 1 or 2 and each $R^6$ group that is present is selected from fluoro, chloro, trifluoromethyl, hydroxy, amino, methyl, ethyl, propyl, isopropyl, butyl, sec-butyl, isobutyl, tert-butyl, cyclopropyl, cyclobutyl, cyclopentyl, hydroxymethyl, 2-hydroxyethyl, methoxymethyl, 2-methoxyethyl, methylaminomethyl, ethylaminomethyl, isopropylaminomethyl, cyclopropylaminomethyl, dimethylaminomethyl, methoxy, ethoxy, methylamino, ethylamino, dimethylamino and diethylamino;

or a pharmaceutically-acceptable salt thereof.

A further particular compound of the invention is a quinoline derivative of the Formula I wherein:—

$X^1$ is O;

p is 2 and the first $R^1$ group is located at the 6-position and is selected from cyano, carbamoyl, methoxy, N-methylcarbamoyl and N,N-dimethylcarbamoyl, and the second $R^1$ group is located at the 7-position and is selected from methoxy, ethoxy, 2-hydroxyethoxy and 2-methoxyethoxy;

q is 0 or q is 1 and the $R^2$ group which is located at the 2-position (relative to the $C(R^3)(R^4)$ group) is selected from fluoro, chloro, cyano, methyl and methoxy;

each of $R^3$ and $R^4$ is hydrogen;

$R^5$ is hydrogen or methyl;

Ring A is 2-oxazolyl, 3-isoxazolyl, 5-isoxazolyl, 2-imidazolyl, 3-pyrazolyl, 4-pyrazolyl, 2-thiazolyl, 3-isothiazolyl, 5-isothiazolyl, 1,2,4-oxadiazol-5-yl and 1,3,4-oxadiazol-5-yl; and r is 1 or 2 and each $R^6$ group that is present is selected from methyl, ethyl, propyl, isopropyl, tert-butyl, cyclopropyl, hydroxymethyl, 2-hydroxyethyl, methoxymethyl, 2-methoxyethyl, methylaminomethyl, ethylaminomethyl, isopropylaminomethyl, cyclopropylaminomethyl, dimethylaminomethyl, amino, methylamino, ethylamino, dimethylamino and diethylamino;

or a pharmaceutically-acceptable salt thereof.

In general, compounds falling within the following compound definitions of the present invention possess substantially better potency against the PDGF receptor family of tyrosine kinases, particularly against the PDGFβ receptor tyrosine kinase than against VEGF receptor tyrosine kinases such as KDR.

A particular novel compound of this aspect of the invention is a quinoline derivative of the Formula I, or a pharmaceutically-acceptable salt thereof, wherein:— p is 0 or p is 1 or 2 and the $R^1$ groups are located at the 6- and/or 7-positions and are selected from halogeno, trifluoromethyl, cyano, hydroxy, amino, carbamoyl, (1-6C)alkoxycarbonyl, (1-8C)alkyl, (2-8C)alkenyl, (2-8C)alkynyl, (1-6C)alkoxy, (2-6C)alkenyloxy, (2-6C)alkynyloxy, (1-6C)alkylamino, di-[(1-6C)alkyl]amino, N-(1-6C)alkylcarbamoyl and N,N-di-[(1-6C)alkyl]carbamoyl, and q is 1 and the $R^2$ group is located at the 2-position (relative to the $C(R^3)(R^4)$ group) and is selected from halogeno, trifluoromethyl, cyano, carbamoyl, hydroxy, amino, (1-8C)alkyl, (2-8C)alkenyl, (2-8C)alkynyl, (1-6C)alkoxy, (1-6C)alkylamino, di-[(1-6C)alkyl]amino, N-(1-6C)alkylcarbamoyl and N,N-di-[(1-6C)alkyl]carbamoyl;

and each of $X^1$, $R^3$, $R^4$, $R^5$, Ring A, r and $R^6$ has any of the meanings defined hereinbefore.

A further particular novel compound of this aspect of the invention is a quinoline derivative of the Formula I, or a pharmaceutically-acceptable salt thereof, wherein:— p is 0 or p is 1 or 2 and the $R^1$ groups are located at the 6- and/or 7-positions and are selected from fluoro, chloro, trifluoromethyl, cyano, hydroxy, amino, carbamoyl, methoxycarbonyl, ethoxycarbonyl, methyl, ethyl, methoxy, ethoxy, methylamino, dimethylamino, N-methylcarbamoyl and N,N-dimethylcarbamoyl, and q is 1 and the $R^2$ group which is located at the 2-position (relative to the $C(R^3)(R^4)$ group) is selected from fluoro, chloro, trifluoromethyl, cyano, carbamoyl, hydroxy, amino, methyl, ethyl, methoxy, ethoxy, methylamino, dimethylamino, N-methylcarbamoyl and N,N-dimethylcarbamoyl;

and each of $X^1$, $R^3$, $R^4$, $R^5$, Ring A, r and $R^6$ has any of the meanings defined hereinbefore.

A further particular novel compound of this aspect of the invention is a quinoline derivative of the Formula I, or a pharmaceutically-acceptable salt thereof, wherein:— p is 0 or p is 1 or 2 and the $R^1$ groups are located at the 6- and/or 7-positions and are selected from fluoro, chloro, cyano, carbamoyl, methoxycarbonyl, methoxy, ethoxy, N-methylcarbamoyl and N,N-dimethylcarbamoyl, and q is 1 and the $R^2$ group which is located at the 2-position (relative to the $C(R^3)(R^4)$ group) is selected from carbamoyl, methoxy, ethoxy, N-methylcarbamoyl and N,N-dimethylcarbamoyl;

and each of $X^1$, $R^3$, $R^4$, $R^5$, Ring A, r and $R^6$ has any of the meanings defined hereinbefore.

A further particular novel compound of this aspect of the invention is a quinoline derivative of the Formula I, or a pharmaceutically-acceptable salt thereof, wherein:— p is 0 or p is 1 or 2 and the $R^1$ groups are located at the 6- and/or 7-positions and are selected from fluoro, cyano, carbamoyl, methoxycarbonyl, methoxy, ethoxy, N-methylcarbamoyl and N,N-dimethylcarbamoyl, and q is 1 and the $R^2$ group which is located at the 2-position (relative to the $C(R^3)(R^4)$ group) is selected from methoxy and ethoxy;

and each of $X^1$, $R^3$, $R^4$, $R^5$, Ring A, r and $R^6$ has any of the meanings defined hereinbefore.

A further particular compound of this aspect of the invention is a quinoline derivative of the Formula I wherein:—

$X^1$ is O;

p is 0 or p is 1 or 2 and the $R^1$ groups are located at the 6- and/or 7-positions and are selected from halogeno, trifluoromethyl, cyano, hydroxy, amino, carbamoyl, (1-6C)alkoxycarbonyl, (1-8C)alkyl, (2-8C)alkenyl, (2-8C)alkynyl, (1-6C)alkoxy, (2-6C)alkenyloxy, (2-6C)alkynyloxy, (1-6C)alkylamino, di-[(1-6C)alkyl]amino, N-(1-6C)alkylcarbamoyl and N,N-di-[(1-6C)alkyl]carbamoyl, q is 1 and the $R^2$ group is located at the 2-position (relative to the $C(R^3)(R^4)$ group) and is selected from halogeno, trifluoromethyl, cyano, carbamoyl, hydroxy, amino, (1-8C)alkyl, (2-8C)alkenyl, (2-8C)alkynyl, (1-6C)alkoxy, (1-6C)

alkylamino, di-[(1-6C)alkyl]amino, N-(1-6C)alkylcarbamoyl and N,N-di-[(1-6C)alkyl]carbamoyl;

each of $R^3$ and $R^4$ is hydrogen;

$R^5$ is hydrogen;

Ring A is a 5-membered monocyclic heteroaryl ring with up to three ring heteroatoms selected from oxygen, nitrogen and sulphur; and r is 0, 1, 2 or 3 and each $R^6$ group that is present, which may be the same or different, is selected from halogeno, trifluoromethyl, cyano, hydroxy, amino, (1-8C)alkyl, (2-8C)alkenyl, (2-8C)alkynyl, (1-6C)alkoxy, (1-6C)alkylamino, di-[(1-6C)alkyl]amino, (2-6C)alkanoylamino and N-(1-6C)alkyl-(2-6C)alkanoylamino;

or a pharmaceutically-acceptable salt thereof.

A further particular compound of this aspect of the invention is a quinoline derivative of the Formula I wherein:—

$X^1$ is O;

p is 0 or p is 1 or 2 and the $R^1$ groups are located at the 6- and/or 7-positions and are selected from fluoro, chloro, trifluoromethyl, cyano, hydroxy, amino, carbamoyl, methoxycarbonyl, ethoxycarbonyl, methyl, ethyl, methoxy, ethoxy, methylamino, dimethylamino, N-methylcarbamoyl and N,N-dimethylcarbamoyl, q is 1 and the $R^2$ group which is located at the 2-position (relative to the $C(R^3)(R^4)$ group) is selected from fluoro, chloro, trifluoromethyl, cyano, carbamoyl, hydroxy, amino, methyl, ethyl, methoxy, ethoxy, methylamino, dimethylamino, N-methylcarbamoyl and N,N-dimethylcarbamoyl;

each of $R^3$ and $R^4$ is hydrogen;

$R^5$ is hydrogen;

Ring A is a furyl, pyrrolyl, thienyl, oxazolyl, isoxazolyl, imidazolyl, pyrazolyl, thiazolyl, isothiazolyl, oxadiazolyl or thiadiazolyl ring; and r is 1 or 2 and each $R^6$ group, which may be the same or different, is selected from fluoro, chloro, trifluoromethyl, cyano, hydroxy, amino, methyl, ethyl, propyl, isopropyl, butyl, sec-butyl, isobutyl, tert-butyl, methoxy, ethoxy, methylamino, ethylamino, dimethylamino and diethylamino;

or a pharmaceutically-acceptable salt thereof.

A further particular compound of this aspect of the invention is a quinoline derivative of the Formula I wherein:—

$X^1$ is O;

p is 0 or p is 1 or 2 and the $R^1$ groups are located at the 6- and/or 7-positions and are selected from fluoro, chloro, cyano, carbamoyl, methoxycarbonyl, methoxy, ethoxy, N-methylcarbamoyl and N,N-dimethylcarbamoyl, q is 1 and the $R^2$ group which is located at the 2-position (relative to the $C(R^3)(R^4)$ group) is selected from carbamoyl, methoxy, ethoxy, N-methylcarbamoyl and N,N-dimethylcarbamoyl;

each of $R^3$ and $R^4$ is hydrogen;

$R^5$ is hydrogen;

Ring A is a furyl, pyrrolyl, thienyl, oxazolyl, isoxazolyl, imidazolyl, pyrazolyl, thiazolyl, isothiazolyl, oxadiazolyl or thiadiazolyl ring that bears one or two $R^6$ groups and one $R^6$ group is located at the 3-position (relative to the $CON(R^5)$ group); and r is 1 or 2 and each $R^6$ group, which may be the same or different, is selected from fluoro, chloro, trifluoromethyl, cyano, hydroxy, amino, methyl, ethyl, propyl, isopropyl, butyl, sec-butyl, isobutyl, tert-butyl, methoxy, ethoxy, methylamino, ethylamino, dimethylamino and diethylamino;

or a pharmaceutically-acceptable salt thereof.

A further particular compound of this aspect of the invention is a quinoline derivative of the Formula I wherein:—

$X^1$ is O;

p is 0 or p is 1 or 2 and the $R^1$ groups are located at the 6- and/or 7-positions and are selected from fluoro, cyano, carbamoyl, methoxycarbonyl, methoxy, ethoxy, N-methylcarbamoyl and N,N-dimethylcarbamoyl, q is 1 and the $R^2$ group which is located at the 2-position (relative to the $C(R^3)(R^4)$ group) is selected from methoxy and ethoxy;

each of $R^3$ and $R^4$ is hydrogen;

$R^5$ is hydrogen;

Ring A is a furyl, pyrrolyl, thienyl, oxazolyl, isoxazolyl, imidazolyl, pyrazolyl, thiazolyl, isothiazolyl, oxadiazolyl or thiadiazolyl ring that bears one or two $R^6$ groups and one $R^6$ group is located at the 3-position (relative to the $CON(R^5)$ group); and r is 1 or 2 and each $R^6$ group, which may be the same or different, is selected from fluoro, chloro, trifluoromethyl, cyano, hydroxy, amino, methyl, ethyl, propyl, isopropyl, butyl, sec-butyl, isobutyl, tert-butyl, methoxy, ethoxy, methylamino, ethylamino, dimethylamino and diethylamino;

or a pharmaceutically-acceptable salt thereof.

A particular compound of this aspect of the invention is a quinoline derivative of the Formula I wherein: —

$X^1$ is O;

p is 0 or p is 1 or 2 and the $R^1$ groups are located at the 6- and/or 7-positions and are selected from fluoro, cyano, carbamoyl, methoxycarbonyl, methoxy, ethoxy, N-methylcarbamoyl and N,N-dimethylcarbamoyl, q is 1 and the $R^2$ group which is located at the 2-position (relative to the $C(R^3)(R^4)$ group) is selected from methoxy and ethoxy;

each of $R^3$ and $R^4$ is hydrogen;

$R^5$ is hydrogen;

Ring A is 2-oxazolyl, 3-isoxazolyl, 5-isoxazolyl, 2-imidazolyl, 3-pyrazolyl, 4-pyrazolyl, 2-thiazolyl, 3-isothiazolyl, 5-isothiazolyl, 1,2,4-oxadiazol-5-yl and 1,3,4-oxadiazol-5-yl; and r is 1 or 2 and each $R^6$ group that is present is selected from methyl, ethyl, propyl, isopropyl, tert-butyl, cyclopropyl, hydroxymethyl, 2-hydroxyethyl, methoxymethyl, 2-methoxyethyl, methylaminomethyl, ethylaminomethyl, isopropylaminomethyl, cyclopropylaminomethyl, dimethylaminomethyl, amino, methylamino, ethylamino, dimethylamino and diethylamino;

or a pharmaceutically-acceptable salt thereof.

A further particular compound of this aspect of the invention is a quinoline derivative of the Formula I wherein:—

$X^1$ is O;

p is 0 or p is 1 or 2 and the $R^1$ groups are located at the 6- and/or 7-positions and are selected from fluoro, cyano, carbamoyl, methoxycarbonyl, methoxy, ethoxy, N-methylcarbamoyl and N,N-dimethylcarbamoyl, q is 1 and the $R^2$ group which is located at the 2-position (relative to the $C(R^3)(R^4)$ group) is a methoxy group;

each of $R^3$ and $R^4$ is hydrogen;

$R^5$ is hydrogen;

Ring A is 2-oxazolyl, 3-isoxazolyl, 5-isoxazolyl, 3-pyrazolyl, 4-pyrazolyl, 2-thiazolyl, 1,2,4-oxadiazol-5-yl and 1,3,4-oxadiazol-5-yl; and r is 1 or 2 and each $R^6$ group that is present is selected from methyl, ethyl, propyl and isopropyl;

or a pharmaceutically-acceptable salt thereof.

Particular compounds of the invention are, for example, the quinoline derivatives of the Formula I that are disclosed within the Examples that are set out hereinafter.

For example, a particular compound of the invention is a quinoline derivative of the Formula I selected from:—
N-(1-ethyl-1H-pyrazol-4-yl)-2-[4-(6-cyano-7-methoxyquinolin-4-yloxy)phenyl]acetamide,
N-(1-ethyl-1H-pyrazol-4-yl)-2-[4-(6-cyano-7-methoxyquinolin-4-yloxy)-2-methoxyphenyl]acetamide,
N-(1-ethyl-1H-pyrazol-4-yl)-2-{4-[6-(N,N-dimethylcarbamoyl)-7-methoxyquinolin-4-yloxy]phenyl}acetamide,
N-[1-(2-methoxyethyl)pyrazol-4-yl]-2-[4-(6,7-dimethoxyquinolin-4-yloxy)phenyl]acetamide,
N-[1-(2-methoxyethyl)pyrazol-4-yl]-2-[4-(6-cyano-7-methoxyquinolin-4-yloxy)phenyl]acetamide,
N-(5-ethyl-1H-pyrazol-3-yl)-2-{4-[6-(N,N-dimethylcarbamoyl)-7-methoxyquinolin-4-yloxy]phenyl}acetamide,
N-(5-ethyl-1H-pyrazol-3-yl)-2-[4-(6-cyano-7-methoxyquinolin-4-yloxy)-2-methoxyphenyl]acetamide,
N-(4,5-dimethylisoxazol-3-yl)-2-[4-(6,7-dimethoxyquinolin-4-yloxy)phenyl]acetamide and
N-(4,5-dimethylisoxazol-3-yl)-2-[4-(6-cyano-7-methoxyquinolin-4-yloxy)phenyl]acetamide;
or a pharmaceutically-acceptable salt thereof.

For example, a further particular compound of the invention is a quinoline derivative of the Formula I selected from: —
N-(1-ethyl-1H-pyrazol-4-yl)-2-(2-methoxy-4-quinolin-4-yloxyphenyl)acetamide,
N-(1-methyl-1H-pyrazol-4-yl)-2-[4-(6-fluoroquinolin-4-yloxy)-2-methoxyphenyl]acetamide,
N-(1-ethyl-1H-pyrazol-4-yl)-2-[4-(6-fluoroquinolin-4-yloxy)-2-methoxyphenyl]acetamide,
N-(1-ethyl-1H-pyrazol-4-yl)-2-[4-(7-fluoroquinolin-4-yloxy)-2-methoxyphenyl]acetamide,
N-(1-ethyl-1H-pyrazol-4-yl)-2-{2-methoxy-4-[6-methoxy-7-(N-methylcarbamoyl)quinolin-4-yloxy]phenyl}acetamide,
N-(1-methyl-1H-pyrazol-4-yl)-2-[2-methoxy-4-(7-methoxyquinolin-4-yloxy)phenyl]acetamide,
N-(1,3-dimethyl-1H-pyrazol-4-yl)-2-[2-methoxy-4-(7-methoxyquinolin-4-yloxy)phenyl]acetamide,
N-(1,5-dimethyl-1H-pyrazol-4-yl)-2-[2-methoxy-4-(7-methoxyquinolin-4-yloxy)phenyl]acetamide,
N-(1,3-dimethyl-1H-pyrazol-4-yl)-2-[4-(6,7-dimethoxyquinolin-4-yloxy)-2-methoxyphenyl]acetamide,
N-(4-methyl-1H-pyrazol-3-yl)-2-[4-(6,7-dimethoxyquinolin-4-yloxy)-2-methoxyphenyl]acetamide,
N-(4-ethyl-1H-pyrazol-3-yl)-2-[4-(6,7-dimethoxyquinolin-4-yloxy)-2-methoxyphenyl]acetamide,
N-(4,5-dimethyl-1H-pyrazol-3-yl)-2-[2-methoxy-4-(7-methoxyquinolin-4-yloxy)phenyl]acetamide,
N-(5-methyl-1H-pyrazol-3-yl)-2-[4-(6-fluoroquinolin-4-yloxy)-2-methoxyphenyl]acetamide,
N-(4,5-dimethyl-1H-pyrazol-3-yl)-2-[4-(6-fluoroquinolin-4-yloxy)-2-methoxyphenyl]acetamide,
N-(4-methylisoxazol-3-yl)-2-[2-methoxy-4-(7-methoxyquinolin-4-yloxy)phenyl]acetamide,
N-(4,5-dimethylisoxazol-3-yl)-2-(2-methoxy-4-quinolin-4-yloxyphenyl)acetamide,
N-(4,5-dimethylisoxazol-3-yl)-2-[2-methoxy-4-(7-methoxyquinolin-4-yloxy)phenyl]acetamide,
N-(4,5-dimethylisoxazol-3-yl)-2-{2-methoxy-4-[7-methoxy-6-(N-methylcarbamoyl)quinolin-4-yloxy]phenyl}acetamide,
N-(4,5-dimethylisoxazol-3-yl)-2-[4-(6-fluoroquinolin-4-yloxy)-2-methoxyphenyl]acetamide,
N-(4-methylthiazol-2-yl)-2-[2-methoxy-4-(6-fluoroquinolin-4-yloxy)phenyl]acetamide and
N-(4-methylthiazol-2-yl)-2-{2-methoxy-4-[6-methoxy-7-(N-methylcarbamoyl)quinolin-4-yloxy]phenyl}acetamide;
or a pharmaceutically-acceptable salt thereof.

A further particular compound of the invention is a quinoline derivative of the Formula I selected from:—
N-(3-pyridyl)-2-[4-(6,7-dimethoxyquinolin-4-yloxy)phenyl]acetamide,
N-(3-pyridyl)-2-[4-(6-cyano-7-methoxyquinolin-4-yloxy)phenyl]acetamide,
N-(4-pyrimidinyl)-2-[4-(6,7-dimethoxyquinolin-4-yloxy)phenyl]acetamide,
N-(3-dimethylaminomethylphenyl)-2-[4-(6,7-dimethoxyquinolin-4-yloxy)phenyl]acetamide,
N-(3-dimethylaminomethylphenyl)-2-[4-(6-cyano-7-methoxyquinolin-4-yloxy)phenyl]acetamide,
N-(4-dimethylaminomethylphenyl)-2-[4-(6,7-dimethoxyquinolin-4-yloxy)phenyl]acetamide and N-(4-dimethylaminomethylphenyl)-2-[4-(6-cyano-7-methoxyquinolin-4-yloxy)phenyl]acetamide;
or a pharmaceutically-acceptable salt thereof.

A quinoline derivative of the Formula I, or a pharmaceutically-acceptable salt thereof, may be prepared by any process known to be applicable to the preparation of chemically-related compounds. Such processes, when used to prepare a quinoline derivative of the Formula I are provided as a further feature of the invention and are illustrated by the following representative process variants in which, unless otherwise stated, each of $X^1$, p, $R^1$, q, $R^2$, $R^3$, $R^4$, $R^5$, Ring A, r and $R^6$ has any of the meanings defined hereinbefore. Necessary starting materials may be obtained by standard procedures of organic chemistry. The preparation of such starting materials is described in conjunction with the following representative process variants and within the accompanying Examples. Alternatively, necessary starting materials are obtainable by analogous procedures to those illustrated which are within the ordinary skill of an organic chemist.

(a) The reaction of a quinoline of the Formula II

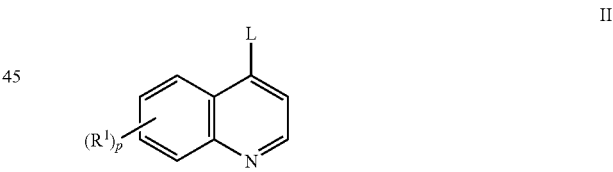

wherein L is a displaceable group and p and $R^1$ have any of the meanings defined hereinbefore except that any functional group is protected if necessary, with a phenylacetamide of the Formula III

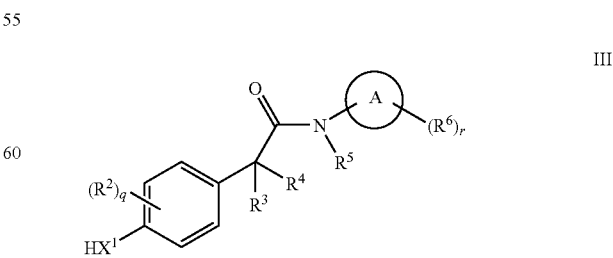

wherein $X^1$, q, $R^2$, $R^3$, $R^4$, $R^5$, Ring A, r and $R^6$ have any of the meanings defined hereinbefore except that any functional group is protected if necessary, whereafter any protecting group that is present is removed.

The reaction may conveniently be carried out in the presence of a suitable acid or in the presence of a suitable base. A suitable acid is, for example, an inorganic acid such as, for example, hydrogen chloride or hydrogen bromide. A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal amide, for example sodium hexamethyldisilazane, or, for example, an alkali metal hydride, for example sodium hydride.

A suitable displaceable group L is, for example, a halogeno, alkoxy, aryloxy or sulphonyloxy group, for example a chloro, bromo, methoxy, phenoxy, pentafluorophenoxy, methanesulphonyloxy or toluene-4-sulphonyloxy group. The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxane, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 0 to 250° C., preferably in the range 0 to 120° C.

Typically, the quinoline of the Formula II may be reacted with a compound of the Formula III in the presence of an aprotic solvent such as N,N-dimethylformamide, conveniently in the presence of a base, for example potassium carbonate or sodium hexamethyldisilazane, and at a temperature in the range, for example, 0 to 150° C., preferably in the range, for example, 0 to 70° C.

The quinoline derivative of the Formula I may be obtained from this process in the form of the free base or alternatively it may be obtained in the form of a salt with the acid of the formula H-L wherein L has the meaning defined hereinbefore. When it is desired to obtain the free base from the salt, the salt may be treated with a suitable base, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1-20 carbon atoms). Examples of carboxy protecting groups include straight or branched chain (1-12C)alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2-6C)alkenyl groups (for example allyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl.

The reader is referred to Advanced Organic Chemistry, 4th Edition, by J. March, published by John Wiley & Sons 1992, for general guidance on reaction conditions and reagents and to Protective Groups in Organic Synthesis, $2^{nd}$ Edition, by T. Green et al., also published by John Wiley & Son, for general guidance on protecting groups.

Quinoline starting materials of the Formula II may be obtained by conventional procedures such as those disclosed in International Patent Applications WO 98/13350 and WO 02/12226. For example, a 1,4-dihydroquinolin-4-one of the Formula IV

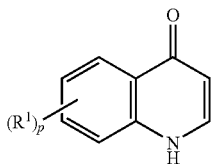

wherein p and $R^1$ have any of the meanings defined hereinbefore except that any functional group is protected if necessary, may be reacted with a halogenating agent such as thionyl chloride, phosphoryl chloride or a mixture of carbon tetrachloride and triphenylphosphine whereafter any protecting group that is present is removed.

The 4-chloroquinoline so obtained may be converted, if required, into a 4-pentafluorophenoxyquinoline by reaction with pentafluorophenol in the presence of a suitable base such as potassium carbonate and in the presence of a suitable solvent such as N,N-dimethylformamide.

Phenylacetamide starting materials of the Formula III may be obtained by conventional procedures. For example, an acetic acid of the Formula V

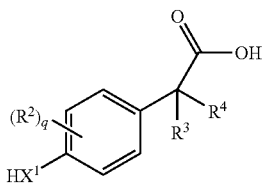

or a reactive derivative thereof, wherein $X^1$, q, $R^2$, $R^3$ and $R^4$ have any of the meanings defined hereinbefore except that any functional group is protected if necessary, may be reacted with an amine of the Formula VI

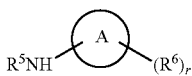

wherein $R^5$, Ring A, r and $R^6$ have any of the meanings defined hereinbefore except that any functional group is protected if necessary, whereafter any protecting group that is present is removed.

A suitable reactive derivative of an acetic acid of the Formula V is, for example, an acyl halide, for example an acyl chloride formed by the reaction of the acid with an inorganic acid chloride, for example thionyl chloride; a mixed anhydride, for example an anhydride formed by the reaction of the acid with a chloroformate such as isobutyl chloroformate; an active ester, for example an ester formed by the reaction of the acid with a phenol such as pentafluorophenol, with an ester such as pentafluorophenyl trifluoroacetate or with an alcohol such as methanol, ethanol, isopropanol, butanol or N-hydroxybenzotriazole; an acyl azide, for example an azide formed by the reaction of the acid with an azide such as diphenylphosphoryl azide; an acyl cyanide, for example a cyanide formed by the reaction of an acid with a cyanide such as diethylphosphoryl cyanide; or the product of the reaction of the acid with a carbodiimide such as dicyclohexylcarbodiimide or 1-(3-dimethylaminopropyl)-3-ethylcarbodiimide or with a uronium compound such as 2-(7-azabenzotriazol-1-yl)-1,1,3,3-tetramethyluronium hexafluorophosphate(V) or 2-(benzotriazol-1-yl)-1,1,3,3-tetramethyluronium tetrafluoroborate.

The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxane, an aromatic solvent such as toluene. Conveniently, the reaction is conveniently carried out in the presence of a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 0 to 120° C., preferably at or near ambient temperature.

Acetic acid derivatives of the Formula V and amines of the Formula VI may be obtained by conventional procedures such as those disclosed in the Examples that are set out hereinafter.

(b) The coupling, conveniently in the presence of a suitable base, of a quinoline of the Formula VII

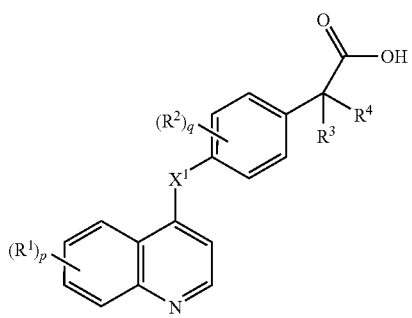

or a reactive derivative thereof as defined hereinbefore, wherein p, $R^1$, $X^1$, q, $R^2$, $R^3$ and $R^4$ have any of the meanings defined hereinbefore except that any functional group is protected if necessary, with an amine of the Formula VI

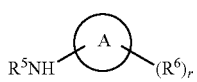

wherein $R^5$, Ring A, r and $R^6$ have any of the meanings defined hereinbefore except that any functional group is protected if necessary, whereafter any protecting group that is present is removed.

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal amide, for example sodium hexamethyldisilazane, or, for example, an alkali metal hydride, for example sodium hydride.

The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxane, an aromatic solvent such as toluene. Conveniently, the reaction is conveniently carried out in the presence of a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 0 to 120° C., preferably at or near ambient temperature.

Quinoline derivatives of the Formula VII and amines of the Formula VI may be obtained by conventional procedures such as those disclosed in the Examples that are set out hereinafter.

(c) For the production of those compounds of the Formula I wherein at least one $R^1$ group is a group of the formula $$Q^1\text{-}X^2\text{—}$$

wherein $Q^1$ is an aryl-(1-6C)alkyl, (3-7C)cycloalkyl-(1-6C)alkyl, (3-7C)cycloalkenyl-(1-6C)alkyl, heteroaryl-(1-6C)alkyl or heterocyclyl-(1-6C)alkyl group or an optionally substituted alkyl group and $X^2$ is an oxygen atom, the coupling, conveniently in the presence of a suitable dehydrating agent, of a quinoline of the Formula VIII

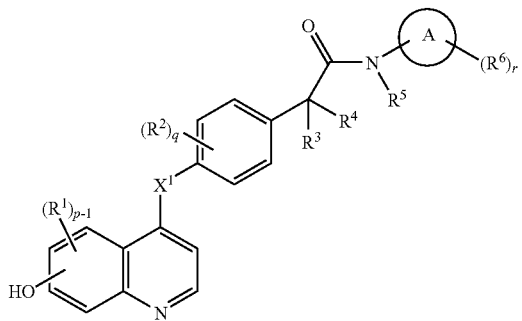

VIII wherein each of p, $R^1$, $X^1$, q, $R^2$, $R^3$, $R^4$, $R^5$, Ring A, r and $R^6$ has any of the meanings defined hereinbefore except that any functional group is protected if necessary, with an appropriate alcohol wherein any functional group is protected if necessary, whereafter any protecting group that is present is removed.

A suitable dehydrating agent is, for example, a carbodiimide reagent such as dicyclohexylcarbodiimide or 1-(3-dimethylaminopropyl)-3-ethylcarbodiimide or a mixture of an azo compound such as diethyl or di-tert-butyl azodicarboxylate and a phosphine such as triphenylphosphine. The reaction is conveniently carried out in the presence of a suitable inert solvent or diluent, for example a halogenated solvent such as methylene chloride, chloroform or carbon tetrachloride and at a temperature in the range, for example, 10 to 150° C., preferably at or near ambient temperature.

Quinoline derivatives of the Formula VIII may be obtained by conventional procedures.

(d) For the production of those compounds of the Formula I wherein a $R^6$ group is a group of the formula —$X^6$—$R^{15}$ wherein $X^6$ has any of the meanings defined hereinbefore and $R^{15}$ is an amino-substituted (1-6C)alkyl group (such as a dimethylaminomethyl, 2-dimethylaminoethyl or 4-methylpiperazin-1-ylmethyl group), the reaction, conveniently in the presence of a suitable base as defined hereinbefore, of a compound of the Formula I wherein a $R^6$ group is a group of the formula —$X^6$—$R^{15}$ wherein $R^{15}$ is a halogeno-substituted (1-6C)alkyl group with an appropriate amine or with a nitrogen-containing heterocyclyl compound.

The reaction is conveniently carried out in the presence of a suitable inert solvent or diluent as defined hereinbefore and at a temperature in the range, for example, 10 to 180° C., conveniently in the range 20 to 120° C., more conveniently at or near ambient temperature.

Compounds of the Formula I wherein a $R^6$ group is a group of the formula —$X^6$—$R^{15}$ wherein $R^{15}$ is a halogeno-substituted (1-6C)alkyl group may be obtained by any of the representative process variants (a), (b) or (c) that are described hereinbefore.

(e) For the production of those compounds of the Formula I wherein a $R^6$ group is a group of the formula —$X^6$—$R^{15}$ wherein $X^6$ has any of the meanings defined hereinbefore and $R^{15}$ is an amino-substituted (1-6C)alkyl group (such as a methylaminomethyl, 2-methylaminoethyl or 2-hydroxyethylaminomethyl group), the reductive amination of a compound of the Formula I wherein a $R^6$ group is a group of the formula —$X^6$—$R^{15}$ wherein $R^{15}$ is a formyl or (2-6C)alkanoyl group.

A suitable reducing agent for the reductive amination reaction is, for example, a hydride reducing agent, for example an alkali metal aluminium hydride such as lithium aluminium hydride or, preferably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride and sodium cyanoborohydride. The reaction is performed at a temperature in the range, for example, 10 to 80° C., conveniently at or near ambient temperature.

Compounds of the Formula I wherein a $R^6$ group is a group of the formula —$X^6$—$R^{15}$ wherein $R^{15}$ is a formyl or (2-6C) alkanoyl group may be obtained by a conventional adaptation of any of the representative process variants (a), (b) or (c) that are described hereinbefore.

(f) For the production of those compounds of the Formula I wherein $R^5$ is a (1-8C)alkyl group, the alkylation, conveniently in the presence of a suitable base as defined hereinbefore, of a compound of the Formula I wherein $R^5$ is hydrogen with a suitable alkylating agent.

The reaction is conveniently carried out in the presence of a suitable inert solvent or diluent as defined hereinbefore and at a temperature in the range, for example, −10° C. to 180° C., conveniently in the range 0 to 100° C., more conveniently at or near ambient temperature.

A suitable alkylating agent is, for example, a compound wherein a (1-8C)alkyl group is attached to a suitable leaving group, for example a chloro, bromo, iodo, methoxy, phenoxy, pentafluorophenoxy, methoxysulphonyloxy, methanesulphonyloxy or toluene-4-sulphonyloxy group.

(g) For the production of those compounds of the Formula I wherein $R^1$ is a carboxy group, the cleavage, conveniently in the presence of a suitable base as defined hereinbefore, of a compound of the Formula I wherein $R^1$ is a (1-6C) alkoxycarbonyl group.

Methods appropriate for the cleavage of a (1-6C)alkoxycarbonyl group include, for example, acid-, base-, metal- or enzymically-catalysed hydrolysis. The reaction is conveniently carried out in the presence of a suitable inert solvent or diluent as defined hereinbefore and at a temperature in the range, for example, −10° C. to 100° C., conveniently at or near ambient temperature. For example, base-catalysed cleavage may be effected at ambient temperature using an alkali metal hydroxide such as lithium hydroxide in an alcohol such as methanol.

(h) For the production of those compounds of the Formula I wherein $R^1$ is a carbamoyl, N-(1-6C)alkylcarbamoyl, N,N-di-[(1-6C)alkyl]carbamoyl or NH-containing heterocyclic group, the coupling, conveniently in the presence of a suitable base as defined hereinbefore, of a compound of the Formula I wherein $R^1$ is a carboxy group, or a reactive derivative thereof as defined hereinbefore, with ammonia or with a (1-6C)alkylamine, a di-(1-6C)alkylamine or a NH-containing heterocycle as appropriate.

The reaction is conveniently carried out in the presence of a suitable inert solvent or diluent as defined hereinbefore and at a temperature in the range, for example, 0° C. to 120° C., conveniently at or near ambient temperature.

(i) For the production of those compounds of the Formula I wherein a $R^6$ group is a di-(1-6C)alkylamino group, the reductive amination of a (1-5C)aldehyde (such as formaldehyde) or a (3-6C)ketone (such as acetone) with a compound of the Formula I wherein a $R^6$ group is an amino or (1-6C)alkylamino group.

A suitable reducing agent for the reductive amination reaction is any of the hydride hydride reducing agents defined hereinbefore, such as an alkali metal borohydride, for example sodium cyanoborohydride or sodium triacetoxyborohydride. The reaction is conveniently performed in a suitable inert solvent or diluent, for example tetrahydrofuran, diethyl ether, methylene chloride, methanol or ethanol. The reaction is performed at a temperature in the range, for example, 10 to 80° C., conveniently at or near ambient temperature.

When a pharmaceutically-acceptable salt of a quinoline derivative of the Formula I is required, for example an acid-addition salt, it may be obtained by, for example, reaction of said quinoline derivative with a suitable acid.

When a pharmaceutically-acceptable pro-drug of a quinoline derivative of the Formula I is required, it may be obtained using a conventional procedure. For example, an in vivo cleavable ester of a quinoline derivative of the Formula I may be obtained by, for example, reaction of a compound of the Formula I containing a carboxy group with a pharmaceutically-acceptable alcohol or by reaction of a compound of the Formula I containing a hydroxy group with a pharmaceutically-acceptable carboxylic acid. For example, an in vivo cleavable amide of a quinoline derivative of the Formula I may be obtained by, for example, reaction of a compound of the Formula I containing a carboxy group with a pharmaceutically-acceptable amine or by reaction of a compound of the Formula I containing an amino group with a pharmaceutically-acceptable carboxylic acid.

Many of the intermediates defined herein are novel and these are provided as a further feature of the invention. For example, many compounds of the Formulae III, VI and VII are novel compounds.

A further particular compound of the invention is a quinoline derivative of the Formula I selected from:—
N-(1-ethyl-1H-pyrazol-4-yl)-2-(2-methoxy-4-quinolin-4-yloxyphenyl)acetamide,
N-(1-ethyl-1H-pyrazol-4-yl)-2-[4-(6-fluoroquinolin-4-yloxy)-2-methoxyphenyl]acetamide,
N-(4,5-dimethylisoxazol-3-yl)-2-[4-(6-fluoroquinolin-4-yloxy)-2-methoxyphenyl]acetamide,
N-(4,5-dimethylisoxazol-3-yl)-2-(2-methoxy-4-quinolin-4-yloxyphenyl)acetamide,
N-(4-methylthiazol-2-yl)-2-(2-methoxy-4-quinolin-4-yloxyphenyl)acetamide and N-(4-methylthiazol-2-yl)-2-[4-(6-fluoroquinolin-4-yloxy)-2-methoxyphenyl]acetamide;
or a pharmaceutically-acceptable salt thereof.

The compounds described immediately hereinbefore are obtainable using any of the processes described hereinbefore. Necessary starting materials may be obtained by standard procedures of organic chemistry. For example, use may be made of 4-chloroquinoline or 4-chloro-6-fluoroquinoline within process variant (a) as described hereinbefore.

As stated hereinbefore, particular compounds of the invention include quinoline derivatives of the Formula I selected from:—
N-(1-ethyl-1H-pyrazol-4-yl)-2-[4-(6-fluoroquinolin-4-yloxy)-2-methoxyphenyl]acetamide,
N-(1-ethyl-1H-pyrazol-4-yl)-2-[4-(7-fluoroquinolin-4-yloxy)-2-methoxyphenyl]acetamide,
N-(1-methyl-1H-pyrazol-4-yl)-2-[2-methoxy-4-(7-methoxyquinolin-4-yloxy)phenyl]acetamide,
N-(1,3-dimethyl-1H-pyrazol-4-yl)-2-[2-methoxy-4-(7-methoxyquinolin-4-yloxy)phenyl]acetamide,
N-(1,5-dimethyl-1H-pyrazol-4-yl)-2-[2-methoxy-4-(7-methoxyquinolin-4-yloxy)phenyl]acetamide,
N-(1,3-dimethyl-1H-pyrazol-4-yl)-2-[4-(6,7-dimethoxyquinolin-4-yloxy)-2-methoxyphenyl]acetamide,
N-(5-methyl-1H-pyrazol-3-yl)-2-[4-(6-fluoroquinolin-4-yloxy)-2-methoxyphenyl]acetamide and N-(4,5-dimethyl-1H-pyrazol-3-yl)-2-[4-(6-fluoroquinolin-4-yloxy)-2-methoxyphenyl]acetamide;
or a pharmaceutically-acceptable salt thereof.

As also stated hereinbefore, a suitable pharmaceutically-acceptable salt of a compound of the Formula I includes, for example, an acid-addition salt of a compound of the Formula I, for example an acid-addition salt with an inorganic or organic acid such as hydrochloric, hydrobromic, sulphuric, trifluoroacetic or citric acid.

A further suitable pharmaceutically-acceptable salt of a compound of the Formula I includes, for example, an acid-addition salt of a compound of the Formula I with an inorganic or organic acid such as phosphoric, glycolic, lactic, malic, tartaric, malonic, fumaric, maleic, mandelic, gluconic, glucuronic, hippuric, methanesulphonic, ethanesulphonic, ethane-1,2-disulphonic, benzenesulphonic or 4-toluenesulphonic acid.

It will be appreciated that, dependent on factors such as the basicity of the compound of the Formula I, the acidity of the acid used to form an acid-addition salt and the relative amounts of each component, the stoichiometry of the acid-addition salt of the compound of the Formula I can involve less than or more than one equivalent of acid. For example, a hemi-, mono-, di- or tri-acid salt may be produced. In general, elemental analysis data may be used to estimate the stoichiometry of any such salt.

For example, when the particular compound of the invention is N-(1-ethyl-1H-pyrazol-4-yl)-2-[4-(6-fluoroquinolin-4-yloxy)-2-methoxyphenyl]acetamide, a suitable pharmaceutically-acceptable salt includes, for example, a crystalline acid-addition salt with an inorganic or organic acid selected from hydrochloric, hydrobromic, phosphoric, citric, tartaric, fumaric, maleic, glucuronic, methanesulphonic, benzenesulphonic and 4-toluenesulphonic acid.

For example, when the particular compound of the invention is N-(1,3-dimethyl-1H-pyrazol-4-yl)-2-[2-methoxy-4-(7-methoxyquinolin-4-yloxy)phenyl]acetamide, a suitable pharmaceutically-acceptable salt includes, for example, a crystalline acid-addition salt with an inorganic or organic acid selected from hydrochloric, hydrobromic, sulphuric, phosphoric, glycolic, lactic, citric, malic, tartaric, malonic, fumaric, maleic, mandelic, gluconic, glucuronic, hippuric, methanesulphonic, ethanesulphonic, ethane-1,2-disulphonic, benzenesulphonic and 4-toluenesulphonic acid, particularly from sulphuric, phosphoric, citric, maleic, methanesulphonic, benzenesulphonic and 4-toluenesulphonic acid.

Such crystalline materials may be analysed using conventional techniques such as X-Ray Powder Diffraction (hereinafter XRPD) analysis, Differential Scanning Calorimetry (hereinafter DSC), Thermal Gravimetric Analysis (hereinafter TGA), Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

Generally, when it is stated that a crystalline acid-addition salt is obtained, the salt is of a substantially homogeneous crystalline form wherein the degree of crystallinity (that may be determined by XRPD means) is conveniently greater than about 80%, more conveniently greater than about 90%, preferably greater than about 95%.

For example, when the particular compound of the invention is N-(1-ethyl-1H-pyrazol-4-yl)-2-[4-(6-fluoroquinolin-4-yloxy)-2-methoxyphenyl]acetamide, a particular pharmaceutically-acceptable salt is a crystalline acid-addition salt with citric acid. In particular, it has been found that a crystalline salt in the form of a mono-citrate may be obtained.

For example, when the particular compound of the invention is N-(1-ethyl-1H-pyrazol-4-yl)-2-[4-(6-fluoroquinolin-4-yloxy)-2-methoxyphenyl]acetamide, a particular pharmaceutically-acceptable salt is a crystalline acid-addition salt with maleic acid. In particular, it has been found that a crystalline salt in the form of a mono-maleate may be obtained.

For example, when the particular compound of the invention is N-(1-ethyl-1H-pyrazol-4-yl)-2-[4-(6-fluoroquinolin-4-yloxy)-2-methoxyphenyl]acetamide, a particular pharmaceutically-acceptable salt is a crystalline acid-addition salt with methanesulphonic acid. In particular, it has been found that a crystalline salt in the form of a mono-mesylate may be obtained.

For example, when the particular compound of the invention is N-(1,3-dimethyl-1H-pyrazol-4-yl)-2-[2-methoxy-4-(7-methoxyquinolin-4-yloxy)phenyl]acetamide, a particular pharmaceutically-acceptable salt is a crystalline acid-addition salt with citric acid. In particular, it has been found that a crystalline salt in the form of a mono-citrate may be obtained.

For example, when the particular compound of the invention is N-(1,3-dimethyl-1H-pyrazol-4-yl)-2-[2-methoxy-4-(7-methoxyquinolin-4-yloxy)phenyl]acetamide, a further particular pharmaceutically-acceptable salt is a crystalline acid-addition salt with maleic acid. In particular, it has been found that a crystalline salt in the form of a mono-maleate may be obtained.

DSC thermogram analysis of said maleate salt showed that the salt has a melting point in the range of about 188-210° C., with an onset of melting at about 188° C. and a melting point peak at about 192° C.

For example, when the particular compound of the invention is N-(1,3-dimethyl-1H-pyrazol-4-yl)-2-[2-methoxy-4-(7-methoxyquinolin-4-yloxy)phenyl]acetamide, a further particular pharmaceutically-acceptable salt is a crystalline acid-addition salt with sulphuric acid. In particular, it has been found that a crystalline salt in the form of a mono-sulphate may be obtained.

DSC thermogram analysis of said sulphate salt showed that the salt has a melting point in the range of about 257-280° C., with an onset of melting at about 257° C. and a melting point peak at about 271° C.

It has also been found that, when said sulphate salt is contacted with water, a hydrated form of the salt is formed.

For example, when the particular compound of the invention is N-(1,3-dimethyl-1H-pyrazol-4-yl)-2-[2-methoxy-4-(7-methoxyquinolin-4-yloxy)phenyl]acetamide, a further particular pharmaceutically-acceptable salt is a crystalline acid-addition salt with methanesulphonic acid. In particular, it has been found that a crystalline salt in the form of a mono-mesylate may be obtained.

For example, when the particular compound of the invention is N-(1,3-dimethyl-1H-pyrazol-4-yl)-2-[2-methoxy-4-(7-methoxyquinolin-4-yloxy)phenyl]acetamide, a further particular pharmaceutically-acceptable salt is a crystalline acid-addition salt with benzenesulphonic acid. In particular, it has been found that a crystalline salt in the form of a mono-benzenesulphonate may be obtained.

It has been noted that said benzenesulphonate salt may be obtained in two or more different crystalline forms. A form of said benzenesulphonate salt was obtained from a suspension of the material in acetone and the DSC thermogram of the resultant benzenesulphonate salt showed a melting point in the range of about 183-190° C., with an onset of melting at about 183° C. and a melting point peak at about 185° C.

For example, when the particular compound of the invention is N-(1,3-dimethyl-1H-pyrazol-4-yl)-2-[2-methoxy-4-(7-methoxyquinolin-4-yloxy)phenyl]acetamide, a further particular pharmaceutically-acceptable salt is a crystalline acid-addition salt with 4-toluenesulphonic acid. In particular, it has been found that a crystalline salt in the form of a mono-4-toluenesulphonate may be obtained.

It has also been found that, when said 4-toluenesulphonate salt is contacted with water, a hydrated form of the salt is formed.

When it is stated that a compound of the Formula I and a pharmaceutically-acceptable acid forms a mono-salt, the molar ratio of each molecule of a compound of the Formula I to each molecule of pharmaceutically-acceptable acid lies in the range from about 0.6:1 to about 1.4:1, conveniently in the range from about 0.75:1 to about 1.25:1, more conveniently in the range from about 0.8:1 to about 1.2:1, generally having about 1 equivalent of the compound of the Formula I to about 1 equivalent of the pharmaceutically-acceptable acid.

For example, when it is stated that a mono-citrate salt is formed, the molar ratio of each molecule of N-(1,3-dimethyl-1H-pyrazol-4-yl)-2-[2-methoxy-4-(7-methoxyquinolin-4-yloxy)phenyl]acetamide to each molecule of citric acid lies in the range from about 0.6:1 to about 1.4:1, conveniently in the range from about 0.75:1 to about 1.25:1, more conveniently in the range from about 0.8:1 to about 1.2:1, generally having about 1 equivalent of N-(1,3-dimethyl-1H-pyrazol-4-yl)-2-[2-methoxy-4-(7-methoxyquinolin-4-yloxy)phenyl]acetamide to about 1 equivalent of citric acid.

Biological Assays

The following assays can be used to measure the effects of the compounds of the present invention as inhibitors of PDGFRα, PDGFRβ and KDR tyrosine kinase enzymes, as inhibitors in vitro of the phosphorylation of PDGFR expressed in MG63 osteosarcoma cells, as inhibitors in vitro of the phosphorylation of KDR expressed in human umbilical vein endothelial cells (HUVECs), as inhibitors in vitro of the proliferation of MG63 osteosarcoma cells, as inhibitors in vitro of the proliferation of HUVECs, and as inhibitors in vivo of the growth in nude mice of xenografts of human tumour tissue such as CaLu-6 and Colo205.

(a) In Vitro Enzyme Assays

The ability of test compounds to inhibit the phosphorylation of a tyrosine containing polypeptide substrate by the tyrosine kinase enzymes PDGFRα, PDGFRβ and KDR was assessed using conventional ELISA assays.

DNA encoding the PDGFRα, PDGFRβ or KDR receptor cytoplasmic domains may be obtained by total gene synthesis (*International Biotechnology Lab.*, 1987, 5(3), 19-25) or by cloning. The DNA fragments may be expressed in a suitable expression system to obtain polypeptide with tyrosine kinase activity. For example, PDGFRα, PDGFRβ and KDR receptor cytoplasmic domains, obtained by expression of recombinant protein in insect cells, can be shown to display intrinsic tyrosine kinase activity. In the case of the VEGF receptor KDR (Genbank Accession No. L04947), a DNA fragment encoding most of the cytoplasmic domain, commencing with methionine 806 and including the termination codon may be cloned into a baculovirus transplacement vector [for example pAcYM1(see The Baculovirus Expression System: A Laboratory Guide, L. A. King and R. D. Possee, Chapman and Hall, 1992) or pAc360 or pBlueBacHis (available from Invitrogen Corporation)]. This recombinant construct may be co-transfected into insect cells [for example *Spodoptera frugiperda* 21 (Sf21) or *Spodoptera frugiperda* 9(Sf9)] with viral DNA (for example Phalmingen BaculoGold) to prepare recombinant baculovirus. Details of the methods for the assembly of recombinant DNA molecules and the preparation and use of recombinant baculovirus can be found in standard texts, for example Sambrook et al., 1989, Molecular cloning—A Laboratory Manual, 2nd edition, Cold Spring Harbour Laboratory Press and O'Reilly et al., 1992, Baculovirus Expression Vectors—A Laboratory Manual, W. H. Freeman and Co, New York).

For expression, Sf9 cells were infected with plaque-pure KDR recombinant virus and harvested 48 hours later. Harvested cells were washed with ice cold phosphate buffered saline solution (PBS) containing 10 mM sodium phosphate pH7.4 buffer, 138 mM sodium chloride and 2.7 mM potassium chloride) and resuspended in ice cold cell diluent comprising 20 mM Hepes pH7.5 buffer, 150 mM sodium chloride, 10% v/v glycerol, 1% v/v Triton X100, 1.5 mM magnesium chloride, 1 mM ethylene glycol-bis(βaminoethyl ether) N,N,N',N'-tetraacetic acid (EGTA) and 1 mM PMSF (phenylmethylsulphonyl fluoride) [the PMSF is added just before use from a freshly-prepared 100 mM solution in methanol] using 1 ml cell diluent per 10 million cells. The suspension was centrifuged for 10 minutes at 13,000 rpm at 4° C. The supernatant (stock enzyme solution) was removed and stored in aliquots at −70° C.

A substrate solution [100 μl of a 2 μg/ml solution of the poly-amino acid Poly(Glu, Ala, Tyr) 6:3:1 (Sigma-Aldrich Company Ltd., Poole, Dorset; Catalogue No. P3899) in phosphate buffered saline (PBS)] was added to each well of a number of Nunc 96-well MaxiSolp immunoplates (Nunc, Roskilde, Denmark; Catalogue No. 439454) and the plates were sealed and stored at 4° C. for 16 hours. The excess of substrate solution was discarded and the wells were washed in turn with PBS containing 0.05% v/v Tween 20 (PBST; 300 μl/well) and twice with Hepes pH7.4 buffer (50 mM, 300 μl/well) before being blotted dry.

Each test compound was dissolved in DMSO and diluted with a 10% solution of DMSO in distilled water to give a series of dilutions (from 40 μM to 0.0012 μM). Aliquots (25 μl) of each dilution of test compound were transferred to wells in the washed assay plates. "Maximum" control wells contained diluted DMSO instead of compound. Aliquots (25 μl) of an aqueous manganese chloride solution (40 mM) containing adenosine-5'-triphosphate (ATP) was added to all test wells except the "blank" control wells which contained magnesium chloride without ATP. For PDGFRα enzyme, an ATP concentration of 14 μM was used; for PDGFRβ enzyme, an ATP concentration of 2.8 μM was used and for KDR enzyme, an ATP concentration of 8 μM was used.

Active human PDGFRα and PDGFRβ recombinant enzyme that had been expressed in Sf9 insect cells was obtained from Upstate Biotechnology Inc., Milton Keynes, UK (product 14-467 for PDGFRα, product 14-463 for PDGFRβ). Active human KDR recombinant enzyme was expressed in Sf9 insect cells as described above.

Each kinase enzyme was diluted immediately prior to use with an enzyme diluent comprising 100 mM Hepes pH7.4 buffer, 0.1 mM sodium orthovanadate, 0.1% Triton X-100 and 0.2 mM dithiothreitol. Aliquots (50 μl) of freshly diluted enzyme were added to each well and the plates were agitated at ambient temperature for 20 minutes. The solution in each well was discarded and the wells were washed twice with PBST. Mouse IgG anti-phosphotyrosine antibody (Upstate Biotechnology Inc.; product 05-321; 100 μl) was diluted by a factor of 1:3667 with PBST containing 0.5% w/v bovine serum albumin (BSA) and aliquots were added to each well. The plates were agitated at ambient temperature for 1.5 hours. The supernatant liquid was discarded and each well was washed with PBST (×2). Horse radish peroxidase (HRP)-linked sheep anti-mouse Ig antibody (Amersham Pharmacia Biotech, Chalfont St Giles, Buckinghamshire, UK; Catalogue No. NXA 931; 100 μl) was diluted by a factor of 1:550 with PBST containing 0.5% w/v BSA and added to each well. The plates were agitated at ambient temperature for 1.5 hours. The supernatant liquid was discarded and the wells were washed with PBST (×2). A sodium perborate (PCSB) capsule (Sigma-Aldrich Company Ltd., Poole, Dorset, UK; Catalogue No. P4922) was dissolved in distilled water (100 ml) to provide phosphate-citrate pH5 buffer (50 mM) containing 0.03% sodium perborate. An aliquot (50 ml) of this buffer was mixed with a 50 mg tablet of 2,2'-azinobis(3-ethylbenzothiazoline-6-sulphonic acid) (ABTS; Roche Diagnostics Ltd., Lewes, East Sussex, UK; Catalogue No. 1204 521). An aliquot (100 μl) of the resultant solution was added to each well. The plates were agitated at ambient temperature for about 20 minutes until the optical density value of the "maximum" control wells, as measured at 405 nm using a plate reading spectrophotometer, was approximately 1.0. "Blank" (no ATP) and "maximun" (no compound) control values were used to determine the dilution range of test compound that gave 50% inhibition of enzyme activity.

(b) In Vitro Phospho-Tyr751 PDGFRβ ELISA Assay

This assay uses a conventional ELISA method to determine the ability of test compounds to inhibit phosphorylation of tyrosine in PDGFRβ.

An MG63 osteosarcoma cell line [American Type Culture Collection (ATCC) CCL 1427] was routinely maintained at 37° C. with 7.5% $CO_2$ in Dulbecco's modified Eagle's growth medium (DMEM; Sigma-Aldrich; Catalogue No. D6546) containing 10% foetal calf serum (FCS; Sigma-Aldrich; Catalogue No. F7524) and 2 mM L-glutamine (Invitrogen Ltd., Paisley, UK; Catalogue No. 25030-024).

For the assay, the cells were detached from the culture flask using a trypsin/ethylenediaminetetraacetic acid (EDTA) mixture (Invitrogen Ltd.; Catalogue No. 15400-054) and resuspended in a test medium comprising DMEM without phenol red (Sigma-Aldrich; Catalogue No. D5921) containing 1% charcoal-stripped foetal calf serum (FCS) (Sigma-Aldrich;

Catalogue No. F7524, stripped by incubation with dextran-coated activated charcoal at 55° C. for 30 minutes with continuous stirring followed by removal of the charcoal by centrifugation and filter sterilisation) and 2 mM L-glutamine (Invitrogen Ltd., Catalogue No. 25030-024) to give $6\times10^4$ cells per ml. Aliquots (100 µl) were seeded into each of the wells of columns 2-12 (excluding column 1) and rows B-G (excluding rows A and H) of a clear 96 well tissue culture plate (Corning Life Sciences, Koolhovenlaan, The Netherlands; Catalogue No. 3595) to give a density of about 6000 cells per well. Aliquots (100 µl) of culture media were placed in the outer wells to minimise edge effects. The cells were incubated overnight at 37° C. with 7.5% $CO_2$ to allow the cells to adhere to the wells.

Test compounds were prepared as 10 mM stock solutions in DMSO and serially diluted as required with DMSO to give a range of concentrations. Aliquots (3 µl) of each compound concentration were added to test medium (300 µl) to create a second dilution range. Aliquots (16 µl) of each resultant compound concentration were added to the cells in each well. "Maximum" control cells received a dilution of DMSO plus test medium only. "Minimum" control cells received a reference PDGFR inhibitor (16 µl). The cells were incubated for 90 minutes at 37° C. with 7.5% $CO_2$.

The resultant cells were stimulated with $PDGF_{BB}$ using the following procedure. A lyophilised powder of $PDGF_{BB}$, (Sigma-Aldrich; Catalogue No. P4306) was mixed with sterile water to provide a stock solution of 10 µg/ml of $PDGF_{BB}$. A dilution of this stock solution into test medium provided a 182 ng/ml $PDGF_{BB}$ solution. Aliquots thereof (44 µl) were added to compound treated cells and to the "Maximum" control cells. The "Minimum" control cells received medium only. The cells were incubated at 37° C. with 7.5% $CO_2$ for 5 minutes. The solution from the wells was removed and the cells were lysed by the addition of 120 µl/well of RIPA buffer comprising 60 mM tris(hydroxymethyl)aminomethane hydrochloride (Tris-HCl), 150 mM sodium chloride, 1 mM EDTA, 1% v/v Igepal CA-630, 0.25% sodium deoxycholate, 1% v/v phosphatase inhibitor cocktail 1 P2850, 1% phosphatase inhibitor cocktail 2 P5726 and 0.5% v/v protease inhibitor cocktail P8340 (all chemicals and inhibitor cocktails were obtainable from the Sigma-Aldrich Company Ltd.). The resultant tissue culture plates were shaken for 5 minutes at ambient temperature to ensure full lysis and then frozen at −20° C. until required.

MaxiSorp ELISA plates (Nunc; Catalogue No. 439454) were coated with PDGFβ antibody (R&D Systems, Abingdon, Oxfordshire, UK; Catalogue No. AF385 comprising lyophilised antibody made up with 100 µl PBS to a final concentration of 100 µl/ml). The antibody was diluted at 1:40 into carbonate-bicarbonate buffer (Sigma-Aldrich; Catalogue No. C3041; one capsule dissolved in 100 ml of distilled water) to give a 2.5 µg/ml solution. Aliquots (50 µl) were added to each well and the plates were placed at 4° C. for 16 hours. The wells were washed 5 times (1 minute soak each time) with 300 µl per well of PBST. The wells were treated with 50 µl of 3% BSA in PBST at ambient temperature for 1 hour and subsequently washed twice with 300 µl per well of PBST.

The tissue culture plates with frozen cell lysate were allowed to warm to 0° C. Aliquots (50 µl) of the MG63 cell lysate were added to the ELISA plates. Each sample was duplicated on separate plates. The ELISA plates were agitated at ambient temperature for 2 hours. The wells were washed twice with 300 µl per well of PBST. A 1:1000 dilution of phospho PDGFRβ antibody (Cell Signaling Technology, Beverley, Mass., USA; Catalogue No. 3161) was made into 1% BSA in PBST. Aliquots (50 µl) of the antibody solutions were added to each of the wells. The plates were agitated at ambient temperature for 1 hour. The plates were washed twice with 300 µl per well of PBST. A 1:2000 dilution of anti-rabbit horseradish peroxidase conjugated secondary antibody (Cell Signaling Technology; Catalogue No. 7074) was made into 1% BSA in PBST. Aliquots (50 µl) of the resultant dilution were added to each well and the plates were agitated at ambient temperature for 1 hour. The plates were washed 5 times with 300 µl per well of PBST. Chemiluminescent substrate was made up according to manufacturers instructions (Pierce Biotechnology Inc., Rockford Ill., USA; Catalogue No. 34080). Aliquots (50 µl) of chemiluminescent substrate solution were added to each of the wells, the plates were agitated for 2 minutes and luminescence was read on a SpectraFluor Plus plate reader (Tecan UK Ltd., Reading, Berkshire, UK). Analysis for each of the compounds was completed by determining a ratio of the 'phospho antibody' plate reading to the 'total antibody' plate reading for each test sample and these ratios were plotted to determine the $IC_{50}$ value of each test compound.

(c) In Vitro Phospho-KDR ELISA Assay

This assay uses a conventional ELISA method to determine the ability of test compounds to inhibit phosphorylation of tyrosine in KDR (VEGFR2).

Human umbilical vein endothelial cells (HUVECs; PromoCell) were routinely incubated at 37° C. with 7.5% $CO_2$ in 'growth medium' comprising MCDB 131 (Gibco Catalogue No. 10372-019; 500 ml) containing L-glutamine (Sigma Catalogue No. G3126; 0.848 g), 1% Penicillin Streptomycin (Gibco Catalogue No. 15140-122) and Fetal Bovine Serum (PAA Laboratories Catalogue No. A15-043; 50 ml).

For the assay, the cells were detached from the culture flask using a trypsin/ethylenediaminetetraacetic acid (EDTA) mixture (Invitrogen Ltd.; Catalogue No. 15400-054) and resuspended in 'test medium' comprising MCDB 131 (500 ml) containing L-glutamine (0.848 g), 1% Penicillin Streptomycin and Fetal Bovine Serum (10 ml). Aliquots (1 ml) were seeded into each well of a 24 well tissue culture plate (Corning Life Sciences; Catalogue No. 3527) to give a density of approximately $3.5\times10^4$ cells per well. The cells were incubated overnight at 37° C. with 7.5% $CO_2$ to allow adherence to the well surface. The following morning the assay medium was decanted and an aliquot (0.5 ml) of 'serum free medium' comprising MCDB 131 (500 ml) containing L-glutamine (0.848 g) and 1% Penicillin Streptomycin was added to each well. The plates were incubated at 37° C. for 2.5 hours.

Test compounds were prepared as 10 mM stock solutions in DMSO and serially diluted with DMSO as required. Aliquots (3 µl) of each concentration of test compound were diluted with 'serum fiee medium' (300 µl). Aliquots (50 µl) of each resultant compound concentration were added to the cells in each well. "Maximum" control cells received only a dilution of DMSO whereas the "minimum" controls received a reference KDR inhibitor to give a final concentration of 1 µM. The cells were incubated for 90 minutes at 37° C. with 7.5% $CO_2$.

The resultant cells were stimulated with VEGF using the following procedure. A lyopliilised powder of VEGF (Sigma-Aldrich; Catalogue No. V7259) was mixed with PBS containing 0.1% filter-sterilised BSA (0.1% BSA/PBS) to provide a stock solution of 10 µg/ml of VEGF. A dilution of this stock solution into 'serum free medium' provided a 1000 ng/ml VEGF solution. Aliquots thereof (50 µl) were added to all wells. The cells were incubated at 37° C. with 7.5% $CO_2$ for 5 minutes. The solution from the wells was removed and the cells were lysed by the addition of 100 µl/well of RIPA buffer comprising 60 mM Tris-HCl, 150 mM sodium chloride, 1 mM EDTA, 1% v/v Igepal CA-630, 0.25% sodium deoxycholate, 1% v/v phosphatase inhibitor cocktail 1 P2850, 1% phosphatase inhibitor cocktail 2 P5726 and 0.5% v/v protease inhibitor cocktail P8340. The resultant tissue culture plates were shaken for 5 minutes at ambient temperature to ensure full lysis before being frozen on dry-ice and stored at −20° C. until required.

MaxiSorp ELISA plates (Nunc; Catalogue No. 439454) were coated with Phospho-VEGFR2 Capture antibody (R&D Systems, Abingdon, Oxfordshire, UK; Human Phospho-VEGFR2 ELISA, Catalogue No. DYC1766). The antibody was diluted in PBS to a concentration of 8 µg/ml, aliquots (100 µl) were added to each well and the plates were stored at ambient temperature for 16 hours. The wells were washed 3 times (1 minute soak each time) with 300 µl per well of PBST. The wells were treated with PBS containing 1% filter-sterilised BSA (1% BSA/PBS; 200 µl) at ambient temperature for 1 hour and subsequently washed 3 times with 300 µl per well of PBST.

The tissue culture plates with frozen cell lysate were allowed to warm to 0° C. Aliquots (100 µl) of the HUVEC cell lysate were added and the ELISA plates were agitated at ambient temperature for 3 hours. The wells were washed 3 times with 300 µl per well of PBST. A dilution of Anti-Phospho-Tyrosine-HRP Detection antibody (R&D Systems; Human Phospho-VEGFR2 ELISA, Catalogue No. DYC 1766) was diluted with 0.1% BSA in Tris-buffered saline solution containing 0.05% v/v Tween 20 (TBST) to make a working concentration of 600 ng/ml. Aliquots (100 µl) of the resultant dilution were added to each well and the plates were agitated at ambient temperature for 2 hours. The plates were washed 4 times with 300 µl per well of PBST. Chemiluminescent substrate was made up according to manufacturers instructions (Pierce Biotechnology Inc., Rockford Ill., USA; Catalogue No. 34080). Aliquots (50 µl) of chemiluminescent substrate solution were added to each of the wells, the plates were agitated for 2 minutes and luminescence was read on a SpectraFluor is Plus plate reader (Tecan UK Ltd.). The resultant data were analysed to determine the $IC_{50}$ value of each test compound.

(d) In Vitro MG63 Osteosarcoma Proliferation Assay

This assay determined the ability of a test compound to inhibit the proliferation of MG63 osteosarcoma cells (ATCC CCL 1427).

MG63 cells were seeded at $1.5 \times 10^3$ cells per well into 96-well clear tissue culture-treated assay plates (Corning Life Sciences; Catalogue No. 3595) to which had been added 60 µl per well of test medium comprising DMEM without phenol red, 1% charcoal-stripped FCS and 2 mM glutamine and the cells were incubated overnight at 37° C. with 7.5% $CO_2$.

Test compounds were solubilised in DMSO to provide a 10 mM stock solution. Aliquots of the stock solution were diluted with the test medium described above and 20 µl aliquots of each dilution were added to appropriate wells. Serial dilutions were made to give a range of test concentrations. Control wells to which DMSO solution only was added were included on each plate. Each plate was duplicated. A lyophilised powder of $PDGF_{BB}$ was mixed with 4 mM aqueous hydrochloric acid containing 0.1% filter-sterilised BSA to provide a stock solution of 10 µg/ml of $PDGF_{BB}$. A dilution of this stock solution into test medium provided a 250 ng/ml $PDGF_{BB}$ solution. Aliquots (20 µl) thereof were added to one set of control wells to give the "maximum" control. Aliquots (20 µl) thereof were added to one set of the duplicate compound-treated plates and these were denoted as the "$PDGF_{BB}$ stimulated" plates. The second set of duplicate compound-treated plates received media only and these were denoted as the "basal" plates. The "minimum" controls received media only. The plates were incubated at 37° C. with 7.5% $CO_2$ for 72 hours.

BrdU labelling reagent (Roche Diagnostics Ltd., Lewes, East Sussex, UK; Catalogue No. 647 229) was diluted by a factor of 1:100 in DMEM medium containing 1% charcoal stripped FCS and aliquots (10 µl) were added to each well to give a final concentration of 10 µM. The plates were incubated at 37° C. for 2 hours. The medium was decanted. A denaturating solution (FixDenat solution, Roche Diagnostics Ltd.; Catalogue No. 647 229; 200 µl) was added to each well and the plates were agitated at ambient temperature for 30 minutes. The supernatant was decanted and the wells were washed with PBS (200 µl per well). Anti-BrdU-Peroxidase solution (Roche Diagnostics Ltd.; Catalogue No. 647 229) was diluted by a factor of 1:100 in antibody diluent (Roche Diagnostics Ltd., Catalogue No. 647 229) and 100 µl of the resultant solution was added to each well. The plates were agitated at ambient temperature for 90 minutes. The wells were washed with PBS (×3; 300 µl) to ensure removal of non-bound antibody conjugate. The plates were blotted dry and tetramethylbenzidine substrate solution (Roche Diagnostics Ltd.; Catalogue No. 647 229; 100 µl) was added to each well. The plates were gently agitated on a plate shaker while the colour developed during a 10 to 20 minute period. Aqueous sulphuric acid (1M; 50 µl) was added to the appropriate wells to stop any further reaction and the absorbance of the wells was measured at 450 nm. The extent of inhibition of cellular proliferation at a range of concentrations of each test compound was determined and an anti-proliferative $IC_{50}$ value was derived.

(e) In Vitro HUVEC Proliferation Assay

This assay determines the ability of a test compound to inhibit the growth factor-stimulated proliferation of human umbilical vein endothelial cells (HUVECs).

HUVECs were isolated in MCDB 131 (Gibco BRL) and 7.5% v/v foetal calf serum (FCS) and were plated out (at passage 2 to 8) in a mixture of MCDB 131, 2% v/v FCS, 3 µg/ml heparin and 1 µg/ml hydrocortisone, at a concentration of 1000 cells/well in 96 well plates. After a minimum of 4 hours, the cells were dosed with the appropriate growth factor (for example VEGF) and with the test compound. The cultures were incubated for 4 days at 37° C. under 7.5% $CO_2$. On day 4, the cell cultures were pulsed with 1 µCi/well of tritiated-thymidine (Amersham product TRA 61) and incubated for 4 hours. The cells were harvested using a 96-well plate harvester (Tomtek) and assayed for incorporation of tritium with a Beta plate counter. Incorporation of radioactivity into cells, expressed as counts per minute (cpm), was used to measure inhibition of growth factor-stimulated cell proliferation by each test compound.

(f) In Vivo Solid Tumour Disease Model

This test measures the capacity of compounds to inhibit solid tumour growth.

CaLu-6 tumour xenografts were established in the flank of female athyinic Swiss nu/nu mice, by subcutaneous injection of $1 \times 10^6$ CaLu-6 cells/mouse in 100 µl of a 50% (v/v) solution of Matrigel in serum free culture medium. Ten days after cellular implant, mice were allocated to groups of 8-10 animals having comparable group mean tumour volumes. Tumours were measured using vernier calipers and volumes were calculated using the formula $$(l \times w) \times \sqrt{(l \times w)} \times (\pi/6)$$

where l is the longest diameter and w the diameter perpendicular to the longest. Test compounds were administered orally once daily for a minimum of 21 days, and control animals received compound diluent only. Tumours were measured twice weekly. The level of growth inhibition was calculated by comparison of the mean tumour volume of the control group versus the treatment group using a Student's T test and/or a Mann-Whitney Rank Sum Test.

Although the pharmacological properties of the compounds of the Formula I vary with structural change as expected, in general activity possessed by compounds of the Formula I, may be demonstrated at the following concentrations or doses in one or more of the above tests (a), (b), (c), (d), (e) and (f):—

Test (a):-   $IC_{50}$ versus PDGFRα tyrosine kinase in the range, for example, 0.1 nM-5 µM;
            $IC_{50}$ versus PDGFRβ tyrosine kinase in the range, for example, 0.1 nM-5 µM;
Test (b):-   $IC_{50}$ versus phospho-Tyr751 formation in PDGFRβ in the range, for example, 0.1 nM-1 µM;
Test (c):-   $IC_{50}$ versus phospho-tyrosine formation in KDR in the range, for example, 0.1 nM-5 µM;
            whilst those compounds having a more selective inhibitory activity against the PDGF receptor family of tyrosine kinases have an $IC_{50}$ versus phospho-tyrosine formation in KDR in the range, for example, 100 nM to greater than 5 µM;
Test (d):-   $IC_{50}$ versus MG63 osteosarcoma proliferation in the range, for example, 1 nM-5 µM;
Test (e):-   $IC_{50}$ versus HUVEC proliferation in the range, for example, 1 nM-5 µM;
Test (f):-   xenograft activity in the range, for example, 1-200 mg/kg/day.

For example, the quinoline compound disclosed as the sixth Compound listed in Table I within Example 4 possesses activity in Test (b) with an $IC_{50}$ versus phospho-Tyr751 formation in PDGFRβ of approximately 2 nM; and activity in Test (c) with an $IC_{50}$ versus phospho-tyrosine formation in KDR of approximately 0.2 µM.

For example, the quinoline compound disclosed as the seventh Compound listed in Table I within Example 4 possesses activity in Test (b) with an $IC_{50}$ versus phospho-Tyr751 formation in PDGFRβ of approximately 2 nM; and activity in Test (c) with an $IC_{50}$ versus phospho-tyrosine formation in KDR of approximately 0.75 µM.

For example, the quinoline compound disclosed as the thirty fifth Compound listed in Table I within Example 4 possesses activity in Test (b) with an $IC_{50}$ versus phospho-Tyr751 formation in PDGFRβ of approximately 5 nM; and activity in Test (c) with an $IC_{50}$ versus phospho-tyrosine formation in KDR of greater than 2 µM.

For example, the quinoline compound disclosed as the thirty sixth Compound listed in Table I within Example 4 possesses activity in Test (b) with an $IC_{50}$ versus phospho-Tyr751 formation in PDGFβ of approximately 5 nM; and activity in Test (c) with an $IC_{50}$ versus phospho-tyrosine formation in KDR of greater than 2 µM.

For example, the quinoline compound disclosed as the thirty seventh Compound listed in Table I within Example 4 possesses activity in Test (b) with an $IC_{50}$ versus phospho-Tyr751 formation in PDGFRβ of approximately 10 nM; and activity in Test (c) with an $IC_{50}$ versus phospho-tyrosine formation in KDR of greater than 2 µM.

For example, the quinoline compound disclosed as the forty ninth Compound listed in Table I within Example 4 possesses activity in Test (b) with an $IC_{50}$ versus phospho-Tyr751 formation in PDGFRβ of approximately 5 nM; and activity in Test (c) with an $IC_{50}$ versus phospho-tyrosine formation in KDR of about 1 µM.

For example, the quinoline compound disclosed as the fifty ninth Compound listed in Table I within Example 4 possesses activity in Test (b) with an $IC_{50}$ versus phospho-Tyr751 formation in PDGFRβ of approximately 5 nM; and activity in Test (c) with an $IC_{50}$ versus phospho-tyrosine formation in KDR of greater than 2 µM.

For example, the quinoline compound disclosed as the third Compound listed in Table II within Example 5 possesses activity in Test (b) with an $IC_{50}$ versus phospho-Tyr751 formation in PDGFRβ of approximately 3 nM; and activity in Test (c) with an $IC_{50}$ versus phospho-tyrosine formation in KDR of approximately 0.7 µM.

For example, the quinoline compound disclosed as the fifty sixth Compound listed in Table II within Example 5 possesses activity in Test (b) with an $IC_{50}$ versus phospho-Tyr751 formation in PDGFRβ of approximately 20 nM; and activity in Test (c) with an $IC_{50}$ versus phospho-tyrosine formation in KDR of greater than 1 µM.

For example, the quinoline compound disclosed as the ninetieth Compound listed in Table II within Example 5 possesses activity in Test (b) with an $IC_{50}$ versus phospho-Tyr751 formation in PDGFRβ of approximately 10 nM; and activity in Test (c) with an $IC_{50}$ versus phospho-tyrosine formation in KDR of greater than 2 µM.

For example, the quinoline compound disclosed as the ninety eigth Compound listed in Table II within Example 5 possesses activity in Test (b) with an $IC_{50}$ versus phospho-Tyr751 formation in PDGFRβ of approximately 10 nM; and activity in Test (c) with an $IC_{50}$ versus phospho-tyrosine formation in KDR of greater than 2 µM.

For example, the quinoline compound disclosed as the ninety ninth Compound listed in Table II within Example 5 possesses activity in Test (b) with an $IC_{50}$ versus phospho-Tyr751 formation in PDGFRβ of approximately 10 nM; and activity in Test (c) with an $IC_{50}$ versus phospho-tyrosine formation in KDR of greater than 2 µM.

For example, the quinoline compound disclosed as Example 17 possesses activity in Test (b) with an $IC_{50}$ versus phospho-Tyr751 formation in PDGFRβ of approximately 10 nM; and activity in Test (c) with an $IC_{50}$ versus phospho-tyrosine formation in KDR of greater than 2 µM.

No untoward toxicological effects are expected when a compound of Formula I, or a pharmaceutically-acceptable salt thereof, as defined hereinbefore is administered at the dosage ranges defined hereinafter.

According to a further aspect of the invention there is provided a pharmaceutical composition which comprises a quinoline derivative of the Formula I, or a pharmaceutically-acceptable salt thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 1 mg to 1 g of active agent (more suitably from 1 to 250 mg, for example from 1 to 100 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the disease state, the age and sex of the animal or patient and the route of administration, according to well known principles of medicine.

In using a compound of the Formula I for therapeutic or prophylactic purposes it will generally be administered so that a daily dose in the range, for example, 1 mg/kg to 100 mg/kg body weight is received, given if required in divided doses. In general, lower doses will be administered when a parenteral route is employed. Thus, for example, for intravenous administration, a dose in the range, for example, 1 mg/kg to 25 mg/kg body weight will generally be used. Similarly, for administration by inhalation, a dose in the range, for example, 1 mg/kg to 25 mg/kg body weight will be used. Oral administration is however preferred, particularly in tablet form. More potent compounds will generally be administered so that a daily oral dose in the range, for example, 1 mg/kg to 25 mg/kg body weight is received. The most potent compounds will generally be administered so that a daily oral dose in the range, for example, 1 mg/kg to 15 mg/kg body weight is received. Typically, unit dosage forms will contain about 10 mg to 0.5 g of a compound of this invention.

As stated above, antagonism of the activity of PDGF receptor kinases, particularly inhibition of the PDGFα and/or PDGFβ receptor tyrosine kinases, is expected to be beneficial in the treatment of a number of cell proliferative disorders such as cancer, especially in inhibiting tumour growth and metastasis and in inhibiting the progression of leukaemia.

We have now found that the novel quinoline derivatives described herein possess potent activity against cell proliferative disorders. It is believed that the compounds provide a useful treatment of cell proliferative disorders, for example to provide an anti-tumour effect, by way of a contribution from inhibition of PDGF receptor tyrosine kinases. In addition, as stated hereinbefore, PDGF is involved in angiogenesis, the process of forming new blood vessels that is critical for continuing tumour growth. It is therefore believed that the compounds of the present invention are expected to be beneficial in the treatment of a number of disease states that are associated with angiogenesis and/or increased vascular permeability such as cancer, especially in inhibiting the development of tumours.

According to this further aspect of the invention there is provided a quinoline derivative of the Formula I, or a pharmaceutically-acceptable salt thereof, as defined hereinbefore for use as a medicament in a warm-blooded animal such as man.

According to a further aspect of the invention, there is provided a quinoline derivative of the Formula I, or a pharmaceutically-acceptable salt thereof, as defined hereinbefore for use in the treatment (or prophylaxis) of cell proliferative disorders or in the treatment (or prophylaxis) of disease states associated with angiogenesis and/or vascular permeability.

According to a further aspect of the invention, there is provided the use of a quinoline derivative of the Formula I, or a pharmaceutically-acceptable salt thereof, as defined hereinbefore in the manufacture of a medicament for use in the treatment (or prophylaxis) of cell proliferative disorders or in the treatment (or prophylaxis) of disease states associated with angiogenesis and/or vascular permeability.

According to this aspect of the invention there is also provided a method for the treatment (or prophylaxis) of cell proliferative disorders in a warm-blooded animal in need of such treatment (or prophylaxis) or for the treatment (or prophylaxis) of disease states associated with angiogenesis and/or vascular permeability in a warm-blooded animal in need of such treatment (or prophylaxis) which comprises administering to said animal an effective amount of a quinoline derivative of the Formula I, or a pharmaceutically-acceptable salt thereof, as defined hereinbefore.

Suitable cell proliferative disorders include neoplastic disorders, for example, cancers of the lung (non-small cell lung cancer, small cell lung cancer and bronchioalveolar cancer), gastrointestine (such as colon, rectal and stomach tumours), prostate, breast, kidney, liver, brain (such as glioblastoma), bile duct, bone, bladder, head and neck, oesophagus, ovary, pancreas, testes, thyroid, cervix and vulva and skin (such as dermatofibrosarcoma protruberans) and in leukaemias and lymphomas such as chronic myelogenous leukaemia (CML), chronic myelomonocytic leukaemia (CMML), acute lymphocytic leukaemia (ALL), chronic neutrophilic leukaemia (CNL), acute myelogenous leukaemia (AML) and multiple myeloma.

According to this aspect of the invention there is also provided a method for treating cell proliferative disorders (such as solid tumour disease) in a warm-blooded animal in need of such treatment which comprises administering to said animal an effective amount of a quinoline derivative of the Formula I, or a pharmaceutically-acceptable salt thereof, as defined hereinbefore.

Other suitable cell proliferative disorders include non-malignant disorders such as blood vessel disease (for example atherosclerosis and restenosis, for example in the process of restenosis subsequent to balloon angioplasty and heart arterial by-pass surgery), fibrotic diseases (for example kidney fibrosis, hepatic cirrhosis, lung fibrosis and multicystic renal dysplasia), glomerulonephritis, benign prostatic hypertrophy, inflammatory diseases (for example rheumatoid arthritis and inflammatory bowel disease), multiple sclerosis, psoriasis, hypersensitivity reactions of the skin, allergic asthma, insulin-dependent diabetes, diabetic retinopathy and diabetic nephropathy.

Suitable disease states associated with angiogenesis and/or vascular permeability include, for example, the undesirable or pathological angiogenesis seen in diabetic retinopathy, psoriasis, cancer, rheumatoid arthritis, atheroma, Kaposi's sarcoma and haemangioma.

According to a further aspect of the invention there is provided a quinoline derivative of the Formula I, or a pharmaceutically-acceptable salt thereof, as defined hereinbefore for use in the treatment (or prevention) of those tumours which are sensitive to inhibition of PDGF receptor enzymes (such as PDGFα and/or PDGFβ receptor tyrosine kinase) that are involved in the signal transduction steps which lead to the proliferation, survival, invasiveness and migratory ability of tumour cells.

According to a further feature of this aspect of the invention there is provided the use of a quinoline derivative of the Formula I, or a pharmaceutically-acceptable salt thereof, as defined hereinbefore in the manufacture of a medicament for use in the treatment (or prevention) of those tumours which are sensitive to inhibition of PDGF receptor enzymes (such as PDGFα and/or PDGFβ receptor tyrosine kinase) that are involved in the signal transduction steps which lead to the proliferation, survival, invasiveness and migratory ability of tumour cells.

According to a further feature of this aspect of the invention there is provided a method for the treatment (or prevention) of a warm-blooded animal having tumours which are sensitive to inhibition of PDGF receptor enzymes (such as PDGFα and/or PDGFβ receptor tyrosine kinase) that are involved in the signal transduction steps which lead to the proliferation, survival, invasiveness and migratory ability of tumour cells which comprises administering to said animal an effective amount of a quinoline derivative of the Formula I, or a pharmaceutically-acceptable salt thereof, as defined hereinbefore.

According to a further aspect of the invention there is provided a quinoline derivative of the Formula I, or a pharmaceutically-acceptable salt thereof, as defined hereinbefore for use in providing a PDGF receptor enzyme inhibitory effect (such as a PDGFα and/or PDGFβ receptor tyrosine kinase inhibitory effect).

According to a further feature of this aspect of the invention there is provided the use of a quinoline derivative of the Formula I, or a pharmaceutically-acceptable salt thereof, as defined hereinbefore in the manufacture of a medicament for use in providing a PDGF receptor enzyme inhibitory effect (such as a PDGFα and/or PDGFβ receptor tyrosine kinase inhibitory effect).

According to a further aspect of the invention there is also provided a method for inhibiting a PDGF receptor enzyme (such as the PDGFα and/or PDGFβ receptor tyrosine kinase) which comprises administering an effective amount of a quinoline derivative of the Formula I, or a pharmaceutically-acceptable salt thereof, as defined hereinbefore.

The anti-cancer treatment defined hereinbefore may be applied as a sole therapy or may involve, in addition to the quinoline derivative of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine, taxoids like taxol and taxotere, and polo kinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZDO530; International Patent Application WO 01/94341) and bosutinib (SKI-606), and metalloproteinase inhibitors like marimastat and inhibitors of urokinase plasminogen activator receptor function];

(iv) inhibitors of growth factor function: for example such inhibitors include growth factor antibodies and growth factor receptor antibodies [for example the anti-erbB2 antibody trastuzumab and the anti-erbB1 antibodies cetuximab (C225) and panitumumab]; such inhibitors also include, for example, tyrosine kinase inhibitors [for example inhibitors of the epidermal growth factor family (for example EGFR family tyrosine kinase inhibitors such as gefitinib (ZD1839), erlotinib (OSI-774) and CI 1033, and erbB2 tyrosine kinase inhibitors such as lapatinib), inhibitors of the hepatocyte growth factor family, inhibitors of the insulin growth factor receptor, other inhibitors of the platelet-derived growth factor family and/or bcr/abl kinase such as imatinib, dasatinib (BMS-354825) and nilotinib (AMN107), inhibitors of cell signalling through MEK, AKT, PI3, c-kit, Flt3, CSF-1R and/or aurora kinases]; such inhibitors also include cyclin dependent kinase inhibitors including CDK2 and CDK4 inhibitors; and such inhibitors also include, for example, inhibitors of serine/threonine kinases (for example Ras/Raf signalling inhibitors such as farnesyl transferase inhibitors, for example sorafenib (BAY 43-9006), tipifarnib (R115777) and lonafamib (SCH66336);

(v) antiangiogenic agents such as those which inhibit the effects of vascular endothelial growth factor, [for example an anti-vascular endothelial cell growth factor antibody such as bevacizumab (Avastin™) or, for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), or, for example, a compound that works by another mechanism (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination suitable for use in the treatment of cell proliferative disorders (such as solid tumour disease) comprising a quinoline derivative of the formula I as defined hereinbefore and an additional anti-tumour agent as defined hereinbefore.

According to this aspect of the invention there is also provided a pharmaceutical product comprising a quinoline derivative of the formula I as defined hereinbefore and an additional anti-tumour agent as defined hereinbefore for the conjoint treatment of cancer.

In particular, the anti-cancer treatment defined hereinbefore may involve the quinoline derivative of the invention in combination with an antiangiogenic agent, for example, an anti-vascular endothelial cell growth factor antibody such as bevacizumab and/or a VEGF receptor tyrosine kinase inhibitor such as vandetanib, vatalanib, sunitinib or AZD2171.

According to this aspect of the invention there is provided a combination suitable for use in the treatment of cell proliferative disorders (such as solid tumour disease) comprising a quinoline derivative of the formula I as defined hereinbefore and an antiangiogenic agent as defined hereinbefore.

According to this aspect of the invention there is also provided a pharmaceutical product comprising a quinoline derivative of the formula I as defined hereinbefore and an antiangiogenic agent as defined hereinbefore for the conjoint treatment of cancer.

The anti-cancer treatment defined hereinbefore may also involve the quinoline derivative of the invention in combination with an anti-invasion agent, for example, a c-Src kinase family inhibitor such as AZD0530 or bosutinib.

According to this aspect of the invention there is provided a combination suitable for use in the treatment of cell proliferative disorders (such as solid tumour disease) comprising a quinoline derivative of the formula I as defined hereinbefore and an anti-invasion agent as defined hereinbefore.

According to this aspect of the invention there is also provided a pharmaceutical product comprising a quinoline derivative of the formula I as defined hereinbefore and an anti-invasion agent as defined hereinbefore for the conjoint treatment of cancer.

The anti-cancer treatment defined hereinbefore may also involve the quinoline derivative of the invention in combination with both an antiangiogenic agent, for example, an anti-vascular endothelial cell growth factor antibody such as bevacizumab and/or a VEGF receptor tyrosine kinase inhibitor such as vandetanib, vatalanib, sunitinib or AZD2171, and an anti-invasion agent, for example, a c-Src kinase family inhibitor such as AZD0530 or bosutinib.

According to this aspect of the invention there is provided a combination suitable for use in the treatment of cell proliferative disorders (such as solid tumour disease) comprising a quinoline derivative of the formula I as defined hereinbefore, an antiangiogenic agent as defined hereinbefore and an anti-invasion agent as defined hereinbefore.

According to this aspect of the invention there is also provided a pharmaceutical product comprising a quinoline derivative of the formula I as defined hereinbefore, an anti-angiogenic agent as defined hereinbefore and an anti-invasion agent as defined hereinbefore for the conjoint treatment of cancer.

In any of the conjoint treatments of cancer described hereinbefore, a bisphosphonate compound may optionally also be present.

Bisphosphonate compounds are diphosphonic acid derivatives that are capable of regulating metal cation (especially calcium) processing within warm-blooded animals such as humans. Accordingly, bisphosphonates are useful in the prevention or treatment of diseases such as osteoporosis and osteolytic bone disease, for example the osteolytic lesions that may occur with metastatic cancers such as renal, thyroid and lung cancers, in particular with breast and prostate cancers. Suitable bisphosphonates include tiludronic acid, ibandronic acid, incadronic acid, risedronic acid, zoledronic acid, clodronic acid, neridronic acid, pamidronic acid and alendronic acid.

Although the compounds of the Formula I are primarily of value as therapeutic agents for use in warm-blooded animals (including man), they are also useful whenever it is required to inhibit the effects of PDGF receptor tyrosine kinase enzymes. Thus, they are useful as pharmacological standards for use in the development of new biological tests and in the search for new pharmacological agents.

The invention will now be illustrated in the following Examples in which, generally:

(i) operations were carried out at ambient temperature, i.e. in the range 17 to 25° C., and under an atmosphere of an inert gas such as nitrogen or argon unless otherwise stated;

(ii) reactions conducted under microwave radiation were performed using an instrument such as a 'Smith Synthesiser' (300 KWatts) on either the normal or high setting, which instrument makes use of a temperature probe to adjust the microwave power ouput automatically in order to maintain the required temperature; alternatively an 'Emrys Optimizer' microwave instrument may be used;

(iii) in general, the course of reactions was followed by thin layer chromatography (TLC) and/or analytical high pressure liquid chromatography (HPLC); the reaction times that are given are not necessarily the minimum attainable;

(iv) when necessary, organic solutions were dried over anhydrous magnesium sulphate, work-up procedures were carried out after removal of residual solids by filtration, evaporations were carried out by rotary evaporation in vacuo;

(v) yields, where present, are not necessarily the maximum attainable, and, when necessary, reactions were repeated if a larger amount of the reaction product was required;

(vi) in general, the structures of the end-products of the Formula I were confirmed by nuclear magnetic resonance (NMR) and/or mass spectral techniques; electrospray mass spectral data were obtained, for example using a Waters ZMD or Waters ZQ LC/mass spectrometer acquiring both positive and negative ion data, generally, only ions relating to the parent structure are reported; proton NMR ($^1$H NMR) chemical shift values were measured on the delta scale, for example using a Bruker Spectrospin DPX300 spectrometer operating at a field strength of 300 MHz; the following abbreviations have been used: s, singlet; d, doublet; t, triplet; q, quartet; m, multiplet; br, broad;

(vii) unless stated otherwise compounds containing an asymmetric carbon and/or sulphur atom were not resolved;

(viii) intermediates were not necessarily fully purified but their structures and purity were assessed by TLC, analytical HPLC, infra-red (IR) and/or NMR analysis;

(ix) column chromatography (by the flash procedure) and medium pressure liquid chromatography (MPLC) were performed on silica gel, for example using Merck Kieselgel silica (Art. 9385) or using columns from Armen Instrument (56890-Saint Ave, France);

(x) preparative HPLC was performed on C18 reversed-phase silica, for example on a Waters 'XterTa' preparative reversed-phase column (5 microns silica, 19 mm diameter, 100 mm length) or on a Novasep SAS 'Prochrom DAC' preparative reversed-phase column using decreasingly polar solvent mixtures as eluent, for example decreasingly polar mixtures of 1% aqueous acetic acid or 1% aqueous ammonium hydroxide (d=0.88) solution and acetonitrile;

(xi) melting points obtained using Differential Scanning Calorimetry were determined using a Mettler DSC820e instrument [Typically, the pan type was aluminium (0.04 ml size) with a pierced lid. The sample weight was approximately 1 to 5 mg. The procedure was carried out under a flow of nitrogen gas (100 ml/min) and the temperature range studied was 25° C. to 325° C. at a constant rate of temperature increase of 10° C. per minute. The skilled person will realise that the precise value of the melting point will be influenced by the purity of the compound, the sample weight, the heating rate and the particle size. It will therefore be appreciated that alternative readings of melting point may be given by other types of equipment or by using conditions different to those described. Hence, the figures quoted herein should not to be taken as absolute values.];

(xii) where certain compounds were obtained as an acid-addition salt, for example a mono-hydrochloride salt or a di-hydrochloride salt, the stoichiometry of the salt was based on the number and nature of the basic groups in the compound; generally, unless otherwise stated, elemental analysis data were not obtained to determine the exact stoichiometry of the salt;

(xiii) the following abbreviations have been used:—
DMF N,N-dimethylformamide
DMA N,N-dimethylacetamide
DMSO dimethyl sulphoxide
THF tetrahydrofuran
NMP N-methylpyrrolidin-2-one

EXAMPLE 1

N-(3-isoxazolyl)-2-[4-(6,7-dimethoxyquinolin-4-yloxy)phenyl]acetamide 1-(3-Dimethylaminopropyl)-3-ethylcarbodiimide hydrochloride (0.226 g) and 2-hydroxypyridine N-oxide (0.131 g) were added in turn to a stirred mixture of 2-[4-(6,7-dimethoxyquinolin-4-yloxy)phenyl]acetic acid (0.2 g), 3-aminoisoxazole (0.064 g), diisopropylethylamine (0.226 g) and DMF (3 ml) at ambient temperature. The resultant mixture was stirred and heated to 60° C. for 16 hours. The mixture was evaporated and the residue was purified by preparative HPLC using a Waters 'Xterra' reversed-phase column (5 microns silica, 30 mm diameter, 150 mm length) using decreasingly polar mixtures of water (containing 0.2% ammonium carbonate) and acetoliitrile as eluent. There was thus obtained the title compound (0.035 g); $^1$H NMR: (DMSOd$_6$) 3.76 (s, 2H), 3.92 (s, 3H), 3.95 (s, 3H), 6.47 (d, 1H), 6.93 (d, 1H), 7.23 (d, 2H), 7.4 (s, 1H), 7.46 (d, 2H), 7.49 (s, 1H), 8.49 (d, 1H), 8.80 (d, 1H), 11.33 (br s, 1H); Mass Spectrum: M+H$^+$ 406.

The 2-[4-(6,7-dimethoxyquinolin-4-yloxy)phenyl]acetic acid used as a starting material was prepared as follows:—

A mixture of 4-chloro-6,7-dimethoxyquinoline (1.28 g; International Patent Application WO 98/13350, Example 2 thereof), 2-(4-hydroxyphenyl)acetic acid (1.73 g), caesium carbonate (7.46 g) and DMF (12.5 ml) was stirred and heated to reflux for 7 hours. The mixture was cooled to ambient temperature and diethyl ether was added. The gummy precipitated solid was dissolved in water and washed with methylene chloride. The aqueous solution was acidified to pH4.5 by the addition of glacial acetic acid. The resultant precipitate was isolated, washed with water and with diethyl ether and dried under vacuum. There was thus obtained the required starting material (1.57 g); $^1$H NMR: (DMSOd$_6$) 3.64 (s, 2H), 3.93 (s, 3H), 3.95 (s, 3H), 6.46 (d, 1H), 7.21 (d, 2H), 7.39 (s, 1H), 7.41 (d, 2H), 7.49 (s, 1H), 8.48 (d, 1H); Mass Spectrum: M+H$^+$ 340.

EXAMPLE 2

N-[1-(2-methoxyethyl)pyrazol-4-yl]-2-[4-(6,7-dimethoxyquinolin-4-yloxy)phenyl]acetamide Diisopropylethylamine (0.124 ml) and 2-(7-azabenzotriazol-1-yl)-1,1,3,3-tetramethyluronium hexafluorophosphate (V) (0.247 g) were added in turn to a stirred mixture of 2-[4-(6,7-dimethoxyquinolin-4-yloxy)phenyl]acetic acid (0.2 g), 4-amino-1-(2-methoxyethyl)pyrazole (0.092 g) and DMF (3 ml) and the resultant mixture was stirred at ambient temperature for 18 hours. The resultant mixture was evaporated and the residue was purified by column cliromatography on silica using a solvent gradient from 100:0 to 24:1 mixtures of methylene chloride and a 3.5M methanolic ammonia solution as eluent. There was thus obtained the title compound as a solid (0.106 g); $^1$H NMR: (DMSOd$_6$) 3.21 (s, 3H), 3.62 (s, 2H), 3.63 (t, 2H), 3.92 (s, 3H), 3.94 (s, 3H), 4.12 (t, 2H), 6.47 (d, 1H), 7.22 (d, 2H), 7.4 (s, 1H), 7.44 (s, 1H), 7.45 (d, 2H), 7.49 (s, 1H), 7.89 (s, 1H), 8.47 (d, 1H), 10.2 (s, 1H); Mass Spectrum: M+H$^+$ 463.

The 4-amino-1-(2-methoxyethyl)pyrazole used as a starting material was prepared as follows:—

4-Nitropyrazole is available commercially from the N. D. Zelinsky Institute, Organic Chemistry, Leninsky prospect 47, 117913 Moscow B-334, Russia. The compound may also be prepared as follows:—

Fuming nitric acid (9.5 ml) was added dropwise to a stirred solution of pyrazole (13.6 g) in glacial acetic acid (51 ml) that had been cooled to −10° C. using an ice-salt bath. A voluminous precipitate was formed. Acetic anhydride (27 ml) was added dropwise and the resultant mixture was stirred at ambient temperature for 2.5 hours. The mixture was poured onto ice and the acidity of the mixture was reduced to pH5 by the addition of potassium carbonate. The precipitate was isolated by filtration. The resultant solid was dissolved in water and the aqueous solution was extracted with diethyl ether. The organic solution was dried over magnesium sulphate and filtered. Petroleum ether (b.p. 60-80° C., 50 ml) was added to the filtrate which was concentrated by evaporation to a volume of about 50 ml. A precipitate formed which was isolated by filtration. This solid was believed to be 1-nitropyrazole (20.6 g); $^1$H NMR: (DMSOd$_6$) 6.71 (s, 1H), 7.88 (s, 1H), 8.81 (s, 1H). The compound may be explosive and should be handled cautiously.

Concentrated sulphuric acid (80 ml) was added dropwise to a stirred sample of 1-nitropyrazole (20.3 g) that was cooled in an ice-bath. The resultant mixture was stirred for 16 hours and allowed to warm to ambient temperature. The mixture was poured onto ice and stirred for 20 minutes. The resultant solid was isolated and washed with water. The filtrate was neutralised by the addition of potassium carbonate and extracted with diethyl ether. The recovered solid was added to the diethyl ether solution and the resultant solution was washed with a saturated aqueous sodium chloride solution, dried over magnesium sulphate and filtered. Petroleum ether (b.p. 60-80° C.) was added to the filtrate which was concentrated by evaporation to a volume of about 50 ml. A precipitate formed which was isolated by filtration. There was thus obtained 4-nitropyrazole (16 g); $^1$H NMR: (DMSOd$_6$+ CF$_3$CO$_2$H) 8.57 (s, 2H).

A mixture of 4-nitropyrazole (0.8 g), 2-methoxyethyl bromide (0.73 ml), potassium carbonate (1.46 g) and acetonitrile (15 ml) was stirred and heated to 60° C. for 6 hours. The resultant mixture was evaporated and the residue was purified by column chromatography on silica using a 99:1 mixture of methylene chloride and ethyl acetate as eluent. There was thus obtained 1-(2-methoxyethyl)-4-nitro-1H-pyrazole (0.98 g); $^1$H NMR: (CDCl$_3$) 3.36 (s, 3H), 3.75 (t, 2H), 4.32 (t, 2H), 8.07 (s, 1H), 8.23 (s, 1H).

A mixture of the material so obtained, 10% palladium on carbon catalyst (0.2 g) and ethanol (50 ml) was stirred under an atmospheres pressure of hydrogen for 45 minutes. The catalyst was removed by filtration and the filtrate was evaporated. There was thus obtained the required starting material as an oil (0.8 g); $^1$H NMR: (DMSOd$_6$) 3.21 (s, 3H), 3.58 (t, 2H), 3.75 (br s, 2H), 4.05 (t, 2H), 6.89 (s, 1H), 7.01 (s, 1H).

EXAMPLE 3

N-(3-methyl-1,2,4-oxadiazol-5-yl)-2-[4-(6,7-dimethoxyquinolin-4-yloxy)phenyl]acetamide Oxalyl chloride (0.5 ml) was added dropwise to a stirred suspension of 2-[4-(6,7-dimethoxyquinolin-4-yloxy)phenyl] acetic acid (0.2 g) in chloroform (5 ml) at ambient temperature under argon. The resultant mixture was heated to reflux for 30 minutes. The mixture was evaporated to leave 2-[4-(6, 7-dimethoxyquinolin-4-yloxy)phenyl]acetyl chloride as a solid. Chloroform (5 ml) and 5-amino-3-methyl-1,2,4 oxadiazole (0.099 g) were added in turn. Pyridine (0.286 ml) was added and the reaction mixture was stirred at ambient temperature for 16 hours. The solvent was evaporated and the residue was purified by preparative HPLC using a Waters 'Xterra' reversed-phase column (5 microns silica, 30 mm diameter, 250 mm length) that was eluted with decreasingly polar mixtures of water (containing 0.2% ammonium carbonate) and acetonitrile as eluent. There was thus obtained the title compound (0.053 g); $^1$H NMR: (DMSOd$_6$) 2.26 (s, 3H), 3.86 (s, 2H), 3.92 (s, 3H), 3.95 (s, 3H), 6.46 (d, 1H), 7.24 (d, 2H), 7.4 (s, 1H), 7.44 (d, 2H), 7.49 (s, 1H), 8.48 (d, 1H), 11.27 (br s, 1H); Mass Spectrum: M+H$^+$ 421.

The 5-amino-3-methyl-1,2,4-oxadiazole used as a starting material was prepared as follows:—

A mixture of acetamide oxime (1.7 g) and trichloroacetic acid anhydride was stirred and heated to 150° C. for 1 hour. The solution was cooled to ambient temperature and partitioned between diethyl ether and water. The organic phase was washed with a saturated solution of sodium bicarbonate, dried over magnesium sulphate and evaporated. The residual oil was distilled under reduced pressure. There was thus obtained 3-methyl-5-trichloromethyl-1,2,4-oxadiazole as an oil (2.66 g); $^1$H NMR: (CDCl$_3$) 2.5 (s, 3H).

A mixture of the material so obtained and a 7M methanolic ammonia solution (30 ml) was stirred at ambient temperature for 16 hours. The resultant mixture was concentrated. The solid so obtained was recrystallised from a toluene solution. There was thus obtained the required starting material (1.28 g); $^1$H NMR: (CDCl$_3$) 2.23 (s, 3H), 5.42 (br s, 2H).

EXAMPLE 4

Using an analogous procedure to that described in Example 1, the appropriate 2-phenylacetic acid was reacted with the appropriate amine to give the compounds described in Table I. Unless otherwise stated, each reaction product was purified by preparative HPLC using a Waters 'Xterra' reversed-phase column and decreasingly polar mixtures of water (containing 0.2% ammonium carbonate) and acetonitrile as eluent. Unless otherwise stated, each amine was a commercially available material.

TABLE I

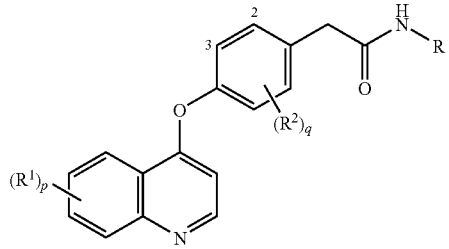

| No. & Note | (R$^1$)$_p$ | (R$^2$)$_q$ | R |
|---|---|---|---|
| [1] | 6,7-dimethoxy | H | pyrazol-4-yl |
| [2] | 6-cyano-7-methoxy | H | pyrazol-4-yl |
| [3] | 6,7-dimethoxy | H | 1-methylpyrazol-4-yl |
| [4] | 6-cyano-7-methoxy | H | 1-methylpyrazol-4-yl |
| [5] | 6,7-dimethoxy | H | 1-ethylpyrazol-4-yl |
| [6] | 6-cyano-7-methoxy | H | 1-ethylpyrazol-4-yl |
| [7] | 6-cyano-7-methoxy | 2-methoxy | 1-ethylpyrazol-4-yl |
| [8] | 6,7-dimethoxy | H | 1-isopropylpyrazol-4-yl |
| [9] | 6-cyano-7-methoxy | H | 1-isopropylpyrazol-4-yl |
| [10] | 6,7-dimethoxy | H | 1-(2-hydroxyethyl)pyrazol-4-yl |
| [11] | 6-cyano-7-methoxy | H | 1-(2-hydroxyethyl)pyrazol-4-yl |
| [12] | 6,7-dimethoxy | H | 5-methylpyrazol-3-yl |
| [13] | 6-cyano-7-methoxy | H | 5-methylpyrazol-3-yl |
| [14] | 6,7-dimethoxy | H | 5-ethylpyrazol-3-yl |
| [15] | 6-cyano-7-methoxy | H | 5-ethylpyrazol-3-yl |
| [16] | 6-cyano-7-methoxy | 2-methoxy | 5-ethylpyrazol-3-yl |
| [17] | 6,7-dimethoxy | H | 1H-pyrazol-3-yl |
| [18] | 6-cyano-7-methoxy | H | 1H-pyrazol-3-yl |
| [19] | 6,7-dimethoxy | H | 1-methylpyrazol-3-yl |
| [20] | 6-cyano-7-methoxy | H | 1-methylpyrazol-3-yl |
| [21] | 6,7-dimethoxy | H | 5-hydroxymethylpyrazol-3-yl |
| [22] | 6-cyano-7-methoxy | H | 5-hydroxymethylpyrazol-3-yl |
| [23] | 6-cyano-7-methoxy | H | 3-isoxazolyl |
| [24] | 6,7-dimethoxy | H | 5-methylisoxazol-3-yl |
| [25] | 6-cyano-7-methoxy | H | 5-methylisoxazol-3-yl |
| [26] | 6,7-dimethoxy | H | 4,5-dimethyloxazol-2-yl |
| [27] | 6,7-dimethoxy | H | 4-methylthiazol-2-yl |
| [28] | 6-cyano-7-methoxy | H | 4-methylthiazol-2-yl |
| [29] | 6-cyano-7-methoxy | H | 4,5-dimethylthiazol-2-yl |
| [30] | 6-carbamoyl-7-methoxy | 2-methoxy | 1-ethylpyrazol-4-yl |
| [31] | 6-(N-methylcarbamoyl)-7-methoxy | 2-methoxy | 1-ethylpyrazol-4-yl |
| [32] | 6-(N-methylcarbamoyl)-7-methoxy | 2-methoxy | 1-methylpyrazol-4-yl |
| [33] | 7-methoxy | 2-methoxy | 1-ethylpyrazol-4-yl |
| [34] | 6-methoxycarbonyl | 2-methoxy | 1-ethylpyrazol-4-yl |
| [35] | 7-methoxy | 2-methoxy | 1-methylpyrazol-4-yl |
| [36] | 7-methoxy | 2-methoxy | 1,3-dimethylpyrazol-4-yl |
| [37] | 7-methoxy | 2-methoxy | 1,5-dimethylpyrazol-4-yl |
| [38] | 6-(N-methylcarbamoyl)-7-methoxy | 2-methoxy | 1,3-dimethylpyrazol-4-yl |
| [39] | 6-(N-methylcarbamoyl)-7-methoxy | 2-methoxy | 1,5-dimethylpyrazol-4-yl |
| [40] | 6-(N-methylcarbamoyl)-7-methoxy | 2-methoxy | 5-ethylpyrazol-3-yl |
| [41] | 7-methoxy | 2-methoxy | 5-ethylpyrazol-3-yl |
| [42] | 7-methoxy | 2-methoxy | 4,5-dimethylpyrazol-3-yl |
| [43] | 6-fluoro | 2-methoxy | 5-ethylpyrazol-3-yl |
| [44] | 7-fluoro | 2-methoxy | 5-ethylpyrazol-3-yl |
| [45] | 6-(N-methylcarbamoyl)-7-methoxy | 2-methoxy | 5-methylisoxazol-3-yl |
| [46] | 7-methoxy | 2-methoxy | 5-methylisoxazol-3-yl |
| [47] | 7-methoxy | 2-methoxy | 5-ethylisoxazol-3-yl |
| [48] | 7-methoxy | 2-methoxy | 4-methylisoxazol-3-yl |

TABLE I-continued

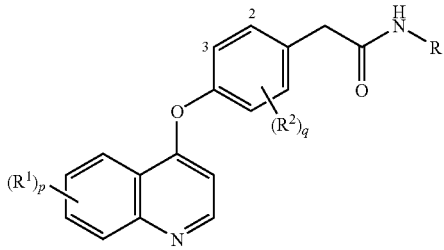

| No. & Note | $(R^1)_p$ | $(R^2)_q$ | R |
|---|---|---|---|
| [49] | 6-(N-methylcarbamoyl)-7-methoxy | 2-methoxy | 4,5-dimethylisoxazol-3-yl |
| [50] | 7-methoxy | 2-methoxy | 4,5-dimethylisoxazol-3-yl |
| [51] | 6-carbamoyl-7-methoxy | 2-methoxy | 5-methylthiazol-2-yl |
| [52] | 7-methoxy | 2-methoxy | 5-methylthiazol-2-yl |
| [53] | 6-carbamoyl-7-methoxy | 2-methoxy | 4-dimethylaminopyridin-2-yl |
| [54] | 7-methoxy | 2-methoxy | 4-dimethylaminopyridin-2-yl |
| [55] | 7-methoxy | 2-methoxy | pyrazin-2-yl |
| [56] | 7-methoxy | 2-methoxy | 3-dimethylaminomethyl-5-methylphenyl |
| [57] | 6-carbamoyl-7-methoxy | 2-methoxy | 5-ethylisoxazol-3-yl |
| [58] | 6,7-dimethoxy | 2-methoxy | 4-methylpyrazol-3-yl |
| [59] | 6,7-dimethoxy | 2-methoxy | 4-ethylpyrazol-3-yl |
| [60] | 7-methoxy | 2-methoxy | 4-ethylpyrazol-3-yl |
| [61] | 6,7-dimethoxy | 2-methoxy | 3-methylpyrazol-4-yl |
| [62] | 7-methoxy | 2-methoxy | 3-methylpyrazol-4-yl |
| [63] | 7-methoxy | 2-methoxy | 3,5-dimethylpyrazol-4-yl |
| [64] | 6-fluoro | 2-methoxy | 3-methylpyrazol-4-yl |
| [65] | 7-methoxy | 2-methoxy | 4-methylpyrazol-3-yl |
| [66] | 6-fluoro | 2-methoxy | 4-methylpyrazol-3-yl |
| [67] | 6-fluoro | 2-methoxy | 4-ethylpyrazol-3-yl |
| [68] | 7-fluoro | 2-methoxy | 4-methylpyrazol-3-yl |

Notes The products gave the characterising data shown below.

[1] $^1$H NMR: (DMSOd$_6$) 3.63 (s, 2H), 3.92 (s, 3H), 3.95 (s, 3H) 6.46 (d, 1H), 7.22 (d, 2H), 7.4 (s, 1H), 7.44 (d, 2H), 7.49 (s, 1H), 7.52 (br s, 1H), 7.84 (br s, 1H), 8.47 (d, 1H), 10.19 (s, 1H), 12.57 (br s, 1H); Mass Spectrum: M+H$^+$405.

The 4-amino-1H-pyrazole used as a starting material was prepared as follows:—

A mixture of 4-nitro-1H-pyrazole (0.7 g), platinum oxide (0.05 g), ethyl acetate (5 ml) and ethanol (15 ml) was stirred under 3 atmospheres pressure of hydrogen for 2 hours. The catalyst was removed by filtration and the filtrate was evaporated. There was thus obtained the required starting material (0.5 g).

[2] $^1$H NMR: (DMSOd$_6$) 3.65 (s, 2H), 4.07 (s, 3H), 6.54 (d, 1H), 7.28 (d, 2H), 7.47 (d, 2H), 7.55 (br s, 1H), 7.62 (s, 1H), 7.81 (br s, 1H), 7.74 (d, 1H), 7.78 (s, 1H), 10.21 (s, 1H), 12.57 (br s, 1H); Mass Spectrum: M−H$^-$ 398.

The 2-[4-(6-cyano-7-methoxyquinolin-4-yloxy)phenyl] acetic acid used as a starting material was prepared as follows:—

A mixture of 4-chloro-6-cyano-7-methoxyquinoline (2 g; International Patent Application WO 02/12226, Example 1 thereof, which concerns analogous procedures to those described for the starting material in Example 1 of International Patent Application WO 98/13350 but where methanol is used instead of 2-methoxyethanol), 2-(4-hydroxyphenyl) acetic acid (2.1 g), potassium carbonate (4.43 g) and DMA (30 ml) was stirred and heated to 100° C. for 4 hours. The mixture was evaporated. The residue was dissolved in water and acidified to pH3 by the addition of dilute aqueous hydrochloric acid. The resultant precipitate was isolated, washed with water and with diethyl ether and dried under vacuum. There was thus obtained the required starting material (3.3 g); $^1$H NMR: (DMSOd$_6$+CF$_3$CO$_2$H) 3.72 (s, 2H), 4.17 (s, 3H), 6.94 (d, 1H), 7.39 (d, 2H), 7.54 (d, 2H), 7.76 (s, 1H), 9.08 (d, 1H), 9.16 (s, 1H); Mass Spectrum: M+H$^+$ 335.

[3] $^1$H NMR: (DMSOd$_6$) 3.62 (s, 2H), 3.78 (s, 3H), 3.92 (s, 3H), 3.95 (s, 3H), 6.46 (d, 1H), 7.22 (d, 2H), 7.4 (s, 1H), 7.41 (s, 1H), 7.44 (d, 2H), 7.49 (s, 1H), 7.86 (s, 1H), 8.47 (d, 1H), 10.19 (br s, 1H); Mass Spectrum: M+H$^+$ 419.

The 4-amino-1-methyl-1H-pyrazole used as a starting material was prepared as follows:—

Dimethyl sulphate (5 ml) was slowly added to a stirred solution of 4-nitropyrazole (2 g) in 1N aqueous sodium hydroxide solution (20 ml) that had been warmed to 30° C. and the resultant mixture was stirred at that temperature for 48 hours. The mixture was cooled to ambient temperature and the precipitate was isolated, washed with cold water and dried under vacuum. There was thus obtained 1-methyl-4-nitro-1H-pyrazole (1.5 g); $^1$H NMR: (DMSOd$_6$) 3.91 (s, 1H), 8.24 (s, 1H), 8.85 (s, 1H).

A mixture of a portion (0.7 g) of the material so obtained, platinum oxide (0.05 g), ethyl acetate (5 ml) and ethanol (15 ml) was stirred under 3 atmospheres pressure of hydrogen for 2 hours. The catalyst was removed by filtration and the filtrate was evaporated. There was thus obtained the required starting material (0.6 g); $^1$H NMR: (DMSOd$_6$) 3.64 (s, 3H), 6.86 (s, 1H), 6.97 (s, 1H).

[4] $^1$H NMR: (DMSOd$_6$) 3.64 (s, 2H), 3.78 (s, 3H), 4.07 (s, 3H), 6.54 (d, 1H), 7.28 (d, 2H), 7.41 (s, 1H), 7.47 (d, 2H), 7.62 (s, 1H), 7.87 (s, 1H), 8.74 (d, 1H), 8.77 (s, 1H), 10.21 (s, 1H); Mass Spectrum: M−H$^-$ 412.

[5] The reaction product was purified by column chromatography on silica using increasingly polar mixtures of ethyl acetate and methanol as eluent and gave the following characterising data:—$^1$H NMR: (DMSOd$_6$) 1.32 (t, 3H), 3.62 (s, 2H), 3.92 (s, 3H), 3.94 (s, 3H), 4.07 (q, 2H), 6.45 (d, 1H), 7.22 (d, 2H), 7.42 (m, 4H), 7.49 (s, 1H), 7.9 (s, 1H), 8.47 (d, 1H); Mass Spectrum: M+H$^+$ 433.

The 4-amino-1-ethyl-1H-pyrazole used as a starting material was prepared as follows:—

Diethyl sulphate (5.23 ml) was slowly added to a stirred solution of 4-nitropyrazole (2.26 g) in 1N aqueous sodium hydroxide solution (22 ml) that had been warmed to 30° C. and the resultant mixture was stirred at that temperature for 48 hours. The mixture was cooled to ambient temperature and the precipitate was isolated, washed with cold water and dried under vacuum. There was thus obtained 1-ethyl-4-nitro-1H-pyrazole (1.71 g); $^1$H NMR: (DMSOd$_6$) 1.4 (t, 3H), 4.2 (q, 2H), 8.25 (s, 1H), 8.9 (s, 1H).

The material so obtained was hydrogenated over platinum oxide using an analogous procedure to that described in the portion of Note [3] immediately above that is concerned with the preparation of starting materials. There was thus obtained the required starting material in 89% yield; $^1$H NMR: (DMSOd$_6$) 1.27 (t, 3H), 3.77 (br s, 2H), 3.92 (q, 2H), 6.87 (s, 1H), 7.01 (s, 1H).

[6] The reaction product was purified by column chromatography on silica using increasingly polar mixtures of ethyl acetate and methanol as eluent and gave the following characterising data:—$^1$H NMR: (DMSOd$_6$) 1.32 (t, 3H), 3.64 (s, 2H), 4.07 (m, 5H), 6.54 (m, 1H), 7.28 (d, 2H), 7.43 (s, 1H), 7.47 (d, 2H), 7.62 (s, 1H), 7.9 (s, 1H), 8.73 (m, 1H), 8.77 (s, 1H), 10.21 (s, 1H); Mass Spectrum: M+H$^+$ 428.

[7] The reaction product was purified by preparative HPLC using a Waters 'Symmetry' C18 reversed-phase column (5 microns silica, 19 mm diameter, 100 mm length) and decreasingly polar mixtures of water (containing 2% acetic acid) and acetonitrile as eluent and gave the following characterising data: —$^1$H NMR: (DMSOd$_6$) 1.33 (t, 3H), 3.6 (s, 2H), 3.77 (s, 3H), 4.06 (q, 2H), 4.08 (s, 3H), 6.6 (d, 1H), 6.87 (d, 1H), 7.0 (s, 1H), 7.35 (d, 1H), 7.42 (s, 1H), 7.62 (s, 1H), 7.88 (s, 1H), 8.76 (d, 1H), 8.77 (s, 1H); Mass Spectrum: M+H$^+$ 458.

The 2-[4-(6-cyano-7-methoxyquinolin-4-yloxy)-2-methoxyphenyl]acetic acid used as a starting material was prepared as follows:—

A mixture of 4-hydroxy-2-methoxybenzaldehyde (5.57 g), benzyl bromide (3.98 ml), potassium iodide (8.22 g), potassium carbonate (6.83 g) and DMA (20 ml) was stirred and heated to 50° C. for 2 hours. The resultant mixture was cooled and evaporated. The residue was purified by column chromatography on silica using increasingly polar mixtures of diethyl ether and ethyl acetate as eluent. There was thus obtained 4-benzyloxy-2-methoxybenzaldehyde (8.05 g); $^1$H NMR: (CDCl$_3$) 3.88 (s, 3H), 5.13 (s, 2H), 6.53 (s, 1H), 6.63 (m, 1H), 7.34-7.44 (m, 5H), 7.81 (d, 1H).

A solution of 4-toluenesulphonyl isocyanide (3.33 g) in 1,2-dimethoxyethane (10 ml) was added portionwise to a stirred solution of potassium tert-butoxide (3.79 g) in 1,2-dimethoxyethane (50 ml) that had been cooled to −78° C. A solution of 4-benzyloxy-2-methoxybenzaldehyde (3.9 g) in 1,2-dimethoxyethane (10 ml) was added whilst the temperature of the reaction mixture was maintained at −78° C. The resultant mixture was allowed to warm to ambient temperature and was stirred for 1 hour. Methanol (85 ml) was added and the mixture was heated to reflux for 2 hours. The mixture was evaporated and the residue was purified by column chromatography on silica using increasingly polar mixtures of methylene chloride and ethyl acetate as eluent. There was thus obtained 2-(4-benzyloxy-2-methoxyphenyl)acetonitrile (3.46 g); $^1$H NMR: (CDCl$_3$) 3.6 (s, 2H), 3.82 (s, 3H), 5.05 (s, 2H), 6.54 (m, 2H), 7.21-7.44 (m, 6H); Mass Spectrum: M+H$^+$ 254.

A mixture of the material so obtained, a 6N aqueous sodium hydroxide solution (40 ml), THF (40 ml) and methanol (40 ml) was stirred and heated to 85° C. for 24 hours. The mixture was concentrated by evaporation. The residual aqueous mixture was acidified to pH2 by the addition of 6N aqueous hydrocloric acid and extracted with methylene chloride. The organic solution was dried over magnesium sulphate and evaporated. There was thus obtained 2-(4-benzyloxy-2-methoxyphenyl)acetic acid (2.36 g); $^1$H NMR: (CDCl$_3$) 3.59 (s, 2H), 3.79 (s, 3H), 5.04 (s, 2H), 6.53 (m, 2H), 7.08 (d, 1H), 7.31-7.44 (m, 5H); Mass Spectrum: M+H$^+$ 272.

A mixture of 2-(4-benzyloxy-2-methoxyphenyl)acetic acid (5 g), 10% platinum-on-carbon catalyst (0.5 g), ethanol (10 ml) and ethyl acetate (90 ml) was stirred under 3 atmospheres pressure of hydrogen for 2.5 hours. The resultant mixture was filtered and the filtrate was evaporated. There was thus obtained 2-(4-hydroxy-2-methoxyphenyl)acetic acid (2.9 g); $^1$H NMR: (DMSOd$_6$) 3.68 (s, 3H), 6.27 (m, 1H), 6.36 (d, 1H), 6.91 (d, 1H); Mass Spectrum: M−H$^−$ 181.

Using an analogous procedure to that described in Note [2] above, 4-chloro-6-cyano-7-methoxyquinoline was reacted with 2-(4-hydroxy-2-methoxyphenyl)acetic acid. There was thus obtained 2-[4-(6-cyano-7-methoxyquinolin-4-yloxy)-2-methoxyphenyl]acetic acid in 86% yield; $^1$H NMR: (DMSOd$_6$) 3.58 (s, 3H), 3.73 (s, 3H), 4.1 (s, 2H), 6.73 (d, 1H), 6.89 (d, 1H), 7.05 (s, 1H), 7.37 (d, 1H), 7.69 (s, 1H), 8.87 (d, 1H), 8.91 (s, 1H); Mass Spectrum: M+H$^+$ 365.

[8] The reaction product was purified by column chromatography on silica using increasingly polar mixtures of ethyl acetate and methanol as eluent and gave the following characterising data:—$^1$H NMR: (DMSOd$_6$) 1.37 (d, 6H), 3.62 (s, 2H), 3.92 (s, 3H), 3.94 (s, 3H), 4.44 (m, 1H), 6.45 (d, 1H), 7.22 (d, 2H), 7.42 (m, 4H), 7.49 (s, 1H), 7.9 (s, 1H), 8.46 (d, 1H); Mass Spectrum: M+H$^+$ 447.

The 4-amino-1-isopropyl-1H-pyrazole used as a starting material was prepared as follows:—

A mixture of 4-nitropyrazole (1.13 g), isopropyl iodide (1 ml), potassium carbonate (1.38 g) and DMF (30 ml) was stirred and heated to 70° C. for 2 hours. The resultant mixture was poured into water and the precipitate was isolated, washed with water and dried under vacuum. There was thus obtained 1-isopropyl-4-nitro-1H-pyrazole (0.845 g); $^1$H NMR: (DMSOd$_6$) 1.44 (d, 6H), 4.59 (m, 1H), 8.26 (s, 1H), 8.93 (s, 1H).

A mixture of a portion (0.8 g) of the material so obtained, platinum oxide (0.1 g), ethyl acetate (10 ml) and ethanol (30 ml) was stirred under 3 atmospheres pressure of hydrogen for 2 hours. The catalyst was removed by filtration and the filtrate was evaporated. There was thus obtained the required starting material as a colourless oil (0.607 g); $^1$H NMR: (DMSOd$_6$) 1.31 (d, 6H), 3.76 (br s, 2H), 4.27 (m, 1H), 6.88 (s, 1H), 7.03 (s, 1H).

[9] The reaction product was purified by column chromatography on silica using increasingly polar mixtures of ethyl acetate and methanol as eluent and gave the following characterising data:—$^1$H NMR: (DMSOd$_6$) 1.37 (d, 6H), 3.64 (s, 2H), 4.07 (s, 3H), 4.44 (m, 1H), 6.53 (d, 1H), 7.28 (d, 2H), 7.42 (s, 1H), 7.47 (d, 2H), 7.62 (s, 1H), 7.9 (s, 1H), 8.73 (d, 1H), 8.77 (s, 1H), 10.21 (s, 1H); Mass Spectrum: M+H$^+$ 442.

[10] The reaction mixture was stirred at ambient temperature for 16 hours rather than being heated to 60° C. The reaction product was purified by column chromatography on silica using increasingly polar mixtures of methylene chloride and a 3.5M methanolic ammonia solution as eluent and gave the following characterising data:—$^1$H NMR: (DMSOd$_6$) 3.62 (s, 2H), 3.67 (d, 1H), 3.69 (d, 1H), 3.92 (s, 3H), 3.95 (s, 3H), 4.08 (t, 2H), 4.85 (t, 1H), 6.46 (d, 1H), 7.22 (d, 2H), 7.4 (s, 1H), 7.43 (s, 1H), 7.44 (d, 2H), 7.49 (s, 1H), 7.9 (s, 1H), 8.49 (d, 1H), 10.19 (s, 1H); Mass Spectrum: M+H$^+$ 449.

The 4-amino-1-(2-hydroxyethyl)pyrazole used as a starting material was prepared as follows:—

A mixture of 4-nitropyrazole (0.8 g), 2-bromoethanol (0.55 ml), potassium carbonate (1.46 g) and acetonitrile (15 ml) was stirred and heated to 60° C. for 6 hours. The resultant mixture was evaporated and the residue was purified by column chromatography on silica using a 4:1 mixture of methylene chloride and ethyl acetate as eluent. There was thus obtained 1-(2-hydroxyethyl)-4-nitro-1H-pyrazole (0.65 g); $^1$H NMR: (CDCl$_3$) 2.28 (t, 1H), 4.07 (m, 2H), 4.3 (m, 2H), 8.1 (s, 1H), 8.75 (s, 1H).

A mixture of the material so obtained, 10% palladium on carbon catalyst (0.15 g) and ethanol (33 ml) was stirred an atmospheres pressure of hydrogen for 30 minutes. The catalyst was removed by filtration and the filtrate was evaporated. There was thus obtained the required starting material as an oil (0.5 g); $^1$H NMR: (DMSOd$_6$) 3.63 (m, 2H), 3.77 (br s, 2H), 3.94 (t, 2H), 4.96 (t, 1H), 6.88 (s, 1H), 7.02 (s, 1H).

[11] The reaction mixture was stirred at ambient temperature for 16 hours rather than being heated to 60° C. The reaction product was purified by column chromatography on silica using increasingly polar mixtures of methylene chloride and a 3.5M methanolic ammonia solution as eluent and gave the following characterising data:—$^1$H NMR: (DMSOd$_6$) 3.64 (s, 2H), 3.67 (d, 1H), 3.69 (d, 1H), 4.04-4.11

(m, 2H), 4.07 (s, 3H), 4.85 (t, 1H), 6.54 (d, 1H), 7.28 (d, 2H), 7.44 (s, 1H), 7.47 (d, 2H), 7.62 (s, 1H), 7.9 (s, 1H), 8.74 (d, 1H), 8.77 (s, 1H), 10.21 (s, 1H); Mass Spectrum: M+H+ 445.

[12] $^1$H NMR: (DMSOd$_6$) 2.18 (s, 3H), 3.64 (s, 2H), 3.92 (s, 3H), 3.94 (s, 3H), 6.25 (br s, 1H), 6.46 (d, 1H), 7.22 (d, 2H), 7.4 (s, 1H), 7.45 (d, 1H), 7.49 (d, 2H), 8.46 (s, 1H), 10.51 (br s, 1H), 11.91 (br s, 1H); Mass Spectrum: M+H+ 419.

[13] $^1$H NMR: (DMSOd$_6$) 2.18 (s, 3H), 3.66 (s, 2H), 4.08 (s, 3H), 6.26 (br s, 1H), 6.54 (d, 1H), 7.28 (d, 2H), 7.48 (d, 2H), 7.62 (s, 1H), 8.73 (d, 1H), 8.78 (s, 1H), 10.53 (br s, 1H), 12.0 (br s, 1H); Mass Spectrum: M+H+ 415.

[14] The reaction product was purified by column chromatography on silica using increasingly polar mixtures of ethyl acetate and methanol as eluent and gave the following characterising data:—$^1$H NMR: (DMSOd$_6$) 1.17 (t, 3H), 2.55 (q, 2H), 3.64 (s, 2H), 3.92 (s, 3H), 3.94 (s, 3H), 6.29 (br s, 1H), 6.46 (d, 1H), 7.22 (d, 2H), 7.4 (s, 1H), 7.45 (d, 2H), 7.49 (s, 1H), 8.46 (d, 1H); Mass Spectrum: M+H+ 433.

The 5-amino-3-ethyl-1H-pyrazole used as a starting material was prepared as follows:—

Acetonitrile (1.17 ml) was added dropwise to a stirred solution of n-butyllithium (1.6M in hexane, 14.06 ml) that had been cooled to −78° C. and the mixture was stirred at that temperature for 1 hour. Ethyl propionate (1.5 ml) was added dropwise and the reaction medium was allowed to warm to −45° C. and stirred at that temperature for 2 hours. The resultant mixture was acidified to pH2 by the addition of 2N aqueous hydrochloric acid and concentrated by evaporation. The residue was extracted with methylene chloride and the organic extract was dried over magnesium sulphate and evaporated. There was thus obtained 3-oxopentanenitrile in 80% yield; $^1$H NMR: (CDCl$_3$) 1.14 (t, 3H), 2.66 (q, 2H), 3.46 (s, 2H).

A mixture of a portion (0.6 g) of the material so obtained, hydrazine hydrate (0.28 ml) and ethanol (45 ml) was heated at 70° C. for 12 hours. The solvent was evaporated and the residue was purified by column chromatography on silica using a 19:1 mixture of methylene chloride and methanol as eluent. There was thus obtained the required starting material in 51% yield; $^1$H NMR: (DMSOd$_6$) 1.04 (t, 3H), 2.41 (q, 2H), 4.4 (br s, 2H).

[15] The reaction product was purified by column chromatography on silica using increasingly polar mixtures of ethyl acetate and methanol as eluent and gave the following characterising data:—$^1$H NMR: (DMSOd$_6$) 1.16 (t, 3H), 2.55 (q, 2H), 3.33 (s, 2H), 4.07 (s, 3H), 6.29 (s, 1H), 6.53 (d, 1H), 7.27 (d, 2H), 7.48 (d, 2H), 7.62 (s, 1H), 8.73 (d, 1H), 8.78 (s, 1H), 10.55 (s, 1H); Mass Spectrum: M+H+ 428.

[16] The reaction product was purified by preparative HPLC using a Waters 'Symmetry' C18 reversed-phase column (5 microns silica, 19 mm diameter, 100 mm length) and decreasingly polar mixtures of water (containing 2% acetic acid) and acetonitrile as eluent and gave the following characterising data:—$^1$H NMR: (DMSOd$_6$) 1.16 (t, 3H), 2.55 (q, 2H), 3.64 (s, 2H), 3.76 (s, 3H), 4.07 (s, 3H), 6.27 (br s, 1H), 6.6 (d, 1H), 6.86 (m, 1H), 6.99 (m, 1H), 7.34 (d, 1H), 7.62 (s, 1H), 8.75 (d, 1H), 8.78 (s, 1H); Mass Spectrum: M−H− 456.

[17] $^1$H NMR: (DMSOd$_6$) 3.67 (s, 2H), 3.92 (s, 3H), 3.94 (s, 3H), 6.47 (d, 1H), 6.49 (br s, 1H), 7.22 (d, 2H), 7.4 (s, 1H), 7.46 (d, 2H), 7.49 (s, 1H), 7.59 (br s, 1H), 8.47 (d, 1H), 10.66 (br s, 1H), 12.33 (br s, 1H); Mass Spectrum: M+H+ 405.

[18] $^1$H NMR: (DMSOd$_6$) 3.69 (s, 2H), 4.07 (s, 3H), 6.49 (br s, 1H), 6.55 (d, 1H), 7.28 (d, 2H), 7.49 (d, 2H), 7.59 (br s, 1H), 7.26 (s, 1H), 8.74 (d, 1H), 8.78 (s, 1H), 10.68 (br s, 1H), 12.34 (br s, 1H); Mass Spectrum: M+H+ 400.

[19] $^1$H NMR: (DMSOd$_6$) 3.65 (s, 2H), 3.73 (s, 3H), 3.92 (s, 3H), 3.94 (s, 3H), 6.42 (d, 1H), 6.46 (d, 1H), 7.22 (d, 2H), 7.4 (s, 1H), 7.45 (d, 2H), 7.49 (s, 1H), 7.54 (d, 1H), 8.47 (d, 1H), 10.65 (s, 1H); Mass Spectrum: M+H+ 419.

[20] $^1$H NMR: (DMSOd$_6$) 3.67 (s, 2H), 3.74 (s, 3H), 4.07 (s, 3H), 6.43 (d, 1H), 6.54 (d, 1H), 7.28 (d, 2H), 7.48 (d, 2H), 7.54 (d, 1H), 7.62 (s, 1H), 8.73 (d, 1H), 8.78 (s, 1H), 10.67 (s, 1H); Mass Spectrum: M+H+ 414.

[21] $^1$H NMR: (DMSOd$_6$) 3.66 (s, 2H), 3.92 (s, 3H), 3.94 (s, 3H), 4.41 (s, 2H), 5.23 (br s, 1H), 6.4 (br s, 1H), 6.47 (d, 1H), 7.22 (d, 2H), 7.4 (s, 1H), 7.45 (d, 2H), 7.49 (s, 1H), 8.47 (d, 1H), 10.57 (br s, 1H), 12.2 (br s, 1H); Mass Spectrum: M+H+ 435.

The 3-amino-5-hydroxymethyl-1H-pyrazole used as a starting material was prepared as follows:—

A mixture of 5-nitropyrazole-3-carboxylic acid (150 g), concentrated sulphuric acid (8 ml) and methanol (1 litre) was heated to reflux for 20 hours. The mixture was cooled to ambient temperature and the solvent was evaporated. The residual solid was dissolved in methylene chloride (800 ml) and solution was washed with a saturated aqueous sodium bicarbonate solution. The organic phase was dried over magnesium sulphate and evaporated. There was thus obtained methyl 5-nitropyrazole-3-carboxylate (116.1 g); $^1$H NMR: (DMSOd$_6$) 3.9 (s, 3H), 7.53 (s, 1H).

A mixture of a portion (20 g) of the material so obtained, 10% palladium on carbon catalyst (2 g) and methanol (500 ml) was stirred under an atmospheres pressure of hydrogen for 2 hours. The catalyst was removed by filtration and the filtrate was evaporated. There was thus obtained methyl 5-aminopyrazole-3-carboxylate as a solid (16.7 g); $^1$H NMR: (DMSOd$_6$) 3.75 (s, 3H), 5.03 (br s, 2H), 5.77 (br s, 1H); Mass Spectrum: M+H+ 142.

Under argon, lithium borohydride (2M in THF, 84.2 ml) was added dropwise to a stirred solution of methyl 5-aminopyrazole-3-carboxylate (9.5 g) in tetrahydrofuran (300 ml). The resultant mixture was heated to reflux for 16 hours. The mixture was cooled and methanol was added dropwise to quench residual reducing agent. The mixture was evaporated. Methanol (200 ml) was added to the residue and insoluble salts were removed by filtration. The filtrate was evaporated and the residue was purified by column chromatography on silica using a solvent gradient of 9:1 to 4:1 of methylene chloride and methanol as eluent. There was thus obtained 3-amino-5-hydroxymethyl-1H-pyrazole (5.6 g) $^1$H NMR: (DMSOd$_6$) 4.27 (s, 2H), 4.3-5.2 (2 br s, 3H), 5.29 (s, 1H).

[22] $^1$H NMR: (DMSOd$_6$) 3.67 (s, 2H), 4.08 (s, 3H), 4.41 (s, 2H), 5.22 (br s, 1H), 6.39 (br s, 1H), 6.54 (d, 1H), 7.28 (d, 2H), 7.49 (d, 2H), 7.62 (s, 1H), 8.74 (d, 1H), 8.77 (s, 1H), 10.6 (br s, 1H), 12.21 (br s, 1H); Mass Spectrum: M+H+ 430.

[23] $^1$H NMR: (DMSOd$_6$) 3.78 (s, 2H), 4.07 (s, 3H), 6.55 (d, 1H), 6.93 (d, 1H), 7.29 (d, 2H), 7.49 (d, 2H), 7.62 (s, 1H), 8.75 (d, 1H), 8.78 (s, 1H), 8.8 (d, 1H), 11.34 (br s, 1H); Mass Spectrum: M−H− 399.

[24] $^1$H NMR: (DMSOd$_6$) 2.37 (s, 3H), 3.73 (s, 2H), 3.92 (s, 3H), 3.95 (s, 3H), 6.47 (s, 1H), 6.62 (s, 1H), 7.23 (d, 2H), 7.4 (s, 1H), 7.44 (d, 2H), 7.49 (s, 1H), 8.47 (d, 1H), 11.17 (br s, 1H); Mass Spectrum: M+H+ 420.

[25] $^1$H NMR: (DMSOd$_6$) 2.37 (s, 3H), 3.76 (s, 2H), 4.07 (s, 3H), 6.55 (d, 1H), 6.63 (s, 1H), 7.29 (d, 2H), 7.48 (d, 2H), 7.62 (s, 1H), 8.74 (d, 1H), 8.77 (s, 1H), 11.19 (br s, 1H); Mass Spectrum: M−H− 413.

[26] The reaction product was purified by column chromatography on silica using increasingly polar mixtures of ethyl acetate and methanol as eluent and gave the following characterising data:—$^1$H NMR: (DMSOd$_6$) 1.97 (s, 3H), 2.17 (s, 3H), 3.72 (br s, 2H), 3.92 (s, 3H), 3.95 (s, 3H), 6.47 (d, 1H), 7.23 (d, 2H), 7.4 (s, 1H), 7.43 (d, 2H), 7.49 (s, 1H), 8.47 (d, 1H); Mass Spectrum: M+H$^+$ 434.

The 2-amino-4,5-dimethyloxazole used as a starting material was prepared as follows:—

A mixture of cyanamide (0.96 ml), 3-hydroxybutan-2-one (1 g) and water (100 ml) was warmed gently to 50° C. until complete dissolution occurred. The temperature of the reaction mixture was kept at 45° C. for 30 minutes. The reaction mixture was cooled to ambient temperature, basified to pH10 by the addition of 2N aqueous sodium hydroxide solution and extracted with diethyl ether. The organic solution was dried over magnesium sulphate and evaporated to give 2-amino-4,5-dimethyloxazole as an oil (0.66 g).

[27] The reaction product was purified by column chromatography on silica using increasingly polar mixtures of ethyl acetate and methanol as eluent and gave the following characterising data:—$^1$H NMR: (DMSOd$_6$) 2.26 (s, 3H), 3.8 (s, 2H), 3.92 (s, 3H), 3.94 (s, 3H), 6.47 (d, 1H), 6.75 (s, 1H), 7.23 (d, 2H), 7.4 (s, 1H), 7.46 (d, 2H), 7.48 (s, 1H), 8.47 (d, 1H); Mass Spectrum: M+H$^+$ 436.

[28] The reaction product was purified by column chromatography on silica using increasingly polar mixtures of ethyl acetate and methanol as eluent and gave the following characterising data:—$^1$H NMR: (DMSOd$_6$) 2.26 (s, 3H), 3.82 (s, 2H), 4.07 (s, 3H), 6.54 (d, 1H), 6.75 (s, 1H), 7.29 (d, 2H), 7.49 (d, 2H), 7.62 (s, 1H), 8.73 (d, 1H), 8.77 (s, 1H); Mass Spectrum: M+H$^+$ 431.

[29] The reaction mixture was heated to 50° C. for 4 hours. The product gave the following characterising data:—$^1$H NMR: (DMSOd$_6$) 2.16 (s, 3H), 2.23 (s, 3H), 3.79 (s, 2H), 4.07 (s, 3H), 6.55 (d, 1H), 7.29 (d, 2H), 7.48 (d, 2H), 7.62 (s, 1H), 8.74 (d, 1H), 8.77 (s, 1H), 12.15 (br s, 1H); Mass Spectrum: M+H$^+$ 445.

[30] After purification by preparative HPLC, the reaction product was purified further by column chromatography on silica using increasingly polar mixtures of methylene chloride and methanol as eluent. The resultant product gave the following characterising data:—$^1$H NMR: (DMSOd$_6$) 1.32 (t, 3H), 3.6 (s, 2H), 3.77 (s, 3H), 4.04 (s, 3H), 4.07 (q, 2H), 6.55 (d, 1H), 6.84 (m, 1H), 6.98 (d, 1H), 7.34 (d, 1H), 7.42 s, 1H), 7.52 (s, 1H), 7.74 (br s, 1H), 7.86 (br s, 1H), 7.88 (s, 1H), 8.68 (d, 1H), 8.7 (s, 1H), 10.04 (s, 1H); Mass Spectrum: M+H$^+$ 476.

The 2-[4-(6-carbamoyl-7-methoxyquinolin-4-yloxy)-2-methoxyphenyl]acetic acid used as a starting material was prepared as follows:—

A mixture of 4-chloro-7-methoxyquinoline-6-carboxamide (1.34 g), 2-(4-hydroxy-2-methoxyphenyl)acetic acid (1.03 g), caesium carbonate (4.4 g) and DMF (12 ml) was stirred and heated to 110° C. for 1.5 hours. The mixture was cooled to ambient temperature. The solvent was concentrated by evaporation and water (50 ml) was added to the residue. The resultant mixture was acidified to pH3.5 by the addition of 6N aqueous hydrochloric acid. The resultant precipitate was isolated, washed with DMF and with water and dried under vacuum. There was thus obtained the required starting material (1.48 g); $^1$H NMR: (DMSOd$_6$) 3.57 (s, 2H), 3.77 (s, 3H), 4.04 (s, 3H), 6.57 (d, 1H), 6.82 (d, 1H), 7.0 (d, 1H), 7.33 (d, 1H), 7.54 (s, 1H), 7.76 (s, 1H), 7.87 (s, 1H), 8.71 (s, 2H); Mass Spectrum: M+H$^+$ 383.

[31] The reaction mixture was stirred at ambient temperature for 16 hours rather than being heated to 60° C. The reaction product was purified by column chromatography on silica using increasingly polar mixtures of methylene chloride and methanol as eluent and gave the following characterising data:—$^1$H NMR: (DMSOd$_6$) 1.33 (t, 3H), 2.85 (d, 3H), 3.59 (s, 3H), 3.77 (s, 3H), 4.03 (s, 3H), 4.07 (q, 2H), 6.55 (d, 1H), 6.83 (d, 1H), 6.97 (s, 1H), 7.34 (d, 1H), 7.42 (s, 1H), 7.52 (s, 1H), 7.88 (s, 1H), 8.37 (q, 1H), 8.63 (s, 1H), 8.67 (s, 1H), 10.04 (s, 1H); Mass Spectrum: M+H$^+$ 490.

The 2-{2-methoxy-4-[7-methoxy-6-(N-methylcarbamoyl)quinolin-4-yloxy]phenyl}acetic acid used as a starting material was prepared as follows:—

A mixture of N-methyl-4-chloro-7-methoxyquinoline-6-carboxamide (1.3 g), 2-(4-hydroxy-2-methoxyphenyl)acetic acid (0.9 g), caesium carbonate (4.01 g) and DMF (15 ml) was stirred and heated to 110° C. for 2.5 hours. The mixture was cooled to ambient temperature and diluted with diethyl ether. The resultant solid was isolated and dissolved in water. The aqueous solution was acidified to pH4 by the addition of 6N aqueous hydrochloric acid. The resultant solid was purified by column chromatography on silica using a solvent gradient of 100:0 to 9:1 of methylene chloride and methanol as eluent. There was thus obtained the required starting material (0.55 g); $^1$H NMR: (DMSOd$_6$) 2.84 (d, 3H), 3.33 (s, 2H), 3.77 (s, 3H), 4.03 (s, 3H), 6.54 (d, 1H), 6.81 (m, 1H), 6.97 (d, 1H), 7.32 (d, 1H), 7.52 (s, 1H), 8.36 (br d, 1H), 8.62 (s, 1H), 8.67 (d, 1H); Mass Spectrum: M+H$^+$ 397.

[32] $^1$H NMR: (DMSOd$_6$) 2.85 (d, 3H), 3.59 (s, 2H), 3.77 (s, 3H), 3.78 (s, 3H), 4.03 (s, 3H), 6.55 (d, 1H), 6.82 (m, 1H), 6.98 (d, 1H), 7.34 (d, 1H), 7.41 (s, 1H), 7.52 (s, 1H), 7.84 (s, 1H), 8.36 (q, 1H), 8.63 (s, 1H), 8.68 (d, 1H), 10.04 (s, 1H); Mass Spectrum: M+H$^+$ 476.

[33] $^1$H NMR: (DMSOd$_6$) 1.32 (t, 3H), 3.59 (s, 2H), 3.76 (s, 3H), 3.94 (s, 3H), 4.07 (q, 2H), 6.52 (d, 1H), 6.79 (m, 1H), 6.96 (d, 1H), 7.29 (m, 1H), 7.32 (d, 1H), 7.41 (d, 1H), 7.42 (s, 1H), 7.87 (s, 1H), 8.2 (d, 1H), 8.62 (d, 1H), 10.04 (s, 1H); Mass Spectrum: M+H$^+$ 433.

The 2-[2-methoxy-4-(7-methoxyquinolin-4-yloxy)phenyl]acetic acid used as starting material was prepared as follows:—

A mixture of 4-chloro-7-methoxyquinoline (*J. Med. Chem.*, 1998, 41, 4918-4926; 1.5 g), tert-butyl 2-(4-hydroxy-2-methoxyphenyl)acetate (2.03 g), 4-dimethylaminopyridine (2.83 g) and chlorobenzene (30 ml) was stirred and heated to 125° C. for 16 hours. The reaction mixture was cooled to ambient temperature and washed with water. The organic solution was evaporated and the resultant residue was purified by column chromatography on silica using a solvent gradient of 3:1 to 1:1 of methylene chloride and diethyl ether as eluent. There was thus obtained tert-butyl 2-[2-methoxy-4-(7-methoxyquinolin-4-yloxy)phenyl]acetate (2 g); $^1$H NMR: (CDCl$_3$) 1.47 (s, 9H), 3.56 (s, 2H), 3.8 (s, 3H), 3.98 (s, 3H), 6.51 (d, 1H), 6.72 (m, 2H), 7.22 (m, 2H), 7.26 (s, 1H), 7.43 (d, 1H), 8.23 (d, 1H), 8.59 (d, 1H); Mass Spectrum: M+H$^+$ 396.

A mixture of the material so obtained, water (0.5 ml) and trifluoroacetic acid (20 ml) was stirred at ambient temperature for 3 hours. The solvent was evaporated. The residue was dissolved in methylene chloride and diisopropylethylamine (3 ml) was added. The resultant solid was recovered and dried under vacuum. There was thus obtained the required starting material (1.48 g); $^1$H NMR: (DMSOd$_6$) 3.55 (s, 2H), 3.76 (s, 3H), 3.94 (s, 3H), 6.52 (d, 1H), 6.77 (m, 1H), 6.96 (d, 1H), 7.3 (m, 2H), 7.41 (d, 1H), 8.19 (d, 1H), 8.62 (d, 1H); Mass Spectrum: M+H$^+$ 340.

The tert-butyl 2-(4-hydroxy-2-methoxyphenyl)acetate used as starting material was prepared as follows:—

A mixture of 2-(4-benzyloxy-2-methoxyphenyl)acetic acid (6.8 g) and toluene (68 ml) and warmed to 90-95° C. Dimethylformamide di-tert-butyl acetal (5.93 ml) was added dropwise and the reaction mixture was heated to 90-95° C. for 1 hour. The solvent was evaporated and the residue was partitioned between diethyl ether and a 10% citric acid solution. The organic solution was washed in turn with water and an aqueous sodium bicarbonate solution, dried over magnesium sulphate and evaporated. There was thus obtained tert-butyl 2-(4-benzyloxy-2-methoxyphenyl)acetate (7.5 g); $^1$H NMR: (DMSOd$_6$) 1.4 (s, 9H), 3.35 (s, 2H), 3.75 (s, 3H), 5.1 (s, 2H), 6.5 (m, 1H), 6.55 (d, 1H), 7.05 (d, 1H), 7.3-7.5 (m, 5H).

A mixture of the material so obtained, 10% palladium-on-carbon catalyst (0.8 g), ethanol (30 ml), methanol (20 ml) and ethyl acetate (100 ml) was stirred under 1.7 atmospheres pressure of hydrogen for 3 hours. The mixture was filtered and the filtrate was evaporated. The resultant oil crystallised on standing for 16 hours. The solid so obtained was triturated under petroleum ether. There was thus obtained tert-butyl 2-(4-hydroxy-2-methoxyphenyl)acetate (5 g); $^1$H NMR: (DMSOd$_6$) 1.35 (s, 9H), 3.3 (s, 2H), 3.7 (s, 3H), 6.3 (m, 1H), 6.4 (d, 1H), 6.9 (d, 1H), 9.3 (s, 1H).

[34] The reaction mixture was stirred at ambient temperature for 16 hours rather than being heated to 60° C. The reaction product was purified by column chromatography on silica using increasingly polar mixtures of methylene chloride and methanol as eluent and gave the following characterising data:—$^1$H NMR: (DMSOd$_6$) 1.33 (t, 3H), 3.61 (s, 2H), 3.78 (s, 3H), 3.95 (s, 3H), 4.07 (q, 2H), 6.74 (d, 1H), 6.89 (m, 1H), 7.04 (d, 1H), 7.37 (d, 1H), 7.42 (s, 1H), 7.88 (s, 1H), 8.14 (d, 1H), 8.29 (m, 1H), 8.83 (d, 1H), 8.97 (d, 1H), 10.05 (s, 1H); Mass Spectrum: M+H$^+$ 461.

The 2-[2-methoxy-4-(6-methoxycarbonylquinolin-4-yloxy)phenyl]acetic acid used as starting material was prepared as follows:—

Methyl 4-aminobenzoate (6 g) was added to a stirred mixture of 5-methoxymethylene-2,2-dimethyl-1,3-dioxane-4,6-dione (7.38 g) and isopropanol (80 ml) and the resultant mixture was stirred and heated to reflux for 10 minutes. The resultant mixture was cooled to ambient temperature and the precipitate was isolated, washed in turn with isopropanol and diethyl ether and dried under vacuum. There was thus obtained 5-(4-methoxycarbonylanilinomethylene)-2,2-dimethyl-1,3-dioxane-4,6-dione (11.3 g); $^1$H NMR: (CDCl$_3$) 1.79 (s, 6H), 3.96 (s, 3H), 7.33 (d, 2H), 8.14 (d, 2H), 8.71 (d, 1H), 11.33 (d, 1H); Mass Spectrum: M−H$^−$ 304.

The material so obtained was added portionwise to a mixture (130 ml) of biphenyl and diphenyl ether ('Dowtherm A') that had been warmed to 260° C. The solution was stirred at that temperature for 5 minutes. The resultant mixture was cooled to ambient temperature. Petroleum ether was added and the precipitate was collected by filtration and washed with petroleum ether. There was thus obtained 6-methoxycarbonyl-1,4-dihydroquinolin-4-one (6.9 g); $^1$H NMR: (DMSOd$_6$) 3.89 (s, 3H), 6.1 (d, 1H), 7.62 (d, 1H), 7.97 (d, 1H), 8.13 (m, 1H), 8.7 (d, 1H); Mass Spectrum: M+H$^+$ 204.

A mixture of a portion (4 g) of the material so obtained and phosphorus oxychloride (4 ml) was stirred and heated to 110° C. for 5 minutes. The mixture was cooled and poured onto ice. The resultant mixture was neutralised by the addition of a saturated aqueous sodium bicarbonate solution. The resultant solid was isolated, dissolved in methylene chloride, dried over magnesium sulphate and evaporated. There was thus obtained 4-chloro-6-methoxycarbonylquinoline (3.65 g); $^1$H NMR: (DMSOd$_6$) 3.97 (s, 3H), 7.9 (d, 1H), 8.22 (d, 1H), 8.32 (m, 1H), 8.8 (d, 1H), 8.98 (d, 1H); Mass Spectrum: M+H$^+$ 222 and 224.

A suspension of 4-chloro-6-methoxycarbonylquinoline (1.3 g), 2-(4-hydroxy-2-methoxyphenyl)acetic acid (1.07 g), caesium carbonate (4.8 g) and DMF (12 ml) was stirred and heated to 100° C. for 3 hours. The resultant mixture was cooled to ambient temperature and diluted with diethyl ether. The solid so obtained was isolated and dissolved in water (60 ml). The aqueous solution so obtained was washed with methylene chloride. The aqueous solution was acidified to pH4 by the addition of 6N aqueous hydrochloric acid. The resultant precipitate was isolated, washed in turn with water and diethyl ether and dried under vacuum. The materials so obtained was purified by column chromatography on silica using a 9:1 mixture of methylene chloride and methanol as eluent. There was thus obtained the required starting material (1.52 g); $^1$H NMR: (DMSOd$_6$) 3.57 (s, 2H), 3.78 (s, 3H), 3.95 (s, 3H), 6.73 (d, 1H), 6.88 (m, 1H), 7.04 (d, 1H), 8.14 (d, 1H), 8.28 (m, 1H), 8.82 (d, 1H), 8.97 (d, 1H); Mass Spectrum: M+H$^+$ 368.

[35] $^1$H NMR: (DMSOd$_6$) 3.59 (s, 2H), 3.76 (s, 3H), 3.78 (s, 3H), 3.94 (s, 3H), 6.52 (d, 1H), 6.79 (m, 1H), 6.96 (d, 1H), 7.29 (m, 1H), 7.32 (d, 1H), 7.4 (s, 1H), 7.41 (d, 1H), 7.84 (s, 1H), 8.2 (d, 1H), 8.62 (d, 1H), 10.03 (s, 1H); Mass Spectrum: M+H$^+$ 419.

[36] $^1$H NMR: (DMSOd$_6$) 2.12 (s, 3H), 3.64 (s, 2H), 3.7 (s, 3H), 3.78 (s, 3H), 3.94 (s, 3H), 6.52 (d, 1H), 6.79 (m, 1H), 6.96 (d, 1H), 7.29 (m, 1H), 7.32 (d, 1H), 7.41 (d, 1H), 7.81 (s, 1H), 8.2 (d, 1H), 8.62 (d, 1H), 9.43 (s, 1H); Mass Spectrum: M+H$^+$ 433; m.p. 165-168° C. (crystallised from ethyl acetate solution).

The 4-amino-1,3-dimethyl-1H-pyrazole used as a starting material was obtainable commercially from Sigma-Aldrich, Gillingham, SP8 4XT, UK). The compound may also be prepared according to the procedure disclosed in Chemical Abstracts volume 94, Abstract No. 103228 (*Zhumal Obshchei Khimii*, 1980, 50, 2106-9).

[37] $^1$H NMR: (DMSOd$_6$) 2.17 (s, 3H), 3.62 (s, 2H), 3.69 (s, 3H) 3.78 (s, 3H), 3.94 (s, 3H), 6.53 (d, 1H), 6.79 (m, 1H), 6.96 (d, 1H), 7.29 (m, 1H), 7.32 (d, 1H), 7.41 (d, 1H), 7.45 (s, 1H), 8.2 (d, 1H), 8.62 (d, 1H), 9.34 (s, 1H); Mass Spectrum: M+H$^+$ 433.

The 4-amino-1,5-dimethyl-1H-pyrazole used as a starting material was prepared as follows:—

Under an atmosphere of argon, diisopropylethylamine (3.49 ml) and diphenylphosphoryl azide (2.37 ml) were added in turn to a stirred mixture of 1,5-dimethyl-1H-pyrazole-4-carboxylic acid (1.4 g), tert-butanol (4 ml) and 1,4-dioxane (40 ml) and the reaction mixture was stirred at ambient temperature for 10 minutes. The resultant mixture was heated to 110° C. for 3 hours. The solvent was evaporated and the reaction product was purified by column chromatography on silica using ethyl acetate as the eluent. There was thus obtained 4-(tert-butoxycarbonylamino)-1,5-dimethyl-1H-pyrazole (0.225 g); $^1$H NMR: (DMSOd$_6$) 1.4 (s, 9H), 2.2 (s, 3H), 3.55 (s, 1H), 6.0 (br s, 1H), 9.3 (br s, 1H).

A mixture of the material so obtained, a 4M solution of hydrogen chloride in 1,4-dioxane (0.96 ml) and methylene chloride (5 ml) was stirred at ambient temperature for 3 days. The resultant solid was collected by filtration, washed with diethyl ether and dried under vacuum. There was thus obtained 4-amino-1,5-dimethyl-1H-pyrazole (0.078 g), as a hydrochloride salt, $^1$H NMR: (DMSOd$_6$) 2.25 (s, 3H), 3.65 (s, 3H), 5.85 (s, 1H).

The 1,5-dimethyl-1H-pyrazole-4-carboxylic acid used as a starting material was obtainable commercially. The compound may also be prepared according to the procedure disclosed in *Australian Journal of Chemistry*, 1983, 36, 135-147.

[38] $^1$H NMR: (DMSOd$_6$) 2.12 (s, 3H), 2.85 (d, 3H), 3.65 (s, 2H), 3.7 (s, 3H), 3.78 (s, 3H), 4.03 (s, 3H), 6.55 (d, 1H), 6.82 (m, 1H), 6.98 (d, 1H), 7.33 (d, 1H), 7.52 (d, 1H), 7.81 (s, 1H), 8.37 (q, 1H), 8.63 (s, 1H), 8.67 (d, 1H), 9.43 (s, 1H); Mass Spectrum: M+H$^+$ 490.

[39] $^1$H NMR: (DMSOd$_6$) 2.17 (s, 3H), 2.85 (d, 3H), 3.62 (s, 2H), 3.69 (s, 3H), 3.78 (s, 3H), 4.03 (s, 3H), 6.56 (d, 1H), 6.82 (m, 1H), 6.98 (d, 1H), 7.34 (d, 1H), 7.45 (s, 1H), 7.52 (s, 1H), 8.37 (q, 1H), 8.63 (s, 1H), 8.67 (s, 1H), 9.34 (s, 1H); Mass Spectrum: M+H$^+$ 490.

[40] $^1$H NMR: (DMSOd$_6$) 1.16 (t, 3H), 2.55 (q, 2H), 2.84 (d, 3H), 3.63 (s, 2H), 3.77 (s, 3H), 4.03 (s, 3H), 6.28 (s, 1H), 6.55 (d, 1H), 6.82 (m, 1H), 6.97 (d, 1H), 7.32 (d, 1H), 7.52 (s, 1H), 8.36 (q, 1H), 8.63 (s, 1H), 8.67 (d, 1H), 10.34 (s, 1H), 11.98 (s, 1H); Mass Spectrum: M+H$^+$ 490.

[41] The reaction mixture was heated to 60° C. for 28 hours. The reaction product gave the following characterising data:—$^1$H NMR: (DMSOd$_6$) 1.16 (t, 3H), 2.55 (q, 2H), 3.62 (s, 2H), 3.76 (s, 3H), 3.94 (s, 3H), 6.28 (br s, 1H), 6.52 (d, 1H), 6.79 (m, 1H), 6.95 (d, 1H), 7.26-7.34 (m, 2H), 7.41 (d, 1H), 8.2 (d, 1H), 8.62 (d, 1H), 10.34 (br s, 1H); Mass Spectrum: M+H$^+$ 433.

[42] The reaction mixture was stirred at ambient temperature for 16 hours rather than being heated to 60° C. The reaction product gave the following characterising data:—$^1$H NMR: (DMSOd$_6$) 1.77 (s, 3H), 2.1 (s, 3H), 3.61 (s, 2H), 3.78 (s, 3H), 3.94 (s, 3H), 6.56 (d, 1H), 6.76 (d, 1H), 6.93 (s, 1H), 7.28 (m, 1H), 7.34 (d, 1H), 7.41 (d, 1H), 8.19 (d, 1H), 8.62 (d, 1H), 9.39 (br s, 1H), 11.88 (br s, 1H); Mass Spectrum: M+H$^+$ 433.

The 3-amino-4,5-dimethyl-1H-pyrazole used as a starting material is described in UK Patent Specification No. 788,140 (within Example 1 thereof).

[43] The reaction mixture was heated to 55° C. for 16 hours. The reaction product was purified by column chromatography on silica using increasingly polar mixtures of ethyl acetate and methanol as eluent and gave the following characterising data: —$^1$H NMR: (DMSOd$_6$) 1.16 (t, 3H), 2.55 (q, 2H), 3.63 (s, 2H), 3.76 (s, 3H), 6.28 (s, 1H), 6.71 (d, 1H), 6.82 (m, 1H), 6.98 (d, 1H), 7.33 (d, 1H), 7.75 (m, 1H), 7.98 (m, 1H), 8.12 (m, 1H), 8.7 (d, 1H), 10.34 (s, 1H); Mass Spectrum: M+H$^+$ 421.

[44] The reaction mixture was heated to 60° C. for 2 hours. The reaction product was purified by column chromatography on silica using a 1:1 mixture of methylene chloride and ethyl acetate as eluent and gave the following characterising data:—$^1$H NMR: (DMSOd$_6$) 1.16 (t, 3H), 2.55 (q, 2H), 3.63 (s, 2H), 3.76 (s, 3H), 6.28 (s, 1H), 6.64 (d, 1H), 6.83 (m, 1H), 6.98 (d, 1H), 7.33 (d, 1H), 7.59 (m, 1H), 7.78 (m, 1H), 8.41 (m, 1H), 8.72 (m, 1H), 10.34 (s, 1H); Mass Spectrum: M+H$^+$ 421.

[45] $^1$H NMR: (DMSOd$_6$) 2.37 (s, 3H), 2.85 (d, 3H), 3.71 (s, 2H), 3.76 (s, 3H), 4.03 (s, 3H), 6.56 (d, 1H), 6.61 (s, 1H), 6.83 (m, 1H), 6.98 (d, 1H), 7.33 (d, 1H), 7.52 (s, 1H), 8.37 (q, 1H), 8.63 (s, 1H), 8.68 (d, 1H), 11.04 (s, 1H); Mass Spectrum: M+H$^+$ 477.

[46] $^1$H NMR: (DMSOd$_6$); 2.37 (s, 3H), 3.71 (s, 2H), 3.75 (s, 3H), 3.94 (s, 3H), 6.53 (d, 1H), 6.61 (s, 1H), 6.79 (m, 1H), 6.96 (d, 1H), 7.29 (m, 1H), 7.32 (d, 1H), 7.42 (d, 1H), 8.2 (d, 1H), 8.63 (d, 1H), 11.03 (s, 1H) Mass Spectrum: M+H$^+$ 420.

[47] $^1$H NMR: (DMSOd$_6$) 1.2 (t, 3H), 2.72 (q, 2H), 3.7 (s, 2H), 3.75 (s, 3H), 3.94 (s, 3H), 6.52 (d, 1H), 6.62 (s, 1H), 6.79 (m, 1H), 6.96 (d, 1H), 7.29 (m, 1H), 7.32 (d, 1H), 7.41 (d, 1H), 8.2 (d, 1H), 8.63 (d, 1H), 11.06 (s, 1H); Mass Spectrum: M+H$^+$ 434.

[48] $^1$H NMR: (DMSOd$_6$) 1.89 (d, 3H), 3.72 (s, 2H), 3.78 (s, 3H), 3.94 (s, 3H), 6.54 (d, 1H), 6.80 (m, 1H), 6.97 (d, 1H), 7.29 (m, 1H), 7.35 (d, 1H), 7.41 (m, 1H), 8.2 (d, 1H), 8.6 (q, 1H), 8.63 (d, 1H), 10.36 (br s, 1H); Mass Spectrum: M+H$^+$ 420.

The 3-amino-4-methylisoxazole used as starting material was prepared as follows:—

Bromine (1.9 ml) was added to a solution of methacrylonitrile (3.65 ml) in methanol (6 ml) that had been cooled to 0° C. The resultant mixture was stirred and heated to 35° C. for 2 hours. The mixture was cooled to 0° C. Hydroxyurea (4.3 g) was added followed by the dropwise addition of a solution of sodium hydroxide (4.72 g) in water (5 ml). The resultant mixture was heated to reflux for 2.5 hours. The mixture was cooled to ambient temperature and partitioned between ethyl acetate and water. The organic solution was dried over magnesium sulphate and evaporated. The residue was purified by column chromatography on silica using a solvent gradient of 1:1 to 0:100 of methylene chloride and ethyl acetate as eluent. There was thus obtained the required starting material (1.11 g); $^1$H NMR: (DMSOd$_6$) 1.81 (d, 3H), 5.43 (br s, 2H), 8.09 (d, 1H); Mass Spectrum: M+H$^+$ 99.

[49] $^1$H NMR: (DMSOd$_6$) 1.8 (s, 3H), 2.3 (s, 3H), 2.85 (d, 3H), 3.71 (s, 2H), 3.78 (s, 3H), 4.03 (s, 3H), 6.57 (d, 1H), 6.83 (m, 1H), 6.99 (d, 1H), 7.36 (d, 1H), 7.52 (s, 1H), 8.36 (q, 1H), 8.63 (s, 1H), 8.68 (d, 1H), 10.27 (br s. 1H); Mass Spectrum: M+H$^+$ 491.

[50] The reaction mixture was heated to 60° C. for 25 hours. The reaction product gave the following characterising data:—$^1$H NMR: (DMSOd$_6$) 1.8 (s, 3H), 2.3 (s, 3H), 3.7 (s, 2H), 3.77 (s, 3H), 3.94 (s, 3H), 6.54 (d, 1H), 6.8 (m, 1H), 6.97 (d, 1H), 7.29 (m, 1H), 7.34 (d, 1H), 7.41 (d, 1H), 8.2 (d, 1H), 8.63 (d, 1H), 10.26 (br s, 1H); Mass Spectrum: M+H$^+$ 434.

[51] The reaction product was purified by column chromatography on silica using increasingly polar mixtures of methylene chloride and methanol as eluent and gave the following characterising data:—$^1$H NMR: (DMSOd$_6$) 2.33 (d, 3H), 3.75 (s, 3H), 3.77 (s, 2H), 4.04 (s, 3H), 6.56 (d, 1H), 6.84 (m, 1H), 7.0 (d, 1H), 7.13 (q, 1H), 7.35 (d, 1H), 7.53 (s, 1H), 7.74 (br s, 1H), 7.86 (br s, 1H), 8.68 (d, 1H), 8.7 (s, 1H), 12.07 (br s, 1H); Mass Spectrum: M+H$^+$ 479.

[52] The reaction mixture was heated to 60° C. for 25 hours. The reaction product gave the following characterising data:—$^1$H NMR: (DMSOd$_6$) 2.33 (s, 3H), 3.75 (s, 3H), 3.77 (s, 2H), 3.94 (s, 3H), 6.54 (d, 1H), 6.8 (m, 1H), 6.97 (d, 1H), 7.13 (s, 1H), 7.29 (m, 1H), 7.33 (s, 1H), 7.42 (d, 1H), 8.2 (d, 1H), 8.63 (d, 1H); Mass Spectrum: M+H$^+$ 436.

[53] $^1$H NMR: (DMSOd$_6$) 2.94 (s, 6H), 3.73 (s, 2H), 3.77 (s, 3H), 4.04 (s, 3H), 6.38 (d, 1H), 6.55 (d, 1H), 6.84 (m, 1H), 6.99 (d, 1H), 7.34 (d, 1H), 7.45 (br s, 1H), 7.53 (s, 1H), 7.74 (br s, 1H), 7.86 (br s, 1H), 7.88 (d, 1H), 8.68 (d, 1H), 8.71 (s, 1H), 10.16 (br s, 1H); Mass Spectrum: M+H$^+$ 502.

[54] $^1$H NMR: (DMSOd$_6$) 2.94 (s, 6H), 3.73 (s, 2H), 3.76 (s, 3H), 3.94 (s, 3H), 6.38 (m, 1H), 6.53 (d, 1H), 6.79 (m, 1H), 6.96 (d, 1H), 7.29 (m, 1H), 7.32 (d, 1H), 7.41 (d, 1H), 7.45 (br s, 1H), 7.88 (d, 1H), 8.2 (d, 1H), 8.63 (d, 1H), 10.14 (s, 1H); Mass Spectrum: M+H$^+$ 459.

[55] The reaction mixture was heated to 60° C. for 28 hours. The reaction product gave the following characterising data:—$^1$H NMR: (DMSOd$_6$) 3.76 (s, 3H), 3.81 (s, 2H), 3.94 (s, 3H), 6.53 (d, 1H), 6.80 (m, 1H), 6.97 (d, 1H), 7.29 (m, 1H), 7.35 (d, 1H), 7.42 (d, 1H), 8.2 (d, 1H), 8.36 (d, 1H), 8.42 (m, 1H), 8.63 (d, 1H), 9.32 (d, 1H), 10.93 (s, 1H); Mass Spectrum: M+H$^+$ 417.

[56] $^1$H NMR: (DMSOd$_6$) 2.13 (s, 6H), 2.26 (s, 3H), 3.29 (s, 2H), 3.65 (s, 2H), 3.77 (s, 3H), 3.94 (s, 3H), 6.52 (d, 1H), 6.78 (s, 1H), 6.80 (m, 1H), 6.96 (d, 1H), 7.29 (m, 1H), 7.34 (d, 1H), 7.35 (s, 1H), 7.37 (s, 1H), 7.41 (d, 1H), 8.21 (d, 1H), 8.62 (d, 1H), 9.98 (s, 1H); Mass Spectrum: M+H$^+$ 486.

[57] In an additional purification step, the reaction product was purified by column chromatography on silica using increasingly polar mixtures of methylene chloride and methanol as eluent. The product gave the following characterising data:—$^1$H NMR: (DMSOd$_6$) 1.2 (t, 3H), 2.72 (q, 2H), 3.71 (s, 2H), 3.76 (s, 3H), 4.04 (s, 3H), 6.55 (d, 1H), 6.62 (s, 1H), 6.83 (m, 1H), 6.99 (d, 1H), 7.34 (d, 1H), 7.52 (s, 1H), 7.74 (br s, 1H), 7.86 (br s, 1H), 8.68 (d, 1H), 8.7 (s, 1H), 11.06 (s, 1H); Mass Spectrum: M+H$^+$ 477.

[58] NMP was used in place of DMF as the reaction solvent and the reaction mixture was heated to 85° C. for 16 hours. The reaction product gave the following characterising data:—$^1$H NMR: (DMSOd$_6$) 1.86 (s, 3H), 3.63 (s, 2H), 3.79 (s, 3H), 3.93 (s, 3H), 3.95 (s, 3H), 6.53 (d, 1H), 6.79 (m, 1H), 6.95 (d, 1H), 7.35 (d, 1H), 7.4 (s, 1H), 7.41 (br m, 1H), 7.51 (s, 1H), 8.48 (d, 1H), 9.62 (br s, 1H); Mass Spectrum: M+H$^+$ 449.

The 3-amino-4-methyl-1H-pyrazole used as a starting material is described in *J. Amer. Chem. Soc.*, 1992, 114, 7695 and *J. Het. Chem.*, 1982, 19, 1267.

[59] NMP was used in place of DMF as the reaction solvent and the reaction mixture was heated to 85° C. for 16 hours. The reaction product gave the following characterising data:—$^1$H NMR: (DMSOd$_6$) 1.08 (t, 3H), 2.29 (q, 2H), 3.62 (s, 2H), 3.78 (s, 3H), 3.93 (s, 3H), 3.95 (s, 3H), 6.53 (d, 1H), 6.77 (m, 1H), 6.94 (d, 1H), 7.35 (d, 1H), 7.4 (s, 1H), 7.42 (brm, 1H), 7.51 (s, 1H), 8.48 (d, 1H); Mass Spectrum: M+H$^+$ 463.

The 3-amino-4-ethyl-1H-pyrazole used as a starting material is described in US Patent Specification No. 2005/0187219 (within Preparative Example 507 thereof).

[60] NMP was used in place of DMF as the reaction solvent and the reaction mixture was heated to 85° C. for 16 hours. The reaction product gave the following characterising data:—$^1$H NMR: (DMSOd$_6$) 1.07 (t, 3H), 2.3 (q, 2H), 3.63 (s, 2H), 3.78 (s, 3H), 3.94 (s, 3H), 6.53 (d, 1H), 6.79 (m, 1H), 6.96 (d, 1H), 7.28 (m, 1H), 7.34 (d, 1H), 7.41 (d, 1H), 8.2 (d, 1H), 8.61 (d, 1H), 9.58 (br s, 1H); Mass Spectrum: M+H$^+$ 433.

[61] NMP was used in place of DMF as the reaction solvent and the reaction mixture was heated to 80° C. for 16 hours. In an additional purification step, the reaction product was purified by column chromatography on silica using increasingly polar mixtures of methylene chloride and methanol as eluent. The product gave the following characterising data:—$^1$H NMR: (DMSOd$_6$) 2.16 (s, 3H), 3.63 (s, 2H), 3.78 (s, 3H), 3.93 (s, 3H), 3.95 (s, 3H), 6.52 (d, 1H), 6.79 (m, 1H), 6.95 (d, 1H), 7.33 (d, 1H), 7.4 (s, 1H), 7.5 (s, 1H), 7.7 (br s, 1H), 8.49 (d, 1H), 9.38 (s, 1H); Mass Spectrum: M+H$^+$ 449.

[62] NMP was used in place of DMF as the reaction solvent and the reaction mixture was heated to 85° C. for 16 hours. The product gave the following characterising data:—$^1$H NMR: (DMSOd$_6$) 2.16 (s, 3H), 3.64 (s, 2H), 3.78 (s, 3H), 3.94 (s, 3H), 6.53 (d, 1H), 6.79 (m, 1H), 6.96 (d, 1H), 7.29 (m, 1H), 7.33 (d, 1H), 7.41 (d, 1H), 7.68 (br s, 1H), 8.2 (d, 1H), 8.62 (d, 1H), 9.39 (s, 1H); Mass Spectrum: M+H$^+$ 419.

[63] NMP was used in place of DMF as the reaction solvent and the reaction mixture was heated to 85° C. for 16 hours. The product gave the following characterising data:—$^1$H NMR: (DMSOd$_6$) 2.01 (s, 6H), 3.59 (s, 2H), 3.79 (s, 3H), 3.94 (s, 3H), 6.54 (d, 1H), 6.79 (m, 1H), 6.96 (d, 1H), 7.29 (m, 1H), 7.35 (d, 1H), 7.41 (d, 1H), 8.2 (d, 1H), 8.62 (d, 1H), 8.97 (s, 1H); Mass Spectrum: M+H$^+$ 433.

[64] NMP was used in place of DMF as the reaction solvent and the reaction mixture was heated to 70° C. for 16 hours. The product gave the following characterising data:—$^1$H NMR: (DMSOd$_6$) 2.17 (s, 3H), 3.64 (s, 2H), 3.78 (s, 3H), 6.71 (d, 1H), 6.83 (m, 1H), 6.99 (d, 1H), 7.35 (d, 1H), 7.57 (br s, 1H), 7.76 (m, 1H), 7.98 (m, 1H), 8.12 (m, 1H), 8.7 (d, 1H), 9.38 (s, 1H), 12.28 (br s, 1H); Mass Spectrum: M+H$^+$ 407.

[65] NMP was used in place of DMF as the reaction solvent and the reaction mixture was heated to 85° C. for 16 hours. The product gave the following characterising data:—$^1$H NMR: (DMSOd$_6$) 1.86 (s, 3H), 3.63 (s, 2H), 3.78 (s, 3H), 3.94 (s, 3H), 6.54 (d, 1H), 6.8 (m, 1H), 6.96 (d, 1H), 7.79 (m, 1H), 7.35 (d, 1H), 7.41 (d, 1H), 7.42 (br s, 1H), 8.21 (d, 1H), 8.62 (d, 1H), 9.61 (br s, 1H); Mass Spectrum: M+H$^+$ 419.

[66] NMP was used in place of DMF as the reaction solvent and the reaction mixture was heated to 70° C. for 16 hours and subsequently to 85° C. for 5 hours. The product gave the following characterising data:—$^1$H NMR: (DMSOd$_6$) 1.88 (s, 3H), 3.64 (s, 2H), 3.79 (s, 3H), 3.75 (d, 1H), 6.81 (d, 1H), 6.96 (s, 1H), 7.37 (br s, 2H), 7.72 (m, 1H), 7.95 (m, 1H), 8.11 (m, 1H), 8.69 (d, 1H), 9.47 (br s, 1H), 12.13 (br s, 1H); Mass Spectrum: M+H$^+$ 407.

[67] NMP was used in place of DMF as the reaction solvent and the reaction mixture was heated to 80° C. for 16 hours. The product gave the following characterising data:—$^1$H NMR: (DMSOd$_6$) 1.07 (t, 3H), 2.32 (q, 2H), 3.63 (s, 2H), 3.79 (s, 3H), 6.75 (d, 1H), 6.81 (d, 1H), 6.96 (s, 1H), 7.37 (br s, 2H), 7.72 (m, 1H), 7.95 (m, 1H), 8.11 (m, 1H), 8.69 (d, 1H), 9.42 (br s, 1H), 12.15 (br s, 1H); Mass Spectrum: M+H$^+$ 421.

[68] NMP was used in place of DMF as the reaction solvent and the reaction mixture was heated to 60° C. for 16 hours. The product gave the following characterising data:—$^1$H NMR: (DMSOd$_6$) 1.87 (s, 3H), 3.64 (s, 2H), 3.79 (s, 3H), 6.66 (d, 1H), 6.84 (m, 1H), 7.0 (d, 1H), 7.38 (d, 1H), 7.40 (br s, 1H), 7.59 (m, 1H), 7.78 (m, 1H), 8.41 (m, 1H), 8.73 (d, 1H), 9.66 (br s, 1H), 12.24 (br s, 1H); Mass Spectrum: M+H$^+$ 407.

EXAMPLE 5

Using an analogous procedure to that described in Example 2, the appropriate 2-phenylacetic acid was reacted with the appropriate amine to give the compounds described in Table II. Unless otherwise stated, each reaction product was purified by column chromatography on silica using increasingly polar mixtures of methylene chloride and a 3.5M methanolic ammonia solution as eluent. Unless otherwise stated, each amine was a commercially available material.

TABLE II

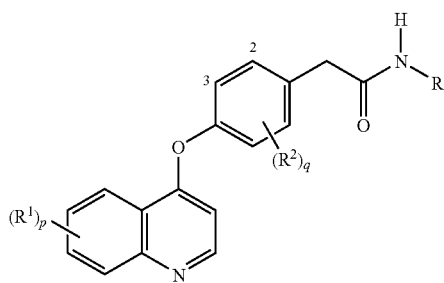

TABLE II-continued

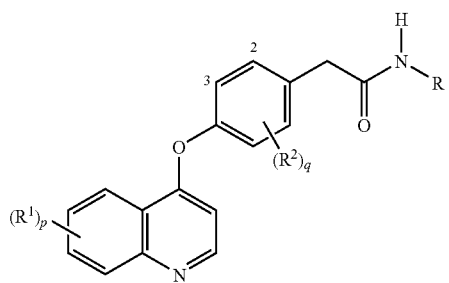

| No. & Note | $(R^1)_p$ | $(R^2)_q$ | R |
|---|---|---|---|
| [1] | 6-carbamoyl-7-methoxy | H | 1-ethylpyrazol-4-yl |
| [2] | 6-(N-methylcarbamoyl)-7-methoxy | H | 1-ethylpyrazol-4-yl |
| [3] | 6-(N,N-dimethylcarbamoyl)-7-methoxy | H | 1-ethylpyrazol-4-yl |
| [4] | 6-methoxycarbonyl-7-methoxy | H | 1-ethylpyrazol-4-yl |
| [5] | 6-cyano-7-methoxy | H | 1-(2-methoxyethyl)pyrazol-4-yl |
| [6] | 6-carbamoyl-7-methoxy | H | 5-ethylpyrazol-3-yl |
| [7] | 6-(N-methylcarbamoyl)-7-methoxy | H | 5-ethylpyrazol-3-yl |
| [8] | 6-(N,N-dimethylcarbamoyl)-7-methoxy | H | 5-ethylpyrazol-3-yl |
| [9] | 6-methoxycarbonyl-7-methoxy | H | 1-ethylpyrazol-3-yl |
| [10] | 6,7-dimethoxy | H | 5-ethylisoxazol-3-yl |
| [11] | 6-cyano-7-methoxy | H | 5-ethylisoxazol-3-yl |
| [12] | 6-carbamoyl-7-methoxy | H | 5-ethylisoxazol-3-yl |
| [13] | 6-(N-methylcarbamoyl)-7-methoxy | H | 5-ethylisoxazol-3-yl |
| [14] | 6-(N,N-dimethylcarbamoyl)-7-methoxy | H | 5-ethylisoxazol-3-yl |
| [15] | 6-methoxycarbonyl-7-methoxy | H | 5-ethylisoxazol-3-yl |
| [16] | 6,7-dimethoxy | H | 4,5-dimethyl-isoxazol-3-yl |
| [17] | 6-cyano-7-methoxy | H | 4,5-dimethyl-isoxazol-3-yl |
| [18] | 6-cyano-7-methoxy | 2-methoxy | 4,5-dimethyloxazol-2-yl |
| [19] | 6-carbamoyl-7-methoxy | H | 4-methylthiazol-2-yl |
| [20] | 6-(N-methylcarbamoyl)-7-methoxy | H | 4-methylthiazol-2-yl |
| [21] | 6-(N,N-dimethylcarbamoyl)-7-methoxy | H | 4-methylthiazol-2-yl |
| [22] | 6-methoxycarbonyl-7-methoxy | H | 4-methylthiazol-2-yl |
| [23] | 6-carbamoyl-7-methoxy | H | 5-methylthiazol-2-yl |
| [24] | 6-(N-methylcarbamoyl)-7-methoxy | H | 5-methylthiazol-2-yl |
| [25] | 6-(N,N-dimethylcarbamoyl)-7-methoxy | H | 5-methylthiazol-2-yl |
| [26] | 6,7-dimethoxy | H | 5-dimethylamino-methylthiazol-2-yl |
| [27] | 6-cyano-7-methoxy | H | 5-dimethylamino-methylthiazol-2-yl |
| [28] | 6,7-dimethoxy | H | 2-pyridyl |
| [29] | 6-cyano-7-methoxy | H | 2-pyridyl |
| [30] | 6,7-dimethoxy | H | 4-dimethylamino-pyridin-2-yl |
| [31] | 6-cyano-7-methoxy | H | 4-dimethylamino-pyridin-2-yl |
| [32] | 6,7-dimethoxy | H | 3-pyridyl |
| [33] | 6-cyano-7-methoxy | H | 3-pyridyl |
| [34] | 6,7-dimethoxy | H | 4-pyridyl |
| [35] | 6,7-dimethoxy | H | 4-pyrimidinyl |
| [36] | 6,7-dimethoxy | H | 5-pyrimidinyl |
| [37] | 6-cyano-7-methoxy | H | 5-pyrimidinyl |
| [38] | 6,7-dimethoxy | H | 4-methylpyrimidin-2-yl |
| [39] | 6,7-dimethoxy | H | 3-pyridazinyl |
| [40] | 6-cyano-7-methoxy | H | 3-pyridazinyl |
| [41] | 6,7-dimethoxy | H | 4-pyridazinyl |
| [42] | 6-cyano-7-methoxy | H | 4-pyridazinyl |
| [43] | 6,7-dimethoxy | H | 2-pyrazinyl |
| [44] | 6-cyano-7-methoxy | H | 2-pyrazinyl |
| [45] | 6,7-dimethoxy | H | 3-dimethylamino-methylphenyl |
| [46] | 6-cyano-7-methoxy | H | 3-dimethylamino-methylphenyl |
| [47] | 6,7-dimethoxy | H | 3-dimethylamino-methyl-4-methylphenyl |
| [48] | 6-cyano-7-methoxy | H | 3-dimethylamino-methyl-4-methylphenyl |
| [49] | 6,7-dimethoxy | H | 3-dimethylamino-methyl-5-methylphenyl |
| [50] | 6-cyano-7-methoxy | H | 3-dimethylamino-methyl-5-methylphenyl |
| [51] | 6,7-dimethoxy | H | 4-dimethylamino-methylphenyl |
| [52] | 6-cyano-7-methoxy | H | 4-dimethylamino-methylphenyl |
| [53] | 6,7-dimethoxy | H | 4-dimethylamino-methyl-3-methylphenyl |
| [54] | 6-cyano-7-methoxy | H | 4-dimethylamino-methyl-3-methylphenyl |
| [55] | 7-(N-methylcarbamoyl)-6-methoxy | 2-methoxy | 1-ethylpyrazol-4-yl |
| [56] | H | 2-methoxy | 1-ethylpyrazol-4-yl |
| [57] | 6,7-dimethoxy | 2-methoxy | 1-ethylpyrazol-4-yl |
| [58] | 6-fluoro | 2-methoxy | 1-methylpyrazol-4-yl |
| [59] | 7-fluoro | 2-methoxy | 1-ethylpyrazol-4-yl |
| [60] | 6-fluoro | 2-methoxy | 1,3-dimethyl-pyrazol-4-yl |
| [61] | 6-fluoro | 2-methoxy | 1,5-dimethyl-pyrazol-4-yl |
| [62] | 7-fluoro | 2-methoxy | 1,5-dimethyl-pyrazol-4-yl |
| [63] | 6-carbamoyl-7-methoxy | 2-methoxy | 5-ethylpyrazol-3-yl |
| [64] | 6,7-dimethoxy | 2-methoxy | 5-ethylpyrazol-3-yl |
| [65] | 7-(N-methylcarbamoyl)-6-methoxy | 2-methoxy | 5-ethylpyrazol-3-yl |
| [66] | H | 2-methoxy | 5-ethylpyrazol-3-yl |
| [67] | 6-(N-methylcarbamoyl)-7-methoxy | 2-methoxy | 5-ethylisoxazol-3-yl |
| [68] | 7-(N-methylcarbamoyl)-6-methoxy | 2-methoxy | 5-ethylisoxazol-3-yl |
| [69] | 6-fluoro | 2-methoxy | 5-methylisoxazol-3-yl |
| [70] | 6-fluoro | 2-methoxy | 5-ethylisoxazol-3-yl |
| [71] | 7-fluoro | 2-methoxy | 5-ethylisoxazol-3-yl |
| [72] | H | 2-methoxy | 4,5-dimethyl-isoxazol-3-yl |
| [73] | 6,7-dimethoxy | 2-methoxy | 4,5-dimethyl-isoxazol-3-yl |

TABLE II-continued

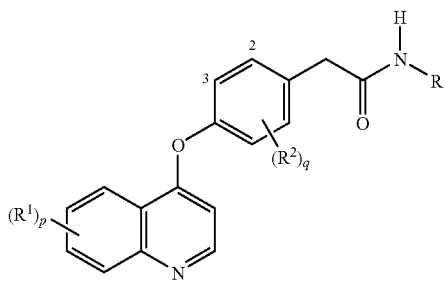

| No. & Note | (R¹)ₚ | (R²)_q | R |
|---|---|---|---|
| [74] | 6-fluoro | 2-methoxy | 4,5-dimethyl-isoxazol-3-yl |
| [75] | 7-fluoro | 2-methoxy | 4,5-dimethyl-isoxazol-3-yl |
| [76] | H | 2-methoxy | 4-methylthiazol-2-yl |
| [77] | 6,7-dimethoxy | 2-methoxy | 4-methylthiazol-2-yl |
| [78] | 6-(N-methylcarbamoyl)-7-methoxy | 2-methoxy | 4-methylthiazol-2-yl |
| [79] | 7-(N-methylcarbamoyl)-6-methoxy | 2-methoxy | 4-methylthiazol-2-yl |
| [80] | 6-(N-methylcarbamoyl)-7-methoxy | 2-methoxy | 5-methylthiazol-2-yl |
| [81] | 6-(N-methylcarbamoyl)-7-methoxy | 2-methoxy | 4-dimethylamino-pyridin-2-yl |
| [82] | 7-(N-methylcarbamoyl)-6-methoxy | 2-methoxy | 4-dimethylamino-pyridin-2-yl |
| [83] | 6-fluoro | 2-methoxy | 4-dimethylamino-pyridin-2-yl |
| [84] | H | 2-methoxy | pyrimidin-4-yl |
| [85] | 6-fluoro | 2-methoxy | pyrazin-2-yl |
| [87] | 6-fluoro | 2-methoxy | 3-dimethylamino-methyl-5-methyl-phenyl |
| [88] | 7-fluoro | 2-methoxy | 3-dimethylamino-methyl-5-methyl-phenyl |
| [89] | 7-(N-methylcarbamoyl)-6-methoxy | 2-methoxy | 3-dimethylamino-methyl-5-methyl-phenyl |
| [90] | 6,7-dimethoxy | 2-methoxy | 1,3-dimethyl-pyrazol-4-yl |
| [91] | 7-fluoro | 2-methoxy | 1-methylpyrazol-4-yl |
| [92] | 6-methoxy | 2-methoxy | 1-methylpyrazol-4-yl |
| [93] | 6-methoxy | 2-methoxy | 1,3-dimethyl-pyrazol-4-yl |
| [94] | 7-ethoxy | 2-methoxy | 1-methylpyrazol-4-yl |
| [95] | 7-fluoro | 2-methoxy | 1,3-dimethyl-pyrazol-4-yl |
| [96] | 6,7-dimethoxy | 2-methoxy | 1,3-dimethyl pyrazol-5-yl |
| [97] | 7-methoxy | 2-methoxy | 1,3-dimethyl-pyrazol-5-yl |
| [98] | 6-fluoro | 2-methoxy | 5-methylpyrazol-3-yl |
| [99] | 6-fluoro | 2-methoxy | 4,5-dimethyl-pyrazol-3-yl |
| [100] | 6-fluoro | 2-methoxy | 1,3-dimethyl-pyrazol-5-yl |
| [101] | 7-fluoro | 2-methoxy | 5-methylpyrazol-3-yl |
| [102] | 7-fluoro | 2-methoxy | 4,5-dimethyl-pyrazol-3-yl |
| [103] | 7-fluoro | 2-methoxy | 1,3-dimethyl-pyrazol-5-yl |
| [104] | 6,7-dimethoxy | 2-methoxy | 4-methylisoxazol-3-yl |
| [105] | 6-fluoro | 2-methoxy | 4-methylisoxazol-3-yl |

TABLE II-continued

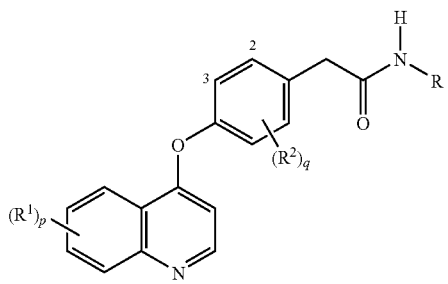

| No. & Note | (R¹)ₚ | (R²)_q | R |
|---|---|---|---|
| [106] | 7-fluoro | 2-methoxy | 4-methylisoxazol-3-yl |

Notes The products gave the characterising data shown below.

[1] $^1$H NMR: (DMSOd$_6$) 1.32 (t, 3H), 3.62 (s, 2H), 4.03 (s, 3H) 4.04-4.1 (m, 2H), 6.48 (d, 1H), 7.26 (d, 2H), 7.42 (s, 1H), 7.46 (d, 2H), 7.54 (s, 1H), 7.74 (br s, 1H), 7.86 (br s, 1H), 7.9 (s, 1H), 8.66 (d, 1H), 8.68 (s, 1H), 10.2 (br s, 1H); Mass Spectrum: M+H$^+$446.

The 2-[4-(6-carbamoyl-7-methoxyquinolin-4-yloxy)phenyl]acetic acid used as a starting material was prepared as follows:—

A mixture of 4-chloro-6-cyano-7-methoxyquinoline (2.5 g) and 12N aqueous hydrochloric acid (50 ml) was stirred and heated to 80° C. for 8 hours. The mixture was cooled to ambient temperature and concentrated by evaporation whereupon a white solid was precipitated. Water (150 ml) was added and the acidity of the mixture was adjusted to pH2.5 by the addition of 4N aqueous sodium hydroxide solution. The mixture was stirred at ambient temperature for 10 minutes. The resultant precipitate was isolated by filtration, washed with ethyl acetate and with diethyl ether and dried under vacuum at 50° C. There was thus obtained 4-chloro-7-methoxyquinoline-6-carboxylic acid (1.9 g); $^1$H NMR: (DMSOd$_6$) 3.99 (s, 3H), 7.59 (s, 1H), 7.66 (d, 1H), 8.4 (s, 1H), 8.83 (d, 1H); Mass Spectrum: M+H$^+$ 238.

Under an atmosphere of argon, oxalyl chloride (1 ml) was added to a stirred suspension of 4-chloro-7-methoxyquinoline-6-carboxylic acid (2.5 g) in methylene chloride (40 ml) and the mixture was stirred at ambient temperature for 10 minutes. Diisopropylethylamine (2 ml) was added and the mixture was stirred at ambient temperature for 10 minutes. Ammonia gas was bubbled through the resultant solution for 5 minutes. The mixture was partitioned between methylene chloride and water. A precipitated solid was isolated by filtration. The organic phase was washed with brine, dried over magnesium sulphate and evaporated. The residue together with the precipitated solid was purified by column chromatography on silica using a solvent gradient of 100:0 to 4:1 of methylene chloride and methanol as eluent. There was thus obtained 4-chloro-7-methoxyquinoline-6-carboxamide (1.26 g); $^1$H NMR: (DMSOd$_6$) 4.04 (s, 3H), 7.6 (s, 1H), 7.66 (d, 1H), 7.81 (br s, 1H), 7.91 (br s, 1H), 8.5 (s, 1H), 8.81 (d, 1H); Mass Spectrum: M+H$^+$ 237 and 239.

A mixture of 4-chloro-7-methoxyquinoline-6-carboxamide (1.26 g), 2-(4-hydroxyphenyl)acetic acid (0.85 g), caesium carbonate (5.47 g) and DMF (15 ml) was stirred and heated to 100° C. for 14 hours. The mixture was cooled to ambient temperature and diethyl ether (50 ml) was added. The precipitate was isolated and dissolved in water and the solution was acidified to pH4.5 by the addition of 6N aqueous hydrochloric acid. The resultant precipitate was isolated, washed with water and with diethyl ether and dried under vacuum. There was thus obtained the required starting material (0.98 g); $^1$H NMR: (DMSOd$_6$) 4.04 (s, 3H), 6.48 (d, 1H), 7.25 (d, 2H), 7.42 (d, 2H), 7.52 (s, 1H), 7.73 (br s, 1H), 7.86 (br s, 1H), 8.67 (m, 2H); Mass Spectrum: M+H$^+$ 353.

[2] $^1$H NMR: (DMSOd$_6$) 1.32 (t, 3H), 2.84 (d, 3H), 3.63 (s, 2H), 4.02 (s, 3H), 4.04-4.1 (m, 2H), 6.48 (d, 1H), 7.25 (d, 2H), 7.42 (s, 1H), 7.46 (d, 2H), 7.52 (s, 1H), 7.9 (s, 1H), 8.34-8.4 (m, 1H), 8.6 (s, 1H), 8.65 (d, 1H), 10.2 (s, 1H); Mass Spectrum: M+H$^+$ 460.

The 2-{4-[7-methoxy-6-(N-methylcarbamoyl)quinolin-4-yloxy]phenyl}acetic acid used as a starting material was prepared as follows:—

Under an atmosphere of argon, oxalyl chloride (1 ml) was added to a stirred suspension of 4-chloro-7-methoxyquinoline-6-carboxylic acid (2.5 g) in methylene chloride (40 ml) and the mixture was stirred at ambient temperature for 10 minutes. Diisopropylethylamine (2 ml) was added and the mixture was stirred at ambient temperature for 10 minutes. Methylamine gas was bubbled through the resultant solution for 5 minutes. The mixture was partitioned between methylene chloride and water. The organic phase was washed with brine, dried over magnesium sulphate and evaporated. The residue was purified by column chromatography on silica using a solvent gradient of 100:0 to 9:1 of methylene chloride and methanol as eluent. There was thus obtained N-methyl-4-chloro-7-methoxyquinoline-6-carboxamide (1.75 g); $^1$H NMR: (DMSOd$_6$) 2.84 (d, 3H), 4.03 (s, 3H), 7.95 (s, 1H), 7.65 (d, 1H), 8.41 (m, 1H), 8.43 (s, 1H), 8.81 (d, 1H); Mass Spectrum: M+H$^+$ 251 and 253.

A mixture of N-methyl-4-chloro-7-methoxyquinoline-6-carboxamide (1.33 g), 2-(4-hydroxyphenyl)acetic acid (0.85 g), caesium carbonate (5.47 g) and DMF (15 ml) was stirred and heated to 100° C. for 14 hours. The mixture was cooled to ambient temperature and diethyl ether (50 ml) was added. The precipitate was isolated and dissolved in water and the solution was acidified to pH4.5 by the addition of 6N aqueous hydrochloric acid. The resultant precipitate was isolated, washed with water and with diethyl ether and dried under vacuum. There was thus obtained the required starting material (1.67 g); $^1$H NMR: (DMSOd$_6$) 2.84 (d, 3H), 3.65 (s, 2H), 4.04 (s, 3H), 6.48 (d, 1H), 7.24 (d, 2H), 7.42 (d, 2H), 7.52 (s, 1H), 8.36 (br s, 1H), 8.6 (s, 1H), 8.66 (d, 1H); Mass Spectrum: M+H$^+$ 367.

[3] The reaction product was purified by column chromatography on silica using increasingly polar mixtures of methylene chloride and methanol as eluent and gave the following characterising data:—$^1$H NMR: (DMSOd$_6$) 1.32 (t, 3H), 2.79 (s, 3H), 3.02 (s, 3H), 2.62 (s, 2H), 3.97 (s, 3H), 4.03-4.11 (m, 2H), 6.59 (d, 1H), 7.25 (d, 2H), 7.42 (s, 1H), 7.45 (d, 2H), 7.5 (s, 1H), 7.9 (s, 1H), 8.04 (s, 1H), 8.64 (d, 1H), 10.2 (s, 1H); Mass Spectrum: M+H$^+$ 474.

The 2-{4-[7-methoxy-6-(N,N-dimethylcarbamoyl)quinolin-4-yloxy]phenyl}acetic acid used as a starting material was prepared as follows:—

Under an atmosphere of argon, oxalyl chloride (0.32 ml) was added to a stirred suspension of 4-chloro-7-methoxyquinoline-6-carboxylic acid (0.3 g) in methylene chloride (6 ml) and the mixture was stirred at ambient temperature for 10 minutes. Diisopropylethylamine (0.44 ml) was added and the mixture was stirred at ambient temperature for 10 minutes. The mixture was evaporated under vacuum and methylene chloride (5 ml) was added to the residue followed by a 2M solution of dimethylamine in THF (2.5 ml). The resultant mixture was stirred at ambient temperature for 20 minutes. The mixture was evaporated and the residue was purified by column chromatography on silica using a solvent gradient of 100:0 to 19:1 of methylene chloride and methanol as eluent. There was thus obtained N,N-dimethyl-4-chloro-7-methoxyquinoline-6-carboxamide (0.257 g); $^1$H NMR: (CDCl$_3$) 2.88 (s, 3H), 3.19 (s, 3H), 4.0 (s, 3H), 7.38 (d, 1H), 7.49 (s, 1H), 8.12 (s, 1H), 8.72 (s, 1H); Mass Spectrum: M+H$^+$ 265 and 267.

A mixture of the materials so obtained, 2-(4-hydroxyphenyl)acetic acid (0.155 g), potassium carbonate (0.402 g) and DMF (3 ml) was stirred and heated to 90° C. for 8 hours. The mixture was cooled to ambient temperature and diethyl ether (30 ml) was added. The precipitate was isolated and dissolved in water and the solution was acidified to pH4.3 by the addition of 6N aqueous hydrochloric acid. The aqueous mixture was extracted with methylene chloride. The organic phase was washed with water, dried over magnesium sulphate and evaporated. There was thus obtained the required starting material (0.2 g); $^1$H NMR: (DMSOd$_6$) 2.8 (s, 3H), 3.02 (s, 3H), 3.63 (s, 2H), 3.97 (s, 3H), 6.49 (d, 1H), 7.23 (d, 2H), 7.41 (d, 2H), 7.51 (s, 1H), 8.04 (s, 1H), 8.64 (d, 1H); Mass Spectrum: M+H$^+$ 381.

[4] $^1$H NMR: (DMSOd$_6$) 1.32 (t, 3H), 3.67 (s, 2H), 3.89 (s, 3H), 4.04 (s, 3H), 4.07 (q, 2H), 6.74 (d, 1H), 7.36 (d, 2H), 7.44 (s, 1H), 7.53 (d, 2H), 7.67 (s, 1H), 7.9 (s, 1H), 8.73 (s, 1H), 8.9 (d, 1H); Mass Spectrum: M+H$^+$ 461.

The 2-[4-(7-methoxy-6-methoxycarbonylquinolin-4-yloxy)phenyl]acetic acid used as a starting material was prepared as follows:—

Using an analogous procedure to that described in Note [2] immediately above, methyl 4-chloro-7-methoxyquinoline-6-carboxylate (International Patent Application WO 98/13350, Example 55 thereof) was reacted with 2-(4-hydroxyphenyl) acetic acid to give the required starting material in 57% yield; $^1$H NMR: (DMSOd$_6$) 3.66 (s, 2H), 3.87 (s, 3H), 3.98 (s, 3H), 6.48 (d, 1H), 7.27 (d, 2H), 7.43 (d, 2H), 7.54 (s, 1H), 8.59 (s, 1H), 8.69 (d, 1H); Mass Spectrum: M+H$^+$ 368.

[5] $^1$H NMR: (DMSOd$_6$) 3.21 (s, 3H), 3.63 (t, 2H), 3.64 (s, 2H), 4.07 (s, 3H), 4.2 (t, 2H), 6.54 (d, 1H), 7.28 (d, 2H), 7.44 (s, 1H), 7.47 (d, 2H), 7.62 (s, 1H), 7.89 (s, 1H), 8.74 (d, 1H), 8.77 (s, 1H), 10.21 (s, 1H).

[6] $^1$H NMR: (DMSOd$_6$) 1.61 (t, 3H), 2.52-2.59 (m, 2H), 3.65 (s, 2H), 4.03 (s, 3H), 6.29 (br s, 1H), 6.48 (d, 1H), 7.26 (d, 2H), 7.47 (d, 2H), 7.52 (s, 1H), 7.73 (br s, 1H), 7.85 (br s, 1H 8.66 (s, 1H), 7.86 (br s, 1H), 8.65 (d, 1H), 8.68 (s, 1H), 10.55 (br s, 1H), 12.02 (s, 1H); Mass Spectrum: M+H$^+$ 446.

[7] $^1$H NMR: (DMSOd$_6$) 1.16 (t, 3H), 2.52-2.59 (m, 2H), 2.84 (d, 3H), 3.65 (s, 2H), 4.02 (s, 3H), 6.48 (d, 1H), 7.25 (d, 2H), 7.47 (d, 2H), 7.51 (s, 1H), 8.33-8.4 (m, 1H), 8.6 (d, 1H), 8.65 (d, 1H), 10.55 (br s, 1H), 12.02 (br s, 1H); Mass Spectrum: M+H$^+$ 460.

[8] $^1$H NMR: (DMSOd$_6$) 1.16 (t, 3H), 2.52-2.59 (m, 2H), 2.79 (s, 3H), 3.02 (s, 3H), 3.65 (s, 2H), 3.97 (s, 3H), 6.28 (br s, 1H), 6.5 (d, 1H), 7.25 (d, 2H), 7.46 (d, 2H), 7.51 (s, 1H), 8.04 (s, 1H), 8.63 (d, 1H), 10.52 (br s, 1H); Mass Spectrum: M+H$^+$ 474.

[9] $^1$H NMR: (DMSOd$_6$) 1.34 (t, 3H), 3.66 (s, 2H), 3.86 (s, 3H), 3.98 (s, 3H), 3.99-4.05 (m, 2H), 6.43 (d, 1H), 6.49 (d, 1H), 7.27 (d, 2H), 7.48 (d, 2H), 7.54 (d, 1H), 7.58 (d, 1H), 8.59 (s, 1H), 8.68 (d, 1H), 10.71 (br s, 1H); Mass Spectrum: M+H$^+$ 461.

The 3-amino-1-ethyl-1H-pyrazole used as a starting material is described in Chemical Abstracts, 1975, 82, 156172 and in International Patent Application WO 2005/060970.

[10] $^1$H NMR: (DMSOd$_6$) 1.2 (t, 3H), 2.71 (d, 1H), 2.74 (d, 1H), 3.74 (s, 2H), 3.92 (s, 3H), 3.95 (s, 3H), 6.47 (d, 1H), 6.63 (s, 1H), 7.23 (d, 2H), 7.4 (s, 1H), 7.45 (d, 2H), 7.49 (s, 1H), 8.47 (d, 1H), 11.2 (br s, 1H); Mass Spectrum: M+H$^+$ 434.

The 3-amino-5-ethylisoxazole used as a starting material is described in International Patent Application WO 2005/026113 (pages 33 and 34 thereof).

[11] $^1$H NMR: (DMSOd$_6$) 1.2 (t, 3H), 2.7 (d, 1H), 2.74 (d, 1H), 3.75 (s, 2H), 4.07 (s, 3H), 6.54 (d, 1H), 6.63 (s, 1H), 7.29 (d, 2H), 7.48 (d, 2H), 7.62 (s, 1H), 8.74 (d, 1H), 8.77 (s, 1H), 11.21 (br s, 1H); Mass Spectrum: M+H$^+$ 429.

[12] $^1$H NMR: (DMSOd$_6$) 1.2 (t, 3H), 2.68-2.76 (m, 2H), 3.75 (s, 2H), 4.03 (s, 3H), 6.49 (d, 1H), 6.64 (br s, 1H), 7.27 (d, 2H), 7.47 (d, 2H), 7.52 (s, 1H), 7.73 (br s, 1H), 7.86 (br s, 1H), 8.66 (d, 1H), 8.67 (s, 1H), 11.21 (br s, 1H); Mass Spectrum: M+H$^+$ 447.

[13] $^1$H NMR: (DMSOd$_6$) 1.2 (t, 3H), 2.68-2.76 (m, 2H), 2.84 (d, 3H), 3.74 (s, 2H), 4.02 (s, 3H), 6.49 (d, 1H), 6.63 (br s, 1H), 7.25 (d, 2H), 7.47 (d, 2H), 7.52 (s, 1H), 8.33-8.39 (m, 1H), 8.6 (s, 1H), 8.66 (d, 1H), 11.21 (br s, 1H); Mass Spectrum: M+H$^+$ 461.

[14] $^1$H NMR: (DMSOd$_6$) 1.21 (t, 3H), 2.69-2.77 (m, 2H), 2.81 (s, 3H), 3.03 (s, 3H), 3.76 (s, 2H), 3.99 (s, 3H), 6.52 (d, 1H), 6.65 (s, 1H), 7.27 (d, 2H), 7.47 (d, 2H), 7.51 (s, 1H), 8.05 (s, 1H), 8.66 (d, 1H), 11.22 (br s, 1H); Mass Spectrum: M+H$^+$ 475.

[15] $^1$H NMR: (DMSOd$_6$) 1.21 (t, 3H), 2.68-2.78 (m, 2H), 3.76 (s, 2H), 3.87 (s, 3H), 3.99 (s, 3H), 6.49 (d, 1H), 6.64 (s, 1H), 7.29 (d, 2H), 7.48 (d, 2H), 7.55 (s, 1H), 8.59 (s, 1H), 8.7 (d, 1H), 11.22 (br s, 1H); Mass Spectrum: M+H$^+$ 462.

[16] $^1$H NMR: (DMSOd$_6$) 1.77 (s, 3H), 2.3 (s, 3H), 3.76 (s, 2H), 3.96 (s, 3H), 3.98 (s, 3H), 6.57 (d, 1H), 7.28 (d, 2H), 7.43 (s, 1H), 7.49 (d, 2H), 7.56 (s, 1H), 8.57 (s, 1H), 10.45 (br s, 1H); Mass Spectrum: M+H$^+$ 434.

The 3-amino-4,5-dimethylisoxazole used as a starting material is described in *Tetrahedron Letters*, 1996, 37, 3339-3342.

[17] $^1$H NMR: (DMSOd$_6$) 1.77 (s, 3H), 2.3 (s, 3H), 3.76 (s, 2H), 4.07 (s, 3H), 6.54 (d, 1H), 7.3 (d, 2H), 7.49 (d, 2H), 7.62 (s, 1H), 8.75 (d, 1H), 8.78 (s, 1H), 10.45 (br 1H); Mass Spectrum: M+H$^+$ 429.

[18] The reaction mixture was diluted with water and the precipitate was isolated, dried and purified by column chromatography on silica using a solvent gradient of 50:50:0 to 9:9:2 of methylene chloride, ethyl acetate and methanol as eluent. The product gave the following characterising data:—$^1$H NMR: (DMSOd$_6$ and CD$_3$CO$_2$D) 1.98 (s, 3H), 2.18 (s, 3H), 3.71 (br s, 2H), 3.77 (s, 3H), 4.08 (s, 3H), 6.61 (d, 1H), 6.86 (m, 1H), 7.0 (d, 1H), 7.35 (d, 1H), 7.62 (s, 1H), 8.76 (d, 1H), 8.77 (s, 1H); Mass Spectrum: M−H$^−$ 457.

[19] $^1$H NMR: (DMSOd$_6$) 2.27 (d, 3H), 3.81 (s, 2H), 4.03 (s, 3H), 6.5 (d, 1H), 6.75 (br s, 1H), 7.28 (d, 2H), 7.48 (d, 2H), 7.52 (s, 1H), 7.72 (br s, 1H), 7.86 (br s, 1H), 8.66 (d, 1H), 8.67 (s, 1H), 12.31 (br s, 1H); Mass Spectrum: M+H$^+$ 449.

[20] $^1$H NMR: (DMSOd$_6$) 2.27 (d, 3H), 2.84 (d, 3H), 3.81 (s, 2H), 4.02 (s, 3H), 6.5 (d, 1H), 6.74-6.78 (m, 1H), 7.27 (d, 2H), 7.48 (d, 2H), 7.52 (s, 1H), 8.33-8.39 (m, 1H), 8.59 (s, 1H), 8.66 (d, 1H), 10.31 (br s, 1H); Mass Spectrum: M+H$^+$ 463.

[21] $^1$H NMR: (DMSOd$_6$) 2.26 (s, 3H), 2.79 (s, 3H), 3.02 (s, 3H), 3.81 (s, 2H), 3.97 (s, 3H), 6.51 (d, 1H), 6.75 (s, 1H), 7.26 (d, 2H), 7.47 (d, 2H), 6.51 (s, 1H), 8.03 (s, 1H), 8.64 (d, 1H); Mass Spectrum: M+H$^+$ 477.

[22] $^1$H NMR: (DMSOd$_6$) 2.27 (d, 3H), 3.82 (s, 2H), 3.86 (s, 3H), 3.98 (s, 3H), 6.5 (d, 1H), 6.76 (br s, 1H), 7.29 (d, 2H), 7.48 (d, 2H), 7.54 (s, 1H), 8.58 (d, 1H), 8.69 (d, 1H); Mass Spectrum: M+H$^+$ 464.

[23] $^1$H NMR: (DMSOd$_6$) 2.33 (d, 3H), 3.81 (s, 2H), 4.03 (s, 3H), 6.50 (d, 1H), 7.14 (br s, 1H), 7.28 (d, 2H), 7.48 (d, 2H), 7.52 (s, 1H), 7.73 (br s, 1H), 7.86 (br s, 1H), 8.66 (d, 1H), 8.67 (s, 1H), 12.2 (br s, 1H); Mass Spectrum: M+H$^+$ 449.

[24] $^1$H NMR: (DMSOd$_6$) 2.33 (d, 3H), 2.84 (d, 3H), 3.81 (s, 2H), 4.02 (s, 3H), 6.5 (d, 1H), 7.13-7.15 (m, 1H), 7.27 (d, 2H), 7.48 (d, 2H), 7.52 (s, 1H), 8.33-8.39 (m, 1H), 8.6 (s, 1H), 8.66 (d, 1H), 12.19 (br s, 1H); Mass Spectrum: M+H$^+$ 463.

[25] $^1$H NMR: (DMSOd$_6$) 2.33 (s, 3H), 2.79 (s, 3H), 3.02 (s, 3H), 3.81 (s, 2H), 3.97 (s, 3H), 6.51 (d, 1H), 7.14 (s, 1H), 7.26 (d, 2H), 7.46 (d, 2H), 7.51 (s, 1H), 8.03 (s, 1H), 8.64 (d, 1H); Mass Spectrum: M+H$^+$ 477.

[26] $^1$H NMR: (DMSOd$_6$+CF$_3$CO$_2$D) 2.74 (s, 6H), 3.94 (s, 2H), 4.05 (s, 3H), 4.07 (s, 3H), 4.51 (s, 2H), 6.87 (d, 1H), 7.42 (d, 2H), 7.59 (d, 2H), 7.65 (s, 1H), 7.66 (s, 1H), 7.76 (s, 1H), 8.83 (d, 1H); Mass Spectrum: M+H$^+$ 479.

The 2-amino-5-dimethylaminomethylthiazole used as a starting material was prepared as follows:—

A mixture of tert-butyl N-[5-(dimethylaminomethyl)thiazol-2-yl]carbamate (*Synth. Comm.*, 2000, 30, 2001-2008; 2.45 g), trifluoroacetic acid (15 ml) and methylene chloride (5 ml) was stirred at ambient temperature for 6 hours. The resultant mixture was evaporated and the residual oil was dissolved in a 5:1 mixture of methylene chloride and ethanol and a 4M solution of hydrogen chloride in 1,4-dioxane (5.95 ml) was added. Diethyl ether was added and the precipitate was isolated, washed with diethyl ether and dried under vacuum. There was thus obtained the required starting material (2.1 g); $^1$H NMR: (DMSOd$_6$+CF$_3$CO$_2$D) 2.75 (s, 6H), 4.37 (s, 2H), 7.53 (s, 1H); Mass Spectrum: M+H$^+$ 158.

[27] A solution of the reaction product (approximately 0.35 mmol) in ethanol (0.3 ml) and methylene chloride (2.7 ml) was treated with a solution of succinic acid (0.5 mmol) in ethanol (3 ml). The resultant solution was evaporated and the residue was triturated under diethyl ether. The resultant solid was isolated and dried under vacuum. There was thus obtained a mono succinate salt which gave the following characterising data:—$^1$H NMR: (DMSOd$_6$+CF$_3$CO$_2$D) 2.43 (s, 4H), 2.76 (s, 6H), 3.94 (s, 2H), 4.17 (s, 3H), 4.52 (s, 2H), 6.94 (d, 1H), 7.42 (d, 2H), 7.6 (d, 2H), 7.65 (s, 1H), 7.77 (s, 1H), 8.07 (d, 1H), 8.14 (s, 1H); Mass Spectrum: M+H$^+$ 474.

[28] $^1$H NMR: (DMSOd$_6$) 3.79 (s, 2H), 3.92 (s, 3H), 3.95 (s, 3H), 6.47 (d, 1H), 7.11 (m, 1H), 2.73 (d, 2H), 7.4 (s, 1), 7.48 (d, 2H), 7.49 (s, 1H), 7.78 (m, 1H), 8.08 (d, 1H), 8.33 (m, 1H), 8.47 (d, 1H), 10.75 (s, 1H); Mass Spectrum: M+H$^+$ 416.

[29] $^1$H NMR: (DMSOd$_6$) 3.81 (s, 2H), 4.07 (s, 3H), 6.55 (d, 1H), 7.11 (m, 1H), 7.29 (d, 2H), 7.52 (d, 2H), 7.62 (s, 1H), 7.75-7.81 (m, 1H), 8.08 (d, 1H), 8.33 (m, 1H), 8.74 (d, 1H), 8.77 (s, 1H), 10.77 (s, 1H); Mass Spectrum: M+H$^+$ 411.

[30] $^1$H NMR: (DMSOd$_6$) 2.94 (s, 6H), 3.75 (s, 2H), 3.92 (s, 3H), 3.94 (s, 3H), 6.38 (m, 1H), 6.47 (d, 1H), 7.23 (d, 2H), 7.4 (s, 1H), 7.43-7.52 (m, 4H), 7.88 (d, 1H), 8.47 (d, 1H), 10.36 (s, 1H); Mass Spectrum: M+H$^+$ 459.

The 2-amino-4-dimethylaminopyridine used as a starting material was prepared as follows:—

A mixture of 2-amino-4-chloropyridine (*Organic Preparation and Procedure*, 1997, 29, 117-122; 0.4 g) and an aqueous solution of dimethylamine (40%) were stirred and heated to 175° C. for 35 minutes in a microwave oven. The resultant reaction mixture was transferred onto a Waters 'β Basic Hypersil' reversed-phase preparative HPLC column (5 microns silica, 30 mm diameter, 250 mm length) that was eluted with decreasingly polar mixtures of water (containing 0.2% ammonium carbonate) and acetonitrile as eluent. There was thus obtained the required starting material in 94% yield; $^1$H NMR: (CDCl$_3$) 2.95 (s, 6H), 4.19 (br s, 2H), 5.68 (m, 1H), 6.05 (m, 1H), 7.77 (m, 1H); Mass Spectrum: M+H$^+$ 138.

[31] The reaction mixture was purified by preparative HPLC using a Waters 'Xterra' reversed-phase column (5 microns silica) using decreasingly polar mixtures of water (containing 0.2% ammonium carbonate) and acetonitrile as eluent. The product gave the following characterising data:—$^1$H NMR: (DMSOd$_6$) 2.94 (s, 6H), 3.76 (s, 2H), 4.07 (s, 3H), 6.38 (m, 1H), 6.54 (m, 1H), 7.28 (d, 2H), 7.46 (s, 1H), 7.5 (d, 2H), 7.62 (s, 1H), 7.88 (m, 1H), 8.73 (m, 1H), 8.78 (s, 1H), 10.38 (s, 1H); Mass Spectrum: M+H$^+$ 454.

[32] $^1$H NMR: (DMSOd$_6$) 3.75 (s, 2H), 3.93 (s, 3H), 3.94 (s, 3H), 6.48 (d, 1H), 7.24 (d, 2H), 7.35 (m, 1H), 7.4 (s, 1H), 7.48 (d, 2H), 7.49 (s, 1H), 8.06 (m, 1H), 8.27 (m, 1H), 8.48 (d, 1H), 8.77 (s, 1H), 10.44 (s, 1H); Mass Spectrum: M+H$^+$ 416.

[33] $^1$H NMR: (DMSOd$_6$) 3.77 (s, 2H), 4.07 (s, 3H), 6.55 (d, 1H), 7.3 (d, 2H), 7.35 (m, 1H), 7.51 (d, 2H), 7.62 (s, 1H), 8.07 (m, 1H), 8.27 (m, 1H), 8.75 (d, 1H), 8.77 (d, 1H), 8.78 (s, 1H), 10.44 (s, 1H); Mass Spectrum: M+H$^+$ 411.

[34] $^1$H NMR: (DMSOd$_6$) 3.77 (s, 2H), 3.93 (s, 3H), 3.95 (s, 3H), 6.48 (d, 1H), 7.24 (d, 2H), 7.4 (s, 1H), 7.47 (d, 2H), 7.49 (s, 1H), 7.59 (d, 2H), 8.43 (d, 2H), 8.48 (d, 1H), 10.59 (br s, 1H); Mass Spectrum: M+H$^+$ 416.

[35] $^1$H NMR: (DMSOd$_6$) 3.84 (s, 2H), 3.92 (s, 3H), 3.95 (s, 3H), 6.48 (d, 1H), 7.24 (d, 2H), 7.4 (s, 1H), 7.47 (d, 2H), 7.49 (s, 1H), 8.06 (m, 1H), 8.48 (d, 1H), 8.65 (d, 1H), 8.9 (d, 1H), 11.2 (br s, 1H); Mass Spectrum: M+H$^+$ 417.

[36] $^1$H NMR: (DMSOd$_6$) 3.8 (s, 2H), 3.92 (s, 3H), 3.95 (s, 3H), 6.48 (d, 1H), 7.25 (d, 2H), 7.4 (s, 1H), 7.48 (d, 2H), 7.49 (s, 1H), 8.48 (d, 1H), 8.9 (s, 1H), 9.03 (s, 2H), 10.65 (br s, 1H); Mass Spectrum: M+H$^+$ 417.

The 5-aminopyrimidine used as a starting material is described in European Patent Application No. 0139477 (Example 1 thereof).

[37] $^1$H NMR: (DMSOd$_6$) 3.82 (s, 2H), 4.07 (s, 3H), 6.54 (d, 1H), 7.3 (d, 2H), 7.51 (d, 2H), 7.62 (s, 1H), 8.75 (d, 1H), 8.78 (s, 1H), 8.9 (s, 1H), 9.03 (s, 2H), 10.67 (br s, 1H); Mass Spectrum: M+H$^+$ 412.

[38] $^1$H NMR: (DMSOd$_6$) 2.41 (s, 3H), 3.86 (s, 2H), 3.92 (s, 3H), 3.95 (s, 3H), 6.46 (d, 1H), 7.22 (d, 2H), 7.07 (d, 1H), 7.4 (s, 1H), 7.46 (d, 2H), 7.49 (s, 1H), 8.47 (d, 1H), 8.5 (d, 1H), 10.73 (br s, 1H); Mass Spectrum: M+H$^+$ 431.

[39] $^1$H NMR: (DMSOd$_6$) 3.86 (s, 2H), 3.92 (s, 3H), 3.94 (s, 3H), 6.48 (d, 1H), 7.24 (d, 2H), 7.4 (s, 1H), 7.49 (s, 1H), 7.5 (d, 2H), 7.68 (m, 1H), 8.31 (m, 1H), 8.48 (d, 1H), 8.97 (m, 1H), 11.4 (br s, 1H); Mass Spectrum: M+H$^+$ 417.

The 3-aminopyridazine used as a starting material is described in *Tetrahedron*, 1993, 49, 599-606.

[40] $^1$H NMR: (DMSOd$_6$) 3.89 (s, 2H), 4.08 (s, 3H), 6.56 (d, 1H), 7.31 (d, 2H), 7.54 (d, 2H), 7.63 (s, 1H), 7.69 (m, 1H), 8.32 (m, 1H), 8.75 (d, 1H), 8.78 (s, 1H), 8.98 (m, 1H), 11.42 (s, 1H); Mass Spectrum: M+H$^+$ 412.

[41] $^1$H NMR: (DMSOd$_6$) 3.82 (s, 2H), 3.92 (s, 3H), 3.95 (s, 3H), 6.48 (d, 1H), 7.24 (d, 2H), 7.4 (s, 1H), 7.47 (d, 2H), 7.49 (s, 1H), 7.94 (m, 1H), 8.48 (d, 1H), 9.03 (m, 1H), 9.31 (m, 1H), 10.86 (br s, 1H); Mass Spectrum: M+H$^+$ 417.

The 4-aminopyridazine used as a starting material is described in U.S. Pat. No. 4,735,650 (within Example 2 thereof).

[42] $^1$H NMR: (DMSOd$_6$) 3.84 (s, 2H), 4.07 (s, 3H), 6.55 (d, 1H), 7.31 (d, 2H), 7.5 (d, 2H), 7.62 (s, 1H), 7.94 (m, 1H), 8.75 (d, 1H), 8.78 (s, 1H), 9.04 (d, 1H), 9.31 (d, 1H), 10.89 (s, 1H); Mass Spectrum: M+H$^+$ 412.

[43] $^1$H NMR: (DMSOd$_6$) 3.84 (s, 2H), 3.92 (s, 3H), 3.95 (s, 3H), 6.48 (d, 1H), 7.27 (d, 2H), 7.4 (s, 1H), 7.48 (d, 2H), 7.49 (s, 1H), 8.37 (d, 1H), 8.42 (m, 1H), 8.48 (d, 1H), 9.34 (d, 1H), 11.07 (br s, 1H); Mass Spectrum: M+H$^+$ 417.

[44] $^1$H NMR: (DMSOd$_6$) 3.86 (s, 2H), 4.07 (s, 3H), 6.55 (d, 1H), 7.3 (d, 2H), 7.52 (d, 2H), 7.62 (s, 1H), 8.38 (d, 1H), 8.48 (br s, 1H), 8.75 (d, 1H), 8.77 (s, 1H), 9.34 (s, 1H), 11.09 (s, 1H); Mass Spectrum: M+H$^+$ 412.

[45] The reaction product was purified by preparative HPLC using a Waters 'Xterra' reversed-phase column (5 microns silica) using decreasingly polar mixtures of water (containing 0.2% ammonium carbonate) and acetonitrile as eluent. The product gave the following characterising data:—$^1$H NMR: (DMSOd$_6$+CF$_3$CO$_2$D) 2.72 (s, 6H), 3.79 (s, 2H), 4.04 (s, 3H), 4.05 (s, 3H), 4.26 (s, 2H), 6.84 (d, 1H), 7.2 (d, 1H), 7.38 (d, 2H), 7.41 (m, 1H), 7.58 (s, 1H), 7.59 (d, 2H), 7.62 (s, 1H), 7.75 (s, 1H), 7.91 (br s, 1H), 8.83 (d, 1H); Mass Spectrum: M+H$^+$ 472.

The 3-dimethylaminomethylaniline used as a starting material was prepared as follows:—

Triethylamine (3.64 g) was added dropwise to a mixture of 3-nitrobenzyl bromide (2.6 g), dimethylamine hydrochloride (1.96 g) and methylene chloride (26 ml) and the resultant mixture was stirred at ambient temperature for 2 hours. The solvent was evaporated and the residue was diluted with water and extracted with ethyl acetate. The organic phase was washed with water, dried over magnesium sulphate and concentrated. There was thus obtained N,N-dimethyl-N-(3-nitrobenzyl)amine (1.6 g); $^1$H NMR: (DMSOd$_6$) 2.18 (s, 6H), 3.34 (s, 2H), 7.63 (t, 1H), 7.75 (d, 1H), 8.12 (m, 2H); Mass Spectrum: M+H$^+$ 181.

Raney nickel (0.8 g) was washed twice with ethanol and added to a solution of N,N-dimethyl-N-(3-nitrobenzyl)amine (1.6 g) in a mixture of methanol (10 ml) and ethanol (50 ml). The mixture was stirred under 1.8 atmospheres pressure of hydrogen at ambient temperature for 1 hour. The reaction mixture was filtered and the filtrate was evaporated. The residue was purified by column chromatography on silica using a solvent gradient from a 19:1 to a 9:1 mixture of methylene chloride and methanol followed by a 9:1 to a 18:3 mixture of methylene chloride and a 7M methanolic ammonia solution as eluent. There was thus obtained 3-dimethylaminomethylaniline (0.85 g); $^1$H NMR: (DMSOd$_6$) 2.11 (s, 6H), 3.2 (s, 2H), 4.96 (br s, 2H), 6.41 (m, 2H), 6.51 (s, 1H), 6.92 (t, 1H); Mass Spectrum: M+H$^+$ 151.

[46] Using an analogous procedure to that described in Note [27] above, the reaction product was treated with succinic acid. The resultant mono succinate salt was isolated and gave the following characterising data:—$^1$H NMR: (DMSOd$_6$+CF$_3$CO$_2$D) 2.44 (s, 4H), 2.75 (s, 6H), 3.81 (s, 2H), 4.17 (s, 3H), 4.28 (s, 2H), 6.92 (d, 1H), 7.2 (d, 1H), 7.41 (d, 2H), 7.44 (m, 1H), 7.58 (d, 1H), 7.6 (d, 2H), 7.78 (s, 1H), 7.92 (br s, 1H), 9.08 (d, 1H), 9.14 (s, 1H); Mass Spectrum: M+H$^+$ 467.

[47] The reaction product was purified by preparative HPLC using a Waters 'Xterra' reversed-phase column (5 microns silica) using decreasingly polar mixtures of water (containing 0.2% ammonium carbonate) and acetonitrile as eluent. The product gave the following characterising data:—$^1$H NMR: (DMSOd$_6$+CF$_3$CO$_2$D) 2.36 (s, 3H), 2.79 (s, 6H), 3.79 (s, 2H), 4.05 (s, 3H), 4.07 (s, 3H), 4.3 (s, 2H), 6.85 (d, 1H), 7.26 (d, 1H), 7.4 (d, 2H), 7.48 (m, 1H), 7.6 (d, 2H), 7.65 (s, 1H), 7.77 (s, 1H), 7.87 (br s, 1H), 8.85 (d, 1H); Mass Spectrum: M+H$^+$ 486.

The 3-dimethylaminomethyl-4-methylaniline used as a starting material was prepared as follows:—

Diborane (2M solution in THF, 24.5 ml) was added dropwise to a stirred solution of N,N-dimethyl-2-methyl-5-nitrobenzamide (3 g) in THF (10 ml). The resultant mixture was stirred and heated to 58° C. for 6 hours. A 6N aqueous hydrochloric acid solution (50 ml) was added and the mixture was stirred at ambient temperature for 16 hours. The mixture was basified by the addition of potassium carbonate and extracted with ethyl acetate. The organic solution was dried over magnesium sulphate and evaporated to leave an oil which was triturated under diethyl ether. There was thus obtained N,N-dimethyl-N-(2-methyl-5-nitrobenzyl)amine as a solid (1.8 g); $^1$H NMR: (CDCl$_3$) 2.27 (s, 6H), 2.45 (s, 3H), 3.43 (s, 2H), 7.29 (m, 1H), 8.02 (m, 1H), 8.16 (m, 1H); Mass Spectrum: M+H$^+$ 195.

A mixture of N,N-dimethyl-N-(2-methyl-5-nitrobenzyl)amine (2.4 g), platinum oxide (0.12 g) and ethyl acetate (40 ml) was stirred under 1.8 atmospheres pressure of hydrogen for 30 minutes. The catalyst was removed by filtration and the filtrate was evaporated. The material so obtained was dried under vacuum at ambient temperature for 2 hours. There was thus obtained 3-dimethylaminomethyl-4-methylaniline as a solid (1.85 g); $^1$H NMR: (DMSOd$_6$+CF$_3$CO$_2$D) 2.42 (s, 3H), 2.81 (s, 6H), 4.37 (s, 2H), 7.36 (m, 1H), 7.43 (m, 2H); Mass Spectrum: M+H$^+$ 165.

[48] Using an analogous procedure to that described in Note [27] above, the reaction product was treated with succinic acid. The resultant salt which contained 1.2 equivalents of succinic acid was isolated and gave the following characterising data:—$^1$H NMR: (DMSOd$_6$+CF$_3$CO$_2$D) 2.35 (s, 3H), 2.43 (s, 4H), 2.8 (s, 6H), 3.79 (s, 2H), 4.17 (s, 3H), 4.3 (s, 2H), 6.91 (d, 1H), 7.26 (d, 1H), 7.4 (d, 2H), 7.46 (m, 1H), 7.6 (d, 2H), 7.78 (s, 1H), 7.87 (d, 1H), 9.08 (d, 1H), 9.14 (s, 1H); Mass Spectrum: M+H$^+$ 481.

[49] The reaction product was purified by preparative HPLC using a Waters 'Xterra' reversed-phase column (5 microns silica) using decreasingly polar mixtures of water (containing 0.2% ammonium carbonate) and acetonitrile as eluent. The product gave the following characterising data:—$^1$H NMR: (DMSOd$_6$+CF$_3$CO$_2$D) 2.33 (s, 3H), 2.77 (s, 6H), 3.74 (s, 2H), 4.05 (s, 3H), 4.07 (s, 3H), 4.22 (s, 2H), 6.85 (d, 1H), 7.04 (br s, 1H), 7.4 (d, 2H), 7.45 (br s, 1H), 7.6 (d, 2H), 7.64 (s, 1H), 7.69 (br s, 1H), 7.77 (s, 1H), 8.84 (d, 1H); Mass Spectrum: M+H$^+$ 486.

The 3-dimethylaminomethyl-5-methylaniline used as a starting material was prepared as follows:—

A mixture of 1,3-dimethyl-5-nitrobenzene (15.15 g), N-bromosuccinimide (2 g), benzoyl peroxide (0.484 g) and carbon tetrachloride (250 ml) was stirred and heated to reflux. Further portions of N-bromosuccinimide (totaling 21 g) were added portionwise during 4 hours to the heated reaction mixture. The mixture was cooled to ambient temperature. Petroleum ether (b.p. 60-80° C.) was added. The mixture was filtered and the filtrate was evaporated to give an oil (25 g) which was shown by NMR analysis to be a mixture of 3-methyl-5-nitrobenzyl bromide (76%), unreacted starting material (~19%) and 3-bromomethyl-5-nitrobenzyl bromide (~15%). This mixture was used in the next step.

A portion (2.3 g) of the oil so obtained was dissolved in ethanol (5 ml) and dimethylamine (6 equivalents) was added portionwise in order to prevent a significant exotherm. The resultant reaction mixture was stirred at ambient temperature for 12 hours. The mixture was evaporated and the residue was purified by column chromatography on silica using increasingly polar mixtures of methylene chloride and diethyl ether as eluent. There was thus obtained N,N-dimethyl-N-(3-methyl-5-nitrobenzyl)amine (0.98 g); $^1$H NMR: (DMSOd$_6$) 2.17 (s, 6H), 2.43 (s, 3H), 3.48 (s, 2H), 7.58 (s, 1H), 7.94 (m, 2H); Mass Spectrum: M+H$^+$ 195.

Using an analogous procedure to that described in the last paragraph of the portion of Note [47] immediately above that is concerned with the preparation of starting materials, N,N-dimethyl-N-(3-methyl-5-nitrobenzyl)amine was hydrogenated to give 3-dimethylaminomethyl-5-methylaniline in 94% yield; $^1$H NMR: (DMSOd$_6$) 2.09 (s, 6H), 2.12 (s, 3H), 3.16 (s, 2H), 4.87 (s, 2H), 6.24 (s, 2H), 6.31 (s, 1H).

[50] Using an analogous procedure to that described in Note [27] above, the reaction product was treated with succinic acid. The resultant salt which contained 1.6 equivalents of succinic acid was isolated and gave the following characterising data:—$^1$H NMR: (DMSOd$_6$+CF$_3$CO$_2$D) 2.32 (s, 3H), 2.43 (s, 4H), 2.74 (s, 6H), 3.79 (s, 2H), 4.17 (s, 3H), 4.22 (s, 2H), 6.91 (d, 2H), 7.03 (br s, 1H), 7.4 (d, 2H), 7.42 (br s, 1H), 7.59 (d, 2H), 7.69 (br s, 1H), 7.77 (s, 1H), 9.07 (d, 1H), 9.13 (s, 1H); Mass Spectrum: M+H$^+$ 481.

[51] The reaction product was purified by preparative HPLC using a Waters 'Xterra' reversed-phase column (5 microns silica) using decreasingly polar mixtures of water (containing 0.2% ammonium carbonate) and acetonitrile as eluent. The product gave the following characterising data:—$^1$H NMR: (DMSOd$_6$+CF$_3$CO$_2$D) 2.72 (s, 6H), 3.81 (s, 2H), 4.05 (s, 3H), 4.07 (s, 3H), 4.24 (s, 2H), 6.87 (d, 1H), 7.41 (d, 2H), 7.46 (d, 2H), 7.61 (d, 2H), 7.64 (s, 1H), 7.74 (d, 2H), 7.78 (s, 1H), 8.84 (d, 1H); Mass Spectrum: M+H$^+$ 472.

The 4-dimethylaminomethylaniline used as a starting material was prepared as follows:—

The 4-dimethylaminomethylaniline used as a starting material was prepared from 4-nitrobenzyl bromide using analogous procedures to those described in Note [45] above for the preparation of 3-dimethylaminomethylaniline. The desired aniline material gave the following characterising data: $^1$H NMR: (DMSOd$_6$) 2.07 (s, 6H), 3.17 (s, 2H), 4.92 (br s, 2H), 6.49 (m, 2H), 6.89 (m, 2H); Mass Spectrum: M+H$^+$ 151.

[52] Using an analogous procedure to that described in Note [27] above, the reaction product was treated with succinic acid. The resultant salt which contained 1.04 equivalents of succinic acid was isolated and gave the following characterising data: —$^1$H NMR: (DMSOd$_6$+CF$_3$CO$_2$D) 2.44 (s, 4H), 2.73 (s, 6H), 3.81 (s, 2H), 4.17 (s, 3H), 4.24 (s, 2H), 6.94 (d, 1H), 7.41 (d, 2H), 7.44 (d, 2H), 7.6 (d, 2H), 7.73 (d, 2H), 7.77 (s, 1H), 9.09 (d, 1H), 9.15 (s, 1H); Mass Spectrum: M+H$^+$ 467.

[53] The reaction product was purified by preparative HPLC using a Waters 'Xterra' reversed-phase column (5 microns silica) using decreasingly polar mixtures of water (containing 0.2% ammonium carbonate) and acetonitrile as eluent. The product gave the following characterising data:—$^1$H NMR: (DMSOd$_6$+CF$_3$CO$_2$D) 2.39 (s, 3H), 2.77 (s, 6H), 3.8 (s, 2H), 4.05 (s, 3H), 4.07 (s, 3H), 4.27 (s, 2H), 6.87 (d, 1H), 7.38-7.44 (m, 3H), 7.55-7.61 (m, 3H), 7.64 (s, 1H), 7.77 (s, 1H), 8.84 (d, 1H); Mass Spectrum: M+H$^+$ 486.

The 4-dimethylaminomethyl-3-methylaniline used as a starting material was prepared as follows:—

A mixture of 1,2-dimethyl-4-nitrobenzene (6.04 g), N-bromosuccinimide (7.12 g), benzoyl peroxide (0.194 g) and carbon tetrachloride (80 ml) was stirred and heated to reflux for 2 hours. The mixture was cooled to ambient temperature. Petroleum ether (b.p. 60-80° C.) was added. The mixture was filtered and the filtrate was evaporated to give an oil comprising a mixture of 2-methyl-4-nitrobenzyl bromide and 2-bromomethyl-4-nitrobenzyl bromide. This mixture was used in the next step.

A portion (2.3 g) of the oil so obtained was dissolved in ethanol (5 ml) and dimethylamine (40% in water, 7.5 ml) was added portionwise in order to prevent a significant exotherm. The resultant reaction mixture was stirred at ambient temperature for 16 hours. The mixture was evaporated and the residue was purified by column chromatography on silica using increasingly polar mixtures of methylene chloride and diethyl ether as eluent. There was thus obtained N,N-dimethyl-N-(2-methyl-4-nitrobenzyl)amine (0.42 g); $^1$H NMR: (CDCl$_3$) 2.27 (s, 6H), 2.45 (s, 3H), 3.46 (s, 2H), 7.49 (d, 1H), 8.0 (d, 1H), 8.02 (s, 1H); Mass Spectrum: M+H$^+$ 195.

A mixture of N,N-dimethyl-N-(2-methyl-4-nitrobenzyl) amine (0.42 g), platinum oxide (0.042 g), ethanol (5 ml) and ethyl acetate (15 ml) was stirred under 1.7 atmospheres pressure of hydrogen for 1 hour. The catalyst was removed by filtration and the filtrate was evaporated. The material so obtained was dried under vacuum at ambient temperature for 2 hours. There was thus obtained 4-dimethylaminomethyl-3-methylaniline as an oil (0.34 g); $^1$H NMR: (DMSOd$_6$) 2.07 (s, 6H), 2.16 (s, 3H), 3.13 (s, 2H), 4.83 (s, 2H), 6.29 (m, 1H), 6.35 (m, 1H), 6.78 (m, 1H); Mass Spectrum: M+H$^+$ 166.

[54] Using an analogous procedure to that described in Note [27] above, the reaction product was treated with succinic acid. The resultant salt which contained 1.2 equivalents of succinic acid was isolated and gave the following characterising data:—$^1$H NMR: (DMSOd$_6$+CF$_3$CO$_2$D) 2.37 (s, 3H), 2.43 (s, 4H), 2.77 (s, 6H), 3.79 (s, 2H), 4.16 (s, 3H), 4.27 (s, 2H), 6.92 (d, 2H), 7.39 (d, 1H), 7.4 (d, 2H), 7.57 (br s, 1H), 7.59 (d, 2H), 7.77 (s, 1H), 9.06 (d, 1H), 9.14 (s, 1H); Mass Spectrum: M+H$^+$ 481.

[55] $^1$H NMR: (DMSOd$_6$) 1.32 (t, 3H), 2.85 (d, 3H), 3.60 (s, 2H), 3.78 (s, 3H), 4.0 (s, 3H), 4.07 (q, 2H), 6.67 (d, 1H), 6.83 (m, 1H), 6.99 (d, 1H), 7.35 (d, 1H), 7.42 (s, 1H), 7.65 (s, 1H), 7.88 (s, 1H), 8.22 (s, 1H), 8.39 (q, 1H), 8.61 (d, 1H), 10.04 (s, 1H), 11.98 (s, 1H); Mass Spectrum: M+H$^+$ 490.

The 2-{2-methoxy-4-[6-methoxy-7-(N-methylcarbamoyl)quinolin-4-yloxy]phenyl}acetic acid used as a starting material was prepared as follows:—

A mixture of methyl 2-methoxy-5-nitrobenzoate (20.3 g), 5% platinum-on-carbon catalyst (1.5 g) and ethyl acetate (300 ml) was stirred under 1.4 atmospheres pressure of hydrogen for 5 hours. The catalyst was removed by filtration and the filtrate was evaporated. There was thus obtained methyl 5-amino-2-methoxybenzoate (17 g); $^1$H NMR: (CDCl$_3$) 3.84 (s, 3H), 3.89 (s, 3H), 6.86 (m, 2H), 7.19 (m, 1H); Mass Spectrum: M+H$^+$ 182.

A mixture of methyl 5-amino-2-methoxybenzoate (17 g; see also *Canadian Journal of Chemistry*, 1973, 51, 162-170), 5-methoxymethylene-2,2-dimethyl-1,3-dioxane-4,6-dione (17.5 g) and isopropanol (170 ml) was stirred at ambient temperature for 10 minutes. A yellow precipitate formed which was isolated by filtration, washed in turn with isopropanol and diethyl ether and dried under vacuum. There was thus obtained 5-(4-methoxy-3-methoxycarbonylanilinomethylene)-2,2-dimethyl-1,3-dioxane-4,6-dione (28.9 g); $^1$H NMR: (CDCl$_3$) 1.76 (s, 6H), 3.93 (s, 3H), 3.95 (s, 3H), 7.05 (d, 1H), 7.35 (m, 1H), 7.74 (d, 1H), 8.56 (d, 1H); Mass Spectrum: M+H$^+$ 336.

5-(4-Methoxy-3-methoxycarbonylanilinomethylene)-2,2-dimethyl-1,3-dioxane-4,6-dione (28.9 g) was added portionwise to a mixture (200 ml) of biphenyl and diphenyl ether ('Dowtherm A') that had been warmed to 260° C. The solution was stirred at that temperature for 5 minutes. The resultant mixture was cooled to ambient temperature and added to a mixture of petroleum ether (250 ml) and diethyl ether (250 ml). The precipitate was collected by filtration and washed with petroleum ether. The material so obtained was purified by column chromatography on silica using increasingly polar solvent mixtures of methylene chloride and methanol (from 10:0 to 17:3) as eluent. There was thus obtained a 7:3 mixture (11.7 g) of 6-methoxy-7-methoxycarbonyl-1,4-dihydroquinolin-4-one and 6-methoxy-5-methoxycarbonyl-1,4-dihydroquinolin-4-one; $^1$H NMR: (DMSOd$_6$) 3.85 (s, 3H), 3.88 (s, 3H), 6.05 (d, 1H), 7.61 (s, 1H), 7.87 (s, 1H), 7.94 (d, 1H) and 3.75 (s, 3H), 3.82 (s, 3H), 5.92 (d, 1H), 7.55 (d, 1H), 7.63 (d, 1H), 7.88 (m, 1H); Mass Spectrum: M+H$^+$ 234.

A portion (9.41 g) of the mixture of quinolin-4-ones so obtained was dissolved in methanol (100 ml). Lithium hydroxide (5.04 g) was added and the mixture was stirred at ambient temperature for 16 hours. The solvent was evaporated and water (100 ml) was added to the residue. The mixture was neutralised to pH7 by the addition of 6N aqueous hydrochloric acid. The aqueous solution was extracted with methylene chloride and with ethyl acetate. The aqueous solution was acidified to pH2 by the addition of 6N aqueous hydrochloric acid. The resultant precipitate was isolated, washed with water and with diethyl ether and dried under vacuum. There was thus obtained 7-carboxy-6-methoxy-1,4-dihydroquinolin-4-one (6.1 g); $^1$H NMR: (DMSOd$_6$) 3.88 (s, 3H), 6.04 (d, 1H), 7.59 (s, 1H), 7.83 (s, 1H), 7.93 (d, 1H), 11.85 (br s, 1H), 13.16 (br s, 1H); Mass Spectrum: M+H$^+$ 220.

A mixture of a portion (2 g) of the material so obtained and phosphorous oxychloride (4.17 ml) was heated to 105° C. for 1 hour. The resultant mixture was cooled to ambient temperature and diluted with methylene chloride (50 ml). The solution so obtained was slowly poured into a 2M solution of methylamine in THF (100 ml) that was cooled in an ice-bath. The mixture was stirred and allowed to warm to ambient temperature. The reaction mixture was washed in turn with a saturated aqueous sodium bicarbonate solution and brine, dried over magnesium sulphate and evaporated. The residue was triturated under diethyl ether. The resultant solid was isolated, washed with diethyl ether and dried under vacuum. There was thus obtained 4-chloro-6-methoxy-7-(N-methylcarbamoyl)quinoline (1.54 g); $^1$H NMR: (DMSOd$_6$) 2.84 (d, 3H), 4.03 (s, 3H), 7.51 (s, 1H), 7.78 (d, 1H), 8.23 (s, 1H), 8.4 (br d, 1H), 8.74 (d, 1H); Mass Spectrum: M+H$^+$ 252 and 254.

A mixture of 4-chloro-6-methoxy-7-(N-methylcarbamoyl)quinoline (1.36 g), tert-butyl 2-(4-hydroxy-2-methoxyphenyl)acetate (1.36 g), caesium carbonate (4 g) and DMF (10 ml) was stirred and heated to reflux for 5 hours. The mixture was cooled to ambient temperature and diluted with diethyl ether (100 ml). The resultant solid was separated and the filtrate was evaporated. The residue was purified by column chromatography on silica using a solvent gradient of 100:0 to 19:1 of methylene chloride and methanol as eluent. There was thus obtained tert-butyl 2-{2-methoxy-4-[6-methoxy-7-(N-methylcarbamoyl)quinolin-4-yloxy] phenyl}acetate (1.2 g); $^1$H NMR (CDCl$_3$) 1.48 (s, 9H), 3.09 (d, 3H), 3.58 (s, 2H), 3.81 (s, 3H), 4.12 (s, 3H), 6.64 (d, 1H), 6.72 (d, 1H), 6.75 (m, 1H), 7.27 (d, 1H), 7.7 (s, 1H), 7.78 (br s, 1H), 8.62 (d, 1H), 8.96 (s, 1H); Mass Spectrum: M+H$^+$ 453.

A mixture of the material so obtained, 4M hydrogen chloride in 1,4-dioxane (25 ml) and methylene chloride (10 ml) was stirred at ambient temperature for 4 hours. The resultant solid was isolated, washed with methylene chloride and dried under vacuum. There was thus obtained 2-{2-methoxy-4-[6-methoxy-7-(N-methylcarbamoyl)quinolin-4-yloxy] phenyl}acetic acid (0.8 g); $^1$H NMR: (DMSOd$_6$) 2.86 (d, 3H), 3.59 (s, 2H), 3.79 (s, 3H), 4.07 (s, 3H), 6.94 (m, 2H), 7.09 (d, 1H), 7.41 (d, 1H), 7.83 (s, 1H), 8.41 (s, 1H), 8.54 (br d, 1H), 8.87 (d, 1H); Mass Spectrum: M+H$^+$ 397.

[56] The reaction product was purified by column chromatography on silica using ethyl acetate as eluent. The product gave the following characterising data:—$^1$H NMR: (DMSOd$_6$) 1.33 (t, 3H), 3.6 (s, 2H), 3.77 (s, 3H), 4.07 (q, 2H), 6.67 (d, 1H), 6.82 (m, 1H), 6.98 (d, 1H), 7.34 (d, 1H), 7.42 (s, 1H), 7.67 (m, 1H), 7.83 (m, 1H), 7.88 (s, 1H), 8.04 (d, 1H), 8.32 (m, 1H), 8.71 (d, 1H), 10.04 (s, 1H); Mass Spectrum: M+H$^+$ 403.

The 2-(2-methoxy-4-quinolin-4-yloxyphenyl)acetic acid used as a starting material was prepared as follows:—

A mixture of 4-chloroquinoline (1.63 g), 2-(4-hydroxy-2-methoxyphenyl)acetic acid (1.82 g), caesium carbonate (8.15 g) and DMF (10 ml) was stirred and heated to 150° C. for 1.5 hours. The solvent was evaporated and the residue was partitioned between water and ethyl acetate. The aqueous solution was acidified to pH3.5 by the addition of 6N aqueous hydrochloric acid. The resultant precipitate was isolated, washed with water and with diethyl ether and dried under vacuum. There was thus obtained the required starting material (2.41 g); $^1$H NMR: (DMSOd$_6$+CD$_3$COOD) 3.57 (s, 2H), 3.77 (s, 3H), 6.76 (d, 1H), 6.83 (m, 1H), 7.0 (d, 1H), 7.33 (d, 1H), 7.44 (m, 1H), 7.91 (m, 1H), 8.09 (d, 1H), 8.38 (d, 1H), 8.78 (d, 1H); Mass Spectrum: M+H$^+$ 310.

[57] The reaction product was purified by column chromatography on silica using a solvent gradient of 100:0:0 to 10:9:1 of methylene chloride, ethyl acetate and methanol as eluent. The product gave the following characterising data:—$^1$H NMR: (DMSOd$_6$) 1.32 (t, 3H), 3.59 (s, 2H), 3.77 (s, 3H), 3.94 (s, 3H), 3.95 (s, 3H), 4.07 (q, 2H), 6.52 (d, 1H), 6.8 (m, 1H), 6.95 (d, 1H), 7.33 (d, 1H), 7.4 (s, 1H), 7.42 (s, 1H), 7.51 (s, 1H), 7.88 (s, 1H), 8.5 (d, 1H), 10.03 (s, 1H); Mass Spectrum: M+H$^+$ 463.

The 2-[2-methoxy-4-(6,7-dimethoxyquinolin-4-yloxy)phenyl]acetic acid used as a starting material was prepared as follows:—

A mixture of 4-chloro-6,7-dimethoxyquinoline (1.12 g), tert-butyl 2-(4-hydroxy-2-methoxyphenyl)acetate (1.19 g), caesium carbonate (6.5 g) and DMF (25 ml) was stirred and heated to reflux for 2.5 hours. The solvent was evaporated and the residue was purified by column chromatography on silica using a solvent gradient of 4:1:0 to 10:9:1 of methylene chloride, diethyl ether and methanol as eluent. There was thus obtained tert-butyl 2-[2-methoxy-4-(6,7-dimethoxyquinolin-4-yloxy)phenyl]acetate (1.4 g); $^1$H NMR: (DMSOd$_6$) 1.41 (s, 9H), 3.53 (s, 2H), 3.76 (s, 3H), 3.93 (s, 3H), 3.95 (s, 3H), 6.49 (d, 1H), 6.77 (m, 1H), 6.95 (d, 1H), 7.28 (d, 1H), 7.4 (s, 1H), 7.5 (s, 1H), 8.48 (d, 1H); Mass Spectrum: M+H$^+$ 426.

A 4M solution of hydrogen chloride in 1,4-dioxane (2.58 ml) was added to a solution of tert-butyl 2-[2-methoxy-4-(6,7-dimethoxyquinolin-4-yloxy)phenyl]acetate (0.43 g) in methylene chloride (2 ml) and the resultant mixture was stirred at ambient temperature for 14 hours. The mixture was diluted with diethyl ether and the solid was isolated and dried under vacuum. There was thus obtained the required starting material (0.33 g); $^1$H NMR: (DMSOd$_6$) 3.6 (s, 2H), 3.79 (s, 3H), 4.04 (s, 3H), 4.05 (s, 3H), 6.87 (d, 1H), 6.95 (m, 1H), 7.11 (s, 1H), 7.41 (d, 1H), 7.68 (s, 1H), 7.74 (s, 1H), 8.8 (d, 1H); Mass Spectrum: M+H$^+$ 370.

[58] $^1$H NMR: (DMSOd$_6$) 3.6 (s, 2H), 3.77 (s, 3H), 3.78 (s, 3H), 6.71 (d, 1H), 6.83 (m, 1H), 6.99 (s, 1H), 7.34 (d, 1H), 7.41 (s, 1H), 7.76 (m, 1H), 7.84 (s, 1H), 7.98 (m, 1H), 8.12 (m, 1H), 8.7 (d, 1H), 10.03 (s, 1H); Mass Spectrum: M+H$^+$ 407.

The 2-[4-(6-fluoroquinolin-4-yl)oxy-2-methoxyphenyl] acetic acid used as starting material was prepared as follows:—

A mixture of 4-chloro-6-fluoroquinoline (U.S. Pat. No. 4,560,692, within example 12 thereof; 2 g), tert-butyl 2-(4-hydroxy-2-methoxyphenyl)acetate (2.62 g), caesium carbonate (6.84 g) and DMF (10 ml) was stirred and heated to 90° C. for 3.5 hours. The mixture was cooled to ambient temperature and partitioned between ethyl acetate and water. The organic solution was washed with water, dried over magnesium sulphate and evaporated. The residue was purified by column chromatography on silica, using a 1:1 mixture of petroleum ether and ethyl acetate as eluent. There was thus obtained tert-butyl 2-[2-methoxy-4-(6-fluoroquinolin-4-yloxy)phenyl]acetate (2.62 g); $^1$H NMR: (DMSOd$_6$) 1.41 (s, 9H), 3.53 (s, 2H), 3.76 (s, 3H), 6.68 (d, 1H), 6.82 (m, 1H), 6.99 (d, 1H), 7.31 (d, 1H), 7.75 (m, 1H), 7.98 (m, 1H), 8.11 (m, 1H), 8.7 (d, 1H).

A mixture of the material so obtained, a 4M solution of hydrogen chloride in 1,4-dioxane (39.5 ml) and methylene chloride (2 ml) was stirred at ambient temperature for 14 hours. The resultant solid was recovered, washed with diethyl ether and dried under vacuum. There was thus obtained the required starting material (2.3 g); $^1$H NMR: 3.59 (s, 2H), 3.78 (s, 3H), 6.93 (m, 1H), 6.97 (d, 1H), 7.09 (d, 1H), 7.4 (d, 1H), 8.05 (m, 1H), 8.25 (m, 1H), 8.34 (m, 1H), 8.96 (d, 1H).

[59] The reaction product was purified by column chromatography on silica using a solvent gradient of 100:0 to 19:1 of ethyl acetate and methanol as eluent. The product gave the following characterising data: —$^1$H NMR: (DMSOd$_6$) 1.32 (t, 3H), 3.6 (s, 2H), 3.77 (s, 3H), 4.07 (q, 2H), 6.64 (d, 1H), 6.84 (m, 1H), 6.99 (d, 1H), 7.35 (d, 1H), 7.42 (s, 1H), 7.59 (m, 1H), 7.78 (m, 1H), 7.87 (s, 1H), 8.4 (m, 1H), 8.73 (d, 1H), 10.04 (s, 1H); Mass Spectrum: M+H$^+$ 421.

The 2-[4-(7-fluoroquinolin-4-yl)oxy-2-methoxyphenyl] acetic acid used as starting material was prepared as follows:—

5-Methoxymethylene-2,2-dimethyl-1,3-dioxane-4,6-dione (33.52 g) was added to a stirred mixture of 3-fluoroaniline (20 g) and isopropanol (250 ml) and the resultant mixture was stirred at ambient temperature for 48 hours. The solvent was evaporated and the residue was diluted in diethyl ether. The resultant precipitate was collected by filtration, washed with diethyl ether and dried under vacuum. There was thus obtained 5-(3-fluoroanilinomethylene)-2,2-dimethyl-1,3-dioxane-4,6-dione (44.57 g); $^1$H NMR: (DMSOd$_6$) 1.7 (s, 6H), 7.1 (m, 1H), 7.4 (m, 2H), 7.06 (m, 1H), 8.6 (s, 1H), 11.25 (s, 1H).

The material so obtained was added portionwise to a mixture (250 ml) of biphenyl and diphenyl ether ('Dowtherm A') that had been warmed to 250° C. The solution was stirred at that temperature for 5 minutes. The resultant mixture was cooled to ambient temperature. Diethyl ether was added and the precipitate was collected by filtration and washed with diethyl ether. The material so obtained was purified by column chromatography on silica using increasingly polar mixtures of methylene chloride and methanol as eluent. There was thus obtained 7-fluoro-1,4-dihydroquinolin-4-one (10.2 g); $^1$H NMR: (DMSOd$_6$) 6.0 (d, 1H), 7.15 (m, 1H), 7.3 (m, 1H), 7.9 (d, 1H), 8.15 (m, 1H).

A mixture of a portion (6.23 g) of the material so obtained and phosphorus oxychloride (70 ml) was stirred and heated to 70° C. for 3 hours. The excess of phosphorus oxychloride was removed by evaporation and the residue was partitioned between methylene chloride and a saturated aqueous sodium bicarbonate solution. The organic solution was dried over magnesium sulphate and evaporated. There was thus obtained 4-chloro-7-fluoroquinoline (6.33 g); $^1$H NMR: (DMSOd$_6$) 7.7 (m, 1H), 7.75 (d, 1H), 7.9 (m, 1H), 8.3 (m, 1H), 8.9 (d, 1H).

A mixture of 4-chloro-7-fluoroquinoline (1.31 g), tert-butyl 2-(4-hydroxy-2-methoxyphenyl)acetate (1.9 g), 4-dimethylaminopyridine (2.65 g) and chlorobenzene (30 ml) was stirred and heated to 125° C. for 18 hours. The mixture was cooled to ambient temperature and diluted with diethyl ether. The resultant precipitate was isolated and purified by column chromatography on silica using a 1:1 mixture of petroleum ether and ethyl acetate as eluent. There was thus obtained tert-butyl 2-[4-(7-fluoroquinolin-4-yl)oxy-2-methoxyphenyl]acetate (1.48 g); $^1$H NMR: (DMSOd$_6$) 1.41 (s, 9H), 3.54 (s, 2H), 3.76 (s, 3H), 6.61 (d, 1H), 6.82 (m, 1H), 6.99 (d, 1H), 7.3 (d, 1H), 7.59 (m, 1H), 7.77 (m, 1H), 8.4 (m, 1H), 8.72 (d, 1H); Mass Spectrum: M+H$^+$ 384.

A mixture of the material so obtained, a 4M solution of hydrogen chloride in 1,4-dioxane (25 ml) and methylene chloride (5 ml) was stirred at ambient temperature for 7 hours. The solvent was evaporated and the residue was triturated under diethyl ether. The resultant solid was recovered and dried under vacuum. There was thus obtained the required starting material (1.38 g); $^1$H NMR: 3.59 (s, 2H), 3.78 (s, 3H), 6.87 (d, 1H), 6.91 (m, 1H), 7.09 (d, 1H), 7.39 (d, 1H), 7.81 (m, 1H), 7.97 (m, 1H), 8.58 (m, 1H), 8.95 (d, 1H); Mass Spectrum: M+H$^+$ 328.

[60] $^1$H NMR: (DMSOd$_6$) 2.12 (s, 3H), 3.65 (s, 2H), 3.7 (s, 3H), 3.78 (s, 3H), 6.71 (d, 1H), 6.83 (m, 1H), 6.99 (d, 1H), 7.34 (d, 1H), 7.76 (m, 1H), 7.81 (s, 1H), 7.98 (m, 1H), 8.12 (m, 1H), 8.7 (d, 1H), 9.43 (s, 1H); Mass Spectrum: M+H$^+$ 421.

[61] $^1$H NMR: (DMSOd$_6$) 2.17 (s, 3H), 3.62 (s, 2H), 3.68 (s, 3H), 3.78 (s, 3H), 6.72 (d, 1H), 6.83 (m, 1H), 6.99 (d, 1H), 7.35 (d, 1H), 7.45 (s, 1H), 7.75 (m, 1H), 7.98 (m, 1H), 8.12 (m, 1H), 8.7 (d, 1H), 9.34 (s, 1H); Mass Spectrum: M+H$^+$ 421.

[62] The reaction product was purified by column chromatography on silica using a solvent gradient of 49:1 to 9:1 of methylene chloride and methanol as eluent. The product gave the following characterising data:—$^1$H NMR: (DMSOd$_6$) 2.18 (s, 3H), 3.62 (s, 2H), 3.69 (s, 3H), 3.78 (s, 3H), 6.65 (d, 1H), 6.83 (m, 1H), 7.0 (d, 1H), 7.35 (d, 1H), 7.45 (s, 1H), 7.59 (m, 1H), 7.78 (m, 1H), 8.41 (m, 1H), 8.73 (d, 1H), 9.34 (s, 1H); Mass Spectrum: M+H$^+$ 421.

[63] The reaction product was purified by column chromatography on silica using a solvent gradient of 100:0:0 to 10:9:1 of methylene chloride, ethyl acetate and methanol as eluent. The product gave the following characterising data:—$^1$H NMR: (DMSOd$_6$) 1.16 (t, 3H), 2.55 (q, 2H), 3.63 (s, 2H), 3.77 (s, 3H), 4.04 (s, 3H), 6.28 (br s, 1H), 6.55 (d, 1H), 6.83 (m, 1H), 6.98 (d, 1H), 7.33 (d, 1H), 7.52 (s, 1H), 7.74 (br s, 1H), 7.86 (br s, 1H), 8.68 (d, 1H), 8.7 (s, 1H), 10.35 (br s, 1H); Mass Spectrum: M+H$^+$ 476.

[64] The reaction mixture was heated to 55° C. for 16 hours. The reaction product was purified by column chromatography on silica using a solvent gradient of 100:0:0 to 10:9:1 of methylene chloride, ethyl acetate and methanol as eluent. The product gave the following characterising data: —$^1$H NMR: (DMSOd$_6$) 1.16 (t, 3H), 2.55 (q, 2H), 3.62 (s, 2H), 3.76 (s, 3H), 3.94 (s, 3H), 3.95 (s, 3H), 6.28 (s, 1H), 6.51 (d, 1H), 6.78 (m, 1H), 6.94 (d, 1H), 7.31 (d, 1H), 7.4 (s, 1H), 7.51 (s, 1H), 8.48 (d, 1H), 10.33 (s, 1H), 11.98 (s, 1H); Mass Spectrum: M+H$^+$ 463.

[65] The reaction mixture was heated to 60° C. for 24 hours. The reaction product gave the following characterising data:—$^1$H NMR: (DMSOd$_6$) 1.16 (t, 3H), 2.56 (q, 2H), 2.85 (d, 3H), 3.63 (s, 2H), 3.77 (s, 3H), 4.0 (s, 3H), 6.28 (s, 1H), 6.67 (d, 1H), 6.82 (m, 1H), 6.97 (d, 1H), 7.33 (d, 1H), 7.65 (s, 1H), 8.21 (s, 1H), 8.39 (q, 1H), 8.6 (d, 1H), 10.34 (s, 1H); Mass Spectrum: M+H$^+$ 490.

[66] The reaction product was purified by column chromatography on silica using ethyl acetate as eluent. The product gave the following characterising data:—$^1$H NMR: (DMSOd$_6$) 1.16 (t, 3H), 2.55 (q, 2H), 3.63 (s, 2H), 3.76 (s, 3H), 6.26 (br s, 1H), 6.66 (d, 1H), 6.81 (m, 1H), 6.97 (d, 1H), 7.32 (d, 1H), 7.68 (m, 1H), 7.83 (m, 1H), 8.04 (d, 1H), 8.32 (d, 1H), 8.71 (d, 1H), 10.34 (br s, 1H); Mass Spectrum: M+H$^+$ 403.

[67] $^1$H NMR: (DMSOd$_6$) 1.2 (t, 3H), 2.72 (q, 2H), 2.85 (d, 3H), 3.71 (s, 2H), 3.76 (s, 3H), 4.03 (s, 3H), 6.55 (d, 1H), 6.62 (s, 1H), 6.83 (m, 1H), 6.98 (d, 1H), 7.34 (d, 1H), 7.52 (s, 1H), 8.37 (q, 1H), 8.63 (s, 1H), 8.68 (d, 1H), 11.06 (s, 1H); Mass Spectrum: M+H$^+$ 491.

[68] $^1$H NMR: (DMSOd$_6$) 1.2 (t, 3H), 2.72 (q, 2H), 2.85 (d, 3H), 3.71 (s, 2H), 3.76 (s, 3H), 4.0 (s, 3H), 6.62 (s, 1H), 6.67 (d, 1H), 6.83 (m, 1H), 6.98 (d, 1H), 7.34 (d, 1H), 7.65 (s, 1H), 8.22 (s, 1H), 8.39 (q, 1H), 8.61 (d, 1H), 11.06 (s, 1H); Mass Spectrum: M+H$^+$ 491.

[69] $^1$H NMR: (DMSOd$_6$) 2.37 (s, 3H), 3.71 (s, 2H), 3.76 (s, 3H), 6.61 (s, 1H), 6.71 (d, 1H), 6.83 (m, 1H), 6.99 (d, 1H), 7.34 (d, 1H), 7.76 (m, 1H), 7.98 (m, 1H), 8.12 (m, 1H), 8.71 (d, 1H), 11.04 (s, 1H); Mass Spectrum: M+H$^+$ 408.

[70] $^1$H NMR: (DMSOd$_6$) 1.2 (t, 3H), 2.72 (q, 2H), 3.71 (s, 2H), 3.76 (s, 3H), 6.62 (s, 1H), 6.71 (d, 1H), 6.83 (m, 1H), 6.99 (d, 1H), 7.34 (d, 1H), 7.76 (m, 1H), 7.98 (m, 1H), 8.12 (m, 1H), 8.7 (d, 1H), 11.06 (s, 1H); Mass Spectrum: M+H$^+$ 422.

[71] The reaction product was purified by column chromatography on silica using ethyl acetate as eluent. The product gave the following characterising data:—$^1$H NMR: (DMSOd$_6$) 1.2 (t, 3H), 2.72 (q, 2H), 3.71 (s, 2H), 3.76 (s, 3H), 6.62 (s, 1H), 6.64 (d, 1H), 6.84 (m, 1H), 7.0 (d, 1H), 7.34 (d, 1H), 7.6 (m, 1H), 7.78 (m, 1H), 8.41 (m, 1H), 8.73 (d, 1H), 11.06 (s, 1H); Mass Spectrum: M+H$^+$ 422.

[72] The reaction product was purified by column chromatography on silica using ethyl acetate as eluent. The product gave the following characterising data:—$^1$H NMR: (DMSOd$_6$) 1.8 (s, 3H) 2.3 (s, 3H), 3.71 (s, 2H), 3.78 (s, 3H), 6.7 (d, 1H), 6.83 (m, 1H), 7.0 (d, 1H), 7.36 (d, 1H), 7.69 (m, 1H) 7.86 (m, 1H), 8.05 (d, 1H), 8.34 (d, 1H), 8.73 (d, 1H), 10.26 (br s, 1H); Mass Spectrum: M+H$^+$ 404.

[73] The reaction product was purified by column chromatography on silica using a solvent gradient of 100:0:0 to 10:9:1 of methylene chloride, ethyl acetate and methanol as eluent. The product gave the following characterising data:—$^1$H NMR: (DMSOd$_6$) 1.81 (s, 3H), 2.3 (s, 3H), 3.7 (s, 2H), 3.77 (s, 3H), 3.93 (s, 3H), 3.95 (s, 3H), 6.54 (d, 1H), 6.8 (d, 1H), 6.96 (s, 1H), 7.34 (d, 1H), 7.4 (s, 1H), 7.5 (s, 1H), 8.49 (d, 1H), 10.26 (br s. 1H); Mass Spectrum: M+H$^+$ 464.

[74] The reaction product was purified by column chromatography on silica using ethyl acetate as eluent. The product gave the following characterising data: —$^1$H NMR: (DMSOd$_6$) 1.8 (s, 3H), 2.3 (s, 3H), 3.71 (s, 2H), 3.78 (s, 3H), 6.73 (d, 1H), 6.84 (m, 1H), 7.0 (d, 1H), 7.36 (d, 1H), 7.76 (m, 1H), 7.98 (m, 1H), 8.12 (m, 1H), 8.7 (d, 1H), 10.27 (br s, 1H); Mass Spectrum: M+H$^+$ 422.

[75] The reaction product was purified by column chromatography on silica using a 3:7 mixture of petroleum ether and ethyl acetate as eluent. The product gave the following characterising data:—$^1$HNMR: (DMSOd$_6$) 1.8 (s, 3H), 2.3 (s, 3H), 3.71 (s, 2H), 3.78 (s, 3H), 6.66 (d, 1H), 6.84 (m, 1H), 7.0 (d, 1H), 7.36 (d, 1H), 7.6 (m, 1H), 7.78 (m, 1H), 8.4 (m, 1H), 8.73 (d, 1H), 10.26 (br s, 1H); Mass Spectrum: M+H$^+$ 422.

[76] The reaction product was purified by column chromatography on silica using ethyl acetate as eluent. The product gave the following characterising data:—$^1$H NMR: (DMSOd$_6$) 2.27 (s, 3H), 3.75 (s, 3H), 3.78 (s, 2H), 6.68 (d, 1H), 6.73 (br s, 1H), 6.83 (m, 1H), 6.99 (d, 1H), 7.35 (d, 1H), 7.67 (m, 1H), 7.83 (m, 1H), 8.04 (d, 1H), 8.32 (m, 1H), 8.71 (d, 1H); Mass Spectrum: M+H$^+$ 406.

[77] The reaction product was purified by column chromatography on silica using a solvent gradient of 100:0:0 to 10:9:1 of methylene chloride, ethyl acetate and methanol as eluent. The product gave the following characterising data:—$^1$H NMR: (DMSOd$_6$) 2.29 (d, 3H), 3.75 (s, 3H), 3.77 (s, 2H), 3.93 (s, 3H), 3.95 (s, 3H), 6.53 (d, 1H), 6.73 (q, 1H), 6.8 (m, 1H), 6.96 (d, 1H), 7.33 (d, 1H), 7.4 (s, 1H), 7.5 (s, 1H), 8.48 (d, 1H), 12.17 (br s, 1H); Mass Spectrum: M+H$^+$ 466.

[78] $^1$H NMR: (DMSOd$_6$) 2.27 (s, 3H), 2.85 (d, 3H), 3.75 (s, 3H), 3.78 (s, 2H), 4.03 (s, 3H), 6.56 (d, 1H), 6.74 (s, 1H), 6.84 (m, 1H), 6.99 (d, 1H), 7.35 (d, 1H), 7.52 (s, 1H), 8.37 (q, 1H), 8.63 (s, 1H), 8.68 (d, 1H); Mass Spectrum: M+H$^+$ 493.

[79] The product was recovered by filtration from the reaction medium and gave the following characterising data:—$^1$H NMR: (DMSOd$_6$) 2.27 (s, 3H), 2.85 (d, 3H), 3.76 (s, 3H), 3.78 (s, 2H), 4.0 (s, 3H), 6.69 (d, 1H), 6.74 (d, 1H), 6.84 (m, 1H), 7.0 (d, 1H), 7.36 (d, 1H), 7.65 (s, 1H), 8.22 (s, 1H), 8.39 (q, 1H), 8.61 (d, 1H), 12.18 (s, 1H); Mass Spectrum: M+H$^+$ 493.

[80] $^1$H NMR: (DMSOd$_6$) 2.34 (s, 3H), 2.85 (d, 3H), 3.75 (s, 3H), 3.78 (s, 2H), 4.03 (s, 3H), 6.57 (d, 1H), 6.84 (m, 1H), 6.99 (d, 1H), 7.13 (s, 1H), 7.35 (d, 1H), 7.52 (s, 1H), 8.37 (q, 1H), 8.63 (s, 1H), 8.68 (d, 1H); Mass Spectrum: M+H$^+$ 493.

[81] $^1$H NMR: (DMSOd$_6$) 2.85 (d, 3H), 2.94 (s, 6H), 3.73 (s, 2H), 3.77 (s, 3H), 4.03 (s, 3H), 6.38 (m, 1H), 6.55 (d, 1H), 6.83 (m, 1H), 6.98 (d, 1H), 7.34 (d, 1H), 7.45 (s, 1H), 7.52 (s, 1H), 7.88 (d, 1H), 8.37 (q, 1H), 8.63 (s, 1H), 8.68 (d, 1H), 10.15 (s, 1H); Mass Spectrum: M+H$^+$ 516.

[82] The product was recovered by filtration from the reaction medium and gave the following characterising data:—$^1$H NMR: (DMSOd$_6$) 2.85 (d, 3H), 2.94 (s, 3H), 3.74 (s, 2H), 3.77 (s, 3H), 4.01 (s, 3H), 6.38 (m, 1H), 6.68 (d, 1H), 6.83 (m, 1H), 6.99 (d, 1H), 7.35 (d, 1H), 7.45 (br s, 1H), 7.65 (s, 1H), 7.88 (d, 1H), 8.22 (s, 1H), 8.39 (q, 1H), 8.61 (d, 1H), 10.14 (s, 1H); Mass Spectrum: M+H$^+$ 516.

[83] $^1$H NMR: (DMSOd$_6$) 2.94 (s, 6H), 3.74 (s, 2H), 3.77 (s, 3H), 6.38 (m, 1H), 6.71 (d, 1H), 6.84 (m, 1H), 6.99 (d, 1H), 7.34 (d, 1H), 7.45 (br s, 1H), 7.75 (m, 1H), 7.88 (d, 1H), 7.99 (m, 1H), 8.12 (m, 1H), 8.7 (d, 1H), 10.15 (s, 1H); Mass Spectrum: M+H$^+$ 447.

[84] The reaction product was purified by column chromatography on silica using ethyl acetate as eluent. The product gave the following characterising data:—$^1$H NMR: (DMSOd$_6$) 3.76 (s, 3H), 3.82 (s, 2H), 6.68 (d, 1H), 6.83 (m, 1H), 7.0 (d, 1H), 7.36 (d, 1H), 7.67 (m, 1H), 7.84 (m, 1H), 8.02-8.07 (m, 2H), 8.33 (m, 1H), 8.64 (d, 1H), 8.72 (d, 1H), 8.89 (d, 1H), 11.07 (br s, 1H); Mass Spectrum: M+H$^+$ 387.

[85] The reaction mixture was heated to 55° C. for 16 hours. The reaction product was purified by column chromatography on silica using increasingly polar mixtures of methylene chloride and ethyl acetate as eluent. The product gave the following characterising data:—$^1$H NMR: (DMSOd$_6$) 3.77 (s, 3H), 3.82 (s, 2H), 6.72 (d, 1H), 6.84 (m, 1H), 7.0 (d, 1H), 7.38 (d, 1H), 7.76 (m, 1H), 7.98 (m, 1H), 8.12 (m, 1H), 8.36 (d, 1H), 8.42 (m, 1H), 8.71 (d, 1H), 9.33 (s, 1H), 10.93 (s, 1H); Mass Spectrum: M+H$^+$ 405.

[86] The reaction product was purified by column chromatography on silica using a solvent gradient of 100:0:0 to 10:9:1 of methylene chloride, ethyl acetate and methanol as eluent. The product gave the following characterising data:—$^1$H NMR: (DMSOd$_6$) 3.77 (s, 3H), 3.81 (s, 2H), 3.94 (s, 3H), 3.95 (s, 3H), 6.53 (d, 1H), 6.80 (m, 1H), 6.96 (d, 1H), 7.35 (d, 1H), 7.4 (s, 1H), 7.51 (s, 1H), 8.36 (d, 1H), 8.42 (m, 1H), 8.5 (d, 1H), 9.33 (s, 1H), 10.92 (s, 1H); Mass Spectrum: M+H$^+$ 447.

[87] $^1$H NMR: (DMSOd$_6$) 2.16 (br s, 6H), 2.26 (s, 3H), 3.32 (br s, 2H), 3.66 (s, 2H), 3.78 (s, 3H), 6.7 (d, 1H), 6.79 (s, 1H), 6.84 (m, 1H), 6.99 (d, 1H), 7.33-7.38 (m, 2H), 7.39 (br s, 1H), 7.76 (m, 1H), 7.98 (m, 1H), 8.12 (m, 1H), 8.7 (d, 1H), 10.0 (s, 1H); Mass Spectrum: M+H$^+$ 474.

[88] The reaction product was purified by column chromatography on silica using a solvent gradient of 19:1 to 9:1 of methylene chloride and methanol as eluent. The product gave the following characterising data:—$^1$H NMR: (DMSOd$_6$) 2.13 (s, 6H), 2.26 (s, 3H), 3.29 (s, 2H), 3.66 (s, 2H), 3.77 (s, 3H), 6.64 (d, 1H), 6.78 (s, 1H), 6.84 (m, 1H), 7.0 (d, 1H), 7.33-7.4 (m, 3H), 7.59 (m, 1H), 7.78 (m, 1H), 8.41 (m, 1H), 8.73 (d, 1H), 9.99 (s, 1H); Mass Spectrum: M+H$^+$ 474.

[89] $^1$H NMR: (DMSOd$_6$) 2.15 (s, 6H), 2.26 (s, 3H), 2.85 (d, 3H), 3.25 (br s, 2H), 3.66 (s, 2H), 3.78 (s, 3H), 4.01 (s, 3H), 6.67 (d, 1H), 6.78 (s, 1H), 6.84 (m, 1H), 6.99 (d, 1H), 3.32-3.42 (m, 3H), 7.65 (s, 1H), 8.22 (s, 1H), 8.39 (q, 1H), 8.61 (s, 1H), 9.99 (s, 1H); Mass Spectrum: M+H$^+$ 543.

[90] $^1$H NMR: (DMSOd$_6$) 2.12 (s, 3H), 3.64 (s, 2H), 3.7 (s, 3H), 3.78 (s, 3H), 3.93 (s, 3H), 3.95 (s, 3H), 6.51 (d, 1H), 6.79 (m, 1H), 6.94 (d, 1H), 7.31 (d, 1H), 7.4 (s, 1H), 7.5 (s, 1H), 7.81 (s, 1H), 8.48 (d, 1H), 9.42 (s, 1H); Mass Spectrum: M+H$^+$ 463.

[91] The reaction mixture was purified by preparative HPLC using a Waters 'Xterra' reversed-phase column (5 microns silica) using decreasingly polar mixtures of water (containing 0.2% ammonium carbonate) and acetonitrile as eluent. The product gave the following characterising data:—$^1$H NMR: (DMSOd$_6$) 3.6 (s, 2H), 3.76 (s, 3H), 3.78 (s, 3H), 6.7 (d, 1H), 6.84 (m, 1H), 6.99 (d, 1H), 7.39-7.44 (m, 2H), 7.59 (m, 1H), 7.78 (m, 1H), 7.84 (s, 1H), 8.4 (m, 1H), 8.73 (d, 1H), 10.04 (s, 1H); Mass Spectrum: M+H$^+$ 407.

[92] The reaction mixture was purified by preparative HPLC as described in Note [91] hereinbefore. The product gave the following characterising data:—$^1$H NMR: (DMSOd$_6$) 3.6 (s, 2H), 3.77 (s, 3H), 3.78 (s, 3H), 3.93 (s, 3H), 6.63 (d, 1H), 6.81 (m, 1H), 6.97 (d, 1H), 7.33 (d, 1H), 7.41 (s, 1H), 7.46 (m, 1H), 7.56 (d, 1H), 7.85 (s, 1H), 7.95 (d, 1H), 8.55 (d, 1H), 10.04 (s, 1H); Mass Spectrum: M+H$^+$ 419.

The 2-[2-methoxy-4-(6-methoxyquinolin-4-yloxy)phenyl]acetic acid used as starting material was prepared as follows:—

A mixture of 4-chloro-6-methoxyquinoline (WO 2006/021448, within Example 48 thereof; 1 g), methyl 2-(4-hydroxy-2-methoxyphenyl)acetate (1.01 g), 4-dimethylaminopyridine (1.89 g) and chlorobenzene (12 ml) was stirred and heated to 140° C. for 14 hours. The reaction mixture was cooled to ambient temperature and diluted with diethyl ether. The mixture was filtered and the filtrate was evaporated. The residue was purified by column chromatography on silica using a solvent gradient from a 1:1 mixture of methylene chloride and ethyl acetate to ethyl acetate alone as eluent. There was thus obtained methyl 2-[2-methoxy-4-(6-methoxyquinolin-4-yloxy)phenyl]acetate (1.05 g); $^1$H NMR: (DMSOd$_6$) 3.63 (s, 3H), 3.66 (s, 2H), 3.77 (s, 3H), 3.93 (s, 3H), 6.64 (d, 1H), 6.8 (m, 1H), 6.98 (d, 1H), 7.32 (d, 1H), 7.46 (m, 1H), 7.56 (d, 1H), 7.94 (d, 1H), 8.55 (d, 1H); Mass Spectrum: M+H$^+$ 354.

A mixture of the material so obtained, sodium hydroxide (0.34 g), THF (1.5 ml), water (0.5 ml) and methanol (7 ml)

was stirred at ambient temperature for 15 hours. The resultant mixture was acidified to pH5 by the addition of 2N aqueous hydrochloric acid. The precipitate was isolated, washed in turn with water and with diethyl ether and dried. There was thus obtained 2-[2-methoxy-4-(6-methoxyquinolin-4-yloxy) phenyl]acetic acid (0.9 g); $^1$H NMR: (DMSOd$_6$) 3.55 (s, 2H), 3.77 (s, 3H), 3.93 (s, 3H), 6.63 (d, 1H), 6.79 (m, 1H), 6.96 (d, 1H), 7.31 (d, 1H), 7.46 (m, 1H), 7.57 (d, 1H), 8.55 (d, 1H); Mass Spectrum: M+H$^+$ 340.

[93] The reaction mixture was purified by preparative HPLC as described in Note [91] hereinbefore. The product gave the following characterising data:—$^1$H NMR: (DMSOd$_6$) 2.12 (s, 3H), 3.65 (s, 2H), 3.7 (s, 3H), 3.78 (s, 3H), 3.93 (s, 3H), 6.63 (d, 1H), 6.81 (m, 1H), 6.97 (d, 1H), 7.33 (d, 1H), 7.46 (m, 1H), 7.57 (d, 1H), 7.81 (s, 1H), 7.95 (d, 1H), 8.55 (d, 1H), 9.43 (s, 1H); Mass Spectrum: M+H$^+$ 433.

[94] The reaction mixture was purified by preparative HPLC as described in Note [91] hereinbefore. The product gave the following characterising data:—$^1$H NMR: (DMSOd$_6$) 1.43 (t, 3H), 3.6 (s, 2H), 3.77 (s, 3H), 3.78 (s, 3H), 4.22 (q, 2H), 6.52 (s, 1H), 6.80 (m, 1H), 6.96 (d, 1H), 7.28 (m, 1H), 7.33 (d, 1H), 7.4 (d, 1H), 7.41 (s, 1H), 7.85 (s, 1H), 8.2 (d, 1H), 8.62 (d, 1H), 10.04 (s, 1H); Mass Spectrum: M+H$^+$ 433.

The 2-[4-(7-ethoxyquinolin-4-yloxy)-2-methoxyphenyl] acetic acid used as starting material was prepared as follows:—

Tributylphosphine (4.57 ml) and 1,1'-(azodicarbonyl)dipiperidine (4.62 g) were added in turn to a stirred mixture of 4-chloro-7-hydroxyquinoline (International Application WO 02/00622, preparation 37 thereof; 2.74 g), ethanol (1.34 ml) and methylene chloride (100 ml) and the resultant mixture was stirred at ambient temperature for 14 hours. The mixture was filtered and the filtrate was concentrated by evaporation. The residue was purified by column chromatography on silica using a 1:1 mixture of methylene chloride and diethyl ether as eluent. There was thus obtained 4-chloro-7-ethoxyquinoline (2.23 g); $^1$H NMR: (DMSOd$_6$) 1.42 (t, 3H), 4.23 (q, 2H), 7.39 (m, 1H), 7.45 (d, 1H), 7.58 (d, 1H), 8.1 (d, 1H), 8.75 (d, 1H); Mass Spectrum: M+H$^+$ 208.

A mixture of methyl 2-(4-hydroxy-2-methoxyphenyl)acetate (1.04 g), 4-chloro-7-ethoxyquinoline (1 g), 4-dimethylaminopyridine (1.76 g) and chlorobenzene (20 ml) was stirred and heated to 125° C. for 16 hours. The mixture was cooled to ambient temperature and filtered. The filtrate was concentrated by evaporation and the residue was purified by column chromatography on silica using a solvent gradient from methylene chloride to a 1:1 mixture methylene chloride and diethyl ether as eluent. There was thus obtained methyl 2-[4-(7-ethoxyquinolin-4-yloxy)-2-methoxyphenyl]acetate (1.66 g).

A solution of sodium hydroxide (0.544 g) in water (10 ml) was added to a stirred suspension of 2-[4-(7-ethoxyquinolin-4-yloxy)-2-methoxyphenyl]acetate (1.66 g) in methanol (30 ml). THF (8 ml) was added and the resultant solution was stirred at ambient temperature for 3 hours. The mixture was concentrated by evaporation and the residue was cooled to 0° C. and acidified to pH2.5 by the addition of a 6N aqueous hydrochloric acid solution. The resultant precipitate was isolated, washed with water and dried under vacuum. There was thus obtained 2-[4-(7-ethoxyquinolin-4-yloxy)-2-methoxyphenyl]acetic acid (1.47 g); $^1$H NMR: (DMSOd$_6$) 1.45 (t, 3H), 3.58 (s, 2H), 3.78 (s, 3H), 4.27 (q, 1H), 6.75 (d, 1H), 6.9 (m, 1H), 7.07 (d, 1H), 7.37 (d, 1H), 7.48 (m, 1H), 7.56 (d, 1H), 8.38 (d, 1H), 8.83 (d, 1H).

[95] The reaction mixture was purified by preparative HPLC using a Waters 'Xterra' reversed-phase column (5 microns silica) using decreasingly polar mixtures of water (containing 0.2% ammonium carbonate) and acetonitrile as eluent. The product gave the following characterising data: —$^1$H NMR: (DMSOd$_6$) 2.13 (s, 3H), 3.65 (s, 2H), 3.69 (s, 3H), 3.78 (s, 3H), 6.64 (d, 1H), 6.83 (m, 1H), 6.99 (d, 1H), 7.34 (d, 1H), 7.59 (m, 1H), 7.78 (m, 1H), 7.81 (s, 1H), 8.4 (m, 1H), 8.72 (d, 1H), 9.43 (s, 1H); Mass Spectrum: M+H$^+$ 421.

[96] The reaction mixture was purified by preparative HPLC using a Waters 'Xterra' reversed-phase column (5 microns silica) using decreasingly polar mixtures of water (containing 0.2% ammonium carbonate) and acetonitrile as eluent. The product gave the following characterising data:—$^1$H NMR: (DMSOd$_6$) 2.08 (s, 3H), 3.58 (s, 3H), 3.68 (s, 2H), 3.78 (s, 3H), 3.93 (s, 3H), 3.95 (s, 3H), 5.96 (s, 1H), 6.54 (d, 1H), 6.79 (m, 1H), 6.96 (d, 1H), 7.34 (d, 1H), 7.4 (s, 1H), 7.5 (s, 1H), 8.49 (d, 1H), 8.93 (s, 1H); Mass Spectrum: M+H$^+$ 463.

[97] The reaction mixture was purified by column chromatography on silica using increasingly polar solvent mixtures obtained by adding methanol to a 1:1 mixture of methylene chloride and ethyl acetate. The product gave the following characterising data:—$^1$H NMR: (DMSOd$_6$) 2.08 (s, 3H), 3.58 (s, 3H), 3.68 (s, 2H), 3.78 (s, 3H), 3.94 (s, 3H), 5.96 (s, 1H), 6.54 (d, 1H), 6.8 (m, 1H), 6.97 (d, 1H), 7.29 (m, 1H), 7.34 (d, 1H), 7.41 (d, 1H), 8.2 (d, 1H), 8.63 (d, 1H), 9.94 (s, 1H); Mass Spectrum: M+H$^+$ 433.

[98] The reaction mixture was purified by preparative HPLC using a Waters 'Xterra' reversed-phase column (5 microns silica) using decreasingly polar mixtures of water (containing 0.2% ammonium carbonate) and acetonitrile as eluent. The product gave the following characterising data:—$^1$H NMR: (DMSOd$_6$) 2.18 (s, 3H), 3.63 (s, 2H), 3.75 (s, 3H), 6.25 (s, 1H), 6.71 (d, 1H), 6.82 (m, 1H), 6.98 (d, 1H), 7.33 (d, 1H), 7.75 (m, 1H), 7.98 (m, 1H), 8.12 (m, 1H), 8.7 (d, 1H), 10.32 (s, 1H), 11.95 (s, 1H); Mass Spectrum: M+H$^+$ 407.

[99] The reaction mixture was purified by preparative HPLC using a Waters 'Xterra' reversed-phase column (5 microns silica) using decreasingly polar mixtures of water (containing 0.2% ammonium carbonate) and acetonitrile as eluent. The product gave the following characterising data:—$^1$H NMR: (DMSOd$_6$) 1.76 (s, 3H), 2.1 (s, 3H), 3.62 (s, 2H), 3.78 (s, 3H), 6.73 (d, 1H), 6.84 (m, 1H), 6.99 (d, 1H), 7.37 (d, 1H), 7.75 (m, 1H), 7.98 (m, 1H), 8.12 (m, 1H), 8.7 (d, 1H), 9.56 (br s, 1H), 12.0 (s, 1H); Mass Spectrum: M+H$^+$ 421.

[100] The reaction mixture was purified by preparative HPLC using a Waters 'Xterra' reversed-phase column (5 microns silica) using decreasingly polar mixtures of water (containing 0.2% ammonium carbonate) and acetonitrile as eluent. The product gave the following characterising data:—$^1$H NMR: (DMSOd$_6$) 2.07 (s, 3H), 3.59 (s, 3H), 3.7 (s, 2H), 3.8 (s, 3H), 5.97 (s, 1H), 6.74 (d, 1H), 6.85 (m, 1H), 7.02 (d, 1H), 7.37 (d, 1H), 7.77 (m, 1H), 7.99 (m, 1H), 8.13 (m, 1H), 8.72 (d, 1H), 9.95 (s, 1H); Mass Spectrum: M+H$^+$ 421.

[101] The reaction mixture was purified by preparative HPLC using a Waters 'Xterra' reversed-phase column (5 microns silica) using decreasingly polar mixtures of water (containing 0.2% ammonium carbonate) and acetonitrile as eluent.

The product gave the following characterising data:—$^1$H NMR: (DMSOd$_6$) 2.18 (s, 3H), 3.63 (s, 2H), 3.76 (s, 3H), 6.25 (br s, 1H), 6.65 (d, 1H), 6.83 (m, 1H), 6.98 (d, 1H), 7.33 (d, 1H), 7.59 (m, 1H), 7.78 (m, 1H), 8.41 (m, 1H), 8.72 (d, 1H), 10.32 (br s, 1H); Mass Spectrum: M+H$^+$ 407.

[102] The reaction mixture was purified by preparative HPLC using a Waters 'Xterra' reversed-phase column (5 microns silica) using decreasingly polar mixtures of water (containing 0.2% ammonium carbonate) and acetonitrile as eluent. The product gave the following characterising data:—$^1$H NMR: (DMSOd$_6$) 1.79 (s, 3H), 2.12 (s, 3H), 3.66 (s, 2H), 3.78 (s, 3H), 6.74 (d, 1H), 6.88 (m, 1H), 7.03 (d, 1H), 7.39 (d, 1H), 7.67 (m, 1H), 7.85 (m, 1H), 8.47 (m, 1H), 8.81 (d, 1H), 8.79 (s, 1H); Mass Spectrum: M+H$^+$ 421.

[103] The reaction mixture was purified by preparative HPLC using a Waters 'Xterra' reversed-phase column (5 microns silica) using decreasingly polar mixtures of water (containing 0.2% ammonium carbonate) and acetonitrile as eluent. The product gave the following characterising data:—$^1$H NMR: (DMSOd$_6$) 2.08 (s, 3H), 3.58 (s, 3H), 3.7 (s, 2H), 3.79 (s, 3H), 5.96 (s, 1H), 6.66 (d, 1H), 6.84 (m, 1H), 7.01 (d, 1H), 7.36 (d, 1H), 7.60 (m, 1H), 7.78 (m, 1H), 8.4 (m, 1H), 8.73 (d, 1H), 9.94 (s, 1H); Mass Spectrum: M+H$^+$ 421.

[104] The reaction mixture was purified by preparative HPLC using a Waters 'Xterra' reversed-phase column (5 microns silica) using decreasingly polar mixtures of water (containing 0.2% ammonium carbonate) and acetonitrile as eluent. The product gave the following characterising data:—$^1$H NMR: (DMSOd$_6$) 1.89 (d, 3H), 3.72 (s, 2H), 3.78 (s, 3H), 3.93 (s, 3H), 3.95 (s, 3H), 6.54 (d, 1H), 6.8 (m, 1H), 6.96 (d, 1H), 7.34 (d, 1H), 7.4 (s, 1H), 7.5 (s, 1H), 8.49 (d, 1H), 8.6 (q, 1H), 10.35 (br s, 1H); Mass Spectrum: M+H$^+$ 450.

[105] The reaction mixture was purified by preparative HPLC using a Waters 'Xterra' reversed-phase column (5 microns silica) using decreasingly polar mixtures of water (containing 0.2% ammonium carbonate) and acetonitrile as eluent. The product gave the following characterising data:—$^1$H NMR: (DMSOd$_6$) 1.89 (d, 3H), 3.72 (s, 2H), 3.79 (s, 3H), 6.73 (d, 1H), 6.84 (m, 1H), 7.0 (d, 1H), 7.37 (d, 1H), 7.76 (m, 1H), 7.98 (m, 1H), 8.12 (m, 1H), 8.6 (q, 1H), 8.71 (d, 1H), 10.36 (br s, 1H); Mass Spectrum: M+H$^+$ 408.

[106] The reaction mixture was purified by preparative HPLC using a Waters 'Xterra' reversed-phase column (5 microns silica) using decreasingly polar mixtures of water (containing 0.2% ammonium carbonate) and acetonitrile as eluent. The product gave the following characterising data:—$^1$H NMR: (DMSOd$_6$) 1.89 (d, 3H), 3.74 (s, 2H), 3.78 (s, 3H), 6.74 (d, 1H), 6.87 (m, 1H), 7.03 (d, 1H), 7.39 (d, 1H), 7.66 (m, 1H), 7.84 (m, 1H), 8.46 (m, 1H), 8.6 (q, 1H), 8.8 (d, 1H), 10.38 (br s, 1H); Mass Spectrum: M+H$^+$ 408.

EXAMPLE 6

Using an analogous procedure to that described in Example 2, the appropriate 2-phenylacetic acid was reacted with the appropriate amine to give the compounds described in Table III. Unless otherwise stated, each reaction product was purified by column chromatography on silica using increasingly polar mixtures of methylene chloride and a 3.5M methanolic ammonia solution as eluent. Unless otherwise stated, each amine was a commercially available material.

TABLE III

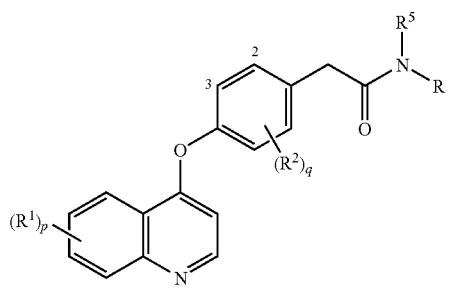

| No. & Note | $(R^1)_p$ | $(R^2)_q$ | $R^5$ | R |
|---|---|---|---|---|
| [1] | 6,7-dimethoxy | H | methyl | 1-methylpyrazol-4-yl |
| [2] | 6-cyano-7-methoxy | H | methyl | 1-methylpyrazol-4-yl |
| [3] | 6-(N,N-dimethyl-carbamoyl)-7-methoxy | H | methyl | 1-methylpyrazol-4-yl |
| [4] | 6,7-dimethoxy | H | methyl | 5-methylisoxazol-3-yl |
| [5] | 6,7-dimethoxy | H | methyl | 5-methylthiazol-2-yl |
| [6] | 6-fluoro | 2-methoxy | methyl | 5-methylthiazol-2-yl |
| [7] | 6,7-dimethoxy | 2-methoxy | methyl | 5-methylthiazol-2-yl |
| [8] | 7-methoxy | 2-methoxy | methyl | 5-methylthiazol-2-yl |
| [9] | 7-fluoro | 2-methoxy | methyl | 5-methylthiazol-2-yl |

Notes The products gave the characterising data shown below.

[1] $^1$H NMR: (DMSOd$_6$) 3.12 (s, 3H), 3.58 (s, 2H), 3.84 (s, 3H) 3.92 (s, 3H), 3.95 (s, 3H), 6.46 (d, 1H), 7.15 (d, 2H), 7.2 (d, 2H), 7.4 (s, 1H), 7.48 (br s, 1H), 7.49 (br s, 1H), 7.85 (s, 1H), 8.48 (d, 1H); Mass Spectrum: M+H$^+$433.

The 1-methyl-4-methylamino-1H-pyrazole used as a starting material was prepared as follows:—

2,4-Dinitrobenzenesulphonyl chloride (3.1 g) was added dropwise to a stirred solution of 4-amino-1-methylpyrazole (2.55 g) in methylene chloride (50 ml) that had been cooled to −5° C. The resultant mixture was stirred at this temperature for 5 minutes. The mixture was washed in turn with water, a 5% aqueous ammonium chloride solution, a saturated aqueous sodium bicarbonate solution and brine. The organic phase was dried over magnesium sulphate and filtered. There was thus obtained a solution of N-(1-methylpyrazol-4-yl)-2,4-dinitrobenzenesulphonamide; Mass Spectrum: M+H$^+$ 328.

Under an atmosphere of argon, triphenylphosphine (6.1 g) and methanol (4.73 ml) were added to the solution of N-(1-methylpyrazol-4-yl)-2,4-dinitrobenzenesulphonamide (about 3.81 g) in methylene chloride (200 ml). The resultant mixture was cooled to 0° C. and di-tert-butyl azodicarboxylate (5.36 g) was added portionwise. The mixture was stirred at 0° C. for 1 hour. Isopropylamine (9.59 ml) was added and the mixture was stirred at ambient temperature for 1 hour. The resultant mixture was evaporated and the residue was purified by column chromatography on silica using a solvent gradient of 50:50:0 to 21:21:8 of methylene chloride, ethyl acetate and methanol respectively as eluent. There was thus obtained 1-methyl-4-methylamino-1H-pyrazole (0.74 g); $^1$H NMR: (CDCl$_3$) 2.75 (s, 3H), 3.81 (s, 3H), 6.91 (s, 1H), 7.13 (s, 1H).

[2] ¹H NMR: (DMSOd₆) 3.12 (s, 3H), 3.59 (d, 2H), 3.84 (s, 3H), 4.07 (s, 3H), 6.53 (d, 1H), 7.2 (d, 2H), 7.24 (d, 2H), 7.48 (s, 1H), 7.61 (s, 1H), 7.85 (s, 1H), 8.75 (m, 2H); Mass Spectrum: M+H⁺ 428.

[3] ¹H NMR: (DMSOd₆) (the major rotameric form gave the following signals) 2.81 (s, 3H), 3.04 (s, 3H), 3.12 (s, 3H), 3.61 (s, 2H), 3.84 (s, 3H), 4.05 (s, 3H), 6.76 (d, 1H), 7.27-7.33 (m, 4H), 7.50 (s, 1H), 7.66 (s, 1H), 7.87 (s, 1H), 8.3 (s, 1H), 8.91 (d, 1H); Mass Spectrum: M+H⁺ 474.

[4] ¹H NMR: (DMSOd₆, at 50° C.) 2.39 (s, 3H), 3.35 (s, 3H), 3.92 (s, 3H), 3.95 (s, 3H), 3.99 (br s, 2H), 6.5 (d, 1H), 6.62 (br s, 1H), 7.18 (d, 2H), 7.34 (d, 2H), 7.4 (s, 1H), 7.49 (s, 1H), 8.49 (d, 1H); Mass Spectrum: M+H⁺ 434.

The 5-methyl-3-methylaminoisoxazole used as a starting material was prepared as follows:—

Under an atmosphere of argon, a 1M solution of lithium hexamethyldisilazane in THF (1.1 ml) was added dropwise to a stirred solution of 3-tert-butoxycarbonylamino-5-methylisoxazole (*Tet. Lett.*, 1996, 37, 3339-3342; 0.2 g) in THF (9 ml) that had been cooled to −5° C. After 10 minutes, a solution of dimethyl sulphate (0.1 ml) in THF (1 ml) was added dropwise and the resultant mixture was stirred at −5° C. for 2 hours. The mixture was evaporated and the residue was partitioned between methylene chloride and water. The organic phase was dried over magnesium sulphate and evaporated to give 3-(N-tert-butoxycarbonyl-N-methylamino)-5-methylisoxazole (0.19 g); ¹H NMR: (CDCl₃) 1.54 (s, 9H), 2.36 (s, 3H), 3.34 (s, 3H), 6.5 (br s, 1H).

A mixture of 3-(N-tert-butoxycarbonyl-N-methylamino)-5-methylisoxazole (0.137 g), a 4M solution of hydrogen chloride in 1,4-dioxane (0.485 ml) and methylene chloride (1.2 ml) was stirred at ambient temperature for 2 hours. The resultant mixture was evaporated and the residue was triturated under diethyl ether. The resultant solid was isolated and dried under vacuum. There was thus obtained 5-methyl-3-methylaminoisoxazole (0.041 g); ¹H NMR: (CDCl₃) 2.29 (s, 3H), 2.85 (s, 3H), 5.49 (s, 1H); Mass Spectrum: M+H⁺ 113.

[5] ¹H NMR: (DMSOd₆) 2.34 (d, 3H), 3.69 (s, 3H), 3.93 (s, 3H), 3.95 (s, 3H), 4.16 (s, 2H), 6.51 (d, 1H), 7.21 (br s, 1H), 7.25 (d, 2H), 7.4 (s, 1H), 7.41 (d, 2H), 7.5 (s, 1H), 8.48 (d, 1H); Mass Spectrum: M+H⁺ 450.

The 5-methyl-2-methylaminothiazole used as a starting material was prepared as follows:—

Pyridine (0.107 ml) was added to a stirred suspension of 2-amino-5-methylthiazole (0.5 g) in acetic anhydride (0.944 ml). The resultant mixture was heated to 100° C. in a microwave oven for 10 minutes. The mixture was cooled to ambient temperature and diethyl ether was added. The precipitate was isolated and dried. There was thus obtained 2-acetamido-5-methylthiazole (0.634 g); ¹H NMR: (CDCl₃) 2.3 (s, 3H), 2.41 (s, 3H), 7.06 (br s, 1H); Mass Spectrum: M+H⁺ 157.

Under an atmosphere of argon, a 1M solution of lithium hexamethyldisilazane in THF (4.24 ml) was added dropwise to a stirred solution of 2-acetamido-5-methylthiazole (0.63 g) in THF (30 ml) that had been cooled to 0° C. After 10 minutes, the mixture was cooled to −30° C. and a solution of dimethyl sulphate (0.4 ml) in THF (4 ml) was added. The resultant mixture was stirred at −30° C. for 1 hour and at ambient temperature for 4 hours. The mixture was evaporated and the residue was purified by column chromatography on silica using a solvent gradient of 9:1 to 3:7 of methylene chloride and ethyl acetate as eluent. There was thus obtained 2-(N-methylacetamido)-5-methylthiazole (0.35 g); ¹H NMR: (CDCl₃) 2.38 (2s, 6H), 3.67 (s, 3H), 7.13 (s, 1H); Mass Spectrum: M+H⁺ 171.

A mixture of 2-(N-methylacetamido)-5-methylthiazole (0.35 g), sodium hydroxide (0.15 g) and methanol (10 ml) was stirred at ambient temperature for 16 hours. The mixture was evaporated. Water (5 ml) and methylene chloride (5 ml) were added and the basicity of the mixture was reduced by the addition of 2N aqueous hydrochloric acid (2 ml). A saturated solution of aqueous sodium bicarbonate was added to bring the pH to 8. The resultant aqueous phase was extracted with methylene chloride. The organic extract was dried over magnesium sulphate and evaporated. There was thus obtained 5-methyl-2-methylaminothiazole (0.26 g); ¹H NMR: (DMSOd₆) 2.19 (s, 3H), 2.75 (s, 3H), 6.67 (s, 1H), 7.22 (s, 1H); Mass Spectrum: M+H⁺ 129.

[6] The reaction product was purified by column chromatography on silica using increasingly polar mixtures of methylene chloride and methanol as eluent. The product gave the following characterising data:—¹H NMR: (DMSOd₆) 2.33 (d, 3H), 3.71 (s, 3H), 3.76 (s, 3H), 4.04 (s, 2H), 6.74 (d, 1H), 6.86 (m, 1H), 7.03 (d, 1H), 7.21 (q, 1H), 7.31 (d, 1H), 7.76 (m, 1H), 7.98 (m, 1H), 8.13 (m, 1H), 8.72 (d, 1H); Mass Spectrum: M+H⁺ 438.

[7] The reaction product was purified by preparative HPLC using a Waters 'Xterra' reversed-phase column (5 microns silica, 19 mm diameter, 100 mm length) and decreasingly polar mixtures of water (containing 0.2% ammonium carbonate) and acetonitrile as eluent. In an additional purification step, the reaction product was purified by column chromatography on silica using increasingly ethyl acetate as eluent. The product gave the following characterising data:—¹H NMR: (DMSOd₆) 2.33 (d, 3H), 3.71 (s, 3H), 3.76 (s, 3H), 3.94 (s, 3H), 3.95 (s, 3H), 4.03 (s, 2H), 6.56 (d, 1H), 6.81 (m, 1H), 6.99 (d, 1H), 7.21 (q, 1H), 7.28 (d, 1H), 7.41 (s, 1H), 7.51 (s, 1H), 8.51 (d, 1H); Mass Spectrum: M+H⁺ 480.

[8] The reaction product was purified by column chromatography on silica using increasingly polar solvent mixtures obtained by adding methanol to a 1:1 mixture of methylene chloride and ethyl acetate. The product gave the following characterising data:—¹H NMR: (DMSOd₆) 2.33 (d, 3H), 3.71 (s, 3H), 3.75 (s, 3H), 3.94 (s, 3H), 4.03 (s, 2H), 6.55 (d, 1H), 6.82 (m, 1H), 7.0 (d, 1H), 7.21 (q, 1H), 7.29 (m, 1H), 7.3 (d, 1H), 7.42 (d, 1H), 8.21 (d, 1H), 8.64 (d, 1H); Mass Spectrum: M+H⁺ 450.

[9] The reaction product was purified by preparative HPLC using a Waters 'Xterra' reversed-phase column (5 microns silica, 19 mm diameter, 100 mm length) and decreasingly polar mixtures of water (containing 0.2% ammonium carbonate) and acetonitrile as eluent. The product gave the following characterising data:—¹H NMR: (DMSOd₆) 2.33 (d, 3H), 3.71 (s, 3H), 3.76 (s, 3H), 4.05 (s, 2H), 6.67 (d, 1H), 6.86 (m, 1H), 7.04 (d, 1H), 7.21 (q, 1H), 7.31 (d, 1H), 7.6 (m, 1H), 7.79 (m, 1H), 8.41 (m, 1H), 8.74 (d, 1H); Mass Spectrum: M+H⁺ 438.

EXAMPLE 7

Using an analogous procedure to that described in Example 3, the appropriate 2-phenylacetic acid was reacted with the appropriate amine to give the compounds described in Table IV. Unless otherwise stated, each reaction product was purified by preparative HPLC using a Waters 'Xterra' reversed-phase column and decreasingly polar mixtures of water (containing 0.2% ammonium carbonate) and acetonitrile as eluent. Unless otherwise stated, each amine was a commercially available material.

TABLE IV

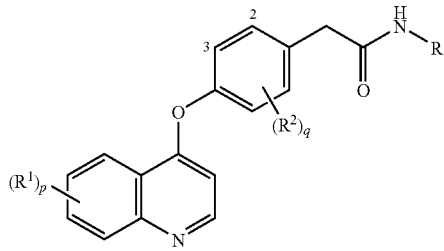

| No. & Note | $(R^1)_p$ | $(R^2)_q$ | R |
|---|---|---|---|
| [1] | 6-cyano-7-methoxy | H | 3-methylisoxazol-5-yl |
| [2] | 6-cyano-7-methoxy | H | 3-ethylisoxazol-5-yl |
| [3] | 6-cyano-7-methoxy | H | 3-methyl-1,2,4-oxadiazol-5-yl |
| [4] | 6,7-dimethoxy | H | 5-methyl-1,3,4-oxadiazol-2-yl |
| [5] | 6-cyano-7-methoxy | H | 5-methyl-1,3,4-oxadiazol-2-yl |
| [6] | 6,7-dimethoxy | H | 2-pyrimidinyl |
| [7] | 6-cyano-7-methoxy | H | 2-pyrimidinyl |
| [8] | 6-fluoro | 2-methoxy | 4-methylthiazol-2-yl |

Notes The products gave the characterising data shown below.

[1] The reaction time was 30 minutes at ambient temperature. The reaction product was purified by column chromatography on silica using increasingly polar mixtures of methylene chloride and ethyl acetate as eluent. The product was obtained in 64% yield and gave the following characterising data:—$^1$H NMR: (DMSOd$_6$) 2.17 (s, 3H), 3.78 (s, 2H), 4.07 (s, 3H) 6.12 (s, 1H), 6.54 (d, 1H), 7.29 (d, 2H), 7.47 (d, 2H), 7.62 (s, 1H), 8.74 (d, 1H), 8.77 (s, 1H), 11.8 (br s, 1H); Mass Spectrum: M+H$^+$ 415.

[2] Diisopropylethylamine was used instead of pyridine and the reaction time was 30 minutes at ambient temperature. The product gave the following characterising data:—$^1$H NMR: (DMSOd$_6$) 1.6 (t, 3H), 2.53-2.6 (m, 2H), 3.78 (s, 2H), 4.07 (s, 3H), 6.16 (s, 1H), 6.54 (d, 1H), 7.29 (d, 2H), 7.48 (d, 2H), 7.62 (s, 1H), 8.75 (d, 1H), 8.77 (s, 1H), 11.82 (br s, 1H); Mass Spectrum: M+H$^+$ 429.

The 5-amino-3-ethylisoxazole used as a starting material was prepared as follows:—

3-Oxopentanenitrile was reacted with hydroxylamine to give the required starting material in 47% yield; $^1$H NMR: (DMSOd$_6$) 1.1 (t, 3H), 2.38 (q, 2H), 4.81 (s, 1H), 6.47 (br s, 2H).

[3] $^1$H NMR: (DMSOd$_6$) 2.26 (s, 3H), 3.87 (s, 2H), 4.07 (s, 3H), 6.55 (d, 1H), 7.3 (d, 2H), 7.48 (d, 2H), 7.62 (s, 1H), 8.75 (d, 1H), 8.78 (s, 1H), 12.27 (br s, 1H); Mass Spectrum: M+H$^+$ 416.

[4] $^1$H NMR: (DMSOd$_6$) 2.44 (s, 3H), 3.8 (s, 2H), 3.93 (s, 3H), 3.95 (s, 3H), 6.48 (d, 1H), 7.24 (d, 2H), 7.4 (s, 1H), 7.44 (d, 2H), 7.49 (s, 1H), 8.48 (d, 1H), 11.60 (br s, 1H); Mass Spectrum: M+H$^+$ 421.

[5] $^1$H NMR: (DMSOd$_6$) 2.44 (s, 3H), 3.82 (s, 2H), 4.07 (s, 3H), 6.55 (d, 1H), 7.3 (d, 2H), 7.48 (d, 2H), 7.62 (s, 1H), 8.75 (d, 1H), 8.78 (s, 1H), 11.77 (br s, 1H); Mass Spectrum: M+H$^+$ 416.

[6] $^1$H NMR: (DMSOd$_6$) 3.87 (s, 2H), 3.92 (s, 3H), 3.95 (s, 3H), 6.47 (d, 1H), 7.19 (t, 1H), 7.23 (d, 2H), 7.4 (s, 1H), 7.47 (d, 2H), 7.49 (s, 1H), 7.48 (d, 1H), 7.67 (d, 2H), 10.84 (br s, 1H); Mass Spectrum: M+H$^+$ 417.

[7] $^1$H NMR: (DMSOd$_6$) 3.88 (s, 2H), 4.07 (s, 3H), 6.54 (d, 1H), 7.2 (m, 1H), 7.29 (d, 2H), 7.5 (d, 2H), 7.62 (s, 1H), 8.67 (s, 1H), 8.68 (s, 1H), 8.74 (d, 1H), 8.78 (s, 1H), 10.85 (s, 1H); Mass Spectrum: M+H$^+$ 412.

[8] Diisopropylethylamine was used instead of pyridine and THF was used as a cosolvent. The reaction product was purified by column chromatography on silica using increasingly polar mixtures of methylene chloride and ethyl acetate as eluent. The product gave the following characterising data:—$^1$H NMR: (DMSOd$_6$) 2.27 (s, 3H), 3.75 (s, 3H), 3.78 (s, 2H), 6.72 (d, 1H), 6.74 (d, 1H), 6.84 (m, 1H), 7.0 (d, 1H), 7.36 (d, 1H), 7.76 (m, 1H), 7.98 (d, 1H), 8.12 (m, 1H), 8.71 (d, 1H), 12.18 (s, 1H); Mass Spectrum: M+H$^+$ 424.

EXAMPLE 8

N-(1-ethylpyrazol-4-yl)-2-[4-(6-carboxy-7-methoxyquinolin-4-yloxy)phenyl]acetamide A mixture of N-(1-ethylpyrazol-4-yl)-2-[4-(7-methoxy-6-methoxycarbonylquinolin-4-yloxy)phenyl]acetamide (0.05 g), lithium hydroxide (0.01 g) and methanol (1 ml) was stirred at ambient temperature for 14 hours. The resultant mixture was acidified to pH2 by the addition of 2N aqueous hydrochloric acid. The precipitate was isolated, washed with water and with diethyl ether and dried under vacuum. There was thus obtained the title compound (0.028 g); $^1$H NMR: (DMSOd$_6$) 1.32 (t, 3H), 3.63 (s, 2H), 3.97 (s, 3H), 4.03-4.11 (m, 2H), 6.48 (d, 1H), 7.27 (d, 2H), 7.42 (s, 1H), 7.46 (d, 2H), 7.5 (s, 1H), 7.9 (s, 1H), 8.54 (s, 1H), 6.67 (d, 1H), 10.21 (s, 1H); Mass Spectrum: M+H$^+$ 447.

EXAMPLE 9

N-(3-amino-1H-pyrazol-5-yl)-2-[4-(6,7-dimethoxyquinolin-4-yloxy)phenyl]acetamide Diisopropylethylamine (0.042 ml) and 2-(7-azabenzotriazol-1-yl)-1,1,3,3-tetramethyluronium hexafluorophosphate (V) (0.091 g) were added in turn to a stirred mixture of 2-[4-(6,7-dimethoxyquinolin-4-yloxy)phenyl]acetic acid (0.068 g), 5-amino-3-(N-tert-butoxycarbonylamino)-1-(3,4-dimethoxybenzyl)pyrazole (0.068 g) and DMF (0.7 ml) and the resultant mixture was stirred at ambient temperature for 2 hours. A 2N aqueous sodium bicarbonate solution was added and the resultant solid was isolated and purified by column chromatography on silica using a solvent gradient of 100:0 to 47:3 of methylene chloride and methanol as eluent. There was thus obtained N-[3-(N-tert-butoxycarbonylamino)-1-(3,4-dimethoxybenzyl)pyrazol-5-yl]-2-[4-(6,7-dimethoxyquinolin-4-yloxy)phenyl]acetamide as a solid (0.095 g); $^1$H NMR: (DMSOd$_6$) 1.42 (s, 9H), 3.65 (s, 3H), 3.67 (s, 3H), 3.92 (s, 3H), 3.95 (s, 3H), 5.02 (s, 2H), 5.76 (s, 2H), 6.32 (m, 1H), 6.39 (m, 1H), 6.57 (m, 1H), 6.73 (m, 1H), 6.84 (m, 1H), 7.2 (m, 2H), 7.41 (m, 3H), 7.49 (s, 1H), 8.43 (m, 1H), 9.5 (br s, 1H), 10.22 (br s, 1H); Mass Spectrum: M+H$^+$ 670.

A mixture of N-[3-(N-tert-butoxycarbonylamino)-1-(3,4-dimethoxybenzyl)pyrazol-5-yl]-2-[4-(6,7-dimethoxyquinolin-4-yloxy)phenyl]acetamide (0.2 g) and trifluoroacetic acid (5 ml) was stirred at ambient temperature for 2 hours. The resultant mixture was evaporated. The residue was purified by column chromatography on silica using a solvent gradient from 49:1 to 9:1 of methylene chloride and a 3M methanolic ammonia solution as eluent. There was thus obtained the title compound (0.045 g); $^1$H NMR: (DMSOd$_6$) 3.63 (s, 2H), 3.93 (s, 3H), 3.95 (s, 3H), 5.05 (br s, 2H), 5.58 (s, 1H), 6.5 (d, 1H), 7.23 (d, 2H), 7.41 (s, 1H), 7.45 (d, 2H), 7.51 (s, 1H), 8.5 (d, 1H), 10.35 (br s, 1H); Mass Spectrum: M+H$^+$ 420.

The 5-amino-3-(N-tert-butoxycarbonylamino)-1-(3,4-dimethoxybenzyl)pyrazole used as a starting material was prepared as follows:—

Diphenylphosphoryl azide (4.23 ml) was added dropwise to a stirred mixture of 1-(3,4-dimethoxybenzyl)-5-nitro-1H-pyrazole-3-carboxylic acid (*Synthesis*, 2003, 1815-1826; 3.55 g), triethylamine (2.73 ml), tert-butanol (25 ml) and 1,4-dioxane (25 ml) and the mixture was stirred at ambient temperature for 1 hour. The resultant mixture was heated to 50° C. for 2.5 hours and subsequently to reflux for 5 hours. The mixture was concentrated and the residue was purified by column chromatography on silica using a gradient of 100:0 to 19:1 of methylene chloride and diethyl ether as eluent. There was thus obtained 3-(N-tert-butoxycarbonylamino)-1-(3,4-dimethoxybenzyl)-5-nitropyrazole (3 g); $^1$H NMR: (DMSOd$_6$) 1.46 (s, 9H), 3.71 (s, 3H), 3.72 (s, 3H), 5.53 (s, 2H), 6.64 (m, 1H), 6.88 (m, 2H), 7.11 (br s, 1H), 10.22 (br s, 1H); Mass Spectrum: M+H$^+$ 379.

A mixture of a portion (0.34 g) of the material so obtained, platinum oxide (0.03 g), ethyl acetate (15 ml) and ethanol (5 ml) was stirred under 1.8 atmospheres pressure of hydrogen gas for 2 hours. The resultant mixture was filtered and the filtrate was evaporated. There was thus obtained the required starting material (0.295 g); $^1$H NMR: (DMSOd$_6$) 1.4 (s, 9H), 3.7 (s, 3H), 3.71 (s, 3H), 4.85 (s, 2H), 5.24 (s, 2H), 5.43 (br s, 1H), 6.64 (m, 1H), 6.84 (m, 1H), 6.86 (m, 1H); Mass Spectrum: M+H$^+$ 349.

EXAMPLE 10

N-(1-ethylpyrazol-3-yl)-2-[4-(6-carboxy-7-methoxyquinolin-4-yloxy)phenyl]acetamide Using an analogous procedure to that described in Example 8, N-(1-ethylpyrazol-3-yl)-2-[4-(7-methoxy-6-methoxycarbonylquinolin-4-yloxy)phenyl]acetamide was reacted with lithium hydroxide to give the title compound in 92% yield; $^1$H NMR: (DMSOd$_6$) 1.34 (t, 3H), 3.67 (s, 2H), 3.99 (s, 3H), 4.0-4.06 (m, 2H), 6.43 (d, 1H), 6.55 (d, 1H), 7.29 (d, 2H), 7.49 (d, 2H), 7.53 (s, 1H), 7.58 (d, 1H), 8.58 (s, 1H), 8.71 (d, 1H), 10.71 (s, 1H); Mass Spectrum: M+H$^+$ 447.

EXAMPLE 11

N-(5-ethylisoxazol-3-yl)-2-[4-(6-carboxy-7-methoxyquinolin-4-yloxy)phenyl]acetamide Using an analogous procedure to that described in Example 8, N-(5-ethylisoxazol-3-yl)-2-[4-(7-methoxy-6-methoxycarbonylquinolin-4-yloxy)phenyl]acetamide was reacted with lithium hydroxide to give the title compound in 78% yield; $^1$H NMR: (DMSOd$_6$) 1.2 (t, 3H), 2.68-2.78 (m, 2H), 3.76 (s, 2H), 3.99 (s, 3H), 6.5 (d, 1H), 6.64 (s, 1H), 7.29 (d, 2H), 7.47 (d, 2H), 7.51 (s, 1H), 8.56 (s, 1H), 8.68 (d, 1H), 11.22 (br s, 1H); Mass Spectrum: M+H$^+$ 448.

EXAMPLE 12

N-(4-methylthiazol-2-yl)-2-[4-(6-carboxy-7-methoxyquinolin-4-yloxy)phenyl]acetamide Using an analogous procedure to that described in Example 8, N-(4-methylthiazol-2-yl)-2-[4-(7-methoxy-6-methoxycarbonylquinolin-4-yloxy)phenyl]acetamide was reacted with lithium hydroxide to give the title compound in 97% yield; $^1$H NMR: (DMSOd$_6$) 2.26 (d, 3H), 3.83 (s, 2H), 4.01 (s, 3H), 6.63 (d, 1H), 6.76 (s, 1H), 7.34 (d, 2H), 7.51 (d, 2H), 7.57 (s, 1H), 8.62 (s, 1H), 8.78 (d, 1H); Mass Spectrum: M+H$^+$ 450.

EXAMPLE 13

N-methyl-N-(4-methylthiazol-2-yl)-2-[4-(6,7-dimethoxyquinolin-4-yloxy)phenyl]acetamide Under an atmosphere of argon, a 1M solution of lithium hexamethyldisilazane in THF (0.52 ml) was added dropwise to a stirred solution of N-(4-methylthiazol-2-yl)-2-[4-(6,7-dimethoxyquinolin-4-yloxy)phenyl]acetamide (0.205 g) in DMF (4 ml) that had been cooled to −5° C. After 5 minutes, a solution of dimethyl sulphate (0.049 ml) in DMF (1 ml) was added dropwise and the resultant mixture was stirred at 0° C. for 30 minutes. The mixture was evaporated and the residue was purified by preparative HPLC using a Waters 'Xterra' reversed-phase column (5 microns silica) using decreasingly polar mixtures of water (containing 0.2% ammonium carbonate) and acetonitrile as eluent. There was thus obtained the title compound (0.105 g); $^1$H NMR: (DMSOd$_6$) 2.29 (d, 3H), 3.73 (s, 3H), 3.93 (s, 3H), 3.95 (s, 3H), 4.17 (s, 2H), 6.5 (d, 1H), 6.82 (s, 1H), 7.52 (d, 2H), 7.4 (s, 1H), 7.42 (d, 2H), 7.5 (s, 1H), 8.49 (d, 1H); Mass Spectrum: M+H$^+$ 450.

EXAMPLE 14

N-methyl-N-(3-pyridyl)-2-[4-(6-cyano-7-methoxyquinolin-4-yloxy)phenyl]acetamide Under an atmosphere of argon, a 1M solution of lithium hexamethyldisilazane in THF (0.27 ml) was added dropwise to a stirred solution of N-(3-pyridyl)-2-[4-(6-cyano-7-methoxyquinolin-4-yloxy)phenyl]acetamide (0.1 g) in DMF (2 ml) that had been cooled to −5° C. After 5 minutes, a solution of dimethyl sulphate (0.026 ml) in DMF (0.5 ml) was added dropwise and the resultant mixture was stirred at 0° C. for 30 minutes. The mixture was evaporated and the residue was purified by preparative HPLC using a Waters 'Xterra' reversed-phase column (5 microns silica) using decreasingly polar mixtures of water (containing 0.2% ammonium carbonate) and acetonitrile as eluent. There was thus obtained the title compound (0.04 g); $^1$H NMR: (CDCl$_3$) 3.34 (s, 3H), 3.52 (s, 2H), 4.08 (s, 3H), 6.51 (d, 1H), 7.07 (d, 2H), 7.18 (d, 2H), 7.42 (m, 1H), 7.53 (br s, 2H), 8.5 (br s, 1H), 8.65 (br s, 1), 8.67 (d, 1H), 8.69 (s, 1H); Mass Spectrum: M+H$^+$ 425.

EXAMPLE 15

N-(3-cyclopropylaminomethyl-5-methylphenyl)-2-[4-(6,7-dimethoxyquinolin-4-yloxy)phenyl]acetamide Using an analogous procedure to that described in Example 2,3-(N-tert-butoxycarbonyl-N-cyclopropylaminomethyl)-5-methylaniline was reacted with 2-[4-(6,7-dimethoxyquinolin-4-yloxy)phenyl]acetic acid. There was thus obtained N-[3-(N-tert-butoxycarbonyl-N-cyclopropylaminomethyl)-5-methylphenyl]-2-[4-(6,7-dimethoxyquinolin-4-yloxy)phenyl]acetamide in 95% yield; $^1$H NMR: (DMSOd$_6$) 0.57 (m, 2H), 0.64 (m, 2H), 1.4 (s, 9H), 2.26 (s, 3H), 2.42 (s, 1H), 3.92 (s, 3H), 3.95 (s, 3H), 4.16 (s, 2H), 4.26 (s, 2H), 6.46 (d, 1H), 6.7 (s, 1H), 7.1 (d, 2H), 7.27 (s, 1H), 7.3 (s, 1H), 7.4 (s, 1H), 7.46 (d, 2H), 7.49 (s, 1H), 8.46 (d, 1H); Mass Spectrum: M+H$^+$ 598.

A mixture of the material so obtained (0.35 g), trifluoroacetic acid (4 ml) and methylene chloride (2 ml) was stirred at ambient temperature for 3 hours. The resultant mixture was evaporated and the residue was dissolved in ethyl acetate and washed with a saturated aqueous sodium bicarbonate solution. The organic phase was dried over magnesium sulphate and evaporated. The residue was purified by preparative HPLC using a Waters 'Xterra' reversed-phase column (5 microns silica) using decreasingly polar mixtures of water (containing 0.2% ammonium carbonate) and acetonitrile as eluent. There was thus obtained the title compound (0.11 g); $^1$H NMR: (DMSOd$_6$) 0.21-0.26 (m, 2H), 0.31-0.37 (m, 2H), 2.0-2.07 (m, 1H), 2.25 (s, 3H), 3.64 (s, 2H), 3.67 (s, 2H), 3.92 (s, 3H), 3.94 (s, 3H), 6.46 (d, 1H), 6.83 (s, 1H), 7.23 (d, 2H), 7.33 (br s, 1H), 7.35 (br s, 1H), 7.4 (s, 1H), 7.47 (d, 2H), 7.49 (s, 1H), 8.47 (d, 1H), 10.08 (s, 1H); Mass Spectrum: M+H$^+$ 498.

The 3-(N-tert-butoxycarbonyl-N-cyclopropylaminomethyl)-5-methylaniline used as a starting material was prepared as follows:—

A mixture (15 g) of 3-methyl-5-nitrobenzyl bromide and 3-bromomethyl-5-nitrobenzyl bromide was dissolved in methylene chloride (15 ml) and added slowly to a stirred mixture of cyclopropylamine (15.3 ml) and ethanol (15 ml) at such a rate that the temperature of the reaction mixture was maintained below 40° C. The resultant reaction mixture was stirred at ambient temperature for 6 hours. The mixture was evaporated and the residue was purified by column chromatography on silica using increasingly polar mixtures of methylene chloride and diethyl ether as eluent. There was thus obtained N-cyclopropyl-N-(3-methyl-5-nitrobenzyl)amine (5.45 g); $^1$H NMR: (DMSOd$_6$) 0.25 (m, 2H), 0.35 (m, 2H), 2.03 (m, 1H), 2.88 (br s, 1H), 3.8 (s, 3H), 7.6 (s, 1H), 7.92 (s, 1H), 7.99 (s, 1H).

A mixture of N-cyclopropyl-N-(3-methyl-5-nitrobenzyl) amine (1 g), di-tert-butyl dicarbonate (1.25 g) and methylene chloride (20 ml) was stirred at ambient temperature for 4 hours. The solvent was evaporated and the residue was purified by column chromatography on silica using methylene chloride as eluent. There was thus obtained N-tert-butoxycarbonyl-N-cyclopropyl-N-(3-methyl-5-nitrobenzyl)amine in 100% yield; $^1$H NMR: (DMSOd$_6$) 0.6 (m, 2H), 0.67 (m, 2H), 1.34 (s, 9H), 2.44 (s, 3H), 2.48 (m, 1H), 4.45 (s, 2H), 7.48 (s, 1H), 7.84 (s, 1H), 7.97 (s, 1H).

A mixture of the material so obtained, platinum oxide (0.2 g) and ethyl acetate (25 ml) was stirred under 1.8 atmospheres pressure of hydrogen for 30 minutes. The catalyst was removed by filtration and the filtrate was evaporated. There was thus obtained 3-(N-tert-butoxycarbonyl-N-cyclopropylaminomethyl)-5-methylaniline; $^1$H NMR: (DMSOd$_6$) 0.56 (m, 2H), 0.63 (m, 2H), 1.4 (s, 9H), 2.12 (s, 3H), 2.37 (m, 1H), 4.16 (s, 2H), 4.95 (s, 2H), 6.16 (s, 1H), 6.21 (s, 1H), 6.24 (s, 1H); Mass Spectrum: M+H$^+$ 277.

EXAMPLE 16

N-(3-cyclopropylaminomethyl-5-methylphenyl)-2-[4-(6-cyano-7-methoxyquinolin-4-yloxy)phenyl]acetamide Using an analogous procedures to those described in Example 15, 2-[4-(6-cyano-7-methoxyquinolin-4-yloxy)phenyl]acetic acid was reacted with 3-(N-tert-butoxycarbonyl-N-cyclopropylaminomethyl)-5-methylaniline and the product was reacted with trifluoroacetic acid. The resultant product was purified by column chromatography on silica using a solvent gradient from 100:0 to 9:1 mixtures of ethyl acetate and methanol as eluent. There was thus obtained the title compound in 48% yield. A portion of the material so obtained was dissolved in methylene chloride and a solution of maleic acid (1 equivalent) in ethanol was added. The resultant solution was evaporated to provide a maleate salt of the title compound which gave the following characterising data:—$^1$H NMR: (DMSOd$_6$) 0.73 (m, 4H), 2.3 (s, 3H), 2.64 (m, 1H), 3.72 (s, 2H), 4.07 (s, 3H), 4.11 (s, 2H), 6.01 (s, 2H), 6.52 (m, 1H), 7.0 (s, 1H), 7.3 (d, 2H), 7.35 (s, 1H), 7.5 (d, 2H), 7.62 (s, 1H), 7.66 (s, 1H), 8.76 (m, 2H), 10.26 (s, 1H); Mass Spectrum: M+H$^+$ 493.

EXAMPLE 17

N-(1-ethylpyrazol-4-yl)-2-[4-(6-fluoroquinolin-4-yloxy)-2-methoxyphenyl]acetamide A mixture of 4-chloro-6-fluoroquinoline (0.11 g), N-(1-ethylpyrazol-4-yl)-2-(4-hydroxy-2-methoxyphenyl)acetamide (0.168 g), caesium carbonate (0.433 g) and DMF (3 ml) was stirred and heated to 120° C. for 2.5 hours. The solvent was evaporated and the residue was purified by column chromatography on silica using a solvent gradient of 100:0 to 93:7 of ethyl acetate and methanol as eluent. There was thus obtained the title compound (0.157 g); $^1$H NMR: (DMSOd$_6$) 1.33 (t, 3H), 3.6 (s, 2H), 3.77 (s, 3H), 4.07 (q, 2H), 6.71 (d, 1H), 6.83 (m, 1H), 6.99 (d, 1H), 7.35 (d, 1H), 7.42 (s, 1H), 7.75 (m, 1H), 7.88 (s, 1H), 7.98 (m, 1H), 8.12 (m, 1H), 8.7 (d, 1H), 10.04 (s, 1H); Mass Spectrum: M+H$^+$ 421.

The N-(1-ethylpyrazol-4-yl)-2-(4-hydroxy-2-methoxyphenyl)acetamide used as starting material was prepared as follows:—

1-(3-Dimethylaminopropyl)-3-ethylcarbodiimide hydrochloride (0.845 g) was added to a stirred mixture of 2-(4-benzyloxy-2-methoxyphenyl)acetic acid (0.4 g), 1-ethyl-4-aminopyrazole hydrochloride (0.239 g), 2-hydroxypyridine N-oxide (0.327 g), diisopropylethylamine (1.03 ml) and DMF (5 ml) and the resultant mixture was stirred at ambient temperature for 16 hours. The solvent was evaporated and the residue was purified by column chromatography on silica using a gradient of 100:0 to 3:7 of methylene chloride and ethyl acetate as eluent. There was thus obtained N-(1-ethylpyrazol-4-yl)-2-(4-benzyloxy-2-methoxyphenyl)acetamide (0.256 g); $^1$H NMR: (DMSOd$_6$) 1.31 (t, 3H), 3.44 (s, 2H), 3.73 (s, 3H), 4.04 (q, 2H), 5.09 (s, 2H), 6.53 (m, 1H), 6.62 (s, 1H), 7.07 (d, 1H), 7.33 (m, 1H), 7.39 (m, 3H), 7.45 (m, 2H), 7.84 (s, 1H), 9.89 (s, 1H); Mass Spectrum: M+H$^+$ 366.

A mixture of the material so obtained, 10% palladium on carbon catalyst (0.1 g), ethyl acetate (10 ml) and ethanol (10 ml) was stirred under 3 atmospheres pressure of hydrogen for 30 minutes. The catalyst was removed and the solvent was evaporated. There was thus obtained the required starting material (0.214 g); $^1$H NMR: (DMSOd$_6$) 1.3 (t, 3H), 3.39 (s, 2H), 3.69 (s, 3H), 4.04 (q, 3H), 6.28 (m, 1H), 6.37 (d, 1H), 6.93 (d, 1H), 7.38 (s, 1H), 7.84 (s, 1H), 9.29 (br s, 1H), 9.84 (s, 1H); Mass Spectrum: M+H$^+$ 276.

EXAMPLE 18

Using an analogous procedure to that described in Example 17, the appropriate 4-chloroquinoline was reacted with the appropriate phenol to give the compounds described in Table V. Unless otherwise stated, each reaction product was purified by column chromatography on silica using increasingly polar solvent mixtures such as ethyl acetate and methanol or methylene chloride and methanol as eluent.

TABLE V

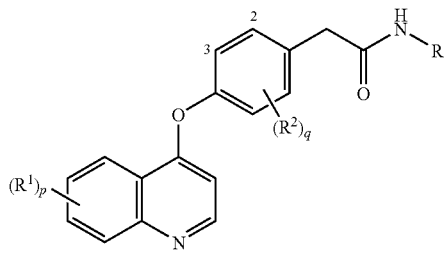

| No. & Note | $(R^1)_p$ | $(R^2)_q$ | R |
|---|---|---|---|
| [1] | 6-methoxy-7-fluoro | 2-methoxy | 1-ethylpyrazol-4-yl |
| [2] | 7-(N-methylcarbamoyl) | 2-methoxy | 1-ethylpyrazol-4-yl |
| [3] | 7-carbamoyl | 2-methoxy | 1-ethylpyrazol-4-yl |
| [4] | 7-(N,N-dimethylcarbamoyl) | 2-methoxy | 1-ethylpyrazol-4-yl |
| [5] | 6-methoxy-7-fluoro | 2-methoxy | 5-ethylpyrazol-3-yl |
| [6] | 7-carbamoyl | 2-methoxy | 5-ethylpyrazol-3-yl |
| [7] | 7-(N-methylcarbamoyl) | 2-methoxy | 5-ethylpyrazol-3-yl |
| [8] | 7-(N,N-dimethylcarbamoyl) | 2-methoxy | 5-ethylpyrazol-3-yl |
| [9] | 6-methoxy | 2-methoxy | 1-ethylpyrazol-4-yl |
| [10] | 6-methoxy | 2-methoxy | 4,5-dimethylisoxazol-3-yl |
| [11] | 7-ethoxy | 2-methoxy | 1,3-dimethylpyrazol-4-yl |
| [12] | 7-methoxy | 2-methoxy | 1-ethyl-methylpyrazol-4-yl |
| [13] | 7-ethoxy | 2-methoxy | 4,5-dimethylisoxazol-3-yl |

Notes The products gave the characterising data shown below.

[1] $^1$H NMR: (DMSOd$_6$) 1.32 (t, 3H), 3.6 (s, 2H), 3.77 (s, 3H) 4.03 (s, 3H), 4.07 (q, 2H), 6.62 (d, 1H), 6.83 (m, 1H), 6.97 (d, 1H), 7.34 (d, 1H), 7.42 (s, 1H), 7.74 (d, 1H), 7.82 (d, 1H), 7.88 (s, 1H), 8.58 (d, 1H), 10.04 (s, 1H); Mass Spectrum: M+H$^+$451.

The 4-chloro-7-fluoro-6-methoxyquinoline used as starting material was prepared as follows:—

5-Methoxymethylene-2,2-dimethyl-1,3-dioxane-4,6-dione (3.72 g) was added to a stirred mixture of 3-fluoro-4-methoxyaniline (2.82 g) and isopropanol (40 ml) and the resultant mixture was stirred and heated to 90° C. for 20 minutes. The reaction mixture was cooled to ambient temperature and the precipitate was collected by filtration, washed in turn with isopropanol and diethyl ether and dried under vacuum. There was thus obtained 5-(3-fluoro-4-methoxyanilinomethylene)-2,2-dimethyl-1,3-dioxane-4,6-dione (5.7 g); $^1$H NMR: (DMSOd$_6$) 1.67 (s, 6H), 3.85 (s, 3H), 7.21 (t, 1H), 7.36 (d, 1H), 7.63 (m, 1H), 8.48 (s, 1H); Mass Spectrum: M+H$^+$ 296.

The material so obtained was added portionwise to a mixture (60 ml) of biphenyl and diphenyl ether ('Dowtherm A') that had been warmed to 230° C. The solution was stirred at that temperature for 10 minutes. The resultant mixture was cooled to ambient temperature. The precipitate was collected by filtration and purified by column chromatography on silica using increasingly polar mixtures of ethyl acetate and methanol as eluent. There was thus obtained 7-fluoro-6-methoxy-1,4-dihydroquinolin-4-one (1.8 g); $^1$H NMR: (DMSOd$_6$) 3.91 (s, 3H), 6.01 (d, 1H), 7.37 (d, 1H), 7.64 (d, 1H), 7.87 (d, 1H); Mass Spectrum: M+H$^+$ 194.

A mixture of the material so obtained and phosphorus oxychloride (15 ml) was stirred and heated to 50° C. for 30 minutes. The excess of phosphorus oxychloride was removed by evaporation and the residue was partitioned between ethyl acetate and a saturated aqueous sodium bicarbonate solution. The organic solution was dried over magnesium sulphate and evaporated. There was thus obtained 4-chloro-7-fluoro-6-methoxyquinoline (1.45 g); $^1$H NMR: (DMSOd$_6$) 4.06 (s, 3H), 7.6 (d, 1H), 7.74 (d, 1H), 7.92 (d, 1H), 8.72 (d, 1H); Mass Spectrum: M+H$^+$ 212 and 214.

[2] $^1$H NMR: (DMSOd$_6$) 1.33 (t, 3H), 2.86 (d, 3H), 3.6 (s, 2H), 3.88 (s, 3H), 4.07 (q, 2H), 6.72 (d, 1H), 6.84 (m, 1H), 7.0 (d, 1H), 7.35 (d, 1H), 7.42 (s, 1H), 7.88 (s, 1H), 8.08 (m, 1H), 8.38 (d, 1H), 8.52 (d, 1H), 8.78 (d, 1H), 8.81 (q, 1H), 10.04 (s, 1H); Mass Spectrum: M+H$^+$ 460.

The 4-chloro-7-(N-methylcarbamoyl)quinoline used as starting material was prepared as follows:—

5-Methoxymethylene-2,2-dimethyl-1,3-dioxane-4,6-dione (3.24 g) was added to a stirred mixture of methyl 3-amino-2-chlorobenzoate (U.S. Pat. No. 6,177,440, columns 227 and 228 thereof; 3.1 g) and isopropanol (75 ml) and the resultant mixture was heated to 80° C. for 10 minutes. The reaction mixture was cooled to ambient temperature and the precipitate was recovered, washed with diethyl ether and dried under vacuum. There was thus obtained 5-(2-chloro-3-methoxycarbonylanilinomethylene)-2,2-dimethyl-1,3-dioxane-4,6-dione (5 g); $^1$H NMR: (DMSOd$_6$); 1.7 (s, 6H), 3.89 (s, 3H), 7.56 (m, 1H), 7.67 (d, 1H), 8.11 (br m, 1H), 8.79 (br m, 1H); Mass Spectrum: M+H$^+$ 340.

The material so obtained was added portionwise to a mixture (60 ml) of biphenyl and diphenyl ether ('Dowtherm A') that had been warmed to 260° C. The solution was stirred at that temperature for 5 minutes. The resultant mixture was cooled to ambient temperature. Petroleum ether was added and the precipitate was recovered, washed with petroleum ether and dried under vacuum. There was thus obtained 8-chloro-7-methoxycarbonyl-1,4-dihydroquinolin-4-one (3.36 g); $^1$H NMR: (DMSOd$_6$) 3.85 (s, 3H), 6.11 (br d, 1H), 7.56 (d, 1H), 7.85 (br d, 1H), 8.06 (d, 1H); Mass Spectrum: M+H$^+$ 238.

A mixture of the material so obtained, 5% palladium on carbon catalyst (2.5 g), ethyl acetate (10 ml) and ethanol (125 ml) was stirred under 4 atmospheres pressure of hydrogen for 8 hours. The mixture was filtered and the filtrate was evaporated. There was thus obtained 7-methoxycarbonyl-1,4-dihydroquinolin-4-one (2.8 g); $^1$H NMR: (DMSOd$_6$) 3.93 (s, 3H), 6.29 (s, 1H), 7.86 (m, 1H), 8.17 (d, 1H), 8.23 (d, 1H), 8.28 (s, 1H); Mass Spectrum: M+H$^+$ 204.

A mixture of 7-methoxycarbonyl-1,4-dihydroquinolin-4-one (1.5 g), lithium hydroxide (1.24 g) and methanol (20 ml) was stirred at ambient temperature for 16 hours. The solution was concentrated by evaporation and 1N aqueous hydrochloric acid (32 ml) was added to the residue. The resultant precipitate was recovered, washed in turn with water, ethyl acetate and diethyl ether and dried under vacuum. There was thus obtained 7-carboxy-1,4-dihydroquinolin-4-one (1.4 g); $^1$H NMR: (DMSOd$_6$) 6.12 (d, 1H), 7.79 (d, 1H), 8.01 (d, 1H), 8.17 (d, 1H), 8.21 (s, 1H); Mass Spectrum: M+H$^+$ 190.

A mixture of 7-carboxy-1,4-dihydroquinolin-4-one (0.45 g) and phosphorus oxychloride (1.09 ml) was heated to reflux for 1 hour. The resultant mixture was cooled to 45° C. and methylene chloride (15 ml) was added. The resultant suspension was added portionwise to a stirred 2M solution of methylamine in THF (23.8 ml) that had been cooled to 0° C. The mixture was stirred at ambient temperature for 30 minutes. The reaction mixture was concentrated by evaporation and the residue was partitioned between methylene chloride and a saturated aqueous sodium bicarbonate solution. The organic phase was dried over magnesium sulphate and evaporated. There was thus obtained 4-chloro-7-(N-methylcarbamoyl)quinoline (0.42 g); $^1$H NMR: (DMSOd$_6$) 2.86 (d, 3H), 7.85

(d, 1H), 8.17 (m, 1H), 8.28 (d, 1H), 8.58 (d, 1H), 8.85 (br d, 1H), 8.93 (d, 1H); Mass Spectrum: M+H⁺ 221 and 223.

[3] $^1$H NMR: (DMSOd$_6$) 1.33 (t, 3H), 3.6 (s, 2H), 3.77 (s, 3H), 4.07 (q, 2H), 6.72 (d, 1H), 6.84 (m, 1H), 7.0 (d, 1H), 7.35 (d, 1H), 7.42 (s, 1H), 7.62 (s, 1H), 7.88 (s, 1H), 8.1 (m, 1H), 8.33 (br s, 1H), 8.37 (d, 1H), 8.58 (d, 1H), 8.78 (d, 1H), 10.04 (s, 1H; Mass Spectrum: M+H⁺ 446.

The 7-carbamoyl-4-chloroquinoline used as starting material was prepared as follows:—

Using analogous procedures to those described in the last portion of Note [2] above that is concerned with the preparation of starting materials, 7-carboxy-1,4-dihydroquinolin-4-one was reacted with phosphorus oxychloride and the reaction product was reacted with a solution of ammonia gas in 1,4-dioxane. There was thus obtained 7-carbamoyl-4-chloroquinoline; $^1$H NMR: (DMSOd$_6$) 7.69 (s, 1H), 7.86 (d, 1H), 8.19 (d, 1H), 8.27 (d, 1H), 8.38 (s, 1H), 8.64 (s, 1H), 8.93 (d, 1H); Mass Spectrum: M+H⁺ 207 and 209.

[4] $^1$H NMR: (DMSOd$_6$) 1.33 (t, 3H), 2.97 (s, 3H), 3.06 (s, 3H), 3.6 (s, 2H), 3.77 (s, 3H), 4.07 (q, 2H), 6.71 (d, 1H), 6.84 (m, 1H), 7.0 (d, 1H), 7.35 (d, 1H), 7.42 (s, 1H), 7.66 (m, 1H), 7.88 (s, 1H), 8.01 (d, 1H), 8.37 (d, 1H), 8.76 (d, 1H), 10.04 (s, 1H); Mass Spectrum: M+H⁺ 474.

The 4-chloro-7-(N,N-dimethylcarbamoyl)quinoline used as starting material was prepared as follows:—

Using analogous procedures to those described in the last portion of Note [2] above that is concerned with the preparation of starting materials, 7-carboxy-1,4-dihydroquinolin-4-one was reacted with phosphorus oxychloride and the reaction product was reacted with a solution of dimethylamine gas in THF. There was thus obtained 4-chloro-7-(N,N-dimethylcarbamoyl)quinoline; $^1$H NMR: (DMSOd$_6$) 2.96 (s, 3H), 3.06 (s, 3H), 7.77 (m, 1H), 7.84 (d, 1H), 8.09 (s, 1H), 8.27 (d, 1H), 8.91 (d, 1H); Mass Spectrum: M+H⁺ 235 and 237.

[5] $^1$H NMR: (DMSOd$_6$) 1.16 (t, 3H), 2.55 (q, 2H), 3.63 (s, 2H), 3.76 (s, 3H), 4.03 (s, 3H), 6.28 (s, 1H), 6.62 (d, 1H), 6.82 (m, 1H), 6.97 (d, 1H), 7.33 (d, 1H), 7.74 (d, 1H), 7.82 (d, 1H), 8.58 (d, 1H), 10.34 (s, 1H); Mass Spectrum: M+H⁺ 451.

The N-(5-ethylpyrazol-3-yl)-2-(4-hydroxy-2-methoxyphenyl)acetamide used as starting material was prepared as follows:—

Using an analogous procedure to that described in the portion of Example 17 that is concerned with the preparation of starting materials, 2-(4-benzyloxy-2-methoxyphenyl)acetic acid was reacted at 75° C. for 3 hours with 3-amino-5-ethylpyrazole to give N-(5-ethylpyrazol-3-yl)-2-(4-benzyloxy-2-methoxyphenyl)acetamide; $^1$H NMR: (DMSOd$_6$) 1.15 (t, 3H), 2.55 (q, 2H), 3.48 (s, 2H), 3.73 (s, 3H), 5.09 (s, 2H), 6.24 (s, 1H), 6.54 (m, 1H), 6.62 (d, 1H), 7.06 (d, 1H), 7.33 (t, 1H), 7.39 (m, 2H), 7.45 (m, 2H), 10.15 (br s, 1H); Mass Spectrum: M+H⁺ 366; which material was hydrogenated to give N-(5-ethylpyrazol-3-yl)-2-(4-hydroxy-2-methoxyphenyl)acetamide; $^1$H NMR: (DMSOd$_6$) 1.15 (t, 3H), 2.53 (q, 2H), 3.43 (s, 2H), 3.68 (s, 3H), 6.24 (br s, 1H), 6.28 (m, 1H), 6.37 (d, 1H), 6.93 (d, 1H), 9.29 (br s, 1H), 10.09 (br s, 1H); Mass Spectrum: M+H⁺ 276.

[6] $^1$H NMR: (DMSOd$_6$) 1.16 (t, 3H), 2.55 (q, 2H), 3.64 (s, 2H), 3.77 (s, 3H), 6.28 (br s, 1H), 6.72 (d, 1H), 6.84 (m, 1H), 6.99 (d, 1H), 7.33 (d, 1H), 7.62 (s, 1H), 8.10 (m, 1H), 8.33 (s, 1H), 8.37 (d, 1H), 8.58 (d, 1H), 8.77 (d, 1H), 10.34 (s, 1H); Mass Spectrum: M+H⁺ 446.

[7] $^1$H NMR: (DMSOd$_6$) 1.16 (t, 3H), 2.55 (q, 2H), 2.86 (d, 3H), 3.63 (s, 2H), 3.76 (s, 3H), 6.27 (s, 1H), 6.72 (d, 1H), 6.84 (m, 1H), 6.99 (d, 1H), 7.33 (d, 1H), 8.07 (m, 1H), 8.38 (d, 1H), 8.52 (d, 1H), 8.77 (d, 1H), 8.81 (q, 1H), 10.35 (br s, 1H), 12.01 (s, 1H); Mass Spectrum: M+H⁺ 460.

[8] $^1$H NMR: (DMSOd$_6$) 1.16 (t, 3H), 2.55 (q, 2H), 2.98 (s, 3H), 3.07 (s, 3H), 3.63 (s, 2H), 3.77 (s, 3H), 6.28 (s, 1H), 6.71 (d, 1H), 6.83 (m, 1H), 6.99 (d, 1H), 7.33 (d, 1H), 6.55 (m, 1H), 8.01 (d, 1H), 8.37 (d, 1H), 8.75 (d, 1H), 10.35 (br s, 1H), 11.98 (s, 1H); Mass Spectrum: M+H⁺ 474.

[9] Chlorobenzene was used in place of DMF and 4-dimethylaminopyridine was added. The reaction mixture was heated to 140° C. for 5 hours. The reaction product gave the following characterising data:—$^1$H NMR: (DMSOd$_6$) 1.33 (t, 3H), 3.6 (s, 2H), 3.77 (s, 3H), 3.93 (s, 3H), 4.06 (q, 2H), 6.63 (d, 1H), 6.81 (m, 1H), 6.96 (d, 1H), 7.33 (d, 1H), 7.42 (s, 1H), 7.46 (m, 1H), 7.56 (d, 1H), 7.88 (s, 1H), 7.95 (d, 1H), 8.56 (d, 1H), 10.04 (s, 1H); Mass Spectrum: M+H⁺ 433.

The 4-chloro-6-methoxyquinoline used as starting material is described in International Patent Application WO 2006/021448 (within Example 48 thereof).

[10] Chlorobenzene was used in place of DMF and 4-dimethylaminopyridine was added. The reaction mixture was heated to 140° C. for 5 hours. The reaction product gave the following characterising data:—$^1$H NMR: (DMSOd$_6$) 1.8 (s, 3H), 2.3 (s, 3H), 3.7 (s, 2H), 3.78 (s, 3H), 3.93 (s, 3H), 6.65 (d, 1H), 6.81 (m, 1H), 6.97 (d, 1H), 7.35 (d, 1H), 7.46 (m, 1H), 7.56 (d, 1H), 7.94 (d, 1H), 8.55 (d, 1H), 10.28 (br s, 1H); Mass Spectrum: M+H⁺ 434.

The N-(4,5-dimethylisoxazol-3-yl)-2-(4-hydroxy-2-methoxyphenyl)acetamide used as starting material was prepared as follows:—

Using a similar procedure to that described in the portion of Example 17 that is concerned with the preparation of starting materials, 2-(4-benzyloxy-2-methoxyphenyl)acetic acid (0.1 g) was reacted with oxalyl chloride (0.093 ml) and DMF (3 drops) in methylene chloride (5 ml). The reaction mixture was stirred at ambient temperature for 1 hour. The mixture was evaporated to give 2-(4-benzyloxy-2-methoxyphenyl)acetyl chloride. A mixture of the material so obtained, 3-amino-4,5-dimethylisoxazole (0.062 g), diisopropylethylamine (0.065 ml), 4-dimethylaminopyridine (0.005 g) and methylene chloride (5 ml) was stirred at ambient temperature for 14 hours. The resultant mixture was evaporated and the residue was purified by column chromatography on silica using increasingly polar mixtures of methylene chloride and ethyl acetate as eluent. There was thus obtained N-(4,5-dimethylisoxazol-3-yl)-2-(4-benzyloxy-2-methoxyphenyl)acetamide; $^1$H NMR: (DMSOd$_6$) 1.77 (s, 3H), 2.28 (s, 3H), 3.55 (s, 2H), 3.74 (s, 3H), 5.09 (s, 2H), 6.54 (m, 1H), 6.63 (d, 1H), 7.09 (d, 1H), 7.33 (m, 1H), 7.39 (m, 2H), 7.45 (m, 2H), 10.15 (br s, 1H); Mass Spectrum: M+H⁺ 367.

Using an analogous procedure to that described in the portion of Example 17 that is concerned with the preparation of starting materials, N-(4,5-dimethylisoxazol-3-yl)-2-(4-benzyloxy-2-methoxyphenyl)acetamide was hydrogenated to give N-(4,5-dimethylisoxazol-3-yl)-2-(4-hydroxy-2-methoxyphenyl)acetamide; $^1$H NMR: (DMSOd$_6$) 1.76 (s, 3H), 2.28 (s, 3H), 3.5 (s, 2H), 3.7 (s, 3H), 6.29 (m, 1H), 6.38 (d, 1H), 6.95 (d, 1H), 9.32 (s, 1H), 10.09 (br s, 1H); Mass Spectrum: M+H⁺ 277.

[11] Chlorobenzene was used in place of DMF and 4-dimethylaminopyridine was added. The reaction mixture was heated to 130° C. for 14 hours. The reaction product gave the following characterising data:—$^1$H NMR: (DMSOd$_6$) 1.42 (t, 3H), 2.12 (s, 3H), 3.64 (s, 2H), 3.7 (s, 3H), 3.77 (s, 3H), 4.21 (q, 2H), 6.51 (d, 1H), 6.79 (m, 1H), 6.95 (d, 1H), 7.27 (m, 1H), 7.32 (d, 1H), 7.39 (d, 1H), 7.81 (s, 1H), 8.19 (d, 1H), 8.61 (d, 1H), 9.43 (s, 1H); Mass Spectrum: M+H⁺ 447.

The N-(1,3-dimethylpyrazol-4-yl)-2-(4-hydroxy-2-methoxyphenyl)acetamide used as starting material was prepared as follows:—

Using an analogous procedure to that described in the portion of Example 17 that is concerned with the preparation of starting materials, 2-(4-benzyloxy-2-methoxyphenyl)acetic acid was reacted with 4-amino-1,3-dimethylpyrazole to give N-(1,3-dimethylpyrazol-4-yl)-2-(4-benzyloxy-2-methoxyphenyl)acetamide; $^1$H NMR: (CDCl$_3$) 2.06 (s, 3H), 3.62 (s, 2H), 3.76 (s, 3H), 3.88 (s, 3H), 5.07 (s, 2H), 6.58 (m, 1H), 6.61 (d, 1H), 7.17 (d, 1H), 7.38 (m, 6H), 7.79 (s, 1H); Mass Spectrum: M+H$^+$ 366; which material was hydrogenated to give N-(1,3-dimethylpyrazol-4-yl)-2-(4-hydroxy-2-methoxyphenyl)acetamide; $^1$H NMR: (DMSOd$_6$) 2.09 (s, 3H), 3.44 (s, 2H), 3.68 (s, 3H), 3.7 (s, 3H), 6.28 (m, 1H), 6.37 (d, 1H), 6.93 (d, 1H), 7.76 (d, 1H), 9.23 (br s, 1H), 9.3 (br s, 1H); Mass Spectrum: M+H$^+$ 276.

[12] Chlorobenzene was used in place of DMF and 4-dimethylaminopyridine was added. The reaction mixture was heated to 130° C. for 14 hours. Purification was carried out using column chromatography on silica using a solvent gradient of 100:0 to 93:7 of ethyl acetate and methanol as eluent. The material so obtained was purified further by preparative HPLC using a Waters 'Xterra' reversed-phase column (5 microns silica, 30 mm diameter, 150 mm length) and decreasingly polar mixtures of water (containing 0.2% ammonium carbonate) and acetonitrile as eluent. The product so obtained gave the following characterising data:—
$^1$H NMR: (DMSOd$_6$) 1.3 (t, 3H), 2.13 (s, 3H), 3.64 (s, 2H), 3.78 (s, 3H), 3.94 (s, 3H), 3.98 (q, 2H), 6.52 (d, 1H), 6.79 (m, 1H), 6.96 (d, 1H), 7.29 (m, 1H), 7.32 (d, 1H), 7.41 (d, 1H), 7.85 (s, 1H), 8.2 (d, 1H), 8.62 (d, 1H), 9.43 (s, 1H); Mass Spectrum: M+H$^+$ 447.

The N-(1,3-dimethylpyrazol-4-yl)-2-(4-hydroxy-2-methoxyphenyl)acetamide used as starting material was prepared as follows:—

Using an analogous procedure to that described in the portion of Example 17 that is concerned with the preparation of starting materials, 2-(4-benzyloxy-2-methoxyphenyl)acetic acid was reacted with 4-amino-1-ethyl-3-methylpyrazole to give N-(1-ethyl-3-methylpyrazol-4-yl)-2-(4-benzyloxy-2-methoxyphenyl)acetamide; $^1$H NMR: (DMSOd$_6$) 1.29 (t, 3H), 2.1 (s, 3H), 3.5 (s, 2H), 3.75 (s, 3H), 3.96 (q, 2H), 5.09 (s, 2H), 6.54 (m, 1H), 6.63 (d, 1H), 7.06 (d, 1H), 7.33 (m, 1H), 7.39 (m, 2H), 7.45 (m, 2H), 7.8 (s, 1H), 9.29 (s, 1H); Mass Spectrum: M+H$^+$ 380; which material was hydrogenated to give N-(1-ethyl-3-methylpyrazol-4-yl)-2-(4-hydroxy-2-methoxyphenyl)acetamide; $^1$H NMR: (DMSOd$_6$) 1.28 (t, 3H), 2.1 (s, 3H), 3.45 (s, 2H), 3.7 (s, 3H), 3.96 (q, 2H), 6.28 (m, 1H), 6.37 (d, 1H), 6.93 (d, 1H), 7.8 (s, 1H), 9.22 (br s, 1H), 9.29 (br s, 1H); Mass Spectrum: M+H$^+$ 290.

[13] Chlorobenzene was used in place of DMF and 4-dimethylaminopyridine was added. The reaction mixture was heated to 130° C. for 14 hours. The reaction product gave the following characterising data:—$^1$H NMR: (DMSOd$_6$) 1.42 (t, 3H), 1.8 (s, 3H), 2.3 (s, 3H), 3.7 (s, 2H), 3.77 (s, 3H), 4.21 (q, 2H), 6.53 (d, 1H), 6.8 (m, 1H), 6.96 (d, 1H), 7.27 (m, 1H), 7.34 (d, 1H), 7.39 (d, 1H), 8.19 (d, 1H), 8.62 (s, 1H), 10.27 (br s, 1H); Mass Spectrum: M+H$^+$ 448.

EXAMPLE 19

N-(1-ethylpyrazol-4-yl)-2-[4-(6-carboxyquinolin-4-yloxy)-2-methoxyphenyl]acetamide Using an analogous procedure to that described in Example 8, N-(1-ethylpyrazol-4-yl)-2-[4-(6-methoxycarbonylquinolin-4-yloxy)-2-methoxyphenyl]acetamide was reacted with lithium hydroxide to give the title compound in 82% yield; $^1$H NMR: (DMSOd$_6$) 1.33 (t, 3H), 3.61 (s, 2H), 3.78 (s, 3H), 4.07 (q, 2H), 6.73 (d, 1H), 6.88 (m, 1H), 7.04 (d, 1H), 7.36 (d, 1H), 7.42 (s, 1H), 7.88 (s, 1H), 8.11 (d, 1H), 8.28 (m, 1H), 8.81 (d, 1H), 8.96 (d, 1H), 10.05 (s, 1H), 13.34 (br s, 1H); Mass Spectrum: M+H$^+$ 447.

EXAMPLE 20

N-(1-ethylpyrazol-4-yl)-2-{2-methoxy-4-[6-(N-methylcarbamoyl)quinolin-4-yloxy]phenyl}acetamide Oxalyl chloride (0.142 ml) was added to a mixture of N-(1-ethylpyrazol-4-yl)-2-[4-(6-carboxyquinolin-4-yloxy)-2-methoxyphenyl]acetamide (0.15 g) and methylene chloride (6 ml) and the resultant mixture was stirred at ambient temperature for 10 minutes. Diethyl ether (10 ml) was added and the resultant precipitate was recovered and dried under vacuum. The material so obtained was suspended in methylene chloride and methylamine gas was passed into the suspension until a clear solution was obtained. The solvent was evaporated and the residue was purified by column chromatography on silica using a gradient of 100:0 to 19:1 of methylene chloride and methanol as eluent. There was thus obtained the title compound (0.102 g); $^1$H NMR: (DMSOd$_6$) 1.33 (t, 3H), 2.85 (d, 3H), 3.61 (s, 2H), 3.78 (s, 3H), 4.07 (q, 2H), 6.7 (d, 1H), 6.87 (m, 1H), 7.01 (d, 1H), 7.37 (d, 1H), 7.42 (s, 1H), 7.88 (s, 1H), 8.08 (d, 1H), 8.24 (m, 1H), 8.77 (d, 1H), 8.82 (q, 1H), 8.87 (d, 1H), 10.06 (s, 1H); Mass Spectrum: M+H$^+$ 460.

EXAMPLE 21

Using an analogous procedure to that described in Example 20, the appropriate carboxy-substituted quinoline was reacted with the appropriate amine or heterocycle to give the compounds described in Table VI. Unless otherwise stated, each reaction product was purified by column chromatography on silica using increasingly polar solvent mixtures such as ethyl acetate and methanol as eluent.

TABLE VI

| No. & Note | (R$^1$)$_p$ | (R$^2$)$_q$ | R |
|---|---|---|---|
| [1] | 6-carbamoyl | 2-methoxy | 1-ethylpyrazol-4-yl |
| [2] | 6-(N,N-dimethylcarbamoyl) | 2-methoxy | 1-ethylpyrazol-4-yl |
| [3] | 6-pyrrolidin-1-ylcarbonyl | 2-methoxy | 1-ethylpyrazol-4-yl |

Notes The products gave the characterising data shown below.

[1] Ammonia gas was passed into the reaction mixture. The product was purified by column chromatography on silica using increasingly polar solvent mixtures of methylene chloride, ethyl acetate and methanol as eluent. The product gave the following characterising data: $^1$H NMR: (DMSOd$_6$) 1.33 (t, 3H), 3.61 (s, 2H), 3.78 (s, 3H), 4.07 (q, 2H), 6.70 (d, 1H), 6.87 (m, 1H), 7.01 (d, 1H), 7.36 (d, 1H), 7.42 (s, 1H), 7.56 (br s, 1H), 7.88 (s, 1H), 8.07 (d, 1H), 8.27 (m, 1H), 8.34 (br s, 1H), 8.77 (d, 1H), 6.91 (d, 1H), 10.05 (s, 1H); Mass Spectrum: M+H$^+$ 446.

[2] Dimethylamine was passed into the reaction mixture. The product was purified by column chromatography on silica using increasingly polar solvent mixtures of methylene chloride, ethyl acetate and methanol as eluent. The product gave the following characterising data: $^1$H NMR: (DMSOd$_6$) 1.33 (t, 3H), 2.98 (s, 3H), 3.05 (s, 3H), 3.6 (s, 2H), 3.77 (s, 3H), 4.07 (q, 2H), 6.71 (d, 1H), 6.85 (m, 1H), 7.0 (d, 1H), 7.35 (d, 1H), 7.42 (s, 1H), 7.83 (m, 1H), 7.88 (s, 1H), 8.07 (d, 1H), 9.31 (d, 1H), 8.76 (d, 1H), 10.04 (s, 1H); Mass Spectrum: M+H$^+$ 474.

[3] Pyrrolidine was added to the reaction mixture. The product was purified by column chromatography on silica using increasingly polar solvent mixtures of methylene chloride, ethyl acetate and methanol as eluent. The product gave the following characterising data: $^1$H NMR: (DMSOd$_6$) 1.32 (t, 3H), 1.74-1.99 (m, 4H), 3.42-3.49 (m, 2H), 3.49-3.57 (m, 2H), 3.6 (s, 2H), 3.77 (s, 3H), 4.07 (q, 2H), 6.72 (d, 1H), 6.84 (d, 1H), 7.0 (s, 1H), 7.34 (d, 1H), 7.42 (s, 1H) 7.88 (s, 1H), 7.94 (d, 1H), 9.07 (d, 1H), 8.42 (s, 1H), 8.76 (d, 1H), 10.04 (s, 1H); Mass Spectrum: M+H$^+$ 500.

EXAMPLE 22

N-(5-amino-1-methylpyrazol-3-yl)-2-[4-(6,7-dimethoxyquinolin-4-yloxy)phenyl]acetamide Diisopropylethylamine (0.105 ml) and 2-(7-azabenzotriazol-1-yl)-1,1,3,3-tetramethyluronium hexafluorophosphate (V) (0.228 g) were added in turn to a stirred mixture of 2-[4-(6,7-dimethoxyquinolin-4-yloxy)phenyl]acetic acid (0.17 g), tert-butyl 3-amino-5-(N-tert-butoxycarbonylamino)-1-methylpyrazole (0.106 g) and DMF (1.7 ml) and the resultant mixture was stirred at ambient temperature for 2 hours. The mixture was concentrated by evaporation and a saturated aqueous sodium bicarbonate solution was added. The resultant solid was isolated and purified by column chromatography on silica using a solvent gradient of 100:0 to 47:3 of methylene chloride and methanol as eluent. There was thus obtained N-[5-(N-tert-butoxycarbonylamino)-1-methylpyrazol-3-yl]-2-[4-(6,7-dimethoxyquinolin-4-yloxy)phenyl]acetamide as a solid (0.205 g); $^1$H NMR: (DMSOd$_6$) 1.46 (s, 9H), 3.55 (s, 3H), 3.65 (s, 2H), 3.93 (s, 3H), 3.95 (s, 3H), 6.34 (s, 1H), 6.47 (d, 1H), 7.22 (d, 2H), 7.4 (s, 1H), 7.45 (d, 2H), 7.5 (s, 1H), 8.47 (d, 1H), 9.31 (br s, 1H), 10.56 (s, 1H); Mass Spectrum: M+H$^+$ 534.

A mixture of the material so obtained, trifluoroacetic acid (2 ml) and methylene chloride (2 ml) was stirred at ambient temperature for 2 hours. The resultant mixture was evaporated. The residue was triturated under a mixture of ethyl acetate and petroleum ether. The resultant precipitate was recovered and dissolved in a mixture of methylene chloride (10 ml) and ethanol (2 ml). A macroporous polystyrene carbonate resin (MP carbonate resin, 2.91 mM/g) was added and the mixture was stirred at ambient temperature for 3 hours. The mixture was filtered and the filtrate was evaporated. The resultant residue was triturated under a mixture of ethanol and petroleum ether to give a precipitate which was isolated and dried under vacuum. There was thus obtained the title compound (0.125 g); $^1$H NMR: (DMSOd$_6$) 3.4 (s, 3H), 3.59 (s, 2H), 3.92 (s, 3H), 3.95 (s, 3H), 5.19 (s, 2H), 5.62 (s, 1H), 6.46 (d, 1H), 7.21 (d, 2H), 7.39 (s, 1H), 7.43 (d, 2H), 7.49 (s, 1H), 8.46 (d, 1H), 10.29 (s, 1H); Mass Spectrum: M+H$^+$ 434.

The 3-amino-5-(N-tert-butoxycarbonylamino)-1-methylpyrazole used as a starting material was prepared as follows:—

Diphenylphosphoryl azide (1.58 ml) and triethylamine (1.02 ml) were added in turn to a stirred mixture of 2-methyl-5-nitropyrazole-3-carboxylic acid (*Bioorganic & Medicinal Chemistry*, 1999, 7, 251-262; 0.838 g), tert-butanol (10 ml) and 1,4-dioxane (10 ml). The resultant mixture was stirred and heated to reflux for 6 hours. The mixture was concentrated by evaporation and the residue was purified by column chromatography on silica using a solvent gradient of 100:0 to 4:1 of methylene chloride and diethyl ether as eluent. There was thus obtained 3-nitro-5-(N-tert-butoxycarbonylamino)-1-methylpyrazole (0.95 g); $^1$H NMR: (DMSOd$_6$) 1.48 (s, 9H), 3.79 (s, 3H), 6.8 (s, 1H), 9.3 (br s, 1H); Mass Spectrum: M-H$^-$ 241.

A mixture of a portion (0.387 g) of the material so obtained, platinum oxide catalyst (0.15 g), ethanol (5 ml) and ethyl acetate (15 ml) was stirred under 3.7 atmospheres pressure of hydrogen for 2 hours. The resultant mixture was filtered and the filtrate was evaporated. There was thus obtained the required starting material (0.34 g); $^1$H NMR: (DMSOd$_6$) 1.44 (s, 9H), 3.56 (s, 3H), 4.41 (s, 2H), 5.28 (s, 1H), 9.03 (br s, 1H); Mass Spectrum: M+H$^+$ 213.

EXAMPLE 23

N-(5-methylamino-1H-pyrazol-3-yl)-2-[4-(6,7-dimethoxyquinolin-4-yloxy)phenyl]acetamide Using an analogous procedure to that described in Example 22, 2-[4-(6,7-dimethoxyquinolin-4-yloxy)phenyl] acetic acid was reacted with 5-amino-3-(N-tert-butoxycarbonyl-N-methylamino)-1-(3,4-dimethoxybenzyl)pyrazole to give N-[3-(N-tert-butoxycarbonyl-N-methylamino)-1-(3,4-dimethoxybenzyl)pyrazol-5-yl]-2-[4-(6,7-dimethoxyquinolin-4-yloxy)phenyl]acetamide as a solid in 66% yield; $^1$H NMR: (DMSOd$_6$) 1.45 (s, 9H), 3.18 (s, 3H), 3.65 (s, 3H), 3.66 (s, 3H), 3.73 (s, 2H), 3.92 (s, 3H), 3.95 (s, 3H), 5.08 (s, 2H), 6.4 (d, 1H), 6.42 (m, 1H), 6.58 (d, 1H), 6.76 (d, 1H), 6.84 (d, 1H), 7.2 (d, 2H), 7.4 (s, 1H), 7.41 (d, 2H), 7.49 (d, 1H), 10.26 (br s, 1H); Mass Spectrum: M+H$^+$ 684.

A mixture of the material so obtained (0.25 g), trifluoroacetic acid (4 ml) and methylene chloride (4 ml) was stirred at ambient temperature for 4 hours. The resultant mixture was evaporated. The residue was triturated under a mixture of ethyl acetate and petroleum ether. The resultant precipitate was recovered and dried under vacuum. There was thus obtained N-[1-(3,4-dimethoxybenzyl)-3-methylaminopyrazol-5-yl]-2-[4-(6,7-dimethoxyquinolin-4-yloxy)phenyl]acetamide (0.216 g); $^1$H NMR: (DMSOd$_6$+CF$_3$CO$_2$D) 2.87 (s, 3H), 3.73 (s, 3H), 3.74 (s, 3H), 3.95 (s, 2H), 4.07 (s, 3H), 4.09 (s, 3H), 5.28 (s, 3H), 6.73 (d, 1H), 6.84 (d, 1H), 6.9 (m, 3H), 7.38 (d, 2H), 7.56 (d, 2H), 7.63 (s, 1H), 7.79 (s, 1H), 8.85 (d, 1H); Mass Spectrum: M+H$^+$ 584.

A mixture of the material so obtained, trifluoroacetic acid (4 ml), meta-cresol (0.314 ml) and thioanisole (0.353 ml) was stirred and heated to reflux for 5 hours. The reaction mixture was concentrated by evaporation and the residue was purified by column chromatography on silica using a solvent gradient of 100:0 to 9:1 of methylene chloride and a 3M methanolic ammonia solution as eluent. There was thus obtained the title compound (0.092 g); $^1$H NMR: (DMSOd$_6$) 2.63 (s, 3H), 3.63 (s, 2H), 3.92 (s, 3H), 3.95 (s, 3H), 5.39 (br s, 1H), 5.58 (s, 1H), 6.47 (d, 2H), 7.4 (s, 1H), 7.45 (d, 2H), 7.5 (s, 1H), 8.47 (d, 1H), 10.35 (s, 1H), 11.1 (br s, 1H); Mass Spectrum: M+H$^+$ 434.

The 5-amino-3-(N-tert-butoxycarbonylamino)-1-(3,4-dimethoxybenzyl)pyrazole used as a starting material was prepared as follows:—

Sodium hydride (60% dispersion in mineral oil, 0.144 g) was added portionwise to a mixture of 3-(N-tert-butoxycarbonylamino)-1-(3,4-dimethoxybenzyl)-5-nitropyrazole (1.14 g) and THF (25 ml) and the mixture was stirred at ambient temperature for 15 minutes. Methyl iodide (0.224 ml) was added followed by DMF (2 ml) and the mixture was stirred at ambient temperature for 45 minutes. The solvent was evaporated and the residue was purified by column chromatography on silica using a solvent gradient of 100:0 to 1:1 petroleum ether and methylene chloride as eluent. There was thus obtained 3-(N-tert-butoxycarbonyl-N-methylamino)-1-(3,4-dimethoxybenzyl)-5-nitropyrazole (0.95 g); $^1$H NMR: (DMSOd$_6$) 1.49 (s, 9H), 3.28 (s, 3H), 3.72 (s, 6H), 5.58 (s, 2H), 6.66 (d, 1H), 6.89 (s, 1H), 6.9 (d, 1H), 7.23 (br s, 1H); Mass Spectrum: M+H$^+$ 393.

A mixture of a portion (0.392 g) of the material so obtained, platinum oxide catalyst (0.039 g), ethanol (5 ml) and ethyl acetate (15 ml) was stirred under 1.7 atmospheres pressure of hydrogen for 2 hours. The catalyst was removed and the filtrate was concentrated by evaporation. There was thus obtained 5-amino-3-(N-tert-butoxycarbonylamino)-1-(3,4-dimethoxybenzyl)pyrazole (0.32 g); $^1$H NMR: (DMSOd$_6$) 1.44 (s, 9H), 3.12 (s, 3H), 3.71 (s, 3H), 3.72 (s, 3H), 4.92 (s, 2H), 5.26 (s, 2H), 5.48 (br s, 1H), 6.65 (m, 1H), 6.86 (m, 1H); Mass Spectrum: M+H$^+$ 363.

EXAMPLE 24

N-(5-dimethylamino-1H-pyrazol-3-yl)-2-[4-(6,7-dimethoxyquinolin-4-yloxy)phenyl]acetamide Sodium triacetoxyborohydride (0.068 g) was added to a mixture of N-[1-(3,4-dimethoxybenzyl)-3-methylaminopyrazol-5-yl]-2-[4-(6,7-dimethoxyquinolin-4-yloxy)phenyl]acetamide (0.139 g), formaldehyde (37% aqueous solution; 0.038 ml), sodium acetate (0.028 g), methanol (2 ml) and methylene chloride (4 ml) and the resultant mixture was stirred at ambient temperature for 2 hours. The mixture was concentrated by evaporation and the residue was purified by column chromatography on silica using a solvent gradient of 100:0 to 93:7 of methylene chloride and 3M methanolic ammonia as eluent. There was thus obtained N-[1-(3,4-dimethoxybenzyl)-3-dimethylaminopyrazol-5-yl]-2-[4-(6,7-dimethoxyquinolin-4-yloxy)phenyl]acetamide (0.06 g); $^1$H NMR: (DMSOd$_6$+CF$_3$CO$_2$D) 3.01 (s, 6H), 3.72 (s, 3H), 3.73 (s, 3H), 3.96 (s, 2H), 4.06 (s, 3H), 4.08 (s, 3H), 5.29 (s, 2H), 5.73 (s, 1H), 6.71 (d, 1H), 6.83 (d, 1H), 6.91 (m, 2H), 7.39 (d, 2H), 7.56 (d, 2H), 7.62 (s, 1H), 7.79 (s, 1H), 8.86 (d, 1H); Mass Spectrum: M+H$^+$ 598.

A mixture of the material so obtained, trifluoroacetic acid (2 ml), meta-cresol (0.084 ml) and thioanisole (0.094 ml) was stirred and heated to reflux for 5 hours. The reaction mixture was concentrated by evaporation and the residue was purified by column chromatography on silica using a solvent gradient of 49:1 to 47:3 of methylene chloride and a 3M methanolic ammonia solution as eluent. There was thus obtained the title compound (0.024 g); $^1$H NMR: (DMSOd$_6$) 2.27 (d, 3H), 3.75 (s, 3H), 3.77 (s, 2H), 3.93 (s, 3H), 3.95 (s, 3H), 6.53 (d, 1H), 6.73 (d, 1H), 6.80 (m, 1H), 6.96 (d, 2H), 7.33 (d, 2H), 7.4, (s, 1H), 7.5 (s, 1H), 8.5 (d, 1H), 12.17 (br s, 1H); Mass Spectrum: M+H$^+$ 448.

EXAMPLE 25

N-(1-ethylpyrazol-4-yl)-2-[4-(6-fluoroquinolin-4-yloxy)-2-methoxyphenyl]propionamide Using an analogous procedure to that described in Example 2, 2-[4-(6-fluoroquinolin-4-yloxy)-2-methoxyphenyl]propionic acid was reacted with 4-amino-1-ethylpyrazole. The resultant mixture was evaporated and the residue was purified by preparative HPLC using a Waters 'Xterra' reversed-phase column (5 microns silica, 30 mm diameter, 150 mm length) using decreasingly polar mixtures of water (containing 0.2% ammonium carbonate) and acetonitrile as eluent. There was thus obtained the title compound as a solid in 39% yield; $^1$H NMR: (DMSOd$_6$) 1.32 (t, 3H), 1.38 (d, 3H), 3.81 (s, 3H), 4.02-4.11 (m, 3H), 6.7 (d, 1H), 6.85 (m, 1H), 7.0 (d, 1H), 7.38-7.44 (m, 2H), 7.75 (m, 1H), 7.90 (s, 1H), 7.96 (m, 1H), 8.12 (m, 1H), 8.69 (d, 1H), 9.97 (s, 1H); Mass Spectrum: M+H$^+$ 435.

The 2-[4-(6-fluoroquinolin-4-yloxy)-2-methoxyphenyl]propionic acid used as a starting material was prepared as follows:—

Dimethylformamide di-tert-butyl acetal (5.93 ml) was added dropwise to a stirred solution of 2-(4-benzyloxy-2-methoxyphenyl)acetic acid (6.8 g) in toluene (68 ml) that had been heated to 90-95° C. The resultant mixture was heated to that temperature range for 1 hour. The mixture was cooled and the solvent was evaporated. The residue was partitioned between diethyl ether and a 10% aqueous citric acid solution. The organic phase was washed with water and with an aqueous sodium bicarbonate solution, dried over magnesium sulphate and evaporated. There was thus obtained tert-butyl 2-(4-benzyloxy-2-methoxyphenyl)acetate (7.5 g); $^1$H NMR Spectrum: (DMSOd$_6$) 1.4 (s, 9H), 3.35 (s, 2H), 3.75 (s, 3H), 5.1 (s, 2H), 6.5 (m, 1H), 6.55 (d, 1H), 7.05 (d, 1H), 7.3-7.5 (m, 5H).

Under an atmosphere of argon, n-butyl lithium (2.5 M in THF, 72 ml) was added dropwise to a stirred solution of tert-butyl 2-(4-benzyloxy-2-methoxyphenyl)acetate (3.28 g) in THF (100 ml) that had been cooled to −78° C. The mixture was stirred at −78° C. for 1 hour. Methyl iodide (1.02 ml) was added at this temperature and the resultant mixture was allowed to warm to ambient temperature over 1 hour. The mixture was diluted with a saturated aqueous ammonium chloride solution and extracted with ethyl acetate. The organic phase was dried over magnesium sulphate and evaporated. The residue was purified by column chromatography on silica using a solvent gradient from petroleum ether to a 17:3 mixture of petroleum ether and ethyl acetate as eluent. There was thus obtained tert-butyl 2-(4-benzyloxy-2-methoxyphenyl)propionate (2.42 g); $^1$H NMR: (CDCl$_3$) 1.37 (d, 3H), 1.4 (s, 9H), 3.78 (s, 3H), 3.83 (q, 1H), 5.04 (s, 2H), 6.52 (m, 2H), 7.1 (d, 1H), 7.32 (m, 1H), 7.38 (m, 2H), 7.43 (m, 2H).

A mixture of the material so obtained, 10% palladium on carbon catalyst (0.25 g), ethyl acetate (25 ml) and methanol (5 ml) was stirred at ambient temperature under an atmospheres pressure of hydrogen for 4 hours. The catalyst was removed by filtration and the filtrate was evaporated. The residue was purified by column chromatography on silica using a solvent gradient from 9:1 to 3:1 of petroleum ether and ethyl acetate as eluent. There was thus obtained tert-butyl 2-(4-hydroxy-2-methoxyphenyl)propionate (1.78 g); $^1$H NMR: (CDCl$_3$)

1.37 (d, 3H), 1.4 (s, 9H), 3.77 (s, 3H), 3.82 (q, 1H), 4.99 (s, 1H), 6.35 (m, 2H), 7.02 (d, 1H).

A mixture of the material so obtained, 4-chloro-6-fluoroquinoline (1.3 g), caesium carbonate (8.89 g) and DMF (15 ml) was stirred and heated to 90° C. for 3.5 hours. The mixture was cooled to ambient temperature, diluted with water, and extracted with ethyl acetate. The organic phase was washed with water, dried over magnesium sulphate and evaporated. The residue was purified by column chromatography on silica using a solvent gradient from 4:1 to 1:1 of petroleum ether and ethyl acetate as eluent. There was thus obtained tert-butyl 2-[4-(6-fluoroquinolin-4-yloxy)-2-methoxyphenyl]propionate (1.86 g); $^1$H NMR: (DMSOd$_6$) 1.35 (s, 9H), 1.36 (d, 3H), 3.77 (s, 3H), 3.84 (q, 1H), 6.69 (d, 1H), 6.83 (m, 1H), 6.99 (d, 1H), 7.29 (d, 1H), 7.75 (m, 1H), 7.96 (m, 1H), 8.11 (m, 1H), 8.7 (d, 1H); Mass Spectrum: M+H$^+$ 398.

A 4M hydrogen chloride solution in 1,4-dioxane (29.25 ml) was added to a solution of tert-butyl 2-[4-(6-fluoroquinolin-4-yloxy)-2-methoxyphenyl]propionate (1.86 g) in methylene chloride (2 ml) and the resultant mixture was stirred at ambient temperature for 14 hours. The solvent was evaporated and the residue triturated under diethyl ether. There was thus obtained 2-[4-(6-fluoroquinolin-4-yloxy)-2-methoxyphenyl]propionic acid (1.78 g); $^1$H NMR: (DMSOd$_6$+ CF$_3$CO$_2$D) 1.41 (d, 3H), 3.82 (s, 3H), 3.89 (q, 1H), 7.01 (d, 1H), 7.15 (m, 2H), 7.44 (d, 1H), 8.17 (m, 1H), 8.36 (m, 1H), 8.41 (m, 1H), 9.12 (d, 1H).

EXAMPLE 26

N-(4,5-dimethylisoxazol-3-yl)-2-[4-(6-fluoroquinolin-4-yloxy)-2-methoxyphenyl]propionamide Using an analogous procedure to that described in Example 2, 2-[4-(6-fluoroquinolin-4-yloxy)-2-methoxyphenyl]propionic acid was reacted with 3-amino-4,5-dimethylisoxazole. The resultant mixture was evaporated and the residue was purified by preparative HPLC using a Waters 'Xterra' reversed-phase column (5 microns silica, 30 mm diameter, 150 mm length) using decreasingly polar mixtures of water (containing 0.2% ammonium carbonate) and acetonitrile as eluent. There was thus obtained the title compound as a solid in 11% yield; $^1$H NMR: (DMSOd$_6$) 1.43 (s, 3H), 1.77 (s, 3H), 2.3 (s, 3H), 3.81 (s, 3H), 4.16 (q, 1H), 6.72 (d, 1H), 6.87 (m, 1H), 7.0 (d, 1H), 7.4 (d, 1H), 7.75 (m, 1H), 7.97 (m, 1H), 8.12 (m, 1H), 8.7 (d, 1H), 10.16 (s, 1H); Mass Spectrum: M+H$^+$ 436.

EXAMPLE 27

N-(1,3-dimethyl-1H-pyrazol-4-yl)-2-[2-methoxy-4-(7-methoxyquinolin-4-yloxy)phenyl]acetamide citrate salt A stirred suspension of N-(1,3-dimethyl-1H-pyrazol-4-yl)-2-[2-methoxy-4-(7-methoxyquinolin-4-yloxy)phenyl] acetamide (0.54 g) in ethanol (5 ml) was heated gently to reflux until a solution was obtained. The resultant solution was stirred and a solution of citric acid monohydrate (0.315 g; 1.2 equivalents) in ethanol (95%, 5 ml) was added. The mixture was allowed to start to cool and tert-butyl methyl ether (10 ml) was added. When the mixture had cooled to ambient temperature, a second portion (2 ml) of tert-butyl methyl ether was added and the resultant mixture was allowed to stand at ambient temperature for 28 hours. The precipitate was collected by filtration and dried to constant weight under vacuum (1.3×10$^{-4}$ atmospheres) at 50° C. during 4 hours.

There was thus obtained the title salt (0.76 g); m.p. 209-212C; $^1$H NMR: (DMSOd$_6$, at 24° C.) 2.12 (s, 3H), 2.65 (d, 2H), 2.75 (d, 2H), 3.64 (s, 2H), 3.7 (s, 3H), 3.78 (s, 3H), 3.94 (s, 3H), 6.53 (d, 1H), 6.79 (m, 1H), 6.96 (d, 1H), 7.3 (m, 1H), 7.32 (d, 1H), 7.41 (d, 1H), 7.81 (s, 1H), 8.21 (d, 1H), 8.63 (d, 1H), 9.43 (s, 1H), 12.39 (br s, 2H);

| Elemental Analysis: | Found C, 57.62; H, 5.29; N, 8.75; |
|---|---|
| C$_{24}$H$_{24}$N$_4$O$_4$1C$_6$H$_8$O$_7$0.21H$_2$O | requires C, 57.34; H, 5.20; N, 8.92%. |

EXAMPLE 28

N-(1,3-dimethyl-1H-pyrazol-4-yl)-2-[2-methoxy-4-(7-methoxyquinolin-4-yloxy)phenyl]acetamide maleate salt A stirred suspension of N-(1,3-dimethyl-1H-pyrazol-4-yl)-2-[2-methoxy-4-(7-methoxyquinolin-4-yloxy)phenyl] acetamide (0.608 g) in ethanol (5 ml) was heated gently to reflux until a solution was obtained. The resultant solution was stirred and a solution of maleic acid (0.18 g; 1.07 equivalents) in ethanol (95%, 5 ml) was added. The mixture was allowed to start to cool and tert-butyl methyl ether (5 ml) was added. When the mixture had cooled to ambient temperature, a second portion (5 ml) of tert-butyl methyl ether was added and the resultant mixture was allowed to stand at ambient temperature for 29 hours. The precipitate was collected by filtration and dried to constant weight under vacuum (1.3×10$^{-4}$ atmospheres) at 50° C. during 4 hours. There was thus obtained the title salt (0.688 g); m.p. 192-199° C.; $^1$H NMR: (DMSOd$_6$, at 24° C.) 2.12 (s, 3H), 3.66 (s, 2H), 3.7 (s, 3H), 3.78 (s, 3H), 3.97 (s, 3H), 6.19 (s, 2H), 6.63 (d, 1H), 6.84 (m, 1H), 7.0 (d, 1H), 7.35 (d, 1H), 7.38 (m, 1H), 7.44 (d, 1H), 7.81 (s, 1H), 8.29 (d, 1H), 8.72 (d, 1H), 9.44 (s, 1H);

| Elemental Analysis: | Found C, 60.64; H, 5.18; N, 9.96; |
|---|---|
| C$_{24}$H$_{24}$N$_4$O$_4$1C$_4$H$_4$O$_4$0.37 H$_2$O | requires C, 60.57; H, 5.22; N, 10.09%. |

DSC thermogram analysis of said maleate salt showed that the salt has a melting point in the range of about 188-210° C., with an onset of melting at about 188° C. and a melting point peak at about 192° C.

EXAMPLE 29

N-(1,3-dimethyl-1H-pyrazol-4-yl)-2-[2-methoxy-4-(7-methoxyquinolin-4-yloxy)phenyl]acetamide sulphate salt A stirred suspension of N-(1,3-dimethyl-1H-pyrazol-4-yl)-2-[2-methoxy-4-(7-methoxyquinolin-4-yloxy)phenyl] acetamide (0.4 g) in acetonitrile (14 ml) was heated gently to reflux until a solution was obtained. The resultant solution was stirred and a 0.5 M solution of sulphuric acid in acetonitrile (1.94 ml; 1.05 equivalents) was added. The mixture was allowed to cool to ambient temperature and was stirred at ambient temperature for 3 days. The precipitate was collected by filtration and dried to constant weight under vacuum (1.3×10$^{-4}$ atmospheres) at 50° C. during 4 hours. There was thus obtained the title salt (0.47 g); m.p. 267-269° C.

The material so obtained was allowed to stand in the open air for 3 hours. The resultant material gave the following characterising data:—m.p. 265-270° C.; $^1$H NMR: (DMSOd$_6$, at 24° C.) 2.13 (s, 3H), 3.68 (s, 2H), 3.7 (s, 3H), 3.79 (s, 3H), 4.04 (s, 3H), 6.88 (d, 1H), 6.95 (m, 1H), 7.11 (d, 1H), 7.42 (d, 1H), 7.52 (d, 1H), 7.58 (m, 1H), 7.8 (s, 1H), 8.48 (d, 1H), 8.94 (d, 1H), 9.46 (s, 1H);

| Elemental Analysis: | Found C, 53.56; H, 4.94; N, 10.38; S, 5.42; |
|---|---|
| $C_{24}H_{24}N_4O_41H_2SO_40.25H_2O$ | requires C, 53.89; H, 4.99; N, 10.47; S, 5.99%. |

DSC thermogram analysis of said sulphate salt showed that the salt has a melting point in the range of about 257-280° C., with an onset of melting at about 257° C. and a melting point peak at about 271° C.

EXAMPLE 30

N-(1,3-dimethyl-1H-pyrazol-4-yl)-2-[2-methoxy-4-(7-methoxyquinolin-4-yloxy)phenyl]acetamide mesylate salt A stirred mixture of N-(1,3-dimethyl-1H-pyrazol-4-yl)-2-[2-methoxy-4-(7-methoxyquinolin-4-yloxy)phenyl]acetamide (1 g), ethyl acetate (16 ml) and ethanol (4 ml) was heated to reflux until a solution was obtained. The resultant solution was stirred and methanesulphonic acid (0.15 ml) was added dropwise. A precipitate started to form which was dissolved by the addition of ethanol (6 ml). Sufficient ethyl acetate was added until a slightly cloudy solution was formed. The resultant solution was filtered whilst hot and the filtrate was allowed to cool to ambient temperature. The mixture was allowed to stand at ambient temperature for 16 hours. The precipitate was collected by filtration and dried to constant weight under vacuum ($1.3 \times 10^{-4}$ atmospheres) at 50° C. during 24 hours. There was thus obtained the title salt (1 g); m.p. onset of melting at about 194° C. and a melting point peak at 206-213° C.; $^1$H NMR: (DMSOd$_6$, at 24° C.) 2.13 (s, 3H), 2.31 (s 3H), 3.68 (s, 2H), 3.7 (s, 3H), 3.79 (s, 3H), 4.04 (s, 3H), 6.88 (d, 1H), 6.95 (m, 1H), 7.11 (d, 1H), 7.42 (d, 1H), 7.53 (d, 1H), 7.58 (m, 1H), 7.8 (s, 1H), 8.48 (d, 1H), 8.94 (d, 1H), 9.46 (s, 1H);

| Elemental Analysis: | Found C, 56.58; H, 5.62; N, 10.49; S, 5.48; |
|---|---|
| $C_{24}H_{24}N_4O_41CH_3SO_3H\ 0.15C_2H_5OH$ | requires C, 56.75; H, 5.44; N, 10.46; S, 5.99%. |

EXAMPLE 31

N-(1,3-dimethyl-1H-pyrazol-4-yl)-2-[2-methoxy-4-(7-methoxyquinolin-4-yloxy)phenyl]acetamide benzenesulphonate salt A stirred suspension of N-(1,3-dimethyl-1H-pyrazol-4-yl)-2-[2-methoxy-4-(7-methoxyquinolin-4-yloxy)phenyl]acetamide (0.5 g) in acetonitrile (10 ml) was heated gently to reflux until a solution was obtained. The resultant solution was stirred and a solution of benzenesulphonic acid (0.205 g) in acetonitrile (1 ml) was added. The mixture was stirred and heated at reflux for 10 minutes. The mixture was allowed to stand and cool to ambient temperature. A precipitate was deposited. The mixture was stored at ambient temperature for 2 days. A spatula was placed into the mixture and a further precipitate was deposited. The mixture of precipitates was collected by filtration and dried to constant weight under vacuum (0.1 mm mercury) at 50° C. during 4 hours. There was thus obtained the title salt as a mixture of two crystalline forms (0.45 g); m.p. partial melting at 159-163° C. and total melting at 188-193° C.

The salt so obtained was dissolved in hot acetonitrile and the solution was allowed to cool to ambient temperature. The resultant precipitate (comprising two different crystalline forms) was isolated by filtration, washed with acetonitrile and dried under vacuum; m.p. partial melting at 150-158° C. and total melting at 180-193° C.

The salt so obtained was dissolved in hot ethanol and the solution was allowed to cool to ambient temperature. A spatula was placed into the solution inducing the deposition of a precipitate. The precipitate was isolated by filtration, washed with ethanol and dried under vacuum at 60° C. There was thus obtained the title salt (0.41 g); m.p. complete melting at 131-134° C., re-solidification at 140-145° C. and complete melting at 180-193° C.; $^1$H NMR: (DMSOd$_6$, at 24° C.) 2.12 (s, 3H), 3.68 (s, 2H), 3.7 (s, 3H), 3.79 (s, 3H), 4.03 (s, 3H), 6.85 (d, 1H), 6.94 (m, 1H), 7.1 (d, 1H), 7.27-7.34 (m, 3H), 7.41 (d, 1H), 7.5 (d, 1H), 7.56 (m, 1H), 7.57-7.61 (m, 2H), 7.8 (s, 1H), 8.46 (d, 1H), 8.91 (d, 1H), 9.45 (s, 1H).

A portion (approximately 0.025 g) of the material so obtained was placed in a vial and acetone (1 ml) was added. The vial was sealed and the mixture was stirred at ambient temperature for 3 days. The lid of the vial was removed and the solvent was allowed to evaporate at ambient temperature resulting in the deposition of a precipitate. The precipitate was isolated. There was thus obtained the title salt, the DSC thermogram of which showed a melting point in the range of about 183-190° C., with an onset of melting at about 183° C. and a melting point peak at about 185° C.

EXAMPLE 32

N-(1,3-dimethyl-1H-pyrazol-4-yl)-2-[2-methoxy-4-(7-methoxyquinolin-4-yloxy)phenyl]acetamide 4-toluenesulphonate salt A stirred suspension of N-(1,3-dimethyl-1H-pyrazol-4-yl)-2-[2-methoxy-4-(7-methoxyquinolin-4-yloxy)phenyl] acetamide (0.605 g) in ethanol (5 ml) was heated to reflux until a solution was obtained. The resultant solution was stirred and a solution of 4-toluenesulphonic acid monohydrate (0.333 g; 1.25 equivalents) in ethanol (95%, 5 ml) was added. The mixture was allowed to start to cool and tert-butyl methyl ether (12 ml) was added. The resultant mixture was allowed to stand at ambient temperature for 29 hours. The precipitate was collected by filtration and dried to constant weight under vacuum ($1.3 \times 10^{-4}$ atmospheres) at 50° C. during 4 hours. There was thus obtained the title salt (0.705 g); m.p. 126-136° C.; $^1$H NMR: (DMSOd$_6$, at 24° C.) 2.13 (s, 3H), 2.28 (s, 3H), 3.68 (s, 2H), 3.7 (s, 3H), 3.79 (s, 3H), 4.03 (s, 3H), 6.87 (d, 1H), 6.95 (m, 1H), 7.08-7.13 (m, 3H), 7.42 (d, 1H), 7.47 (d, 2H), 7.51 (d, 1H), 7.58 (m, 1H), 7.8 (s, 1H), 8.47 (d, 1H), 8.93 (d, 1H), 9.46 (s, 1H);

| Elemental Analysis: | Found C, 58.11; H, 5.60; N, 8.65; S, 5.13; |
|---|---|
| $C_{24}H_{24}N_4O_41CH_3C_6H_4SO_3H2.07H_2O$ | requires 58.00; H, 5.67; N, 8.73; S, 4.99%. |

The invention claimed is:
1. A quinoline derivative of the Formula I

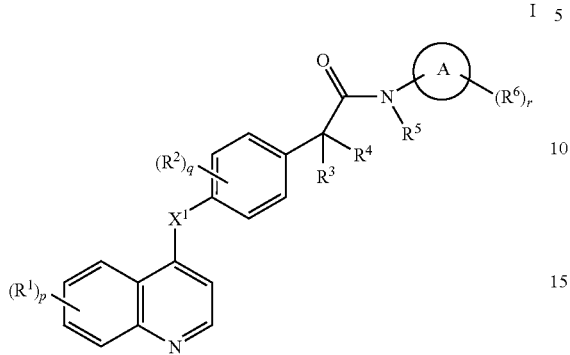

wherein
X¹ is O or N(R⁷) where R⁷ is hydrogen or (1-8C)alkyl;
p is 0, 1, 2 or 3;
each R¹ group, which may be the same or different, is selected from halogeno, trifluoromethyl, cyano, hydroxy, mercapto, amino, carboxy, (1-6C)alkoxycarbonyl, carbamoyl, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, N-(1-6C)alkylcarbamoyl, N,N-di-[(1-6C)alkyl]carbamoyl, N-(1-6C)alkylsulphamoyl, N,N-di-[(1-6C)alkyl]sulphamoyl, (2-6C)alkanoyl, (2-6C)alkanoylamino and N-(1-6C)alkyl-(2-6C)alkanoylamino,
or from a group of the formula:

Q¹-X²— wherein X² is selected from O, S, SO, SO₂, N(R⁸), CO, CON(R⁸), N(R⁸)CO, OC(R⁸)₂ and N(R⁸)C(R⁸)₂, wherein each R⁸ is hydrogen or (1-8C)alkyl, and Q¹ is aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl,
and wherein any aryl, (3-8C)cycloalkyl, (3-8C)cycloalkenyl, heteroaryl or heterocyclyl group within a R¹ substituent optionally bears 1, 2 or 3 substituents, which may be the same or different, selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (2-6C)alkanoylamino, N-(1-6C)alkyl-(2-6C)alkanoylamino, N-(1-6C)alkylureido, N'-(1-6C)alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino,
or from a group of the formula:

—X³—R⁹ wherein X³ is a direct bond or is selected from O and N(R¹⁰), wherein R¹⁰ is hydrogen or (1-8C)alkyl, and R⁹ is halogeno-(1-6C)alkyl, hydroxy-(1-6C)alkyl, mercapto-(1-6C)alkyl, (1-6C)alkoxy-(1-6C)alkyl, (1-6C)alkylthio-(1-6C)alkyl, (1-6C)alkylsulphinyl-(1-6C)alkyl, (1-6C)alkylsulphonyl-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, (1-6C)alkoxycarbonylamino-(1-6C)alkyl, ureido-(1-6C)alkyl, N-(1-6C)alkylureido-(1-6C)alkyl, N'-(1-6C)alkylureido-(1-6C)alkyl, N',N'-di-[(1-6C)alkyl]ureido-(1-6C)alkyl, N,N'-di-[(1-6C)alkyl]ureido-(1-6C)alkyl or N,N',N'-tri-[(1-6C)alkyl]ureido-(1-6C)alkyl,
or from a group of the formula:

—X⁴-Q² wherein X⁴ is a direct bond or is selected from O, CO and N(R¹¹), wherein R¹¹ is hydrogen or (1-8C)alkyl, and Q² is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, hydroxy, (1-8C)alkyl and (1-6C)alkoxy,
and wherein any aryl, heteroaryl or heterocyclyl group within a substituent on R¹ optionally bears a (1-3C)alkylenedioxy group,
and wherein any heterocyclyl group within a R¹ substituent optionally bears 1 or 2 oxo or thioxo substituents,
and wherein any CH, CH₂ or CH₃ group within a R¹ substituent optionally bears on each said CH, CH₂ or CH₃ group one or more halogeno or (1-8C)alkyl substituents and/or a substituent selected from hydroxy, mercapto, amino, cyano, carboxy, carbamoyl, ureido, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, N-(1-6C)alkylureido, N'-(1-6C)alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino,
and wherein adjacent carbon atoms in any (2-6C)alkylene chain within a R¹ substituent are optionally separated by the insertion into the chain of a group selected from O, S, SO, SO₂, N(R¹²), CO, CH(OR¹²), CON(R¹²), N(R¹²)CO, N(R¹²)CON(R¹²), SO₂N(R¹²), N(R¹²)SO₂, CH=CH and C≡C wherein R¹² is hydrogen or (1-8C)alkyl, or, when the inserted group is N(R¹²), R¹² may also be (2-6C)alkanoyl;
q is 0, 1 or 2;
each R² group, which may be the same or different, is selected from halogeno, trifluoromethyl, cyano, carboxy, hydroxy, amino, carbamoyl, (1-8C)alkyl, (2-8C)alkenyl, (2-8C)alkynyl, (1-6C)alkoxy, (1-6C)alkylamino, di-[(1-6C)alkyl]amino, N-(1-6C)alkylcarbamoyl, N,N-di-[(1-6C)alkyl]carbamoyl, halogeno-(1-6C)alkyl, hydroxy-(1-6C)alkyl, (1-6C)

alkoxy-(1-6C)alkyl, cyano-(1-6C)alkyl, carboxy-(1-6C)alkyl, (1-6C)alkoxycarbonyl-(1-6C)alkyl, amino-(1-6C)alkyl, (1-6C)alkylamino-(1-6C)alkyl, di-[(1-6C)alkyl]amino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (2-6C)alkanoylamino-(1-6C)alkyl and N-(1-6C)alkyl-(2-6C)alkanoylamino-(1-6C)alkyl;

$R^3$ is hydrogen, (1-8C)alkyl, (2-8C)alkenyl or (2-8C)alkynyl;

$R^4$ is hydrogen, (1-8C)alkyl, (2-8C)alkenyl, (2-8C)alkynyl, halogeno-(1-6C)alkyl, hydroxy-(1-6C)alkyl, (1-6C)alkoxy-(1-6C)alkyl, cyano-(1-6C)alkyl, carboxy-(1-6C)alkyl, amino-(1-6C)alkyl, (1-6C)alkylamino-(1-6C)alkyl, di-[(1-6C)alkyl]amino-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, (1-6C)alkoxycarbonyl-(1-6C)alkyl, (2-6C)alkanoylamino-(1-6C)alkyl or N-(1-6C)alkyl-(2-6C)alkanoylamino-(1-6C)alkyl;

or $R^3$ and $R^4$ together with the carbon atom to which they are attached form a (3-8C)cycloalkyl group;

$R^5$ is hydrogen, (1-8C)alkyl, (2-8C)alkenyl or (2-8C)alkynyl or a group of the formula:

—$X^5$—$R^{13}$ wherein $X^5$ is a direct bond or is selected from O and N($R^{14}$), wherein $R^{14}$ is hydrogen or (1-8C)alkyl, and $R^{13}$ is halogeno-(1-6C)alkyl, hydroxy-(1-6C)alkyl, (1-6C)alkoxy-(1-6C)alkyl or cyano-(1-6C)alkyl;

Ring A is a 5-membered monocyclic heteroaryl ring with up to three ring heteroatoms selected from oxygen, nitrogen and sulphur;

r is 0, 1, 2 or 3; and each $R^6$ group, which may be the same or different, is selected from halogeno, trifluoromethyl, cyano, hydroxy, mercapto, amino, carboxy, carbamoyl, sulphamoyl, ureido, (1-8C)alkyl, (2-8C)alkenyl, (2-8C)alkynyl, (1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—$X^6$—$R^{15}$ wherein $X^6$ is a direct bond or is selected from O and N($R^{16}$), wherein $R^{16}$ is hydrogen or (1-8C)alkyl, and $R^{15}$ is halogeno-(1-6C)alkyl, hydroxy-(1-6C)alkyl, mercapto-(1-6C)alkyl, (1-6C)alkoxy-(1-6C)alkyl, (1-6C)alkylthio-(1-6C)alkyl, (1-6C)alkylsulphinyl-(1-6C)alkyl, (1-6C)alkylsulphonyl-(1-6C)alkyl, cyano-(1-6C)alkyl, amino-(1-6C)alkyl, (1-6C)alkylamino-(1-6C)alkyl, di-[(1-6C)alkyl]amino-(1-6C)alkyl, (2-6C)alkanoylamino-(1-6C)alkyl, N-(1-6C)alkyl-(2-6C)alkanoylamino-(1-6C)alkyl, carboxy-(1-6C)alkyl, (1-6C)alkoxycarbonyl-(1-6C)alkyl, carbamoyl-(1-6C)alkyl, N-(1-6C)alkylcarbamoyl-(1-6C)alkyl, N,N-di-[(1-6C)alkyl]carbamoyl-(1-6C)alkyl, sulphamoyl-(1-6C)alkyl, N-(1-6C)alkylsulphamoyl-(1-6C)alkyl, N,N-di-[(1-6C)alkyl]sulphamoyl-(1-6C)alkyl, ureido-(1-6C)alkyl, N-(1-6C)alkylureido-(1-6C)alkyl, N'-(1-6C)alkylureido-(1-6C)alkyl, N',N'-di-[(1-6C)alkyl]ureido-(1-6C)alkyl, N,N'-di-[(1-6C)alkyl]ureido-(1-6C)alkyl, N,N',N'-tri-[(1-6C)alkyl]ureido-(1-6C)alkyl, (1-6C)alkanesulphonylamino-(1-6C)alkyl or N-(1-6C)alkyl-(1-6C)alkanesulphonylamino-(1-6C)alkyl, or from a group of the formula:

—$X^7$-$Q^3$ wherein $X^7$ is a direct bond or is selected from O, S, SO, $SO_2$, N($R^{17}$), CO, CH(O$R^{17}$), CON($R^{17}$), N($R^{17}$)CO, N($R^{17}$)CON($R^{17}$), $SO_2$N($R^{17}$), N($R^{17}$)$SO_2$, C($R^{17}$)$_2$O, C($R^{17}$)$_2$S and C($R^{17}$)$_2$N($R^{17}$), wherein each $R^{17}$ is hydrogen or (1-8C)alkyl, and $Q^3$ is aryl, aryl-(1-6C)alkyl, (3-8C)cycloalkyl, (3-8C)cycloalkyl-(1-6C)alkyl, (3-8C)cycloalkenyl, (3-8C)cycloalkenyl-(1-6C)alkyl, heteroaryl, heteroaryl-(1-6C)alkyl, heterocyclyl or heterocyclyl-(1-6C)alkyl, or two $R^6$ groups together form a bivalent group that spans adjacent ring positions on Ring A selected from OC($R^{18}$)$_2$O, OC($R^{18}$)$_2$C($R^{18}$)$_2$O, OC($R^{18}$)$_2$C($R^{18}$)$_2$, C($R^{18}$)$_2$OC($R^{18}$)$_2$, C($R^{18}$)$_2$C($R^{18}$)$_2$C($R^{18}$)$_2$, C($R^{18}$)$_2$C($R^{18}$)$_2$C($R^{18}$)$_2$C($R^{18}$)$_2$, OC($R^{18}$)$_2$N($R^{19}$), N($R^{19}$)C($R^{18}$)$_2$N($R^{19}$), N($R^{19}$)C($R^{18}$)$_2$C($R^{18}$)$_2$, N($R^{19}$)C($R^{18}$)$_2$C($R^{18}$)$_2$C($R^{18}$)$_2$, O C($R^{18}$)$_2$C($R^{18}$)$_2$N($R^{19}$), C($R^{18}$)$_2$N($R^{19}$)C($R^{18}$)$_2$, CO.N($R^{18}$)C($R^{18}$)$_2$, N($R^{18}$)CO.C($R^{18}$)$_2$, N($R^{19}$)C($R^{18}$)$_2$CO, CO.N($R^{18}$)CO, N($R^{19}$)N($R^{18}$)CO, N($R^{18}$)CO.N($R^{18}$), O.CO.N($R^{18}$), O.CO.C($R^{18}$)$_2$ and CO.OC($R^{18}$)$_2$ wherein each $R^{18}$ is hydrogen, (1-8C)alkyl, (2-8C)alkenyl or (2-8C)alkynyl, and wherein $R^{19}$ is hydrogen, (1-8C)alkyl, (2-8C)alkenyl, (2-8C)alkynyl or (2-6C)alkanoyl, and wherein any aryl, (3-8C)cycloalkyl, (3-8C)cycloalkenyl, heteroaryl or heterocyclyl group within an $R^6$ group optionally bears 1, 2 or 3 substituents, which may be the same or different, selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (2-6C)alkanoylamino, N-(1-6C)alkyl-(2-6C)alkanoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino and N-(1-6C)alkyl-(1-6C)alkanesulphonylamino, or from a group of the formula:

—$X^8$—$R^{20}$ wherein $X^8$ is a direct bond or is selected from O and N($R^{21}$), wherein $R^{21}$ is hydrogen or (1-8C)alkyl, and $R^{20}$ is halogeno-(1-6C)alkyl, hydroxy-(1-6C)alkyl, mercapto-(1-6C)alkyl, (1-6C)alkoxy-(1-6C)alkyl, (1-6C)alkylthio-(1-6C)alkyl, (1-6C)alkylsulphinyl-(1-6C)alkyl, (1-6C)alkylsulphonyl-(1-6C)alkyl, cyano-(1-6C)alkyl, amino-(1-6C)alkyl, (1-6C)alkylamino-(1-6C)alkyl, di-[(1-6C)alkyl]amino-(1-

6C)alkyl, (2-C)alkanoylamino-(1-6C)alkyl or N-(1-6C)alkyl-(2-6C)alkanoylamino-(1-6C) alkyl, or from a group of the formula:

—X⁹-Q⁴ wherein X⁹ is a direct bond or is selected from O, CO and N(R²²), wherein R²² is hydrogen or (1-8C)alkyl, and Q⁴ is aryl, aryl-(1-6C)alkyl, heteroaryl, heteroaryl-(1-6C)alkyl, heterocyclyl or heterocyclyl-(1-6C)alkyl which optionally bears 1 or 2 substituents, which may be the same or different, selected from halogeno, hydroxy, (1-8C)alkyl and (1-6C)alkoxy, and wherein any aryl, heteroaryl or heterocyclyl group within an R⁶ group optionally bears a (1-3C)alkylenedioxy group, and wherein any heterocyclyl group within an R⁶ group optionally bears 1 or 2 oxo or thioxo substituents, and wherein any CH, CH₂ or CH₃ group within an R⁶ group optionally bears on each said CH, CH₂ or CH₃ group one or more halogeno or (1-8C)alkyl substituents and/or a substituent selected from hydroxy, mercapto, amino, cyano, carboxy, carbamoyl, ureido, (2-8C)alkenyl, (2-8C)alkynyl, (1-6C)alkoxy, (1-6C) alkylthio, (1-6C)alkylsulphinyl, (1-6C)alkylsulphonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C) alkyl-(2-6C)alkanoylamino, N'-(1-6C)alkylureido, N',N'-di-[(1-6C)alkyl]ureido, N-(1-6C)alkylureido, N,N'-di-[(1-6C)alkyl]ureido, N,N',N'-tri-[(1-6C) alkyl]ureido, N-(1-6C)alkylsulphamoyl, N-(1-6C) alkylsulphamoyl, N,N-di-[(1-6C)alkyl]sulphamoyl, (1-6C)alkanesulphonylamino and N-(1-6C)alkyl-(1-6C)alkanesulphonylamino, and wherein adjacent carbon atoms in any (2-6C)alkylene chain within an R⁶ group are optionally separated by the insertion into the chain of a group selected from O, S, SO, SO₂, N(R²³), N(R²³)CO, CON(R²³), N(R²³)CON(R²³), CO, CH(OR²³), N(R²³)SO₂, SO₂N(R²³), CH=CH and C≡C wherein R²³ is hydrogen or (1-8C)alkyl, or, when the inserted group is N(R²³), R²³ may also be (2-6C)alkanoyl;

or a pharmaceutically-acceptable salt thereof.

2. The quinoline derivative of the Formula I according to claim 1 wherein:

R¹ substituents may only be located at the 6- and/or 7-positions on the quinoline ring;

and each of X¹, R¹, R², R³, R⁴, R⁵, Ring A, r and R⁶ has any of the meanings defined in claim 1.

3. The quinoline derivative of the Formula I according to claim 1 wherein:

p is 1 or 2 and the R¹ groups are located at the 6- and/or 7-positions and the R¹ group at the 6-position is selected from halogeno, trifluoromethyl, cyano, hydroxy, amino, carboxy, (1-6C)alkoxycarbonyl, carbamoyl, (1-8C)alkyl, (2-8C)alkenyl, (2-8C)alkynyl, (1-6C)alkoxy, (2-6C) alkenyloxy, (2-6C)alkynyloxy, (1-6C)alkylamino, di-[(1-6C)alkyl]amino, N-(1-6C)alkylcarbamoyl and N,N-di-[(1-6C)alkyl] carbamoyl, and the R¹ group at the 7-position is selected from halogeno, trifluoromethyl, cyano, hydroxy, amino, carboxy, (1-6C)alkoxycarbonyl, carbamoyl, (1-8C)alkyl, (2-8C)alkenyl, (2-8C)alkynyl, (1-6C)alkoxy, (2-6C) alkenyloxy, (2-6C)alkynyloxy, (1-6C)alkylamino, di-[(1-6C)alkyl]amino, N-(1-6C)alkylcarbamoyl and N,N-di-[(1-6C)alkyl]carbamoyl, or from a group of the formula:

Q¹-X²— wherein X² is selected from O, N(R⁸), CO, CON (R⁸), N(R⁸)CO and OC(R⁸)₂ wherein R⁸ is hydrogen or (1-8C)alkyl, and Q¹ is aryl, aryl-(1-6C)alkyl, (3-8C)cycloalkyl-(1-6C)alkyl, heteroaryl, heteroaryl-(1-6C)alkyl, heterocyclyl or heterocyclyl-(1-6C)alkyl, and wherein any aryl, (3-8C)cycloalkyl, heteroaryl or heterocyclyl group within a substituent on R¹ optionally bears 1, 2 or 3 substituents, which may be the same or different, selected from halogeno, trifluoromethyl, hydroxy, amino, carbamoyl, (1-8C)alkyl, (2-8C)alkenyl, (2-8C)alkynyl, (1-6C) alkoxy, (1-6C)alkylsulphonyl, (1-6C)alkylamino, di-[(1-6C)alkyl]amino, (2-6C)alkanoyl, N-(1-6C) alkylcarbamoyl, N,N-di-[(1-6C)alkyl]carbamoyl, (2-6C)alkanoylamino and N-(1-6C)alkyl-(2-6C) alkanoylamino, or from a group of the formula:

—X³—R⁹ wherein X³ is a direct bond or is selected from O and N(R¹⁰), wherein R¹⁰ is hydrogen or (1-8C) alkyl, and R⁹ is halogeno-(1-6C)alkyl, hydroxy-(1-6C)alkyl, (1-6C)alkoxy-(1-6C)alkyl, (1-6C) alkylsulphonyl-(1-6C)alkyl, cyano-(1-6C)alkyl, amino-(1-6C)alkyl, (1-6C)alkylamino-(1-6C) alkyl, di-[(1-6C)alkyl]amino-(1-6C)alkyl, (2-6C)alkanoylamino-(1-6C)alkyl or N-(1-6C) alkyl-(2-6C)alkanoylamino-(1-6C)alkyl, or from a group of the formula:

—X⁴-Q² wherein X⁴ is a direct bond or is selected from O, CO and N(R¹¹), wherein R¹¹ is hydrogen or (1-8C)alkyl, and Q² is heterocyclyl or heterocyclyl-(1-6C)alkyl which optionally bears 1 or 2 substituents, which may be the same or different, selected from halogeno, (1-8C)alkyl and (1-6C) alkoxy, and wherein any heterocyclyl group within a substituent on R¹ optionally bears a (1-3C)alkylenedioxy group, and wherein any heterocyclyl group within a substituent on R¹ optionally bears 1 or 2 oxo substituents, and wherein any CH, CH₂ or CH₃ group within a R¹ substituent optionally bears on each said CH, CH₂ or CH₃ group one or more halogeno or (1-8C)alkyl groups and/or a substituent selected from hydroxy, amino, cyano, carboxy, carbamoyl, ureido, (1-6C) alkoxy, (1-6C)alkylthio, (1-6C)alkylsulphinyl, (1-6C)alkylsulphonyl, (1-6C)alkylamino, di-[(1-6C) alkyl]amino, (1-6C)alkoxycarbonyl, N-(1-6C)alkylcarbamoyl, N,N-di-[(1-6C)alkyl]carbamoyl, (2-6C) alkanoyl, (2-6C)alkanoylamino, N-(1-6C)alkyl-(2-6C)alkanoylamino, N-(1-6C)alkylsulphamoyl, N,N-di-[(1-6C)alkyl]sulphamoyl, (1-6C) alkanesulphonylamino and N-(1-6C)alkyl-(1-6C) alkanesulphonylamino, and wherein adjacent carbon atoms in any (2-6C)alkylene chain within a R¹ substituent are optionally separated by the insertion into the chain of a group selected from O, N(R¹²), CON(R¹²), N(R¹²)CO, CH=CH and C≡C wherein $R^{12}$ is hydrogen or (1-8C)alkyl, or, when the inserted group is $N(R^{12})$, $R^{12}$ may also be (2-6C)alkanoyl;

and each of $X^1$, $R^2$, $R^3$, $R^4$, $R^5$, Ring A, r and $R^6$ has any of the meanings defined in claim 1.

4. The quinoline derivative of the Formula I according to claim 1 wherein:

$X^1$ is O;

p is 2 and the $R^1$ groups are located at the 6- and 7-positions and the $R^1$ group at the 6-position is selected from cyano, hydroxy, methoxycarbonyl, ethoxycarbonyl, carbamoyl, methoxy, ethoxy, propoxy, N-methylcarbamoyl, N-ethylcarbamoyl, N,N-dimethylcarbamoyl, N,N-diethylcarbamoyl, pyrrolidin-1-ylcarbonyl, morpholinocarbonyl, piperidinocarbonyl and piperazin-1-ylcarbonyl, and the $R^1$ group at the 7-position is selected from methoxy, ethoxy, propoxy, 2-pyrrolidin-1-ylethoxy, 3-pyrrolidin-1-ylpropoxy, 4-pyrrolidin-1-ylbutoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 4-morpholinobutoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 4-piperidinobutoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 3-(1,2,3,6-tetrahydropyridin-1-yl)propoxy, 2-piperazin-1-ylethoxy, 3-piperazin-1-ylpropoxy, 2-homopiperazin-1-ylethoxy and 3-homopiperazin-1-ylpropoxy, and wherein any heterocyclyl group within a substituent on $R^1$ optionally bears 1 or 2 substituents, which may be the same or different, selected from fluoro, chloro, trifluoromethyl, hydroxy, amino, methyl, ethyl, methoxy, methylenedioxy, ethylidenedioxy and isopropylidenedioxy, and a pyrrolidin-2-yl, pyrrolidin-3-yl, piperidin-3-yl, piperidin-4-yl, piperazin-1-yl or homopiperazin-1-yl group within a $R^1$ substituent is optionally N-substituted with methyl, ethyl, propyl, allyl, 2-propynyl, methylsulphonyl, acetyl, propionyl, isobutyryl, 2-fluoroethyl, 2,2-difluoroethyl, 2,2,2-trifluoroethyl or cyanomethyl, and wherein any heterocyclyl group within a substituent on $R^1$ optionally bears 1 or 2 oxo substituents, and wherein any $CH$, $CH_2$ or $CH_3$ group within a $R^1$ substituent optionally bears on each said $CH$, $CH_2$ or $CH_3$ group one or more chloro groups or a substituent selected from hydroxy, amino, methoxy, methylsulphonyl, methylamino, dimethylamino, diisopropylamino, N-ethyl-N-methylamino and N-isopropyl-N-methylamino;

q is 0 or q is 1 and the $R^2$ group is selected from fluoro, chloro, trifluoromethyl, cyano, hydroxy, amino, methyl, methoxy, methylamino and dimethylamino;

each of $R^3$ and $R^4$ is hydrogen;

$R^5$ is hydrogen, methyl or ethyl;

Ring A is a furyl, pyrrolyl, thienyl, oxazolyl, isoxazolyl, imidazolyl, pyrazolyl, thiazolyl, isothiazolyl, oxadiazolyl or thiadiazolyl ring; and r is 0 or r is 1 or 2 and one $R^6$ group is located at the 3-position (relative to the $CON(R^5)$ group), and each $R^6$ group, which may be the same or different, is selected from fluoro, chloro, trifluoromethyl, cyano, hydroxy, amino, methyl, ethyl, propyl, isopropyl, butyl, sec-butyl, isobutyl, tert-butyl, methoxy, ethoxy, methylamino, ethylamino, dimethylamino and diethylamino, or r is 1 or 2 and one $R^6$ group is located at the 3-position (relative to the $CON(R^5)$ group) and is a group of the formula:

—$X^6$—$R^{15}$ wherein $X^6$ is a direct bond or O and $R^{15}$ is hydroxymethyl, 1-hydroxyethyl, 2-hydroxyethyl, 3-hydroxypropyl, methoxymethyl, 1-methoxyethyl, 2-methoxyethyl, 1-methoxy-1-methylethyl, 3-methoxypropyl, cyanomethyl, 1-cyanoethyl, 2-cyanoethyl, 3-cyanopropyl, aminomethyl, 1-aminoethyl, 2-aminoethyl, 3-aminopropyl, methylaminomethyl, 1-methylaminoethyl, 2-methylaminoethyl, 3-methylaminopropyl, ethylaminomethyl, 1-ethylaminoethyl, 2-ethylaminoethyl, 1-ethylamino-1-methylethyl, 3-ethylaminopropyl, isopropylaminomethyl, 1-isopropylaminoethyl, dimethylaminomethyl, 1-dimethylaminoethyl, 2-dimethylaminoethyl, 3-dimethylaminopropyl, phenyl, benzyl, cyclopropyl, cyclopentyl, cyclohexyl, thienyl, imidazolyl, thiazolyl, thiadiazolyl, pyrrolidinyl, morpholinyl, tetrahydro-1,4-thiazinyl, piperidinyl, homopiperidinyl, piperazinyl, homopiperazinyl, pyrrolidinylmethyl, 2-(pyrrolidinyl)ethyl, 3-(pyrrolidinyl)propyl, morpholinylmethyl, 2-(morpholinyl)ethyl, 3-(morpholinyl)propyl, piperidinylmethyl, 2-(piperidinyl)ethyl, 3-(piperidinyl)propyl, homopiperidinylmethyl, piperazinylmethyl, 2-(piperazinyl)ethyl, 3-(piperazinyl)propyl or homopiperazinylmethyl, provided that, when $X^6$ is O, there are at least two carbon atoms between $X^6$ and any heteroatom in the $R^{15}$ group, and wherein any aryl, (3-8C)cycloalkyl, heteroaryl or heterocyclyl group within the $R^6$ group optionally bears a substituent selected from fluoro, chloro, trifluoromethyl, hydroxy, amino, methyl, methoxy, methylamino and dimethylamino and any such aryl, (3-8C)cycloalkyl, heteroaryl or heterocyclyl group within the $R^6$ group optionally bears a further substituent selected from hydroxymethyl, cyanomethyl, aminomethyl, methylaminomethyl and dimethylaminomethyl, and any second $R^6$ group that is present is selected from fluoro, chloro, trifluoromethyl, cyano, hydroxy, amino, methyl, methoxy, methylamino and dimethylamino;

or a pharmaceutically-acceptable salt thereof.

5. The quinoline derivative of the Formula I according to claim 1 wherein:

$X^1$ is O;

p is 2 and the first $R^1$ group is located at the 6-position and is selected from cyano, carbamoyl, methoxy, N-methylcarbamoyl and N,N-dimethylcarbamoyl, and the second $R^1$ group is located at the 7-position and is selected from methoxy, ethoxy, 2-hydroxyethoxy and 2-methoxyethoxy;

q is 0 or q is 1 and the $R^2$ group which is located at the 2-position (relative to the $C(R^3)(R^4)$ group) is selected from fluoro, chloro, cyano, methyl and methoxy;

each of $R^3$ and $R^4$ is hydrogen;

$R^5$ is hydrogen or methyl;

Ring A is 2-oxazolyl, 3-isoxazolyl, 5-isoxazolyl, 2-imidazolyl, 3-pyrazolyl, 4-pyrazolyl, 2-thiazolyl, 3-isothiazolyl, 5-isothiazolyl, 1,2,4-oxadiazol-5-yl and 1,3,4-oxadiazol-5-yl; and r is 1 or 2 and each $R^6$ group that is present is selected from methyl, ethyl, propyl, isopropyl, tert-butyl, cyclopropyl, hydroxymethyl, 2-hydroxyethyl, methoxymethyl, 2-methoxyethyl, methylaminomethyl, ethylaminomethyl, isopropylaminomethyl, cyclopropylaminomethyl, dimethylaminomethyl, amino, methylamino, ethylamino, dimethylamino and diethylamino;

or a pharmaceutically-acceptable salt thereof.

6. The quinoline derivative of the Formula I according to claim 1 wherein:

p is 0 or p is 1 or 2 and the $R^1$ groups are located at the 6- and/or 7-positions and are selected from halogeno, trifluoromethyl, cyano, hydroxy, amino, carbamoyl, (1-6C)alkoxycarbonyl, (1-8C)alkyl, (2-8C)alkenyl, (2-8C)alkynyl, (1-6C)alkoxy, (2-6C)alkenyloxy, (2-6C)alkynyloxy, (1-6C)alkylamino, di-[(1-6C)alkyl]amino, N-(1-6C)alkylcarbamoyl and N,N-di-[(1-6C)alkyl]carbamoyl, and q is 1 and the $R^2$ group is located at the 2-position (relative to the $C(R^3)(R^4)$ group) and is selected from halogeno, trifluoromethyl, cyano, carbamoyl, hydroxy, amino, (1-8C)alkyl, (2-8C)alkenyl, (2-8C)alkynyl, (1-6C)alkoxy, (1-6C)alkylamino, di-[(1-6C)alkyl]amino, N-(1-6C)alkylcarbamoyl and N,N-di-[(1-6C)alkyl]carbamoyl;

and each of $X^1$, $R^3$, $R^4$, $R^5$, Ring A, r and $R^6$ has any of the meanings defined in claim 1.

7. The quinoline derivative of the Formula I according to claim 1 wherein:

p is 0 or p is 1 or 2 and the $R^1$ groups are located at the 6- and/or 7-positions and are selected from fluoro, chloro, cyano, carbamoyl, methoxycarbonyl, methoxy, ethoxy, N-methylcarbamoyl and N,N-dimethylcarbamoyl, and q is 1 and the $R^2$ group which is located at the 2-position (relative to the $C(R^3)(R^4)$ group) is selected from carbamoyl, methoxy, ethoxy, N-methylcarbamoyl and N,N-dimethylcarbamoyl;

and each of $X^1$, $R^3$, $R^4$, $R^5$, Ring A, r and $R^6$ has any of the meanings defined in claim 1.

8. The quinoline derivative of the Formula I according to claim 1 wherein:

$X^1$ is O;

p is 0 or p is 1 or 2 and the $R^1$ groups are located at the 6- and/or 7-positions and are selected from halogeno, trifluoromethyl, cyano, hydroxy, amino, carbamoyl, (1-6C)alkoxycarbonyl, (1-8C)alkyl, (2-8C)alkenyl, (2-8C)alkynyl, (1-6C)alkoxy, (2-6C)alkenyloxy, (2-6C)alkynyloxy, (1-6C)alkylamino, di-[(1-6C)alkyl]amino, N-(1-6C)alkylcarbamoyl and N,N-di-[(1-6C)alkyl]carbamoyl, q is 1 and the $R^2$ group is located at the 2-position (relative to the $C(R^3)(R^4)$ group) and is selected from halogeno, trifluoromethyl, cyano, carbamoyl, hydroxy, amino, (1-8C)alkyl, (2-8C)alkenyl, (2-8C)alkynyl, (1-6C)alkoxy, (1-6C)alkylamino, di-[(1-6C)alkyl]amino, N-(1-6C)alkylcarbamoyl and N,N-di-[(1-6C)alkyl]carbamoyl;

each of $R^3$ and $R^4$ is hydrogen;

$R^5$ is hydrogen;

Ring A is a 5-membered monocyclic heteroaryl ring with up to three ring heteroatoms selected from oxygen, nitrogen and sulphur; and r is 0, 1, 2 or 3 and each $R^6$ group that is present, which may be the same or different, is selected from halogeno, trifluoromethyl, cyano, hydroxy, amino, (1-8C)alkyl, (2-8C)alkenyl, (2-8C)alkynyl, (1-6 C)alkoxy, (1-6 C)alkylamino, di- [(1-6 C)alkyl] amino, (2-6 C)alkanoylamino and N-(1-6C)alkyl-(2-6C)alkanoylamino;

or a pharmaceutically-acceptable salt thereof.

9. The quinoline derivative of the Formula I according to claim 1 wherein:

$X^1$ is O;

p is 0 or p is 1 or 2 and the $R^1$ groups are located at the 6- and/or 7-positions and are selected from fluoro, chloro, trifluoromethyl, cyano, hydroxy, amino, carbamoyl, methoxycarbonyl, ethoxycarbonyl, methyl, ethyl, methoxy, ethoxy, methylamino, dimethylamino, N-methylcarbamoyl and N,N-dimethylcarbamoyl, q is 1 and the $R^2$ group which is located at the 2-position (relative to the $C(R^3)(R^4)$ group) is selected from fluoro, chloro, trifluoromethyl, cyano, carbamoyl, hydroxy, amino, methyl, ethyl, methoxy, ethoxy, methylamino, dimethylamino, N-methylcarbamoyl and N,N-dimethylcarbamoyl;

each of $R^3$ and $R^4$ is hydrogen;

$R^5$ is hydrogen;

Ring A is a furyl, pyrrolyl, thienyl, oxazolyl, isoxazolyl, imidazolyl, pyrazolyl, thiazolyl, isothiazolyl, oxadiazolyl or thiadiazolyl ring; and r is 1 or 2 and each $R^6$ group, which may be the same or different, is selected from fluoro, chloro, trifluoromethyl, cyano, hydroxy, amino, methyl, ethyl, propyl, isopropyl, butyl, sec-butyl, isobutyl, tert-butyl, methoxy, ethoxy, methylamino, ethylamino, dimethylamino and diethylamino;

or a pharmaceutically-acceptable salt thereof.

10. The quinoline derivative of the Formula I according to claim 1 wherein:

$X^1$ is O;

p is 0 or p is 1 or 2 and the $R^1$ groups are located at the 6- and/or 7-positions and are selected from fluoro, cyano, carbamoyl, methoxycarbonyl, methoxy, ethoxy, N-methylcarbamoyl and N,N-dimethylcarbamoyl, q is 1 and the $R^2$ group which is located at the 2-position (relative to the $C(R^3)(R^4)$ group) is selected from methoxy and ethoxy;

each of $R^3$ and $R^4$ is hydrogen;

$R^5$ is hydrogen;

Ring A is a furyl, pyrrolyl, thienyl, oxazolyl, isoxazolyl, imidazolyl, pyrazolyl, thiazolyl, isothiazolyl, oxadiazolyl or thiadiazolyl ring that bears one or two $R^6$ groups and one $R^6$ group is located at the 3-position (relative to the $CON(R^5)$ group); and r is 1 or 2 and each $R^6$ group, which may be the same or different, is selected from fluoro, chloro, trifluoromethyl, cyano, hydroxy, amino, methyl, ethyl, propyl, isopropyl, butyl, sec-butyl, isobutyl, tert-butyl, methoxy, ethoxy, methylamino, ethylamino, dimethylamino and diethylamino;

or a pharmaceutically-acceptable salt thereof.

11. The quinoline derivative of the Formula I according to claim 1 wherein:

$X^1$ is O;

p is 0 or p is 1 or 2 and the $R^1$ groups are located at the 6-and/or 7-positions and are selected from fluoro, cyano, carbamoyl, methoxycarbonyl, methoxy, ethoxy, N-methylcarbamoyl and N,N-dimethylcarbamoyl, q is 1 and the $R^2$ group which is located at the 2-position (relative to the $C(R^3)(R^4)$ group) is a methoxy group;

each of $R^3$ and $R^4$ is hydrogen;

$R^5$ is hydrogen;

Ring A is 2-oxazolyl, 3-isoxazolyl, 5-isoxazolyl, 3-pyrazolyl, 4-pyrazolyl, 2-thiazolyl, 1,2,4-oxadiazol-5-yl and 1,3,4-oxadiazol-5-yl; and r is 1 or 2 and each $R^6$ group that is present is selected from methyl, ethyl, propyl and isopropyl;

or a pharmaceutically-acceptable salt thereof.

12. The quinoline derivative of the Formula I according to claim 1 selected from:

N-(1-ethyl-1H-pyrazol-4-yl)-2-(2-methoxy-4-quinolin-4-yloxyphenyl)acetamide,

N-(1-methyl-1H-pyrazol-4-yl)-2-[4-(6-fluoroquinolin-4-yloxy)-2-methoxyphenyl]acetamide, N-(1-ethyl-1H-pyrazol-4-yl)-2-[4-(6-fluoroquinolin-4-yloxy)-2-methoxyphenyl]acetamide, N-(1-ethyl-1H-pyrazol-4-yl)-2-[4-(7-fluoroquinolin-4-yloxy)-2-methoxyphenyl]acetamide, N-(1-ethyl-1H-pyrazol-4-yl)-2-{2-methoxy-4-[6-methoxy-7-(N-methylcarbamoyl)quinolin-4-yloxy]phenyl}acetamide, N-(1-methyl-1H-pyrazol-4-yl)-2-[2-methoxy-4-(7-methoxyquinolin-4-yloxy)phenyl]acetamide, N-(1,3-dimethyl-1H-pyrazol-4-yl)-2-[2-methoxy-4-(7-methoxyquinolin-4-yloxy)phenyl]acetamide, N-(1,5-dimethyl-1H-pyrazol-4-yl)-2-[2-methoxy-4-(7-methoxyquinolin-4-yloxy)phenyl]acetamide, N-(1,3-dimethyl-1H-pyrazol-4-yl)-2-[4-(6,7-dimethoxyquinolin-4-yloxy)-2-methoxyphenyl]acetamide, N-(4-methyl-1H-pyrazol-3-yl)-2-[4-(6,7-dimethoxyquinolin-4-yloxy)-2-methoxyphenyl]acetamide, N-(4-ethyl-1H-pyrazol-3-yl)-2-[4-(6,7-dimethoxyquinolin-4-yloxy)-2-methoxyphenyl]acetamide, N-(4,5-dimethyl-1H-pyrazol-3-yl)-2-[2-methoxy-4-(7-methoxyquinolin-4-yloxy)phenyl]acetamide, N-(5-methyl-1H-pyrazol-3-yl)-2-[4-(6-fluoroquinolin-4-yloxy)-2-methoxyphenyl]acetamide, N-(4,5-dimethyl-1H-pyrazol-3-yl)-2-[4-(6-fluoroquinolin-4-yloxy)-2-methoxyphenyl]acetamide, N-(4-methylisoxazol-3-yl)-2-[2-methoxy-4-(7-methoxyquinolin-4-yloxy)phenyl]acetamide, N-(4,5-dimethylisoxazol-3-yl)-2-(2-methoxy-4-quinolin-4-yloxyphenyl)acetamide, N-(4,5-dimethylisoxazol-3-yl)-2-[2-methoxy-4-(7-methoxyquinolin-4-yloxy)phenyl]acetamide, N-(4,5-dimethylisoxazol-3-yl)-2-{2-methoxy-4-[7-methoxy-6-(N-methylcarbamoyl)quinolin-4-yloxy]phenyl}acetamide, N-(4,5-dimethylisoxazol-3-yl)-2-[4-(6-fluoroquinolin-4-yloxy)-2-methoxyphenyl]acetamide, N-(4-methylthiazol-2-yl)-2-[2-methoxy-4-(6-fluoroquinolin-4-yloxy)phenyl]acetamide and N-(4-methylthiazol-2-yl)-2-{2-methoxy-4-[6-methoxy-7-(N-methylcarbamoyl)quinolin-4-yloxy]phenyl}acetamide;

and pharmaceutically-acceptable saltst thereof.

13. A process for the preparation of a quinoline derivative of the Formula I, or a pharmaceutically-acceptable salt thereof, according to claim 1 which comprises:

(a) the reaction of a quinoline of the Formula II

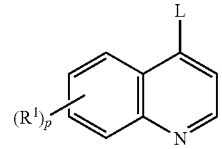

II wherein L is a displaceable group and p and $R^1$ have any of the meanings defined in claim 1 except that any functional group is protected if necessary, with a phenylacetamide of the Formula III

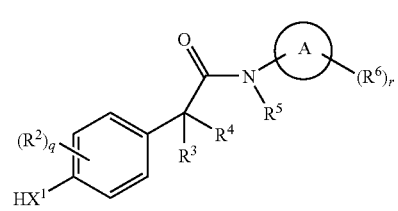

III wherein $X^1$, q, $R^2$, $R^3$, $R^4$, $R^5$, Ring A, r and $R^6$ have any of the meanings defined in claim 1 except that any functional group is protected if necessary, whereafter any protecting group that is present is removed;

(b) the coupling of a quinoline of the Formula VII

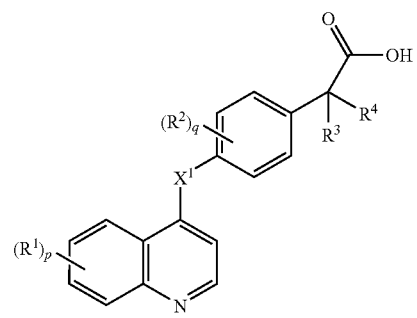

VII or a reactive derivative thereof, wherein p, $R^1$, $X^1$, q, $R^2$, $R^3$ and $R^4$ have any of the meanings defined in claim 1 except that any functional group is protected if necessary, with an amine of the Formula VI

VI wherein $R^5$, Ring A, r and $R^6$ have any of the meanings defined in claim 1 except that any functional group is protected if necessary, whereafter any protecting group that is present is removed;

(c) for the production of those compounds of the Formula I wherein at least one $R^1$ group is a group of the formula $Q^1$-$X^2$— wherein $Q^1$ is an aryl-(1-6C)alkyl, (3-7C)cycloalkyl-(1-6C)alkyl, (3-7C)cycloalkenyl-(1-6C)alkyl, heteroaryl-(1-6C)alkyl or heterocyclyl-(1-6C)alkyl group or an optionally substituted alkyl group and $X^2$ is an oxygen atom, the coupling of a quinoline of the Formula VIII

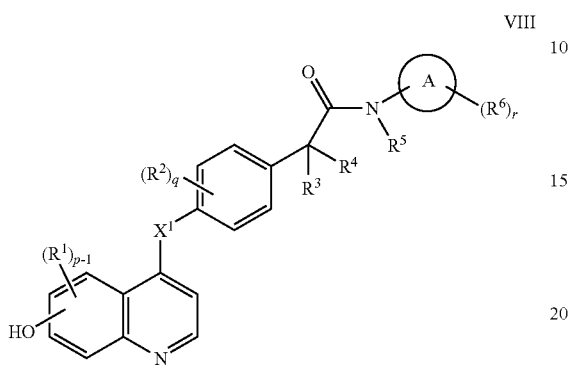

VIII wherein each of p, $R^1$, $X^1$, q, $R^2$, $R^3$, $R^4$, $R^5$, Ring A, r and $R^6$ has any of the meanings defined in claim 1 except that any functional group is protected if necessary, with an appropriate alcohol wherein any functional group is protected if necessary, whereafter any protecting group that is present is removed;

(d) for the production of those compounds of the Formula I wherein a $R^6$ group is a group of the formula —$X^6$—$R^{15}$ wherein $X^6$ has any of the meanings defined in claim 1 and $R^{15}$ is an amino-substituted (1-6C)alkyl group, the reaction of a compound of the Formula I wherein a $R^6$ group is a group of the formula —$X^6$—$R^{15}$ wherein $R^{15}$ is a halogeno-substituted (1-6C)alkyl group with an appropriate amine or with a nitrogen-containing heterocyclyl compound;

(e) for the production of those compounds of the Formula I wherein a $R^6$ group is a group of the Formula —$X^6$—$R^{15}$ wherein $X^6$ has any of the meanings defined in claim 1 and $R^{15}$ is an amino-substituted (1-6C)alkyl group, the reductive amination of a compound of the Formula I wherein a $R^6$ group is a group of the formula —$X^6$—$R^{15}$ wherein $R^{15}$ is a formyl or (2-6C)alkanoyl group;

(f) for the production of those compounds of the Formula I wherein $R^5$ is a (1-8C)alkyl group, the alkylation of a compound of the Formula I wherein $R^5$ is hydrogen with a suitable alkylating agent;

(g) for the production of those compounds of the Formula I wherein $R^1$ is a carboxy group, the cleavage of a compound of the Formula I wherein $R^1$ is a (1-6C)alkoxycarbonyl group;

(h) for the production of those compounds of the Formula I wherein $R^1$ is a carbamoyl, N-(1-6C)alkylcarbamoyl, N,N-di-[(1-6C)alkyl]carbamoyl or NH-containing heterocyclic group, the coupling of a compound of the Formula I wherein $R^1$ is a carboxy group, or a reactive derivative thereof, with ammonia or with a (1-6C)alkylamine, a di-(1-6C)alkylamine or a NH-containing heterocycle as appropriate; or (i) for the production of those compounds of the Formula I wherein a $R^6$ group is a di-(1-6C)alkylamino group, the reductive amination of a (1-5C)aldehyde or a (3-6C) ketone with a compound of the Formula I wherein a $R^6$ group is an amino or (1-6C)alkylamino group;

and optionally forming a pharmaceutically-acceptable salt of a quinoline derivative of the Formula I by reaction of said quinoline derivative with a suitable acid.

14. A pharmaceutical composition which comprises a quinoline derivative of the Formula I, or a pharmaceutically-acceptable salt thereof, according to claim 1 in association with a pharmaceutically-acceptable diluent or carrier.

15. The quinoline derivative of the Formula I according to claim 1 selected from:

2-(4-[(6,7-dimethoxyquinolin-4-yl)oxy]phenyl)-N-[1-(propan-2-yl)-1H-pyrazol-4-yl]acetamide;

2-{4-[(6,7-dimethoxyquinolin-4-yl)oxy]phenyl}-N-(5-ethyl-1H-pyrazol-3-yl)acetamide;

2-{4-[(6,7-dimethoxyquinolin-4-yl)oxy]phenyl}-N-(5-ethyl-1,2-oxazol-3-yl)acetamide;

4-(4-{2-[(5-ethyl-1,2-oxazol-3-yl)amino]-2-oxoethyl}phenoxy)-7-methoxyquinoline-6-carboxamide;

4-(4-{2-[(5-ethyl-1,2-oxazol-3-yl)amino]-2-oxoethyl}-3-methoxyphenoxy)-7-methoxy-N-methylquinoline-6-carboxamide; and 4-(4-{2[(5-ethyl-1H-pyrazol-3-yl)amino]-2-oxoethyl}-3-methoxyphenoxy)-N-methylquinoline-7-carboxamide;

and pharmaceutically-acceptable salts thereof.

* * * * *